United States Patent
Buesking et al.

(10) Patent No.: US 11,685,744 B2
(45) Date of Patent: Jun. 27, 2023

(54) CDK INHIBITORS AND THEIR USE AS PHARMACEUTICALS

(71) Applicant: Prelude Therapeutics, Incorporated, Wilmington, DE (US)

(72) Inventors: Andrew W. Buesking, Wilmington, DE (US); Andrew Paul Combs, Kennett Square, PA (US); Jincong Zhuo, Garnet Valley, PA (US); Ryan Holmes, Wilmington, DE (US); Sarah Pawley, Landenberg, PA (US); Xiaowei Wu, Wilmington, DE (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 0 days.

(21) Appl. No.: 17/480,323

(22) Filed: Sep. 21, 2021

(65) Prior Publication Data
US 2022/0089608 A1 Mar. 24, 2022

Related U.S. Application Data

(60) Provisional application No. 63/221,959, filed on Jul. 15, 2021, provisional application No. 63/081,126, filed on Sep. 21, 2020.

(51) Int. Cl.
| | |
|---|---|
| *A61K 31/4188* | (2006.01) |
| *A61K 31/4196* | (2006.01) |
| *A61K 31/506* | (2006.01) |
| *A61K 31/5355* | (2006.01) |
| *A61K 31/551* | (2006.01) |
| *A61K 31/565* | (2006.01) |
| *A61P 35/00* | (2006.01) |
| *C07D 495/04* | (2006.01) |
| *C07D 519/00* | (2006.01) |

(52) U.S. Cl.
CPC ........ *C07D 495/04* (2013.01); *A61K 31/4188* (2013.01); *A61K 31/4196* (2013.01); *A61K 31/506* (2013.01); *A61K 31/5355* (2013.01); *A61K 31/551* (2013.01); *A61K 31/565* (2013.01); *A61P 35/00* (2018.01); *C07D 519/00* (2013.01)

(58) Field of Classification Search
CPC ............... C07D 495/04; C07D 519/00; A61K 31/4188; A61K 31/4196; A61K 31/506; A61K 31/5355; A61K 31/551; A61K 31/565; A61P 35/00
See application file for complete search history.

(56) References Cited

U.S. PATENT DOCUMENTS

| | | | |
|---|---|---|---|
| 3,657,744 A | 4/1972 | Ersek | |
| 4,739,762 A | 4/1988 | Palmaz | |
| 4,992,445 A | 2/1991 | Lawter et al. | |
| 5,001,139 A | 3/1991 | Lawter et al. | |
| 5,023,252 A | 6/1991 | Hsieh | |
| 5,040,548 A | 8/1991 | Yock | |
| 5,061,273 A | 10/1991 | Yock | |
| 5,195,984 A | 3/1993 | Schatz | |
| 5,292,331 A | 3/1994 | Boneau | |
| 5,451,233 A | 8/1995 | Yock | |
| 5,496,346 A | 3/1996 | Horewski | |
| 5,674,278 A | 10/1997 | Boneau | |
| 5,879,382 A | 3/1999 | Boneau | |
| 6,344,053 B1 | 2/2002 | Boneau | |

FOREIGN PATENT DOCUMENTS

| | | | |
|---|---|---|---|
| CN | 112457326 A | * 3/2021 | ............. A61P 35/00 |
| WO | 2009036082 | 3/2009 | |
| WO | 2009046416 | 4/2009 | |
| WO | 2014149164 | 9/2014 | |
| WO | 2017114351 | 7/2017 | |
| WO | 2017133701 | 8/2017 | |
| WO | 2019223632 | 11/2019 | |

OTHER PUBLICATIONS

CN-112457326-A; (2021) WIPO English machine translation—Description: p. 1-31.*
Berge_etal_J_Pharm Sci_1977.
Bronner_etal_Bioorg_MedChem_Lett_2019.
Cho_etal_J_Med_Chem_2010.
De_Gooijer_etal_Invest_New_Drugs_2015.
Parrish, Pokorny et al. 2015.
Raub_etal_Drug_Metabolism _Disposition_2015.
Remington's_Pharmaceutical_Science_17_ed_chapter_76.

* cited by examiner

Primary Examiner — John M Mauro
(74) Attorney, Agent, or Firm — BakerHostetler

(57) ABSTRACT

The disclosure is directed to compounds of Formula I

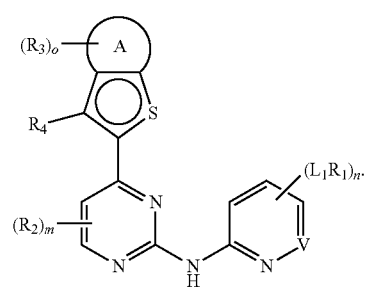

Pharmaceutical compositions comprising compounds of Formula I, as well as methods of their use and preparation, are also described.

54 Claims, No Drawings

CDK INHIBITORS AND THEIR USE AS PHARMACEUTICALS

CROSS REFERENCE TO RELATED APPLICATIONS

This application claims the benefit of U.S. Provisional Application No. 63/081,126, filed Sep. 21, 2020, the entirety of which is incorporated by reference herein, and U.S. Provisional Application No. 63/221,959, filed Jul. 15, 2021, the entirety of which is incorporated by reference herein.

TECHNICAL FIELD

The disclosure is directed to CDK inhibitors and methods of their use.

BACKGROUND

Cyclin-dependent kinases (CDKs) are a family of conserved serine/threonine kinases that play critical roles in cell cycle and gene transcription regulation (Malumbres 2014). Among the cell cycle CDK subfamily, CDK4 and CDK6 are the master regulators that control entry of cells from the first gap phase (G1) to the DNA synthesis phase (S). During this process, cyclin D protein levels increase, complex with CDK4/6 and activate their kinase activities. Activated CDK4/6 complexes phosphorylate retinoblastoma protein (RB1) and other RB1-like proteins, reduce their binding affinities and release RB1-containing transcription repressor complexes from E2F transcription factors, resulting in activation of E2F controlled cell cycle genes and progression of cell cycle (Lapenna and Giordano 2009, Asghar, Witkiewicz et al. 2015).

Given the central roles CDK4/6 play in cell cycle regulation, disfunction of which is a hallmark of cancer (Hanahan and Weinberg 2011), dysregulation of CDK4/6 pathway has been frequently observed in cancer, such as (epi)genetic inactivation of endogenous CDK4/6 inhibitor p16INK4A and amplification/overexpression of CDK4/6 as well as cyclin D proteins (Lapenna and Giordano 2009, Malumbres and Barbacid 2009, Asghar, Witkiewicz et al. 2015, O'Leary, Finn et al. 2016). CDK4/6 have been intensively investigated as potential therapeutic targets for cancer treatment and the recent approval of CDK4/6 selective inhibitors, namely, Palbociclib (U.S. Food & Drug Administration. 2017), Ribociclib (U.S. Food & Drug Administration. 2017), and Abemaciclib (U.S. Food & Drug Administration. 2018), in combination with endocrine therapies, to treat hormone receptor (HR) positive and human epidermal growth factor receptor 2 (HER2) negative metastatic breast cancer further validated this thesis.

Central nervous system (CNS) diseases such as glioblastoma (GBM) and brain metastases are challenging malignancies with urgent unmet needs. GBM is the most common and aggressive primary brain cancer in adults with overall 5-year survival rate less than 6% (Ostrom, Gittleman et al. 2016). Large scale genomic studies revealed that the cyclin D-CDK4/6-RB1 pathway is alternated in majority of gliomas and represents one of the most perturbed pathways (Cancer Genome Atlas Research 2008, Brennan, Verhaak et al. 2013), suggesting CDK4/6 may be good targets for GBM. Brain metastases, on the other hand, may arise from an estimated of 20% of all cancer patients but still lacks effective treatments (Achrol, Rennert et al. 2019). Interestingly, genomic studies also identified CDK pathway as one of three most altered and actionable genetic alternations in brain metastases (Brastianos, Carter et al. 2015, Valiente, Ahluwalia et al. 2018).

However, despite positive preclinical data supporting targeting CDK4/6 to treat GBM (Yin, Li et al. 2018, Bronner, Merrick et al. 2019), and initial signs of brain penetration of Abemaciclib in patients (Patnaik, Rosen et al. 2016, Sahebjam, Rhun et al. 2016), clinical development of CDK4/6 inhibitors in the clinic for GBM or brain metastases are still in early stage or unsuccessful (Anders, Rhun et al. 2019, Nguyen, Searle et al. 2019, Sahebjam, Le Rhun et al. 2019), likely due to their inability to penetrate the blood-brain barrier (BBB) (de Gooijer, Zhang et al. 2015, Parrish, Pokorny et al. 2015, Raub, Wishart et al. 2015).

Additional small molecule CDK4/6 inhibitors are needed.

SUMMARY OF THE INVENTION

The disclosure is directed to compounds of Formula I:

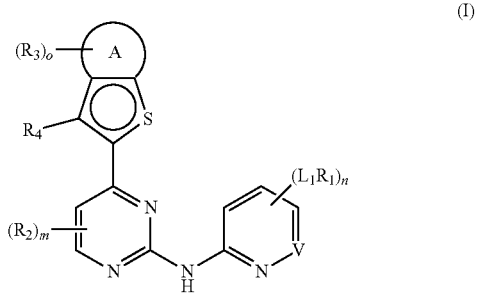

(I)

or a pharmaceutically acceptable salt thereof, wherein
ring A is a 5-7-membered heteroaryl;
V=CL$_1$R$_1$ or N
n is 1 or 2 or 3;
m is 1 or 2;
o is 1, 2, 3, 4, or 5;
each L$_1$ is independently a bond, O, NR or C$_1$-C$_6$ alkylene, wherein R is H or C$_1$-C$_6$alkyl;
each R$_1$ is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR$^b$), —B(OR$^c$)(OR$^d$) or —S(O)$_2$R$^b$;
each R$_2$ is independently H, D, halogen, C$_1$-C$_8$ alkoxide C$_1$-C$_8$ alkyl, haloalkyl, or CN and
each R$_3$ is independently H, D, halogen, oxo, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, or heterocycloalkenyl, —OR$^a$, —OR$^b$, SR$^b$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR), —B(OR$^d$)(OR$^c$) or —S(O)$_2$R$^b$;
each R$^a$ is independently H, D, —C(O)R$^b$, —C(O)OR$^c$, —C(O)NR$^c$R$^d$, —C(=NR)NR$^b$R$^c$, —C(=NOR$^b$)NR$^b$R$^c$, —C(=NCN)NR$^b$R$^c$, —P(OR$^c$)$_2$, —P(O)R$^b$R$^b$, —P(O)R$^c$R$^b$, —S(O)R$^b$, —S(O)NR$^c$R$^d$, —S(O)$_2$R$^b$, —S(O)$_2$NR$^c$R$^d$, SiR$_3$, —C$_1$-C$_{10}$alkyl, —C$_2$-C$_{10}$ alkenyl, —C$_2$-C$_{10}$ alkynyl, aryl, cycloalkyl, cycloalkenyl, heteroaryl, heterocycloalkyl, or heterocycloalkenyl;

each $R^b$, is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, heteroaryl, cycloalkyl, cycloalkenyl, heterocycloalkyl, or heterocycloalkenyl;

or $R^c$ and $R^d$, together with the atom to which they are both attached, form a monocyclic or multicyclic heterocycloalkyl, or a monocyclic or multicyclic heterocyclo-alkenyl group;

each $R_4$ is independently H, D, halogen, $C_1$-$C_8$ alkoxide or $C_1$-$C_8$ alkyl, haloalkyl and CN.

Stereoisomers of the compounds of Formula I, and the pharmaceutical salts and solvates thereof, are also contemplated, described, and encompassed herein. Methods of using compounds of Formula I are described, as well as pharmaceutical compositions including the compounds of Formula I.

DETAILED DESCRIPTION OF ILLUSTRATIVE EMBODIMENTS

The disclosure may be more fully appreciated by reference to the following description, including the following definitions and examples. Certain features of the disclosed compositions and methods which are described herein in the context of separate aspects, may also be provided in combination in a single aspect. Alternatively, various features of the disclosed compositions and methods that are, for brevity, described in the context of a single aspect, may also be provided separately or in any subcombination.

At various places in the present specification, substituents of compounds of the invention are disclosed in groups or in ranges. It is specifically intended that the invention include each and every individual subcombination of the members of such groups and ranges. For example, the term "$C_1$-$C_6$ alkyl" is specifically intended to individually disclose methyl, ethyl, $C_3$ alkyl, $C_4$ alkyl, $C_5$ alkyl, and $C_6$ alkyl. "$C_0$ alkyl" refers to a covalent bond.

It is further intended that the compounds of the invention are stable. As used herein "stable" refers to a compound that is sufficiently robust to survive isolation to a useful degree of purity from a reaction mixture, and preferably capable of formulation into an efficacious therapeutic agent.

It is further appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

The term "alkyl," when used alone or as part of a substituent group, refers to a straight- or branched-chain hydrocarbon group having from 1 to 12 carbon atoms ("$C_1$-$C_{12}$"), preferably 1 to 6 carbons atoms ("$C_1$-$C_6$"), in the group. Examples of alkyl groups include methyl (Me, $C_1$alkyl), ethyl (Et, $C_2$alkyl), n-propyl ($C_3$alkyl), isopropyl ($C_3$alkyl), butyl ($C_4$alkyl), isobutyl ($C_4$alkyl), sec-butyl ($C_4$alkyl), tert-butyl ($C_4$alkyl), pentyl ($C_5$alkyl), isopentyl ($C_5$alkyl), tert-pentyl ($C_5$alkyl), hexyl ($C_6$alkyl), isohexyl ($C_6$alkyl), and the like. Alkyl groups of the disclosure can be unsubstituted or substituted. In those embodiments wherein the alkyl group is substituted, the alkyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "halo" or halogen, refers to chloro, fluoro, bromo, or iodo.

The term "cycloalkyl" when used alone or as part of a substituent group refers to cyclic-containing, non-aromatic hydrocarbon groups having from 3 to 10 carbon atoms ("$C_3$-$C_{10}$"), preferably from 3 to 6 carbon atoms ("$C_3$-$C_6$"). Cycloalkyl groups of the disclosure include monocyclic groups, as well as multicyclic groups such as bicyclic and tricyclic groups. In those embodiments having at least one multicyclic cycloalkyl group, the cyclic groups can share one common atom (i.e., spirocyclic). In other embodiments having at least one multicyclic cycloalkyl group, the cyclic groups share two common atoms. Examples of cycloalkyl groups include, for example, cyclopropyl ($C_3$), cyclobutyl ($C_4$), cyclopropylmethyl ($C_4$), cyclopentyl ($C_5$), cyclohexyl ($C_6$), 1-methylcyclopropyl ($C_4$), 2-methylcyclopentyl ($C_4$), adamantanyl ($C_{10}$), spiro[3.3]heptanyl, bicyclo[3.3.0]octanyl, and the like. Cycloalkyl groups of the disclosure can be unsubstituted or substituted. In those embodiments wherein the cycloalkyl group is substituted, the cycloalkyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "heterocycloalkyl" when used alone or as part of a substituent group refers to any three to ten membered monocyclic or bicyclic, saturated ring structure containing at least one heteroatom selected from the group consisting of O, N and S. Heterocycloalkyl groups of the disclosure include monocyclic groups, as well as multicyclic groups such as bicyclic and tricyclic groups. In those embodiments having at least one multicyclic heterocycloalkyl group, the cyclic groups can share one common atom (i.e., spirocyclic). In other embodiments having at least one multicyclic heterocycloalkyl group, the cyclic groups share two common atoms. The term —$C_3$-$C_6$ heterocycloalkyl refers to a heterocycloalkyl group having between three and six carbon ring atoms. The term —$C_3$-$C_{10}$ heterocycloalkyl refers to a heterocycloalkyl group having between three and 10 rin atoms. The heterocycloalkyl group may be attached at any heteroatom or carbon atom of the ring such that the result is a stable structure. Examples of suitable heterocycloalkyl groups include, but are not limited to, azepanyl, aziridinyl, azetidinyl, pyrrolidinyl, dioxolanyl, imidazolidinyl, pyrazolidinyl, piperazinyl, piperidinyl, dioxanyl, morpholinyl, dithianyl, thiomorpholinyl, oxazepanyl, oxiranyl, oxetanyl, quinuclidinyl, tetrahydrofuranyl, tetrahydropyranyl, piperazinyl, azepanyl, diazepanyl, oxepanyl, dioxepanyl, azocanyl diazocanyl, oxocanyl, dioxocanyl, azaspiro[2.2]pentanyl, oxaazaspiro[3.3]heptanyl, oxaspiro[3.3]heptanyl, dioxaspiro[3.3]heptanyl, and the like. Heteroycloalkyl groups of the disclosure can be unsubstituted or substituted. In those embodiments wherein the heterocycloalkyl group is substituted, the heterocycloalkyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-

$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "heterocycloalkenyl" when used alone or as part of a substituent group refers to any three to ten membered monocyclic or bicyclic, partially saturated ring structure containing at least one heteroatom selected from the group consisting of O, N and S. Heterocycloalkenyl groups of the disclosure include monocyclic groups, as well as multicyclic groups such as bicyclic and tricyclic groups. In those embodiments having at least one multicyclic heterocycloalkyenyl group, the cyclic groups can share one common atom (i.e., spirocyclic). In other embodiments having at least one multicyclic heterocycloalkenyl group, the cyclic groups share two common atoms. The term —$C_3$-$C_6$ heterocycloalkenyl refers to a heterocycloalkenyl group having between three and six carbon atoms. The term —$C_3$-$C_{10}$ heterocycloalkenyl refers to a heterocycloalkenyl group having between three and ten ring atoms. The heterocycloalkenyl group may be attached at any heteroatom or carbon atom of the ring such that the result is a stable structure. Heteroycloalkenyl groups of the disclosure can be unsubstituted or substituted. In those embodiments wherein the heterocycloalkenyl group is substituted, the heterocycloalkenyl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "heteroaryl" when used alone or as part of a substituent group refers to a mono- or bicyclic-aromatic ring structure including carbon atoms as well as up to five heteroatoms selected from nitrogen, oxygen, and sulfur. Heteroaryl rings can include a total of 5, 6, 7, 8, 9, or 10 ring atoms. The term —$C_5$-$C_{10}$ heteroaryl refers to a heteroaryl group containing five to ten ring atoms. Examples of heteroaryl groups include but are not limited to, pyrrolyl, furyl, thiophenyl (thienyl), oxazolyl, imidazolyl, pyrazolyl, isoxazolyl, isothiazolyl, triazolyl, thiadiazolyl, pyrazolyl, pyridinyl, pyridazinyl, pyrimidinyl, pyrazinyl, pyranyl, furazanyl, indolizinyl, indolyl, and the like. Heteroaryl groups of the disclosure can be unsubstituted or substituted. In those embodiments wherein the heteroaryl group is substituted, the heteroaryl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

The term "aryl" when used alone or as part of a substituent group refers to a mono- or bicyclic-aromatic carbon ring structure. Aryl rings can include a total of 5, 6, 7, 8, 9, or 10 ring atoms. Examples of aryl groups include but are not limited to, phenyl, napthyl, and the like. Aryl groups of the disclosure can be unsubstituted or substituted. In those embodiments wherein the aryl group is substituted, the aryl group can be substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

When a range of carbon atoms is used herein, for example, $C_1$-$C_6$, all ranges, as well as individual numbers of carbon atoms are encompassed, for example, "$C_{1-3}$" includes $C_{1-3}$, $C_{1-2}$, $C_{2-3}$, $C_1$, $C_2$, and $C_3$. The term "$C_{1-6}$alk" refers to an aliphatic linker having 1, 2, 3, 4, 5, or 6 carbon atoms and includes, for example, —CH$_2$—, —CH(CH$_3$)—, —CH(CH$_3$)—CH$_2$—, and —C(CH$_3$)$_2$—. The term "—$C_0$alk-" refers to a bond.

The term "$C_0$-$C_6$alk" when used alone or as part of a substituent group refers to an aliphatic linker having 0, 1, 2, 3, 4, 5 or 6 carbon atoms. The term "—$C_1$alk-", for example, refers to a —CH$_2$—. The term "—$C_0$alk-" refers to a bond.

As used herein, each —$C_1$-$C_6$alkyl, —$C_1$-$C_{10}$ alkyl, —$C_2$-$C_6$alkenyl, —$C_2$-$C_{10}$alkenyl, —$C_2$-$C_6$alkynyl, —$C_2$-$C_{10}$alkynyl, aryl, heteroaryl, cycloalkyl, cycloalkenyl, heterocycloalkenyl, and heterocycloalkyl can be optionally substituted with 1, 2, or 3 substituents independently selected from —OH, —CN, amino, halo, $C_1$-$C_6$alkyl, $C_1$-$C_6$alkoxy, $C_1$-$C_6$haloalkyl, and $C_1$-$C_6$haloalkoxy. Additional substitutents include —C(O)NH($C_1$-$C_6$alkyl), —C(O)N($C_1$-$C_6$alkyl)$_2$, —OC(O)NH($C_1$-$C_6$alkyl), —OC(O)N($C_1$-$C_6$alkyl)$_2$, —S(O)$_2$NH($C_1$-$C_6$alkyl), and —S(O)$_2$N($C_1$-$C_6$alkyl)$_2$.

As used herein, "alkoxy" refers to an —O-alkyl group. Example alkoxy groups include methoxy, ethoxy, propoxy (e.g., n-propoxy and isopropoxy), t-butoxy, and the like.

As used herein, "hydroxylalkyl" refers to an alkyl group substituted by OH.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically active starting materials are known in the art, such as by resolution of racemic mixtures or by stereoselective synthesis. Geometric isomers of olefins, C=N double bonds, and the like can also be present in the compounds described herein, and all such stable isomers are contemplated in the present invention. Geometric isomers of the compounds of the present invention are described and may be isolated as a mixture of isomers or as separated isomeric forms.

Compounds of the invention may also include tautomeric forms. All tautomeric forms are encompassed.

In some embodiments, the compounds of the present invention may exist as rotational isomers. In some embodiments, the compounds of the present invention exist as mixtures of rotational isomers in any proportion. In other embodiments, the compounds of the present invention exist as particular rotational isomers, substantially free of other rotational isomers.

Compounds of the invention can also include all isotopes of atoms occurring in the intermediates or final compounds. Isotopes include those atoms having the same atomic number but different mass numbers. For example, isotopes of hydrogen include tritium and deuterium.

In some embodiments, the compounds of the invention, and salts thereof, are substantially isolated. By "substantially isolated" is meant that the compound is at least partially or substantially separated from the environment in which it was formed or detected. Partial separation can include, for example, a composition enriched in the compound of the invention. Substantial separation can include compositions containing at least about 50%, at least about 60%, at least about 70%, at least about 80%, at least about 90%, at least about 95%, at least about 97%, or at least about 99% by weight of the compound of the invention, or salt thereof. Methods for isolating compounds and their salts are routine in the art.

The present invention also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the conventional non-toxic salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418 and *Journal of Pharmaceutical Science*, 66, 2 (1977), each of which is incorporated herein by reference in its entirety.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of an agent and that is compatible therewith. Examples of excipients include calcium carbonate, calcium phosphate, various sugars and types of starch, cellulose derivatives, gelatin, vegetable oils, and polyethylene glycols.

A "solvate" refers to a physical association of a compound of Formula I with one or more solvent molecules.

"Subject" includes humans. The terms "human," "patient," and "subject" are used interchangeably herein.

"Treating" or "treatment" of any disease or disorder refers, in one embodiment, to ameliorating the disease or disorder (i.e., arresting or reducing the development of the disease or at least one of the clinical symptoms thereof). In another embodiment "treating" or "treatment" refers to ameliorating at least one physical parameter, which may not be discernible by the subject. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to delaying the onset of the disease or disorder.

"Compounds of the present disclosure," and equivalent expressions, are meant to embrace compounds of Formula I as described herein, as well as its subgenera, which expression includes the stereoisomers (e.g., entaniomers, diastereomers) and constitutional isomers (e.g., tautomers) of compounds of Formula I as well as the pharmaceutically acceptable salts, where the context so permits.

As used herein, the term "isotopic variant" refers to a compound that contains proportions of isotopes at one or more of the atoms that constitute such compound that is greater than natural abundance. For example, an "isotopic variant" of a compound can be radiolabeled, that is, contain one or more radioactive isotopes, or can be labeled with non-radioactive isotopes such as for example, deuterium (2H or D), carbon-13 ($^{13}$C), nitrogen-15 ($^{15}$N), or the like. It will be understood that, in a compound where such isotopic substitution is made, the following atoms, where present, may vary, so that for example, any hydrogen may be $^2$H/D, any carbon may be $^{13}$C, or any nitrogen may be $^{15}$N, and that the presence and placement of such atoms may be determined within the skill of the art.

It is also to be understood that compounds that have the same molecular formula but differ in the nature or sequence of bonding of their atoms or the arrangement of their atoms in space are termed "isomers." Isomers that differ in the arrangement of their atoms in space are termed "stereoisomers," for example, diastereomers, enantiomers, and atropisomers. The compounds of this disclosure may possess one or more asymmetric centers; such compounds can therefore be produced as individual (R)- or (S)-stereoisomers at each asymmetric center, or as mixtures thereof. Unless indicated otherwise, the description or naming of a particular compound in the specification and claims is intended to include all stereoisomers and mixtures, racemic or otherwise, thereof. Where one chiral center exists in a structure, but no specific stereochemistry is shown for that center, both enantiomers, individually or as a mixture of enantiomers, are encompassed by that structure. Where more than one chiral center exists in a structure, but no specific stereochemistry is shown for the centers, all enantiomers and diastereomers, individually or as a mixture, are encompassed by that structure. The methods for the determination of stereochemistry and the separation of stereoisomers are well-known in the art.

The disclosure is directed to compounds of Formula I:

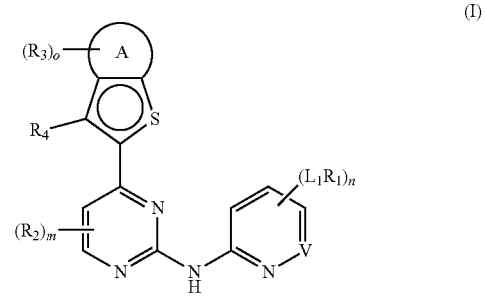

or a pharmaceutically acceptable salt or solvate or N-oxide thereof;
ring A is a 5-7-membered heteroaryl;
V=CL$_1$R$_1$ or N
n is 1 or 2 or 3;
m is 1 or 2;
o is 1, 2, 3, 4, or 5;
each L$_1$ is independently a bond, O, NR or C$_1$-C$_6$ alkylene, wherein R is H or C$_1$-C$_6$alkyl;
each R$_1$ is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR$^b$), —B(OR$^c$)(OR$^d$) or —S(O)$_2$R$^b$;

each R$_2$ is independently H, D, halogen, C$_1$-C$_8$ alkoxide C$_1$-C$_8$ alkyl, haloalkyl, or CN and each R$_3$ is independently H, D, halogen, oxo, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, or heterocycloalkenyl, —OR$^a$, —OR$^b$, SR$^b$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR), —B(OR$^d$)(OR$^c$) or —S(O)$_2$R$^b$;

each R$^a$ is independently H, D, —C(O)R$^b$, —C(O)OR$^c$, —C(O)NR$^c$R$^d$, —C(=NR)NR$^b$R$^c$, —C(=NOR$^b$)NR$^b$R$^c$, —C(=NCN)NR$^b$R$^c$, —P(OR$^c$)$_2$, —P(O)R$^c$R$^b$, —P(O)OR$^c$R$^b$, —S(O)R$^b$, —S(O)NR$^c$R$^d$, —S(O)$_2$R$^b$, —S(O)$_2$NR$^c$R$^d$, SiR$_3$, —C$_1$-C$_{10}$alkyl, —C$_2$-C$_{10}$ alkenyl, —C$_2$-C$_{10}$ alkynyl, aryl, cycloalkyl, cycloalkenyl, heteroaryl, heterocycloalkyl, or heterocycloalkenyl;

each R$^b$ is independently H, D, —C$_1$-C$_6$ alkyl, —C$_2$-C$_6$ alkenyl, —C$_2$-C$_6$ alkynyl, aryl, cycloalkyl, cycloalkenyl, heteroaryl, heterocycloalkyl, or heterocycloalkenyl;

each R$^c$ or R$^d$ is independently H, D, —C$_1$-C$_{10}$ alkyl, —C$_2$-C$_6$ alkenyl, —C$_2$-C$_6$ alkynyl, —OC$_1$-C$_6$alkyl, —O-cycloalkyl, aryl, heteroaryl, cycloalkyl, cycloalkenyl, heterocycloalkyl, or heterocycloalkenyl;

or R$^c$ and R$^d$, together with the atom to which they are both attached, form a monocyclic or multicyclic heterocycloalkyl, or a monocyclic or multicyclic heterocyclo-alkenyl group; each R$_4$ is independently H, D, halogen, C$_1$-C$_8$ alkoxide or C$_1$-C$_8$ alkyl, haloalkyl and CN.

In some embodiments, ring A in Formula (I) is a 5-7-membered heteroaryl. In some embodiments, ring A is a 5-membered heteroaryl. In other embodiments, ring A is a 6-membered heteroaryl. In yet other embodiments, ring A is a 7-membered heteroaryl.

In some embodiments, ring A is a 5-membered heteroaryl having at least one N atom. In some embodiments, the 5-membered heteroaryl having at least one N atom is an imidazole. In other embodiments, ring A is a 6-membered heteroaryl having at least one N atom. In other embodiments, the 6-membered heteroaryl having at least two N atom is a pyrimidine or a pyridazine.

In some embodiments, V in Formula (I) is N or CL$_1$R$^1$. In some embodiments, V is N. In other embodiments, V is CL$_1$R$^1$.

In some embodiments, n in Formula (I) is 1, 2 or 3. In some embodiments, n is 1. In other embodiments, n is 2. In yet other embodiments, n is 3.

In some embodiments, m in Formula (I) is 1 or 2. In some embodiments, m is 1. In other embodiments, m is 2.

In some embodiments, o in Formula (I) is 1, 2, 3, 4 or 5. In some embodiments, o is 1. In some embodiments, o is 2. In other embodiments, o is 3. In other embodiments, o is 4. In yet other embodiments, o is 5.

In some embodiments, each L$^1$ in Formula I is independently a bond, O, NR or C$_1$-C$_6$ alkylene, wherein R is H or C$_1$-C$_6$alkyl. In some embodiments, L$^1$ is a bond. In some embodiments, L$^1$ is O. In some embodiments, L$^1$ is NR. In some embodiments, L$^1$ is C$_1$-C$_6$ alkylene. In some embodiments, L$^1$ is methylene. In some embodiments, R is H. In some embodiments, R is C$_1$-C$_6$alkyl. In some embodiments, R is methyl.

In some embodiments, each R$_1$ in Formula I is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR$^b$), —B(OR$^c$)(OR$^d$) or —S(O)$_2$R$^b$. In some embodiments, R$_1$ is H. In some embodiments, R$_1$ is D. In some embodiments, R$_1$ is halogen. In some embodiments, R$_1$ is —OH. In some embodiments, R$_1$ is —CN. In some embodiments, R$_1$ is NO$_2$. In some embodiments, R$_1$ is —C$_1$-C$_6$alkyl. In some embodiments, R$_1$ is —C$_2$-C$_6$alkenyl. In some embodiments, R$_1$ is —C$_2$-C$_6$alkynyl. In some embodiments, R$_1$ is aryl. In some embodiments, R$_1$ is heteroaryl. In some embodiments, R$_1$ is cycloalkyl. In some embodiments, R$_1$ is cycloalkenyl. In some embodiments, R$_1$ is heterocycloalkenyl. In some embodiments, R$_1$ is —OR$^a$, —SR$^a$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^c$)(OR$^d$), —S(O)$_2$R$^b$ and the like.

In other embodiments, R$_1$ is heterocycloalkyl. In other embodiments, R$_1$ is a 6-membered heterocyclalkyl. In some embodiments, R$_1$ is a piperazine. In yet other embodiments, R$_1$ is a 7-membered heterocyclalkyl. In yet other embodiments, R$_1$ is a spiro-fused group. In yet other embodiments, R$_1$ is a diazaspiroheptane.

In some embodiments, each R$_2$ in Formula I is independently H, D, halogen, C$_1$-C$_8$ alkoxide, C$_1$-C$_8$ alkyl, haloalkyl, or —CN. In some embodiments, R$_2$ is H. In some embodiments, R$_2$ is D. In other embodiments, R$_2$ is halogen. In other embodiments, R$_2$ is fluoro. In yet other embodiments, R$_2$ is C$_1$-C$_8$ alkoxide. In yet other embodiments, R$_2$ is C$_1$-C$_8$ alkyl. In yet other embodiments, R$_2$ is haloalkyl. In yet other embodiments, R$_2$ is —CN.

In some embodiments, each R$_3$ in Formula I is independently H, D, halogen, oxo, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, or heterocycloalkenyl, —OR$^a$, —OR$^b$, —SR$^b$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR)R$^b$, —SF$_5$, —P(O)R$^b$R$^b$, —P(O)(OR$^b$)(OR$^b$), —B(OR$^d$)(OR$^c$) or —S(O)$_2$R$^b$.

In some embodiments of the disclosure, at least one R$_3$ moiety will be directly bonded to the remainder of the compound of Formula (I) via a carbon atom. In particularly preferred aspects of these embodiments, each R$_3$ bonded through a carbon atom is independently H, D, halogen, oxo, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, or heterocycloalkenyl, —OR$^a$, —OR$^b$, —SR$^b$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O)R$^b$R$^b$, —P(O)(OR$^b$)(OR$^b$), —B(OR$^d$)(OR$^c$) or —S(O)$_2$R$^b$.

In some embodiments of the disclosure, at least one R$_3$ moiety will be directly bonded to the remainder of the compound of Formula (I) via a nitrogen atom. In particularly preferred aspects of these embodiments, each R$_3$ bonded through a nitrogen atom is independently H, D, oxo, —OH, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, or heterocycloalkenyl, —OR$^a$, —OR$^b$, —NR$^c$R$^d$, —NR$^a$R$^c$, —S(O)$_2$NR$^d$, or —S(O)$_2$R$^b$.

In some embodiments, $R_3$ is H. In some embodiments, $R_3$ is D. In some embodiments, $R_3$ is halogen. In some embodiments, $R_3$ is oxo. In some embodiments, $R_3$ is bound to a nitrogen atom and $R_3$ is oxo. In some embodiments, $R_3$ is —OH. In some embodiments, $R_3$ is —CN. In some embodiments, $R_3$ is $NO_2$. In some embodiments, $R_3$ is —$C_1$-$C_6$alkyl. In some embodiments, $R_3$ is —$C_2$-$C_6$alkenyl. In some embodiments, $R_3$ is —$C_2$-$C_6$alkynyl. In other embodiments, $R_3$ is $C_0$-$C_1$alk-aryl. In other embodiments, $R_3$ is $C_0$-$C_1$alk-heteroaryl. In other embodiments, $R_3$ is cycloalkyl. In other embodiments, $R_3$ is $C_{3-10}$cycloalkyl. In other embodiments, $R_3$ is cycloalkenyl. In other embodiments, $R_3$ is heterocycloalkyl. In other embodiments, $R_3$ is heterocycloalkenyl. In yet other embodiments, $R_3$ is $OR^a$, —$OR^b$, —$SR^b$, —$NR^cR^d$, —$NR^aR^c$, —$C(O)R^b$, —$OC(O)R^b$, —$C(O)OR^b$, —$C(O)NR^cR^d$, —$S(O)R^b$, —$S(O)_2R^b$, —$S(O)_2NR^cR^d$, —$S(O)(=NR)R^b$, —$SF_5$, —$P(O)R^bR^b$, —$P(O)(OR^b)(OR)$, —$B(OR^d)(OR^c)$, —$S(O)_2R^b$ and the like. In some aspects, at least one $R_3$ is hydroxyalkyl. In other aspects, $R_3$ is $C_1$-$C_6$alkyl, for example, isopropyl. In other aspects, $R_3$ is oxo. In other aspects, $R_3$ is oxo bound to a nitrogen atom. In some aspects $R_3$ is OR.

In some embodiments, each $R^a$ in Formula I is independently H, D, —$C(O)R^b$, —$C(O)OR^c$, —$C(O)NR^cR^d$, —$C(=NR)NR^bR^c$, —$C(=NOR)NR^bR^c$, —$C(=NCN)NRR^c$, —$P(OR^c)_2$, —$P(O)R^bR^b$, —$P(O)OR^cOR^b$, —$S(O)R^b$, —$S(O)NR^cR^d$, —$S(O)_2R^b$, —$S(O)_2NR^cR^d$, $SiR_3$, —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, or heterocycloalkenyl.

In some embodiments, $R^a$ is H. In some embodiments, $R^a$ is D. In some embodiments, $R^a$ is —$C(O)R^b$. In some embodiments, $R^a$ is —$C(O)OR^c$. In some embodiments, $R^a$ is —$C(O)NR^cR^d$. In some embodiments, $R^a$ is —$C(=NR)NR^bR^c$. In some embodiments, $R^a$ is $C(=NOR^b)NR^bR^c$. In some embodiments, $R^a$ is —$C(=NCN)NR^bR^c$.

In other embodiments, $R^a$ is —$P(OR^c)_2$, —$P(O)R^bR^b$, —$P(O)OR^cR^b$, —$S(O)R^b$, —$S(O)NR^cR^d$, —$S(O)_2R^b$, —$S(O)_2NR^cR^d$, $SiR_3$, and the like. In yet other embodiments, $R^a$ is —$C_1$-$C_{10}$alkyl, —$C_2$-$C_{10}$ alkenyl, —$C_2$-$C_{10}$ alkynyl, aryl, cycloalkyl, cycloalkenyl, heteroaryl, heterocycloalkyl, heterocycloalkenyl, and the like.

In some embodiments, each $R^b$ in Formula I is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl. In some embodiments, $R^b$ is H. In some embodiments, $R^b$ is D. In some embodiments, $R^b$ is —$C_1$-$C_6$ alkyl. In some embodiments, $R^b$ is —$C_2$-$C_6$ alkenyl. In some embodiments, $R^b$ is —$C_2$-$C_6$ alkynyl. In other embodiments, $R^b$ is aryl. In other embodiments, $R^b$ is cycloalkyl. In other embodiments, $R^b$ is cycloalkenyl. In other embodiments, $R^b$ is heteroaryl. In other embodiments, $R^b$ is heterocycloalkyl. In other embodiments, $R^b$ is heterocycloalkenyl.

In some embodiments, each $R^c$ or $R^d$ in Formula I is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl. In some embodiments, $R^c$ or $R^d$ is H. In some embodiments, $R^c$ or $R^d$ is D. In some embodiments, $R^c$ or $R^d$ is —$C_1$-$C_{10}$ alkyl. In some embodiments, $R^c$ or $R^d$ is —$C_2$-$C_6$ alkenyl. In some embodiments, $R^c$ or $R^d$ is —$C_2$-$C_6$ alkynyl. In other embodiments, $R^c$ or $R^d$ is —$OC_1$-$C_6$alkyl. In other embodiments, $R^c$ or $R^d$ is —O-cycloalkyl. In other embodiments, $R^c$ or $R^d$ is aryl. In other embodiments, $R^c$ or $R^d$ is cycloalkyl. In other embodiments, $R^c$ or $R^d$ is cycloalkenyl. In other embodiments, $R^c$ or $R^d$ is heteroaryl. In other embodiments, $R^c$ or $R^d$ is heterocycloalkyl. In other embodiments, $R^c$ or $R^d$ is heterocycloalkenyl.

In yet other embodiments, $R^c$ and $R^d$, together with the atom to which they are both attached, form a monocyclic or multicyclic heterocycloalkyl, or a monocyclic or multicyclic heterocyclo-alkenyl group. In yet other embodiments, $R^c$ and $R^d$ form a monocyclic heterocycloalkyl. In yet other embodiments, $R^c$ and $R^d$ form a multicyclic heterocycloalkyl. In yet other embodiments, $R^c$ and $R^d$ form a monocyclic heterocyclo-alkenyl group. In yet other embodiments, $R^c$ and $R^d$ form a multicyclic heterocyclo-alkenyl group.

In some embodiments, each $R_4$ in Formula I is independently H, D, halogen, $C_1$-$C_8$ alkoxide or $C_1$-$C_8$ alkyl, haloalkyl and —CN. In some embodiments, $R_4$ is H. In some embodiments, $R_4$ is D. In some embodiments, $R_4$ is halogen. In some embodiments, $R_4$ is —$C_1$-$C_8$ alkoxide. In other embodiments, $R_4$ is —$C_1$-$C_8$ alkyl. In other embodiments, $R_4$ is methyl. In other embodiments, $R_4$ is haloalkyl. In other embodiments, $R_4$ is —CN.

In some embodiments, the compounds of Formula (I) are the pharmaceutically acceptable salts. In some embodiments, the compounds of Formula (I) are solvates. In some embodiments, the compounds of Formula (I) are N-oxides of the compounds of Formula (I).

In some embodiments, the compounds of Formula (I) are represented by compounds of Formula II

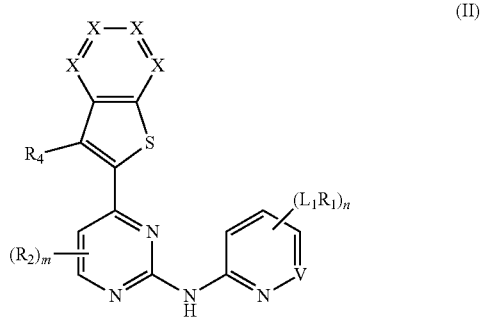

(II)

or a pharmaceutically acceptable salt thereof, wherein
each X is independently N, N-oxide or $CR_3$ and at least one X is N or N-oxide; and wherein each $R_4$, $R_3$, $(R_2)_m$, V and $(L_1R_1)_n$ is defined with respect to Formula (I).

In some embodiments, each X in Formula II is N. In other embodiments, one X in Formula II is N-oxide and three Xs in Formula II are $CR_3$. In other embodiments, one X in Formula II is N and three Xs in Formula II are $CR_3$. In yet other embodiments, two Xs in Formula II are N and two Xs in Formula II are $CR_3$. In yet other embodiments, three Xs in Formula II are N and one X in Formula II is $CR_3$.

In some embodiments, the compounds of Formula (I) are represented by compounds of Formula III

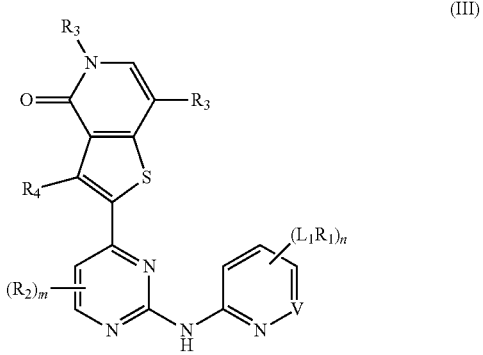

(III)

(IIIa)

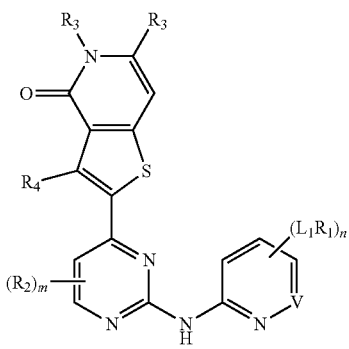

(IIIb)

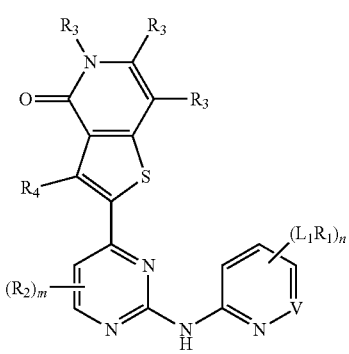

or a pharmaceutically acceptable salt thereof, wherein wherein each $R_4$, $R_3$, $(R_2)_m$, V and $(L_1R_1)_n$ is defined with respect to Formula (I).

In some embodiments, the compounds of Formula (I) are represented by compounds of Formula IV (IV)

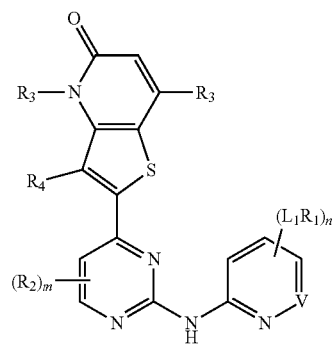

(IVa)

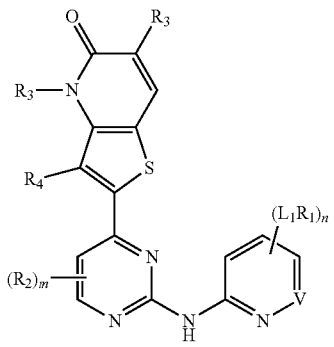

(IVb)

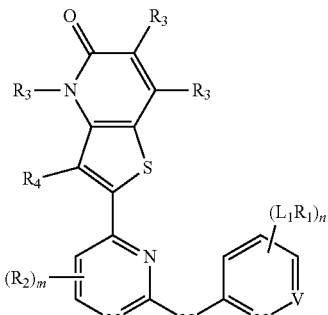

or a pharmaceutically acceptable salt thereof, wherein wherein each $R_4$, $R_3$, $(R_2)_m$, V and $(L_1R^1)_n$ is defined with respect to Formula (I).

In some embodiments, the compounds of Formula (I) are represented by compounds of Formula V (V)

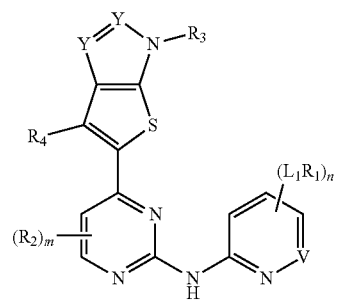

or a pharmaceutically acceptable salt thereof, wherein
each Y is independently N or $CR_3$ and at least one Y is N; and
wherein each $R_4$, $R_3$, $(R_2)_m$, V and $(L_1R_1)_n$ is defined with respect to Formula (I).

In some embodiments, each Y in Formula V is N. In other embodiments, one Y in Formula V is N the other Y in Formula V is $CR_3$. In yet other embodiments, each Y in Formula V is $CR_3$.

In some embodiments, the compounds of Formula (I) are represented by compounds of Formula VI (VI)

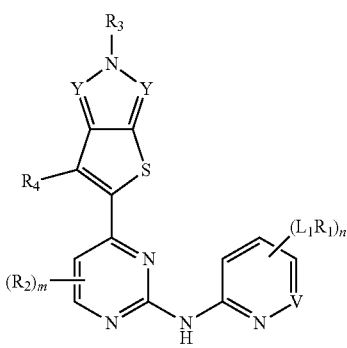

or a pharmaceutically acceptable salt thereof, wherein
each Y is independently N or $CR_3$ and at least one Y is N; and wherein each $R_4$, $R_3$, $(R_2)_m$, V and $(L_1R_1)n$ is defined with respect to Formula (I).

In some embodiments, each Y in Formula VI is N. In other embodiments, one Y in Formula VI is N the other Y in Formula VI is $CR_3$. In yet other embodiments, each Y in Formula VI is $CR_3$.

In some embodiments, the compounds of Formula (I) are represented by compounds of Formula VIII

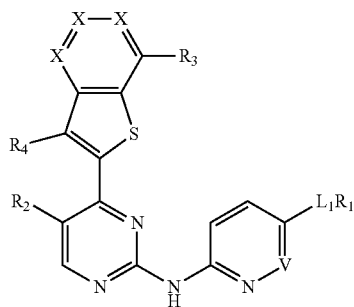

(VIII)

or a pharmaceutically acceptable salt thereof, wherein
each X is independently N, N-oxide or $CR_3$ and at least one X is N or N-oxide; and
wherein each $R_4$, $R_3$, $R_2$, V and $L_1R_1$ is defined with respect to Formula (I).

In some embodiments, each X in Formula VIII is N. In some embodiments, one X in Formula VIII is N-oxide and two Xs in Formula VIII are $CR_3$. In other embodiments, one X in Formula VIII is N and two Xs in Formula VIII are $CR_3$. In other embodiments, two Xs in Formula VIII are N and one X in Formula VIII is $CR_3$.

In some embodiments, the compounds of Formula (I) are represented by compounds of Formula IX

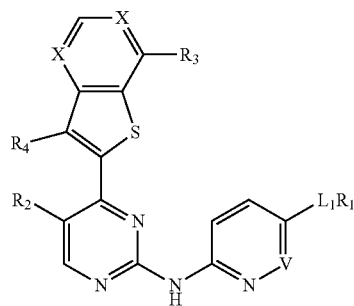

(IX)

or a pharmaceutically acceptable salt thereof, wherein
each X is independently N, N-oxide or $CR_3$ and at least one X is N or N-oxide; and
wherein each $R_4$, $R_3$, $R_2$, V and $L_1R_1$ is defined with respect to Formula (I).

In some embodiments, each X in Formula IX is N. In other embodiments, one X in Formula IX is N-oxide and one X in Formula IX is $CR_3$. In yet other embodiments, one X in Formula IX is N and one X in Formula IX is $CR_3$.

In some embodiments, the compounds of Formula (I) are represented by compounds of Formula X

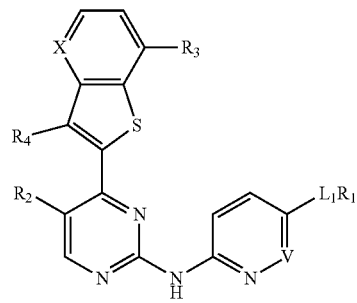

(X)

or a pharmaceutically acceptable salt thereof, wherein
each X is independently N, N-oxide or $CR_3$ and at least one X is N or N-oxide; and
wherein each $R_4$, $R_3$, $R_2$, V and $L_1R_1$ is defined with respect to Formula (I).

In some embodiments, the X in Formula X is N. In other embodiments, the X in Formula X is N-oxide.

In some embodiments, the compounds of Formula (I) are represented by compounds of Formula XI

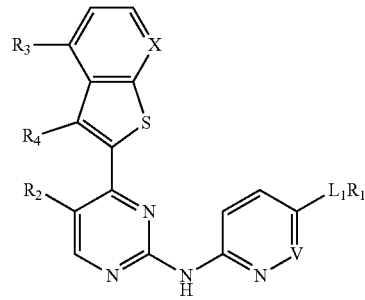

(XI)

or a pharmaceutically acceptable salt thereof, wherein
each X is independently N, N-oxide or $CR_3$ and at least one X is N or N-oxide; and wherein each $R_4$, $R_3$, $R_2$, V and $L_1R_1$ is defined with respect to Formula (I).

In some embodiments, the X in Formula XI is N. In other embodiments, the X in Formula XI is N-oxide.

In some embodiments, the compounds of Formula (I) are represented by compounds of Formula XII

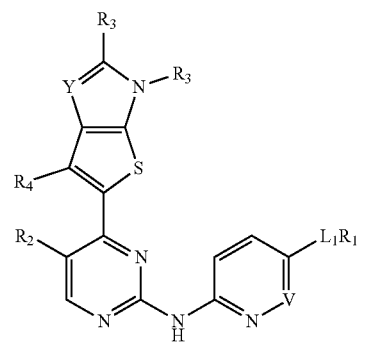

(XII)

or a pharmaceutically acceptable salt thereof, wherein
Y is N or $CHR_3$; and wherein each $R_4$, $R_3$, $R_2$, V and $L_1R_1$ is defined with respect to Formula (I).

In some embodiments, the Y in Formula XII is N. In other embodiments, the Y in Formula XII is CHR$_3$.

In some embodiments, the compounds of Formula (I) are represented by compounds of Formula XIII

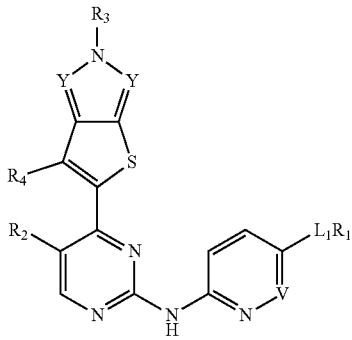

(XIII)

or a pharmaceutically acceptable salt thereof, wherein
Y is N or CHR$_3$; and wherein each R$_4$, R$_3$, R$_2$, V and L$_1$R$_1$ is defined with respect to Formula (I).

In some embodiments, each Y in Formula XIII is N. In other embodiments, one Y in Formula XIII is N the other Y in Formula XIII is CR$_3$. In yet other embodiments, each Y in Formula XIII is CR$_3$.

In other embodiments, the compounds of Formula (I) are represented by compounds of Formula XV

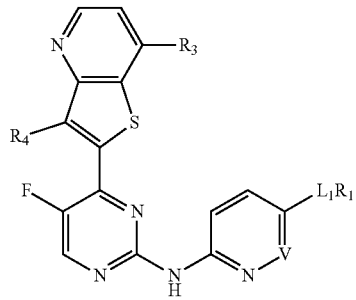

(XV)

or a pharmaceutically acceptable salt thereof, wherein
each R$_4$, R$_3$, V and L$_1$R$_1$ is defined with respect to Formula (I).

In other embodiments, the compounds of Formula (I) are represented by compounds of Formula XVI

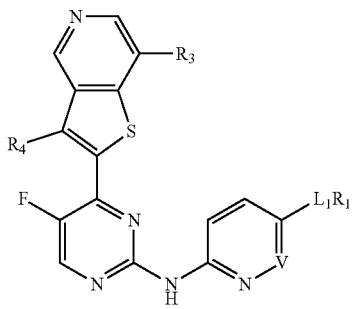

(XVI)

or a pharmaceutically acceptable salt thereof, wherein
each R$_4$, R$_3$, V and L$_1$R$_1$ is defined with respect to Formula (I).

In other embodiments, the compounds of Formula (I) are represented by compounds of Formula XVII

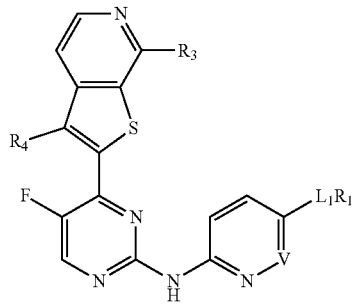

(XVII)

or a pharmaceutically acceptable salt thereof, wherein
each R$_4$, R$_3$, V and L$_1$R$_1$ is defined with respect to Formula (I).

In other embodiments, the compounds of Formula (I) are represented by compounds of Formula XVIII

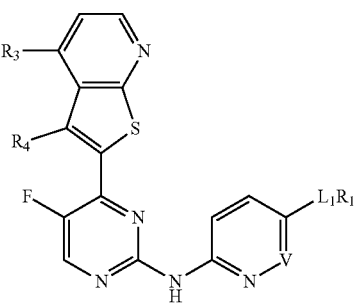

(XVIII)

or a pharmaceutically acceptable salt thereof, wherein
each R$_4$, R$_3$, V and L$_1$R$_1$ is defined with respect to Formula (I).

In other embodiments, the compounds of Formula (I) are represented by compounds of Formula XIX

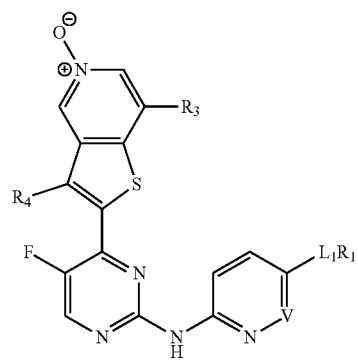

(XIX)

or a pharmaceutically acceptable salt thereof, wherein
each R$_4$, R$_3$, V and L$_1$R$_1$ is defined with respect to Formula (I).

In other embodiments, the compounds of Formula (I) are represented by compounds of Formula XX

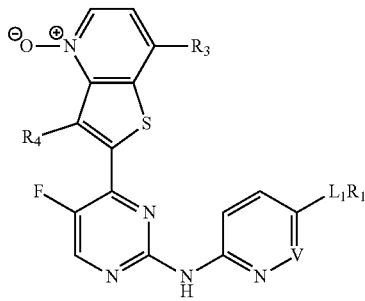

(XX)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXI

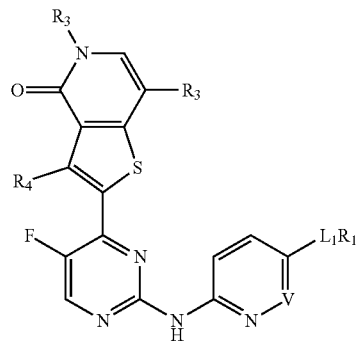

(XXI)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXII

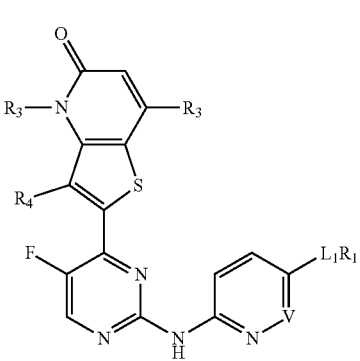

(XXII)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXIII

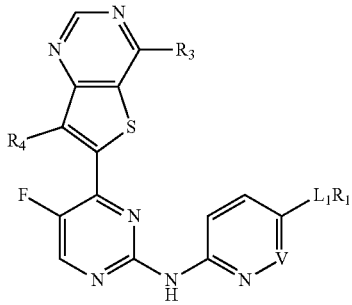

(XXIII)

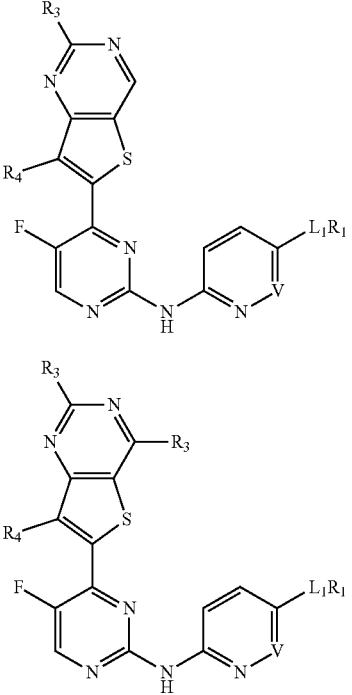

(XXIIIa)

(XXIIIb)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXIV

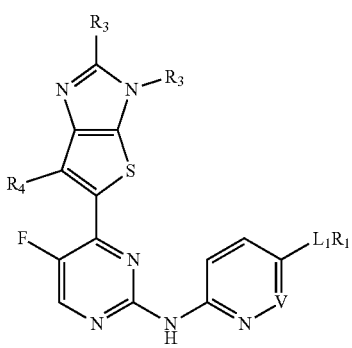

(XXIV)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXV

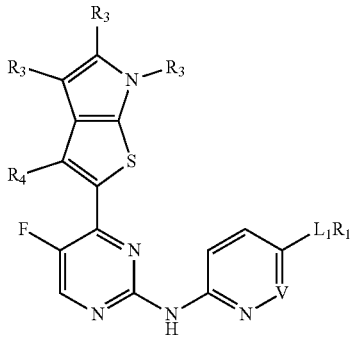

(XXV)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXVI

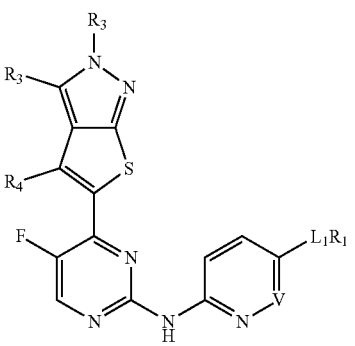

(XXVI)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXVII

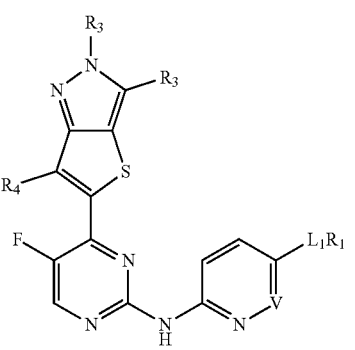

(XXVII)

or a pharmaceutically acceptable salt thereof, wherein each $R_4$, $R_3$, V and $L_1R_1$ is defined with respect to Formula (I).

In other embodiments, the compounds of Formula (I) are represented by compounds of Formula XXIX

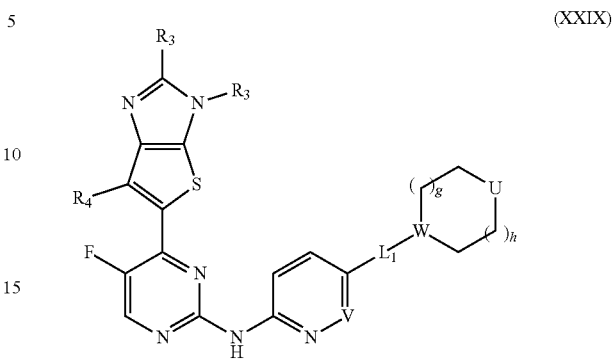

(XXIX)

or a pharmaceutically acceptable salt thereof, wherein

W is CH or N;

U is $C(R_{10})_2$, $NR_{10}$, or O;

$R_{10}$ is H, halogen (preferably fluoro), $C_{1-6}$alkyl, or $C_{1-6}$alkoxide;

each g and h is independently 0, 1, 2 or 3; and each $R_4$, $R_3$, V and $L_1$ is defined with respect to Formula (I).

In some embodiments, W of Formula XXIX is CH. In other embodiments, W of Formula XXIX is N.

In some embodiments, U of Formula XXIX is $C(R_{10})_2$. In other embodiments, U of Formula XXIX is $NR_{10}$. In yet other embodiments, U of Formula XXIX is O.

In some embodiments, $R_{10}$ of Formula XXIX is H. In some embodiments, $R_{10}$ of Formula XXIX is halogen. In other embodiments, $R_{10}$ of Formula XXIX is fluoro. In some embodiments, $R_{10}$ of Formula XXIX is $C_{1-6}$alkyl. In other embodiments, $R_{10}$ of Formula XXIX is methyl or ethyl.

In some embodiments, $R_{10}$ of Formula XXIX is $C_{1-6}$alkoxide.

In some embodiments, when U of Formula XXIX is $C(R_{10})_2$, each $R_{10}$ is H. In some embodiments, when U of Formula XXIX is $C(R_{10})_2$, each $R_{10}$ is methyl. In some embodiments, when U of Formula XXIX is $C(R_{10})_2$, one $R_{10}$ is methyl and one $R_{10}$ is hydrogen. In some embodiments, when U of Formula XXIX is $C(R_{10})_2$, each $R_{10}$ is halogen. In some embodiments, when U of Formula XXIX is $C(R_{10})_2$, one $R_{10}$ is halogen and one $R_{10}$ is hydrogen. In other embodiments, when U of Formula XXIX is $C(R_{10})_2$, each $R_{10}$ is fluoro. In other embodiments, when U of Formula XXIX is $C(R_{10})_2$, one $R_{10}$ is fluoro and one $R_{10}$ is hydrogen.

In some embodiments, U of Formula XXIX is $NCH_3$. In other embodiments, U of Formula XXIX is $NCH_2CH_3$.

In some embodiments, g in Formula XXIX is 0, 1, 2 or 3. In some embodiments, g in Formula XXIX is 0. In some embodiments, g in Formula XXIX is 1. In other embodiments, g in Formula XXIX is 2. In other embodiments, g in Formula XXIX is 3.

In some embodiments, h in Formula XXIX is 0, 1, 2 or 3. In some embodiments, h in Formula XXIX is 0. In some embodiments, h in Formula XXIX is 1. In other embodiments, h in Formula XXIX is 2. In other embodiments, h in Formula XXIX is 3.

In other embodiments, the compounds of Formula (I) are represented by compounds of Formula XXX

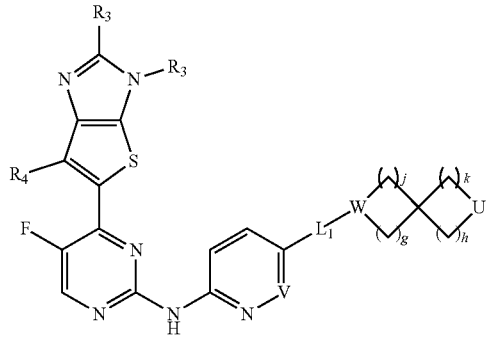
(XXX)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g, h, j and k is independently 0, 1, 2 or 3; and
each $R_4$, $R_3$, V and $L_1$ is defined with respect to Formula (I).

In some embodiments, W of Formula XXX is CH. In other embodiments, W of Formula XXX is N.

In some embodiments, U of Formula XXX is $C(R_{10})_2$. In other embodiments, U of Formula XXX is $NR_{10}$. In yet other embodiments, U of Formula XXX is O.

In some embodiments, $R_{10}$ of Formula XXX is H. In some embodiments, $R_{10}$ of Formula XXX is halogen. In other embodiments, $R_{10}$ of Formula XXX is fluoro. In some embodiments, $R_{10}$ of Formula XXX is $C_{1-6}$alkyl. In other embodiments, $R_{10}$ of Formula XXX is methyl or ethyl. In some embodiments, $R_{10}$ of Formula XXX is $C_{1-6}$alkoxide.

In some embodiments, when U of Formula XXX is $C(R_{10})_2$, each $R_{10}$ is H. In some embodiments, when U of Formula XXX is $C(R_{10})_2$, each $R_{10}$ is methyl. In some embodiments, when U of Formula XXX is $C(R_{10})_2$, one $R_{10}$ is methyl and one $R_{10}$ is hydrogen. In some embodiments, when U of Formula XXX is $C(R_{10})_2$, each $R_{10}$ is halogen. In some embodiments, when U of Formula XXX is $C(R_{10})_2$, one $R_{10}$ is halogen and one $R_{10}$ is hydrogen. In other embodiments, when U of Formula XXX is $C(R_{10})_2$, each $R_{10}$ is fluoro. In other embodiments, when U of Formula XXX is $C(R_{10})_2$, one $R_{10}$ is fluoro and one $R_{10}$ is hydrogen.

In some embodiments, U of Formula XXX is $NCH_3$. In other embodiments, U of Formula XXX is $NCH_2CH_3$.

In some embodiments, g in Formula XXX is 0, 1, 2 or 3. In some embodiments, g in Formula XXX is 0. In some embodiments, g in Formula XXX is 1. In other embodiments, g in Formula XXX is 2. In other embodiments, g in Formula XXX is 3.

In some embodiments, h in Formula XXX is 0, 1, 2 or 3. In some embodiments, h in Formula XXX is 0. In some embodiments, h in Formula XXX is 1. In other embodiments, h in Formula XXX is 2. In other embodiments, h in Formula XXX is 3.

In some embodiments, j in Formula XXX is 0, 1, 2 or 3. In some embodiments, j in Formula XXX is 0. In some embodiments, j in Formula XXX is 1. In other embodiments, j in Formula XXX is 2. In other embodiments, j in Formula XXX is 3.

In some embodiments, k in Formula XXX is 0, 1, 2 or 3. In some embodiments, k in Formula XXX is 0. In some embodiments, k in Formula XXX is 1. In other embodiments, k in Formula XXX is 2. In other embodiments, k in Formula XXX is 3.

In other embodiments, the compounds of Formula (I) are represented by compounds of Formula XXXI

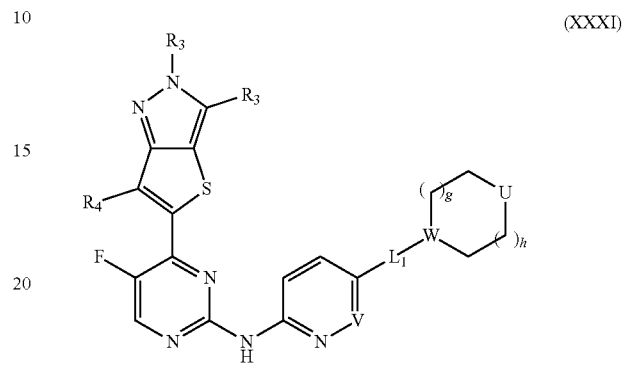
(XXXI)

or a pharmaceutically acceptable salt thereof, wherein
W is CH or N;
U is $C(R_{10})_2$, $NR_{10}$, or 0;
$R_{10}$ is H, halogen (preferably fluoro), $C_{1-6}$alkyl, or $C_{1-6}$alkoxide;
each g and h is independently 0, 1, 2 or 3; and
each $R_4$, $R_3$, V and $L_1$ is defined with respect to Formula (I).

In some embodiments, W of Formula XXXI is CH. In other embodiments, W of Formula XXXI is N.

In some embodiments, U of Formula XXXI is $C(R_{10})_2$. In other embodiments, U of Formula XXXI is $NR_{10}$. In yet other embodiments, U of Formula XXXI is O.

In some embodiments, $R_{10}$ of Formula XXXI is H. In some embodiments, $R_{10}$ of Formula XXXI is halogen. In other embodiments, $R_{10}$ of Formula XXXI is fluoro. In some embodiments, $R_{10}$ of Formula XXXI is $C_{1-6}$alkyl. In other embodiments, $R_{10}$ of Formula XXXI is methyl or ethyl.

In some embodiments, $R_{10}$ of Formula XXXI is $C_{1-6}$alkoxide.

In some embodiments, when U of Formula XXXI is $C(R_{10})_2$, each $R_{10}$ is H. In some embodiments, when U of Formula XXXI is $C(R_{10})_2$, each $R_{10}$ is methyl. In some embodiments, when U of Formula XXXI is $C(R_{10})_2$, one $R_{10}$ is methyl and one $R_{10}$ is hydrogen. In some embodiments, when U of Formula XXXI is $C(R_{10})_2$, each $R_{10}$ is halogen. In some embodiments, when U of Formula XXXI is $C(R_{10})_2$, one $R_{10}$ is halogen and one $R_{10}$ is hydrogen. In other embodiments, when U of Formula XXXI is $C(R_{10})_2$, each $R_{10}$ is fluoro. In other embodiments, when U of Formula XXXI is $C(R_{10})_2$, one $R_{10}$ is fluoro and one $R_{10}$ is hydrogen.

In some embodiments, U of Formula XXXI is $NCH_3$. In other embodiments, U of Formula XXXI is $NCH_2CH_3$.

In some embodiments, g in Formula XXXI is 0, 1, 2 or 3. In some embodiments, g in Formula XXXI is 0. In some embodiments, g in Formula XXXI is 1. In other embodiments, g in Formula XXXI is 2. In other embodiments, g in Formula XXXI is 3.

In some embodiments, h in Formula XXXI is 0, 1, 2 or 3. In some embodiments, h in Formula XXXI is 0. In some embodiments, h in Formula XXXI is 1. In other embodiments, h in Formula XXXI is 2. In other embodiments, h in Formula XXXI is 3.

In other embodiments, the compounds of Formula (I) are represented by compounds of Formula XXXII

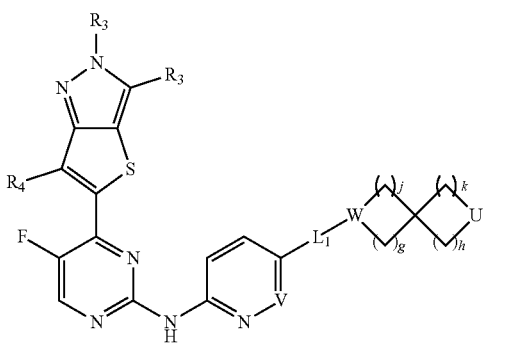

(XXXII)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g, h, j and k is independently 0, 1, 2 or 3; and
each $R_4$, $R_3$, V and $L_1$ is defined with respect to Formula (I).

In some embodiments, W of Formula XXXII is CH. In other embodiments, W of Formula XXXII is N.

In some embodiments, U of Formula XXXII is $C(R_{10})_2$. In other embodiments, U of Formula XXXII is $NR_{10}$. In yet other embodiments, U of Formula XXXII is O.

In some embodiments, $R_{10}$ of Formula XXXII is H. In some embodiments, $R_{10}$ of Formula XXXII is halogen. In other embodiments, $R_{10}$ of Formula XXXII is fluoro. In some embodiments, $R_{10}$ of Formula XXXII is $C_{1-6}$alkyl. In other embodiments, $R_{10}$ of Formula XXXII is methyl or ethyl. In some embodiments, $R_{10}$ of Formula XXXII is $C_{1-6}$alkoxide.

In some embodiments, when U of Formula XXXII is $C(R_{10})_2$, each $R_{10}$ is H. In some embodiments, when U of Formula XXXII is $C(R_{10})_2$, each $R_{10}$ is methyl. In some embodiments, when U of Formula XXXII is $C(R_{10})_2$, one $R_{10}$ is methyl and one $R_{10}$ is hydrogen. In some embodiments, when U of Formula XXXII is $C(R_{10})_2$, each $R_{10}$ is halogen. In some embodiments, when U of Formula XXXII is $C(R_{10})_2$, one $R_{10}$ is halogen and one $R_{10}$ is hydrogen. In other embodiments, when U of Formula XXXII is $C(R_{10})_2$, each $R_{10}$ is fluoro. In other embodiments, when U of Formula XXXII is $C(R_{10})_2$, one $R_{10}$ is fluoro and one $R_{10}$ is hydrogen.

In some embodiments, U of Formula XXXII is $NCH_3$. In other embodiments, U of Formula XXXII is $NCH_2CH_3$.

In some embodiments, g in Formula XXXII is 0, 1, 2 or 3. In some embodiments, g in Formula XXXII is 0. In some embodiments, g in Formula XXXII is 1. In other embodiments, g in Formula XXXII is 2. In other embodiments, g in Formula XXXII is 3.

In some embodiments, h in Formula XXXII is 0, 1, 2 or 3. In some embodiments, h in Formula XXXII is 0. In some embodiments, h in Formula XXXII is 1. In other embodiments, h in Formula XXXII is 2. In other embodiments, h in Formula XXXII is 3.

In some embodiments, j in Formula XXXII is 0, 1, 2 or 3. In some embodiments, j in Formula XXXII is 0. In some embodiments, j in Formula XXXII is 1. In other embodiments, j in Formula XXXII is 2. In other embodiments, j in Formula XXXII is 3.

In some embodiments, k in Formula XXXII is 0, 1, 2 or 3. In some embodiments, k in Formula XXXII is 0. In some embodiments, k in Formula XXXII is 1. In other embodiments, k in Formula XXXII is 2. In other embodiments, k in Formula XXXII is 3.

In other embodiments, the compounds of Formula (I) are represented by compounds of Formula XXXV

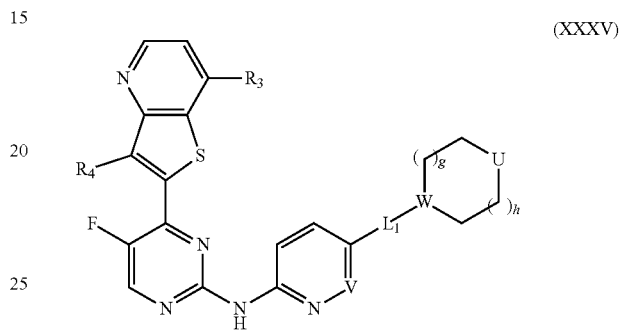

(XXXV)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g and h is independently 0, 1, 2 or 3; and
each $R_4$, $R_3$, V and $L_1$ is defined with respect to Formula (I).

In some embodiments, W of Formula XXXV is CH. In other embodiments, W of Formula XXXV is N.

In some embodiments, U of Formula XXXV is $C(R_{10})_2$. In other embodiments, U of Formula XXXV is $NR_{10}$. In yet other embodiments, U of Formula XXXV is O.

In some embodiments, $R_{10}$ of Formula XXXV is H. In some embodiments, $R_{10}$ of Formula XXXV is halogen. In other embodiments, $R_{10}$ of Formula XXXV is fluoro. In some embodiments, $R_{10}$ of Formula XXXV is $C_{1-6}$alkyl. In other embodiments, $R_{10}$ of Formula XXXV is methyl or ethyl. In some embodiments, $R_{10}$ of Formula XXXV is $C_{1-6}$alkoxide.

In some embodiments, when U of Formula XXXV is $C(R_{10})_2$, each $R_{10}$ is H. In some embodiments, when U of Formula XXXV is $C(R_{10})_2$, each $R_{10}$ is methyl. In some embodiments, when U of Formula XXXV is $C(R_{10})_2$, one $R_{10}$ is methyl and one $R_{10}$ is hydrogen. In some embodiments, when U of Formula XXXV is $C(R_{10})_2$, each $R_{10}$ is halogen. In some embodiments, when U of Formula XXXV is $C(R_{10})_2$, one $R_{10}$ is halogen and one $R_{10}$ is hydrogen. In other embodiments, when U of Formula XXXV is $C(R_{10})_2$, each $R_{10}$ is fluoro. In other embodiments, when U of Formula XXXV is $C(R_{10})_2$, one $R_{10}$ is fluoro and one $R_{10}$ is hydrogen.

In some embodiments, U of Formula XXXV is $NCH_3$. In other embodiments, U of Formula XXXV is $NCH_2CH_3$.

In some embodiments, g in Formula XXXV is 0, 1, 2 or 3. In some embodiments, g in Formula XXXV is 0. In some embodiments, g in Formula XXXV is 1. In other embodiments, g in Formula XXXV is 2. In other embodiments, g in Formula XXXV is 3.

In some embodiments, h in Formula XXXV is 0, 1, 2 or 3. In some embodiments, h in Formula XXXV is 0. In some embodiments, h in Formula XXXV is 1. In other embodiments, h in Formula XXXV is 2. In other embodiments, h in Formula XXXV is 3.

In other embodiments, the compounds of Formula (I) are represented by compounds of Formula XXXVI

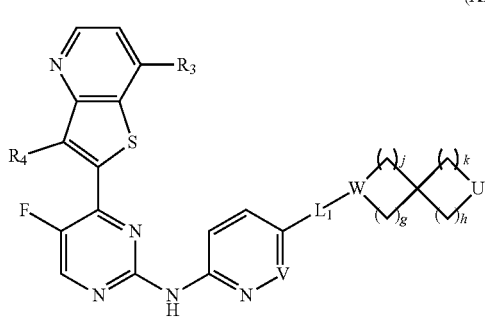

(XXXVI)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g, h, j and k is independently 0, 1, 2 or 3; and
each $R_4$, $R_3$, V and $L_1$ is defined with respect to Formula (I).

In some embodiments, W of Formula XXXVI is CH. In other embodiments, W of Formula XXXVI is N.

In some embodiments, U of Formula XXXVI is $C(R_{10})_2$. In other embodiments, U of Formula XXXVI is $NR_{10}$. In yet other embodiments, U of Formula XXXVI is O.

In some embodiments, $R_{10}$ of Formula XXXVI is H. In some embodiments, $R_{10}$ of Formula XXXVI is halogen. In other embodiments, $R_{10}$ of Formula XXXVI is fluoro. In some embodiments, $R_{10}$ of Formula XXXVI is $C_{1-6}$alkyl. In other embodiments, $R_{10}$ of Formula XXXVI is methyl or ethyl. In some embodiments, $R_{10}$ of Formula XXXVI is $C_{1-6}$alkoxide.

In some embodiments, when U of Formula XXXVI is $C(R_{10})_2$, each $R_{10}$ is H. In some embodiments, when U of Formula XXXVI is $C(R_{10})_2$, each $R_{10}$ is methyl. In some embodiments, when U of Formula XXXVI is $C(R_{10})_2$, one $R_{10}$ is methyl and one $R_{10}$ is hydrogen. In some embodiments, when U of Formula XXXVI is $C(R_{10})_2$, each $R_{10}$ is halogen. In some embodiments, when U of Formula XXXVI is $C(R_{10})_2$, one $R_{10}$ is halogen and one $R_{10}$ is hydrogen. In other embodiments, when U of Formula XXXVI is $C(R_{10})_2$, each $R_{10}$ is fluoro. In other embodiments, when U of Formula XXXVI is $C(R_{10})_2$, one $R_{10}$ is fluoro and one $R_{10}$ is hydrogen.

In some embodiments, U of Formula XXXVI is $NCH_3$. In other embodiments, U of Formula XXXVI is $NCH_2CH_3$.

In some embodiments, g in Formula XXXVI is 0, 1, 2 or 3. In some embodiments, g in Formula XXXVI is 0. In some embodiments, g in Formula XXXVI is 1. In other embodiments, g in Formula XXXVI is 2. In other embodiments, g in Formula XXXVI is 3.

In some embodiments, h in Formula XXXVI is 0, 1, 2 or 3. In some embodiments, h in Formula XXXVI is 0. In some embodiments, h in Formula XXXVI is 1. In other embodiments, h in Formula XXXVI is 2. In other embodiments, h in Formula XXXVI is 3.

In some embodiments, j in Formula XXXVI is 0, 1, 2 or 3. In some embodiments, j in Formula XXXVI is 0. In some embodiments, j in Formula XXXVI is 1. In other embodiments, j in Formula XXXVI is 2. In other embodiments, j in Formula XXXVI is 3.

In some embodiments, k in Formula XXXVI is 0, 1, 2 or 3. In some embodiments, k in Formula XXXVI is 0. In some embodiments, k in Formula XXXVI is 1. In other embodiments, k in Formula XXXVI is 2. In other embodiments, k in Formula XXXVI is 3.

In other embodiments, the compounds of Formula (I) are represented by compounds of Formula XXXVII

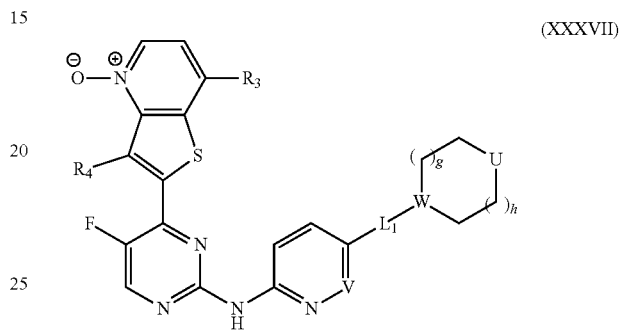

(XXXVII)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g and h is independently 0, 1, 2 or 3; and
each $R_4$, $R_3$, V and $L_1$ is defined with respect to Formula (I).

In some embodiments, W of Formula XXXVII is CH. In other embodiments, W of Formula XXXVII is N.

In some embodiments, U of Formula XXXVII is $C(R_{10})_2$. In other embodiments, U of Formula XXXVII is $NR_{10}$. In yet other embodiments, U of Formula XXXVII is O.

In some embodiments, $R_{10}$ of Formula XXXVII is H. In some embodiments, $R_{10}$ of Formula XXXVII is halogen. In other embodiments, $R_{10}$ of Formula XXXVII is fluoro. In some embodiments, $R_{10}$ of Formula XXXVII is $C_{1-6}$alkyl. In other embodiments, $R_{10}$ of Formula XXXVII is methyl or ethyl. In some embodiments, $R_{10}$ of Formula XXXVII is $C_{1-6}$alkoxide.

In some embodiments, when U of Formula XXXVII is $C(R_{10})_2$, each $R_{10}$ is H. In some embodiments, when U of Formula XXXVII is $C(R_{10})_2$, each $R_{10}$ is methyl. In some embodiments, when U of Formula XXXVII is $C(R_{10})_2$, one $R_{10}$ is methyl and one $R_{10}$ is hydrogen. In some embodiments, when U of Formula XXXVII is $C(R_{10})_2$, each $R_{10}$ is halogen. In some embodiments, when U of Formula XXXVII is $C(R_{10})_2$, one $R_{10}$ is halogen and one $R_{10}$ is hydrogen. In other embodiments, when U of Formula XXXVII is $C(R_{10})_2$, each $R_{10}$ is fluoro. In other embodiments, when U of Formula XXXVII is $C(R_{10})_2$, one $R_{10}$ is fluoro and one $R_{10}$ is hydrogen.

In some embodiments, U of Formula XXXVII is $NCH_3$. In other embodiments, U of Formula XXXVII is $NCH_2CH_3$.

In some embodiments, g in Formula XXXVII is 0, 1, 2 or 3. In some embodiments, g in Formula XXXVII is 0. In some embodiments, g in Formula XXXVII is 1. In other embodiments, g in Formula XXXVII is 2. In other embodiments, g in Formula XXXVII is 3.

In some embodiments, h in Formula XXXVII is 0, 1, 2 or 3. In some embodiments, h in Formula XXXVII is 0. In some embodiments, h in Formula XXXVII is 1. In other embodiments, h in Formula XXXVII is 2. In other embodiments, h in Formula XXXVII is 3.

In other embodiments, the compounds of Formula (I) are represented by compounds of Formula XXXVIII

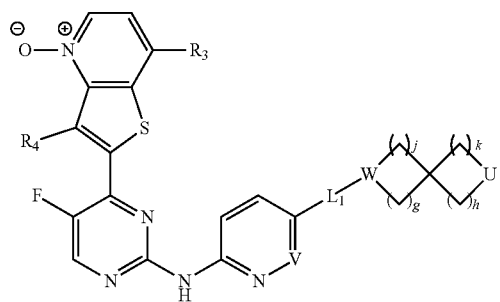

(XXXVIII)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g, h, j and k is independently 0, 1, 2 or 3; and
each $R_4$, $R_3$, V and $L_1$ is defined with respect to Formula (I).

In some embodiments, W of Formula XXXVIII is CH. In other embodiments, W of Formula XXXVIII is N.

In some embodiments, U of Formula XXXVIII is $C(R_{10})_2$. In other embodiments, U of Formula XXXVIII is $NR_{10}$. In yet other embodiments, U of Formula XXXVIII is O.

In some embodiments, $R_{10}$ of Formula XXXVIII is H. In some embodiments, $R_{10}$ of Formula XXXVIII is halogen. In other embodiments, $R_{10}$ of Formula XXXVIII is fluoro. In some embodiments, $R_{10}$ of Formula XXXVIII is $C_{1-6}$alkyl. In other embodiments, $R_{10}$ of Formula XXXVIII is methyl or ethyl. In some embodiments, $R_{10}$ of Formula XXXVIII is $C_{1-6}$alkoxide.

In some embodiments, when U of Formula XXXVIII is $C(R_{10})_2$, each $R_{10}$ is H. In some embodiments, when U of Formula XXXVIII is $C(R_{10})_2$, each $R_{10}$ is methyl. In some embodiments, when U of Formula XXXVIII is $C(R_{10})_2$, one $R_{10}$ is methyl and one $R_{10}$ is hydrogen. In some embodiments, when U of Formula XXXVIII is $C(R_{10})_2$, each $R_{10}$ is halogen. In some embodiments, when U of Formula XXXVIII is $C(R_{10})_2$, one $R_{10}$ is halogen and one $R_{10}$ is hydrogen. In other embodiments, when U of Formula XXXVIII is $C(R_{10})_2$, each $R_{10}$ is fluoro. In other embodiments, when U of Formula XXXVIII is $C(R_{10})_2$, one $R_{10}$ is fluoro and one $R_{10}$ is hydrogen.

In some embodiments, U of Formula XXXVIII is $NCH_3$. In other embodiments, U of Formula XXXVIII is $NCH_2CH_3$.

In some embodiments, g in Formula XXXVIII is 0, 1, 2 or 3. In some embodiments, g in Formula XXXVIII is 0. In some embodiments, g in Formula XXXVIII is 1. In other embodiments, g in Formula XXXVIII is 2. In other embodiments, g in Formula XXXVIII is 3.

In some embodiments, h in Formula XXXVIII is 0, 1, 2 or 3. In some embodiments, h in Formula XXXVIII is 0. In some embodiments, h in Formula XXXVIII is 1. In other embodiments, h in Formula XXXVIII is 2. In other embodiments, h in Formula XXXVIII is 3.

In some embodiments, j in Formula XXXVIII is 0, 1, 2 or 3. In some embodiments, j in Formula XXXVIII is 0. In some embodiments, j in Formula XXXVIII is 1. In other embodiments, j in Formula XXXVIII is 2. In other embodiments, j in Formula XXXVIII is 3.

In some embodiments, k in Formula XXXVIII is 0, 1, 2 or 3. In some embodiments, k in Formula XXXVIII is 0. In some embodiments, k in Formula XXXVIII is 1. In other embodiments, k in Formula XXXVIII is 2. In other embodiments, k in Formula XXXVIII is 3.

In other embodiments, the compounds of Formula (I) are represented by compounds of Formula XXXIX

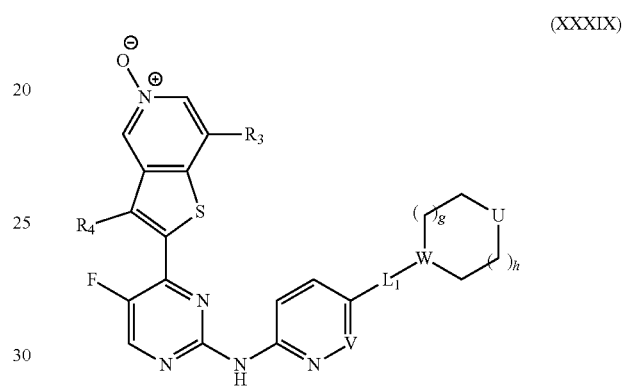

(XXXIX)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g and h is independently 0, 1, 2 or 3; and
each $R_4$, $R_3$, V and $L_1$ is defined with respect to Formula (I).

In some embodiments, W of Formula XXXIX is CH. In other embodiments, W of Formula XXXIX is N.

In some embodiments, U of Formula XXXIX is $C(R_{10})_2$. In other embodiments, U of Formula XXXIX is $NR_{10}$. In yet other embodiments, U of Formula XXXIX is O.

In some embodiments, $R_{10}$ of Formula XXXIX is H. In some embodiments, $R_{10}$ of Formula XXXIX is halogen. In other embodiments, $R_{10}$ of Formula XXXVII is fluoro. In some embodiments, $R_{10}$ of Formula XXXIX is $C_{1-6}$alkyl. In other embodiments, $R_{10}$ of Formula XXXIX is methyl or ethyl. In some embodiments, $R_{10}$ of Formula XXXIX is $C_{1-6}$alkoxide.

In some embodiments, when U of Formula XXXIX is $C(R_{10})_2$, each $R_{10}$ is H. In some embodiments, when U of Formula XXXIX is $C(R_{10})_2$, each $R_{10}$ is methyl. In some embodiments, when U of Formula XXXIX is $C(R_{10})_2$, one $R_{10}$ is methyl and one $R_{10}$ is hydrogen. In some embodiments, when U of Formula XXXIX is $C(R_{10})_2$, each $R_{10}$ is halogen. In some embodiments, when U of Formula XXXIX is $C(R_{10})_2$, one $R_{10}$ is halogen and one $R_{10}$ is hydrogen. In other embodiments, when U of Formula XXXIX is $C(R_{10})_2$, each $R_{10}$ is fluoro. In other embodiments, when U of Formula XXXIX is $C(R_{10})_2$, one $R_{10}$ is fluoro and one $R_{10}$ is hydrogen.

In some embodiments, U of Formula XXXIX is $NCH_3$. In other embodiments, U of Formula XXXIX is $NCH_2CH_3$.

In some embodiments, g in Formula XXXIX is 0, 1, 2 or 3. In some embodiments, g in Formula XXXIX is 0. In some embodiments, g in Formula XXXIX is 1. In other embodiments, g in Formula XXXIX is 2. In other embodiments, g in Formula XXXIX is 3.

In some embodiments, h in Formula XXXIX is 0, 1, 2 or 3. In some embodiments, h in Formula XXXIX is 0. In some embodiments, h in Formula XXXIX is 1. In other embodiments, h in Formula XXXIX is 2. In other embodiments, h in Formula XXXIX is 3.

In other embodiments, the compounds of Formula (I) are represented by compounds of Formula XL (XL)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g, h, j and k is independently 0, 1, 2 or 3; and
each $R_4$, $R_3$, V and $L_1$ is defined with respect to Formula (I).

In some embodiments, W of Formula XL is CH. In other embodiments, W of Formula XL is N.

In some embodiments, U of Formula XL is $C(R_{10})_2$. In other embodiments, U of Formula XL is $NR_{10}$. In yet other embodiments, U of Formula XL is O.

In some embodiments, $R_{10}$ of Formula XL is H. In some embodiments, $R_{10}$ of Formula XL is halogen. In other embodiments, $R_{10}$ of Formula XL is fluoro. In some embodiments, $R_{10}$ of Formula XL is $C_{1-6}$alkyl. In other embodiments, $R_{10}$ of Formula XL is methyl or ethyl. In some embodiments, $R_{10}$ of Formula XL is $C_{1-6}$alkoxide.

In some embodiments, when U of Formula XL is $C(R_{10})_2$, each $R_{10}$ is H. In some embodiments, when U of Formula XL is $C(R_{10})_2$, each $R_{10}$ is methyl. In some embodiments, when U of Formula XL is $C(R_{10})_2$, one $R_{10}$ is methyl and one $R_{10}$ is hydrogen. In some embodiments, when U of Formula XL is $C(R_{10})_2$, each $R_{10}$ is halogen. In some embodiments, when U of Formula XL is $C(R_{10})_2$, one $R_{10}$ is halogen and one $R_{10}$ is hydrogen. In other embodiments, when U of Formula XL is $C(R_{10})_2$, each $R_{10}$ is fluoro. In other embodiments, when U of Formula XL is $C(R_{10})_2$, one $R_{10}$ is fluoro and one $R_{10}$ is hydrogen.

In some embodiments, U of Formula XL is $NCH_3$. In other embodiments, U of Formula XL is $NCH_2CH_3$.

In some embodiments, g in Formula XL is 0, 1, 2 or 3. In some embodiments, g in Formula XL is 0. In some embodiments, g in Formula XL is 1. In other embodiments, g in Formula XL is 2. In other embodiments, g in Formula XL is 3.

In some embodiments, h in Formula XL is 0, 1, 2 or 3. In some embodiments, h in Formula XL is 0. In some embodiments, h in Formula XL is 1. In other embodiments, h in Formula XL is 2. In other embodiments, h in Formula XL is 3.

In some embodiments, j in Formula XL is 0, 1, 2 or 3. In some embodiments, j in Formula XL is 0. In some embodiments, j in Formula XL is 1. In other embodiments, j in Formula XL is 2. In other embodiments, j in Formula XL is 3.

In some embodiments, k in Formula XL is 0, 1, 2 or 3. In some embodiments, k in Formula XL is 0. In some embodiments, k in Formula XL is 1. In other embodiments, k in Formula XL is 2. In other embodiments, k in Formula XL is 3.

In other embodiments, the compounds of Formula (I) are represented by compounds of Formula XLI (XLI)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g and h is independently 0, 1, 2 or 3; and
each $R_4$, $R_3$, V and $L_1$ is defined with respect to Formula (I).

In some embodiments, W of Formula XLI is CH. In other embodiments, W of Formula XLI is N.

In some embodiments, U of Formula XLI is $C(R_{10})_2$. In other embodiments, U of Formula XLI is $NR_{10}$. In yet other embodiments, U of Formula XLI is O.

In some embodiments, $R_{10}$ of Formula XLI is H. In some embodiments, $R_{10}$ of Formula XLI is halogen. In other embodiments, $R_{10}$ of Formula XLI is fluoro. In some embodiments, $R_{10}$ of Formula XLI is $C_{1-6}$alkyl. In other embodiments, $R_{10}$ of Formula XLI is methyl or ethyl. In some embodiments, $R_{10}$ of Formula XLI is $C_{1-6}$alkoxide.

In some embodiments, when U of Formula XLI is $C(R_{10})_2$, each $R_{10}$ is H. In some embodiments, when U of Formula XLI is $C(R_{10})_2$, each $R_{10}$ is methyl. In some embodiments, when U of Formula XLI is $C(R_{10})_2$, one $R_{10}$ is methyl and one $R_{10}$ is hydrogen. In some embodiments, when U of Formula XLI is $C(R_{10})_2$, each $R_{10}$ is halogen. In some embodiments, when U of Formula XLI is $C(R_{10})_2$, one $R_{10}$ is halogen and one $R_{10}$ is hydrogen. In other embodiments, when U of Formula XLI is $C(R_{10})_2$, each $R_{10}$ is fluoro. In other embodiments, when U of Formula XLI is $C(R_{10})_2$, one $R_{10}$ is fluoro and one $R_{10}$ is hydrogen.

In some embodiments, U of Formula XLI is $NCH_3$. In other embodiments, U of Formula XLI is $NCH_2CH_3$.

In some embodiments, g in Formula XLI is 0, 1, 2 or 3. In some embodiments, g in Formula XLI is 0. In some embodiments, g in Formula XLI is 1. In other embodiments, g in Formula XLI is 2. In other embodiments, g in Formula XLI is 3.

In some embodiments, h in Formula XLI is 0, 1, 2 or 3. In some embodiments, h in Formula XLI is 0. In some embodiments, h in Formula XLI is 1. In other embodiments, h in Formula XLI is 2. In other embodiments, h in Formula XLI is 3.

In other embodiments, the compounds of Formula (I) are represented by compounds of Formula XLII

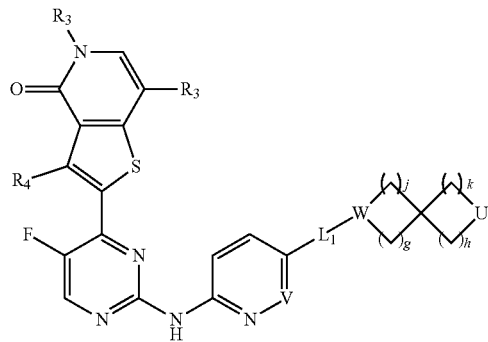

(XLII)

or a pharmaceutically acceptable salt thereof, wherein

W is CH or N;

U is $C(R_{10})_2$, $NR_{10}$, or O;

$R_{10}$ is H, halogen (preferably fluoro), $C_{1-6}$alkyl, or $C_{1-6}$alkoxide;

each g, h, j and k is independently 0, 1, 2 or 3; and each $R_4$, $R_3$, V and $L_1$ is defined with respect to Formula (I).

In some embodiments, W of Formula XLII is CH. In other embodiments, W of Formula XLII is N.

In some embodiments, U of Formula XLII is $C(R_{10})_2$. In other embodiments, U of Formula XLII is $NR_{10}$. In yet other embodiments, U of Formula XLII is O.

In some embodiments, $R_{10}$ of Formula XLII is H. In some embodiments, $R_{10}$ of Formula XLII is halogen. In other embodiments, $R_{10}$ of Formula XLII is fluoro. In some embodiments, $R_{10}$ of Formula XLII is $C_{1-6}$alkyl. In other embodiments, $R_{10}$ of Formula XLII is methyl or ethyl. In some embodiments, $R_{10}$ of Formula XLII is $C_{1-6}$alkoxide.

In some embodiments, when U of Formula XLII is $C(R_{10})_2$, each $R_{10}$ is H. In some embodiments, when U of Formula XLII is $C(R_{10})_2$, each $R_{10}$ is methyl. In some embodiments, when U of Formula XLII is $C(R_{10})_2$, one $R_{10}$ is methyl and one $R_{10}$ is hydrogen. In some embodiments, when U of Formula XLII is $C(R_{10})_2$, each $R_{10}$ is halogen. In some embodiments, when U of Formula XLII is $C(R_{10})_2$, one $R_{10}$ is halogen and one $R_{10}$ is hydrogen. In other embodiments, when U of Formula XLII is $C(R_{10})_2$, each $R_{10}$ is fluoro. In other embodiments, when U of Formula XLII is $C(R_{10})_2$, one $R_{10}$ is fluoro and one $R_{10}$ is hydrogen.

In some embodiments, U of Formula XLII is $NCH_3$. In other embodiments, U of Formula XLII is $NCH_2CH_3$.

In some embodiments, g in Formula XLII is 0, 1, 2 or 3. In some embodiments, g in Formula XLII is 0. In some embodiments, g in Formula XLII is 1. In other embodiments, g in Formula XLII is 2. In other embodiments, g in Formula XLII is 3.

In some embodiments, h in Formula XLII is 0, 1, 2 or 3. In some embodiments, h in Formula XLII is 0. In some embodiments, h in Formula XLII is 1. In other embodiments, h in Formula XLII is 2. In other embodiments, h in Formula XLII is 3.

In some embodiments, j in Formula XLII is 0, 1, 2 or 3. In some embodiments, j in Formula XLII is 0. In some embodiments, j in Formula XLII is 1. In other embodiments, j in Formula XLII is 2. In other embodiments, j in Formula XLII is 3.

In some embodiments, k in Formula XLII is 0, 1, 2 or 3. In some embodiments, k in Formula XLII is 0. In some embodiments, k in Formula XLII is 1. In other embodiments, k in Formula XLII is 2. In other embodiments, k in Formula XLII is 3.

In other embodiments, the compounds of Formula (I) are represented by compounds of Formula XLIII

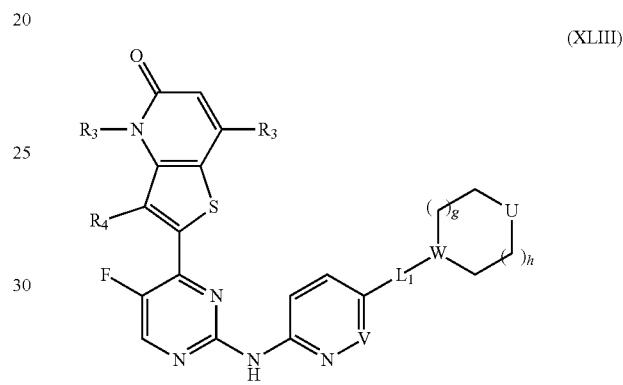

(XLIII)

or a pharmaceutically acceptable salt thereof, wherein

W is CH or N;

U is $C(R_{10})_2$, $NR_{10}$, or O;

$R_{10}$ is H, halogen (preferably fluoro), $C_{1-6}$alkyl, or $C_{1-6}$alkoxide;

each g and h is independently 0, 1, 2 or 3; and each $R_4$, $R_3$, V and $L_1$ is defined with respect to Formula (I).

In some embodiments, W of Formula XLIII is CH. In other embodiments, W of Formula XLIII is N.

In some embodiments, U of Formula XLIII is $C(R_{10})_2$. In other embodiments, U of Formula XLIII is $NR_{10}$. In yet other embodiments, U of Formula XLIII is O.

In some embodiments, $R_{10}$ of Formula XLIII is H. In some embodiments, $R_{10}$ of Formula XLIII is halogen. In other embodiments, $R_{10}$ of Formula XLIII is fluoro. In some embodiments, $R_{10}$ of Formula XLI is $C_{1-6}$alkyl. In other embodiments, $R_{10}$ of Formula XLIII is methyl or ethyl. In some embodiments, $R_{10}$ of Formula XLIII is $C_{1-6}$alkoxide.

In some embodiments, when U of Formula XLIII is $C(R_{10})_2$, each $R_{10}$ is H. In some embodiments, when U of Formula XLIII is $C(R_{10})_2$, each $R_{10}$ is methyl. In some embodiments, when U of Formula XLIII is $C(R_{10})_2$, one $R_{10}$ is methyl and one $R_{10}$ is hydrogen. In some embodiments, when U of Formula XLIII is $C(R_{10})_2$, each $R_{10}$ is halogen. In some embodiments, when U of Formula XLIII is $C(R_{10})_2$, one $R_{10}$ is halogen and one $R_{10}$ is hydrogen. In other embodiments, when U of Formula XLIII is $C(R_{10})_2$, each $R_{10}$ is fluoro. In other embodiments, when U of Formula XLIII is $C(R_{10})_2$, one $R_{10}$ is fluoro and one $R_{10}$ is hydrogen.

In some embodiments, U of Formula XLIII is $NCH_3$. In other embodiments, U of Formula XLIII is $NCH_2CH_3$.

In some embodiments, g in Formula XLIII is 0, 1, 2 or 3. In some embodiments, g in Formula XLIII is 0. In some embodiments, g in Formula XLIII is 1. In other embodiments, g in Formula XLIII is 2. In other embodiments, g in Formula XLIII is 3.

In some embodiments, h in Formula XLIII is 0, 1, 2 or 3. In some embodiments, h in Formula XLIII is 0. In some embodiments, h in Formula XLIII is 1. In other embodiments, h in Formula XLIII is 2. In other embodiments, h in Formula XLIII is 3.

In other embodiments, the compounds of Formula (I) are represented by compounds of Formula XLIV

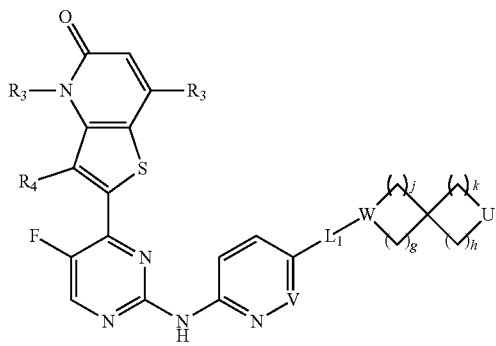

(XLIV)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide;
each g, h, j and k is independently 0, 1, 2 or 3; and
each $R_4$, $R_3$, V and $L_1$ is defined with respect to Formula (I).

In some embodiments, W of Formula XLIV is CH. In other embodiments, W of Formula XLIV is N.

In some embodiments, U of Formula XLIV is $C(R_{10})_2$. In other embodiments, U of Formula XLIV is $NR_{10}$. In yet other embodiments, U of Formula XLIV is O.

In some embodiments, $R_{10}$ of Formula XLIV is H. In some embodiments, $R_{10}$ of Formula XLIV is halogen. In other embodiments, $R_{10}$ of Formula XLIV is fluoro. In some embodiments, $R_{10}$ of Formula XLIV is $C_{1-6}$alkyl. In other embodiments, $R_{10}$ of Formula XLIV is methyl or ethyl.

In some embodiments, $R_{10}$ of Formula XLIV is $C_{1-6}$alkoxide.

In some embodiments, when U of Formula XLIV is $C(R_{10})_2$, each $R_{10}$ is H. In some embodiments, when U of Formula XLIV is $C(R_{10})_2$, each $R_{10}$ is methyl. In some embodiments, when U of Formula XLIV is $C(R_{10})_2$, one $R_{10}$ is methyl and one $R_{10}$ is hydrogen. In some embodiments, when U of Formula XLIV is $C(R_{10})_2$, each $R_{10}$ is halogen. In some embodiments, when U of Formula XLIV is $C(R_{10})_2$, one $R_{10}$ is halogen and one $R_{10}$ is hydrogen. In other embodiments, when U of Formula XLIV is $C(R_{10})_2$, each $R_{10}$ is fluoro. In other embodiments, when U of Formula XLIV is $C(R_{10})_2$, one $R_{10}$ is fluoro and one $R_{10}$ is hydrogen.

In some embodiments, U of Formula XLIV is $NCH_3$. In other embodiments, U of Formula XLIV is $NCH_2CH_3$.

In some embodiments, g in Formula XLIV is 0, 1, 2 or 3. In some embodiments, g in Formula XLIV is 0. In some embodiments, g in Formula XLIV is 1. In other embodiments, g in Formula XLIV is 2. In other embodiments, g in Formula XLIV is 3.

In some embodiments, h in Formula XLIV is 0, 1, 2 or 3. In some embodiments, h in Formula XLIV is 0. In some embodiments, h in Formula XLIV is 1. In other embodiments, h in Formula XLIV is 2. In other embodiments, h in Formula XLIV is 3.

In some embodiments, j in Formula XLIV is 0, 1, 2 or 3. In some embodiments, j in Formula XLIV is 0. In some embodiments, j in Formula XLIV is 1. In other embodiments, j in Formula XLIV is 2. In other embodiments, j in Formula XLIV is 3.

In some embodiments, k in Formula XLIV is 0, 1, 2 or 3. In some embodiments, k in Formula XLIV is 0. In some embodiments, k in Formula XLIV is 1. In other embodiments, k in Formula XLIV is 2. In other embodiments, k in Formula XLIV is 3.

In yet other embodiments, the compounds of Formula (I) are represented by compounds of Formula XLV

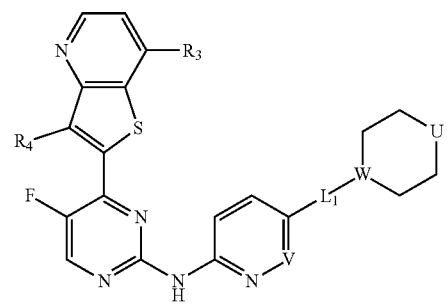

(XLV)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula XLV is CH. In other embodiments, W of Formula XLV is N.

In some embodiments, U of Formula XLV is $C(R_{10})_2$. In other embodiments, U of Formula XLV is $NR_{10}$. In yet other embodiments, U of Formula XLV is O.

In some embodiments, $R_{10}$ of Formula XLV is H. In some embodiments, $R_{10}$ of Formula XLV is halogen. In other embodiments, $R_{10}$ of Formula XLV is fluoro. In some embodiments, $R_{10}$ of Formula XLV is $C_{1-6}$alkyl. In other embodiments, $R_{10}$ of Formula XLV is methyl or ethyl. In some embodiments, $R_{10}$ of Formula XLV is $C_{1-6}$alkoxide.

In some embodiments, when U of Formula XLV is $C(R_{10})_2$, each $R_{10}$ is H. In some embodiments, when U of Formula XLV is $C(R_{10})_2$, each $R_{10}$ is methyl. In some embodiments, when U of Formula XLV is $C(R_{10})_2$, one $R_{10}$ is methyl and one $R_{10}$ is hydrogen. In some embodiments, when U of Formula XLV is $C(R_{10})_2$, each $R_{10}$ is halogen. In some embodiments, when U of Formula XLV is $C(R_{10})_2$, one $R_{10}$ is halogen and one $R_{10}$ is hydrogen. In other embodiments, when U of Formula XLV is $C(R_{10})_2$, each $R_{10}$ is fluoro. In other embodiments, when U of Formula XLV is $C(R_{10})_2$, one $R_{10}$ is fluoro and one $R_{10}$ is hydrogen.

In some embodiments, U of Formula XLV is $NCH_3$. In other embodiments, U of Formula XLV is $NCH_2CH_3$.

In yet other embodiments, the compounds of Formula (I) are represented by compounds of Formula XLVI

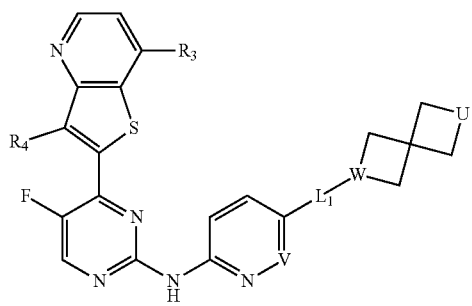

(XLVI)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula XLVI is CH. In other embodiments, W of Formula XLVI is N.

In some embodiments, U of Formula XLVI is $C(R_{10})_2$. In other embodiments, U of Formula XLVI is $NR_{10}$. In yet other embodiments, U of Formula XLVI is O.

In some embodiments, $R_{10}$ of Formula XLVI is H. In some embodiments, $R_{10}$ of Formula XLVI is halogen. In other embodiments, $R_{10}$ of Formula XLVI is fluoro. In some embodiments, $R_{10}$ of Formula XLVI is $C_{1-6}$alkyl. In other embodiments, $R_{10}$ of Formula XLVI is methyl or ethyl.

In some embodiments, $R_{10}$ of Formula XLV is $C_{1-6}$alkoxide.

In some embodiments, when U of Formula XLVI is $C(R_{10})_2$, each $R_{10}$ is H. In some embodiments, when U of Formula XLVI is $C(R_{10})_2$, each $R_{10}$ is methyl. In some embodiments, when U of Formula XLVI is $C(R_{10})_2$, one $R_{10}$ is methyl and one $R_{10}$ is hydrogen. In some embodiments, when U of Formula XLVI is $C(R_{10})_2$, each $R_{10}$ is halogen. In some embodiments, when U of Formula XLVI is $C(R_{10})_2$, one $R_{10}$ is halogen and one $R_{10}$ is hydrogen. In other embodiments, when U of Formula XLVI is $C(R_{10})_2$, each $R_{10}$ is fluoro. In other embodiments, when U of Formula XLVI is $C(R_{10})_2$, one $R_{10}$ is fluoro and one $R_{10}$ is hydrogen.

In some embodiments, U of Formula XLVI is $NCH_3$. In other embodiments, U of Formula XLVI is $NCH_2CH_3$.

In yet other embodiments, the compounds of Formula (I) are represented by compounds of Formula XLVII

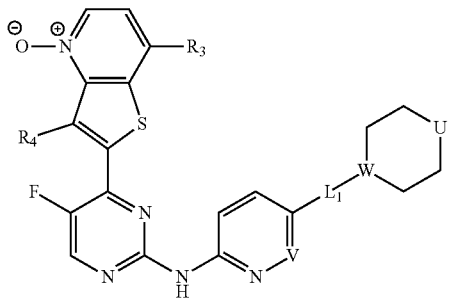

(XLVII)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula XLVII is CH. In other embodiments, W of Formula XLVII is N.

In some embodiments, U of Formula XLVII is $C(R_{10})_2$. In other embodiments, U of Formula XLVII is $NR_{10}$. In yet other embodiments, U of Formula XLVII is O.

In some embodiments, $R_{10}$ of Formula XLVII is H. In some embodiments, $R_{10}$ of Formula XLVII is halogen. In other embodiments, $R_{10}$ of Formula XLVII is fluoro. In some embodiments, $R_{10}$ of Formula XLVII is $C_{1-6}$alkyl. In other embodiments, $R_{10}$ of Formula XLVII is methyl or ethyl.

In some embodiments, $R_{10}$ of Formula XLVII is $C_{1-6}$alkoxide.

In some embodiments, when U of Formula XLVII is $C(R_{10})_2$, each $R_{10}$ is H. In some embodiments, when U of Formula XLVII is $C(R_{10})_2$, each $R_{10}$ is methyl. In some embodiments, when U of Formula XLVII is $C(R_{10})_2$, one $R_{10}$ is methyl and one $R_{10}$ is hydrogen. In some embodiments, when U of Formula XLVII is $C(R_{10})_2$, each $R_{10}$ is halogen. In some embodiments, when U of Formula XLVII is $C(R_{10})_2$, one $R_{10}$ is halogen and one $R_{10}$ is hydrogen. In other embodiments, when U of Formula XLVII is $C(R_{10})_2$, each $R_{10}$ is fluoro. In other embodiments, when U of Formula XLVII is $C(R_{10})_2$, one $R_{10}$ is fluoro and one $R_{10}$ is hydrogen.

In some embodiments, U of Formula XLVII is $NCH_3$. In other embodiments, U of Formula XLVII is $NCH_2CH_3$.

In yet other embodiments, the compounds of Formula (I) are represented by compounds of Formula XLVIII

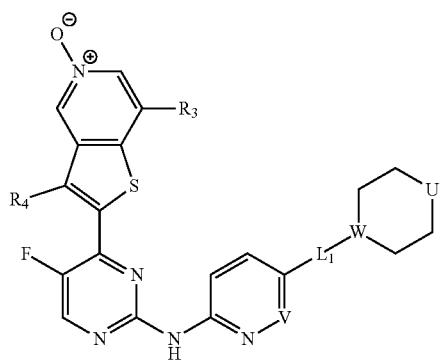

(XLVIII)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula XLVIII is CH. In other embodiments, W of Formula XLVIII is N.

In some embodiments, U of Formula XLVIII is $C(R_{10})_2$. In other embodiments, U of Formula XLVIII is $NR_{10}$. In yet other embodiments, U of Formula XLVIII is O.

In some embodiments, $R_{10}$ of Formula XLVIII is H. In some embodiments, $R_{10}$ of Formula XLVIII is halogen. In other embodiments, $R_{10}$ of Formula XLVIII is fluoro. In some embodiments, $R_{10}$ of Formula XLVIII is $C_{1-6}$alkyl. In other embodiments, $R_{10}$ of Formula XLVIII is methyl or ethyl. In some embodiments, $R_{10}$ of Formula XLVIII is $C_{1-6}$alkoxide.

In some embodiments, when U of Formula XLVIII is $C(R_{10})_2$, each $R_{10}$ is H. In some embodiments, when U of Formula XLVIII is $C(R_{10})_2$, each $R_{10}$ is methyl. In some embodiments, when U of Formula XLVIII is $C(R_{10})_2$, one $R_{10}$ is methyl and one $R_{10}$ is hydrogen. In some embodiments, when U of Formula XLVIII is $C(R_{10})_2$, each $R_{10}$ is halogen. In some embodiments, when U of Formula XLVIII is $C(R_{10})_2$, one $R_{10}$ is halogen and one $R_{10}$ is hydrogen. In other embodiments, when U of Formula XLVIII is $C(R_{10})_2$, each $R_{10}$ is fluoro. In other embodiments, when U of Formula XLVIII is $C(R_{10})_2$, one $R_{10}$ is fluoro and one $R_{10}$ is hydrogen.

In some embodiments, U of Formula XLVIII is $NCH_3$. In other embodiments, U of Formula XLVIII is $NCH_2CH_3$.

In yet other embodiments, the compounds of Formula (I) are represented by compounds of Formula XLIX

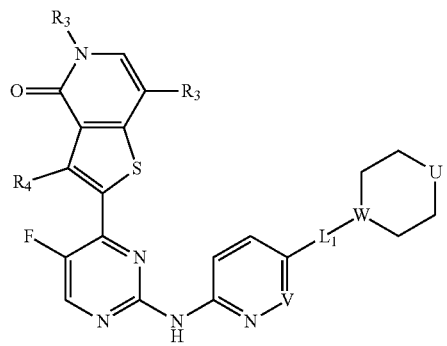

(XLIX)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula XLIX is CH. In other embodiments, W of Formula XLIX is N.

In some embodiments, U of Formula XLIX is $C(R_{10})_2$. In other embodiments, U of Formula XLIX is $NR_{10}$. In yet other embodiments, U of Formula XLIX is O.

In some embodiments, $R_{10}$ of Formula XLIX is H. In some embodiments, $R_{10}$ of Formula XLIX is halogen. In other embodiments, $R_{10}$ of Formula XLIX is fluoro. In some embodiments, $R_{10}$ of Formula XLIX is $C_{1-6}$alkyl. In other embodiments, $R_{10}$ of Formula XLIX is methyl or ethyl.

In some embodiments, $R_{10}$ of Formula XLIX is $C_{1-6}$alkoxide.

In some embodiments, when U of Formula XLIX is $C(R_{10})_2$, each $R_{10}$ is H. In some embodiments, when U of Formula XLIX is $C(R_{10})_2$, each $R_{10}$ is methyl. In some embodiments, when U of Formula XLIX is $C(R_{10})_2$, one $R_{10}$ is methyl and one $R_{10}$ is hydrogen. In some embodiments, when U of Formula XLIX is $C(R_{10})_2$, each $R_{10}$ is halogen. In some embodiments, when U of Formula XLIX is $C(R_{10})_2$, one $R_{10}$ is halogen and one $R_{10}$ is hydrogen. In other embodiments, when U of Formula XLIX is $C(R_{10})_2$, each $R_{10}$ is fluoro. In other embodiments, when U of Formula XLIX is $C(R_{10})_2$, one $R_{10}$ is fluoro and one $R_{10}$ is hydrogen.

In some embodiments, U of Formula XLIX is $NCH_3$. In other embodiments, U of Formula XLIX is $NCH_2CH_3$.

In yet other embodiments, the compounds of Formula (I) are represented by compounds of Formula L

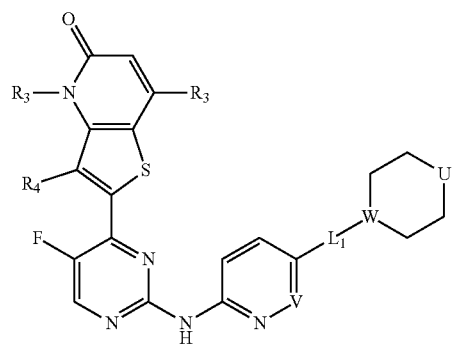

(L)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula L is CH. In other embodiments, W of Formula XLIX is N.

In some embodiments, U of Formula L is $C(R_{10})_2$. In other embodiments, U of Formula L is $NR_{10}$. In yet other embodiments, U of Formula L is O.

In some embodiments, $R_{10}$ of Formula L is H. In some embodiments, $R_{10}$ of Formula L is halogen. In other embodiments, $R_{10}$ of Formula L is fluoro. In some embodiments, $R_{10}$ of Formula L is $C_{1-6}$alkyl. In other embodiments, $R_{10}$ of Formula L is methyl or ethyl. In some embodiments, $R_{10}$ of Formula L is $C_{1-6}$alkoxide.

In some embodiments, when U of Formula L is $C(R_{10})_2$, each $R_{10}$ is H. In some embodiments, when U of Formula L is $C(R_{10})_2$, each $R_{10}$ is methyl. In some embodiments, when U of Formula L is $C(R_{10})_2$, one $R_{10}$ is methyl and one $R_{10}$ is hydrogen. In some embodiments, when U of Formula L is $C(R_{10})_2$, each $R_{10}$ is halogen. In some embodiments, when U of Formula L is $C(R_{10})_2$, one $R_{10}$ is halogen and one $R_{10}$ is hydrogen. In other embodiments, when U of Formula L is $C(R_{10})_2$, each $R_{10}$ is fluoro. In other embodiments, when U of Formula L is $C(R_{10})_2$, one $R_{10}$ is fluoro and one $R_{10}$ is hydrogen.

In some embodiments, U of Formula L is $NCH_3$. In other embodiments, U of Formula L is $NCH_2CH_3$.

In yet other embodiments, the compounds of Formula (I) are represented by compounds of Formula LI

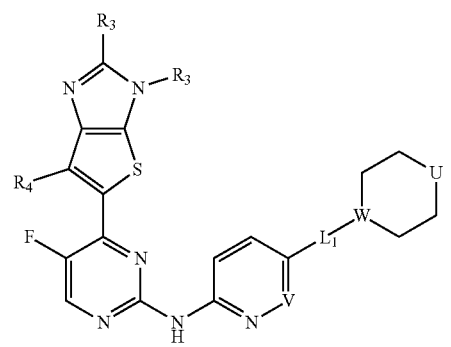

(LI)

or a pharmaceutically acceptable salt thereof, wherein
W is CH or N;
U is $C(R_{10})_2$, $NR_{10}$, or O;

$R_{10}$ is H, halogen (preferably fluoro), $C_{1-6}$alkyl, or $C_{1-6}$alkoxide; and each $R_4$, $R_3$, V and $L_1$ is defined with respect to Formula (I).

In some embodiments, W of Formula LI is CH. In other embodiments, W of Formula LI is N.

In some embodiments, U of Formula LI is $C(R_{10})_2$. In other embodiments, U of Formula LI is $NR_{10}$. In yet other embodiments, U of Formula LI is O.

In some embodiments, $R_{10}$ of Formula LI is H. In some embodiments, $R_{10}$ of Formula LI is halogen. In other embodiments, $R_{10}$ of Formula LI is fluoro. In some embodiments, $R_{10}$ of Formula LI is $C_{1-6}$alkyl. In other embodiments, $R_{10}$ of Formula LI is methyl or ethyl. In some embodiments, $R_{10}$ of Formula LI is $C_{1-6}$alkoxide.

In some embodiments, when U of Formula LI is $C(R_{10})_2$, each $R_{10}$ is H. In some embodiments, when U of Formula LI is $C(R_{10})_2$, each $R_{10}$ is methyl. In some embodiments, when U of Formula LI is $C(R_{10})_2$, one $R_{10}$ is methyl and one $R_{10}$ is hydrogen. In some embodiments, when U of Formula LI is $C(R_{10})_2$, each $R_{10}$ is halogen. In some embodiments, when U of Formula LI is $C(R_{10})_2$, one $R_{10}$ is halogen and one $R_{10}$ is hydrogen. In other embodiments, when U of Formula LI is $C(R_{10})_2$, each $R_{10}$ is fluoro. In other embodiments, when U of Formula LI is $C(R_{10})_2$, one $R_{10}$ is fluoro and one $R_{10}$ is hydrogen.

In some embodiments, U of Formula LI is $NCH_3$. In other embodiments, U of Formula LI is $NCH_2CH_3$.

The following are particularly preferred

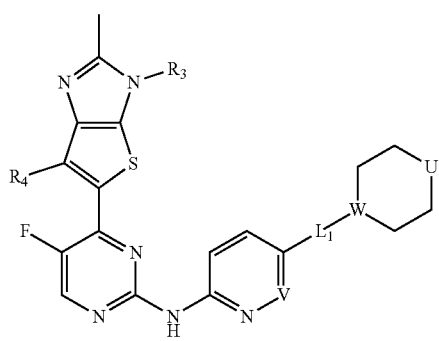

(LIa)

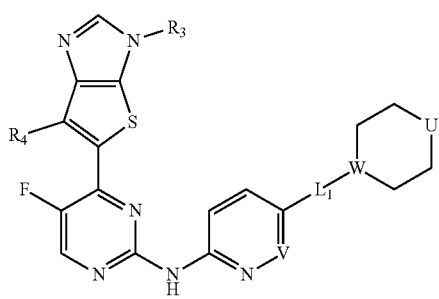

(LIb)

In yet other embodiments, the compounds of Formula (I) are represented by compounds of Formula LII

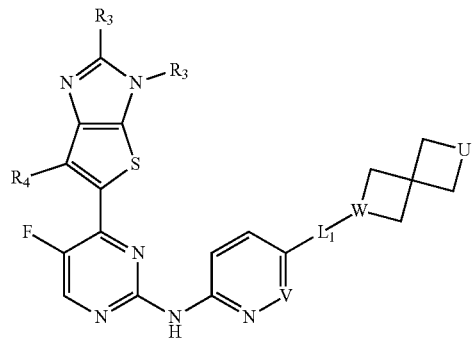

(LII)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula LII is CH. In other embodiments, W of Formula LII is N.

In some embodiments, U of Formula LII is $C(R_{10})_2$. In other embodiments, U of Formula LII is $NR_{10}$. In yet other embodiments, U of Formula LII is O.

In some embodiments, $R_{10}$ of Formula LII is H. In some embodiments, $R_{10}$ of Formula LII is halogen. In other embodiments, $R_{10}$ of Formula LII is fluoro. In some embodiments, $R_{10}$ of Formula LII is $C_{1-6}$alkyl. In other embodiments, $R_{10}$ of Formula LII is methyl or ethyl. In some embodiments, $R_{10}$ of Formula LII is $C_{1-6}$alkoxide.

In some embodiments, when U of Formula LII is $C(R_{10})_2$, each $R_{10}$ is H. In some embodiments, when U of Formula LII is $C(R_{10})_2$, each $R_{10}$ is methyl. In some embodiments, when U of Formula LII is $C(R_{10})_2$, one $R_{10}$ is methyl and one $R_{10}$ is hydrogen. In some embodiments, when U of Formula LII is $C(R_{10})_2$, each $R_{10}$ is halogen. In some embodiments, when U of Formula LII is $C(R_{10})_2$, one $R_{10}$ is halogen and one $R_{10}$ is hydrogen. In other embodiments, when U of Formula LII is $C(R_{10})_2$, each $R_{10}$ is fluoro. In other embodiments, when U of Formula LII is $C(R_{10})_2$, one $R_{10}$ is fluoro and one $R_{10}$ is hydrogen.

In some embodiments, U of Formula LII is $NCH_3$. In other embodiments, U of Formula LII is $NCH_2CH_3$.

The following are particularly preferred

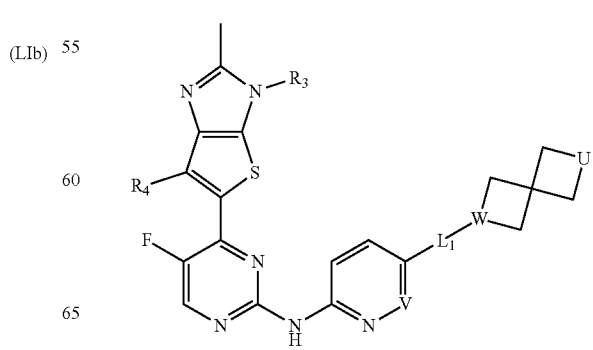

(LIIa)

In yet other embodiments, the compounds of Formula (I) are represented by compounds of Formula LIII

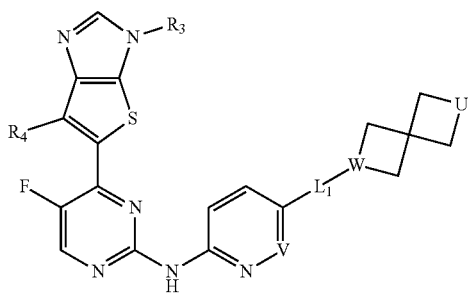
(LIIb)

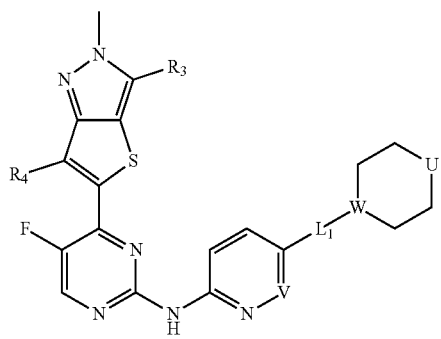
(LIII)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula LIII is CH. In other embodiments, W of Formula LIII is N.

In some embodiments, U of Formula LIII is $C(R_{10})_2$. In other embodiments, U of Formula LIII is $NR_{10}$. In yet other embodiments, U of Formula LIII is O.

In some embodiments, $R_{10}$ of Formula LIII is H. In some embodiments, $R_{10}$ of Formula LIII is halogen. In other embodiments, $R_{10}$ of Formula LIII is fluoro. In some embodiments, $R_{10}$ of Formula LIII is $C_{1-6}$alkyl. In other embodiments, $R_{10}$ of Formula LIII is methyl or ethyl. In some embodiments, $R_{10}$ of Formula LIII is $C_{1-6}$alkoxide.

In some embodiments, when U of Formula LIII is $C(R_{10})_2$, each $R_{10}$ is H. In some embodiments, when U of Formula LIII is $C(R_{10})_2$, each $R_{10}$ is methyl. In some embodiments, when U of Formula LIII is $C(R_{10})_2$, one $R_{10}$ is methyl and one $R_{10}$ is hydrogen. In some embodiments, when U of Formula LIII is $C(R_{10})_2$, each $R_{10}$ is halogen. In some embodiments, when U of Formula LIII is $C(R_{10})_2$, one $R_{10}$ is halogen and one $R_{10}$ is hydrogen. In other embodiments, when U of Formula LIII is $C(R_{10})_2$, each $R_{10}$ is fluoro. In other embodiments, when U of Formula LIII is $C(R_{10})_2$, one $R_{10}$ is fluoro and one $R_{10}$ is hydrogen.

In some embodiments, U of Formula LIII is $NCH_3$. In other embodiments, U of Formula LIII is $NCH_2CH_3$.

In yet other embodiments, the compounds of Formula (I) are represented by compounds of Formula LIV

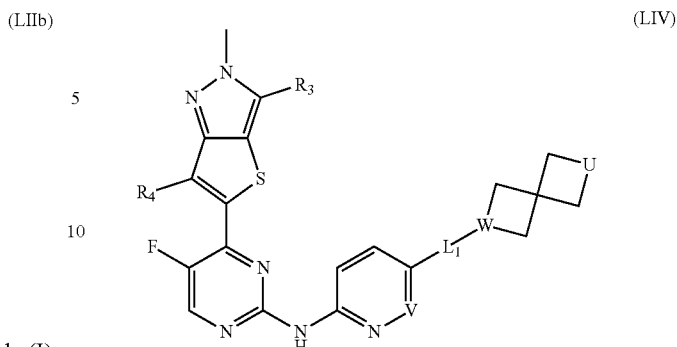
(LIV)

or a pharmaceutically acceptable salt thereof, wherein
W is CH or N;
U is $C(R_{10})_2$, $NR_{10}$, or O;
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, W of Formula LIV is CH. In other embodiments, W of Formula LIV is N.

In some embodiments, U of Formula LIV is $C(R_{10})_2$. In other embodiments, U of Formula LIV is $NR_{10}$. In yet other embodiments, U of Formula LIV is O.

In some embodiments, $R_{10}$ of Formula LIV is H. In some embodiments, $R_{10}$ of Formula LIV is halogen. In other embodiments, $R_{10}$ of Formula LIV is fluoro. In some embodiments, $R_{10}$ of Formula LIV is $C_{1-6}$alkyl. In other embodiments, $R_{10}$ of Formula LIV is methyl or ethyl. In some embodiments, $R_{10}$ of Formula LIV is $C_{1-6}$alkoxide.

In some embodiments, when U of Formula LIV is $C(R_{10})_2$, each $R_{10}$ is H. In some embodiments, when U of Formula LIV is $C(R_{10})_2$, each $R_{10}$ is methyl. In some embodiments, when U of Formula LIV is $C(R_{10})_2$, one $R_{10}$ is methyl and one $R_{10}$ is hydrogen. In some embodiments, when U of Formula LIV is $C(R_{10})_2$, each $R_{10}$ is halogen. In some embodiments, when U of Formula LIV is $C(R_{10})_2$, one $R_{10}$ is halogen and one $R_{10}$ is hydrogen. In other embodiments, when U of Formula LIV is $C(R_{10})_2$, each $R_{10}$ is fluoro. In other embodiments, when U of Formula LIV is $C(R_{10})_2$, one $R_{10}$ is fluoro and one $R_{10}$ is hydrogen.

In some embodiments, U of Formula LIV is $NCH_3$. In other embodiments, U of Formula LIV is $NCH_2CH_3$.

In yet other embodiments, the compounds of Formula (I) are represented by compounds of Formula LVII

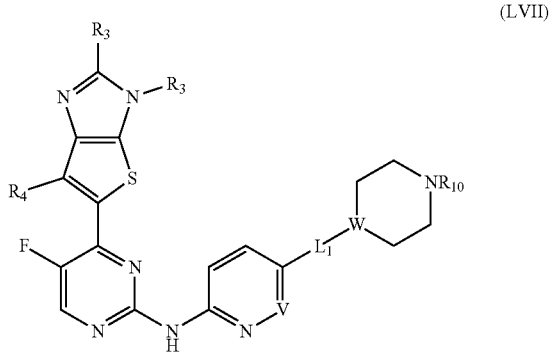
(LVII)

or a pharmaceutically acceptable salt thereof, wherein
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, $R_{10}$ of Formula LVII is H. In some embodiments, $R_{10}$ of Formula LVII is $C_{1-6}$alkyl. In other embodiments, $R_{10}$ of Formula LVII is methyl. In other embodiments, $R_{10}$ of Formula LI is ethyl.

Particularly preferred compounds are

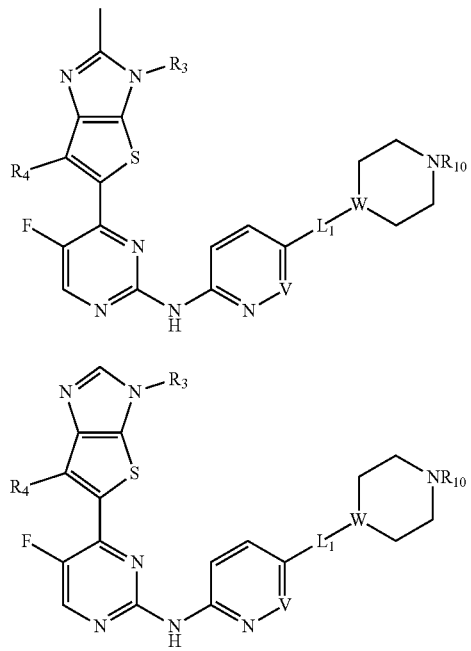

(LVIIa)

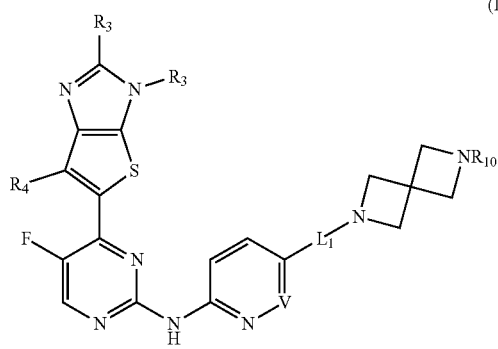

(LVIIb)

In yet other embodiments, the compounds of Formula (I) are represented by compounds of Formula LVIII

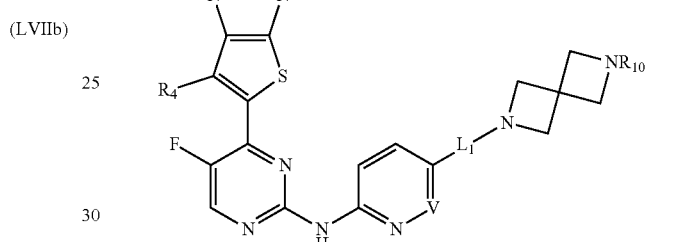

(LVIII)

or a pharmaceutically acceptable salt thereof, wherein $R_{10}$ is H, halogen (preferably fluoro), $C_{1-6}$alkyl, or $C_{1-6}$alkoxide; and each $R_4$, $R_3$, V and $L_1$ is defined with respect to Formula (I).

In some embodiments, $R_{10}$ of Formula LVIII is H. In some embodiments, $R_{10}$ of Formula LVIII is $C_{1-6}$alkyl. In other embodiments, $R_{10}$ of Formula LVIII is methyl. In other embodiments, $R_{10}$ of Formula LVIII is ethyl.

Particularly preferred compounds are

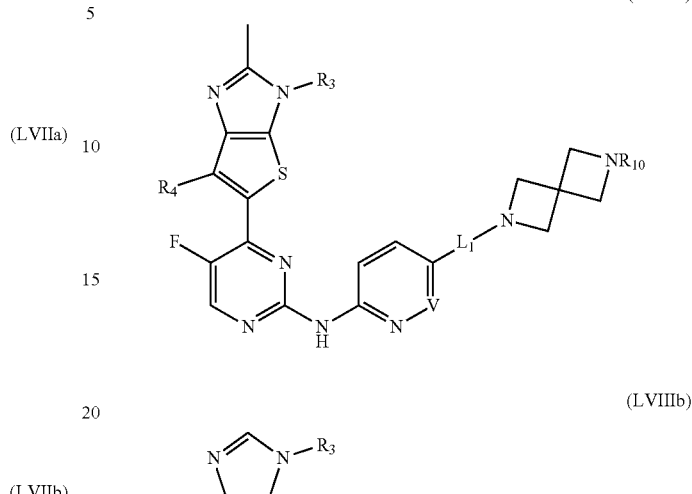

(LVIIIa)

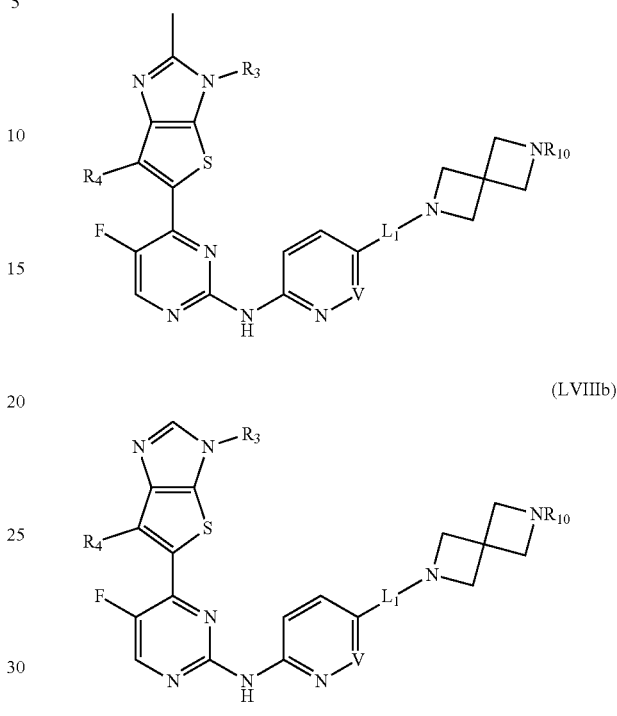

(LVIIIb)

In yet other embodiments, the compounds of Formula (I) are represented by compounds of Formula LIX

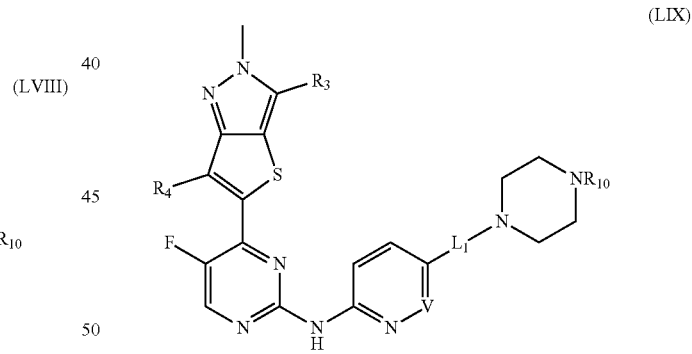

(LIX)

or a pharmaceutically acceptable salt thereof, wherein $R_{10}$ is H, halogen (preferably fluoro), $C_{1-6}$alkyl, or $C_{1-6}$alkoxide; and each $R_4$, $R_3$, V and $L_1$ is defined with respect to Formula (I).

In some embodiments, $R_{10}$ of Formula LIX is H. In some embodiments, $R_{10}$ of Formula LIX is $C_{1-6}$alkyl. In other embodiments, $R_{10}$ of Formula LIX is methyl. In other embodiments, $R_{10}$ of Formula LIX is ethyl.

In yet other embodiments, the compounds of Formula (I) are represented by compounds of Formula LX

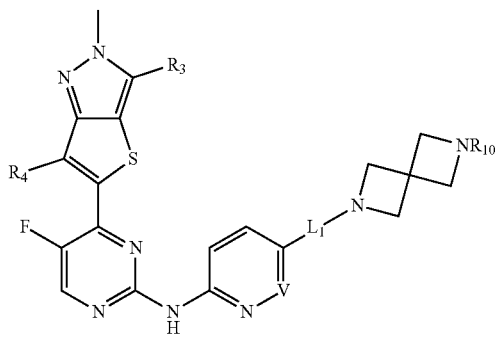

(LX)

or a pharmaceutically acceptable salt thereof, wherein
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, $R_{10}$ of Formula LX is H. In some embodiments, $R_{10}$ of Formula LX is $C_{1-6}$alkyl. In other embodiments, $R_{10}$ of Formula LX is methyl. In other embodiments, $R_{10}$ of Formula LX is ethyl.

In yet other embodiments, the compounds of Formula (I) are represented by compounds of Formula LXIII

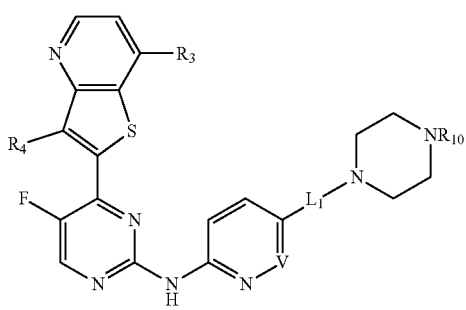

(LXIII)

or a pharmaceutically acceptable salt thereof, wherein
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, $R_{10}$ of Formula LXIII is H. In some embodiments, $R_{10}$ of Formula LXIII is $C_{1-6}$alkyl. In other embodiments, $R_{10}$ of Formula LXIII is methyl. In other embodiments, $R_{10}$ of Formula LXIII is ethyl.

In yet other embodiments, the compounds of Formula (I) are represented by compounds of Formula LXIV

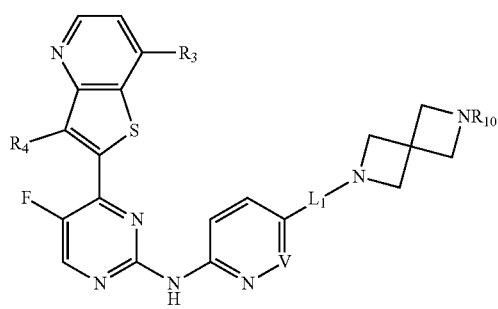

(LXIV)

or a pharmaceutically acceptable salt thereof, wherein
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, $R_{10}$ of Formula LXIV is H. In some embodiments, $R_{10}$ of Formula LXIV is $C_{1-6}$alkyl. In other embodiments, $R_{10}$ of Formula LXIV is methyl. In other embodiments, $R_{10}$ of Formula LXIV is ethyl.

In yet other embodiments, the compounds of Formula (I) are represented by compounds of Formula LXV

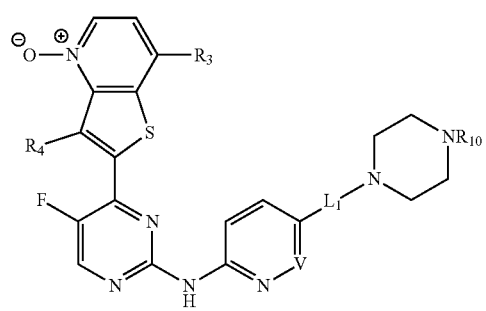

(LXV)

or a pharmaceutically acceptable salt thereof, wherein
$R_{10}$ is H, halogen (preferably fluoro), $C_{1-6}$alkyl, or $C_{1-6}$alkoxide; and each $R_4$, $R_3$, V and $L_1$ is defined with respect to Formula (I).

In some embodiments, $R_{10}$ of Formula LXV is H. In some embodiments, $R_{10}$ of Formula LXV is $C_{1-6}$alkyl. In other embodiments, $R_{10}$ of Formula LXV is methyl. In other embodiments, $R_{10}$ of Formula LXV is ethyl.

In yet other embodiments, the compounds of Formula (I) are represented by compounds of Formula LXVI

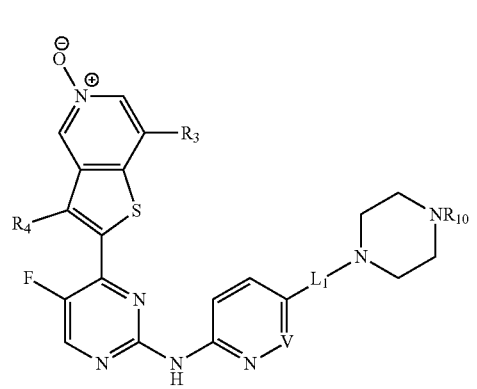

(LXVI)

or a pharmaceutically acceptable salt thereof, wherein
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, $R_{10}$ of Formula LXVI is H. In some embodiments, $R_{10}$ of Formula LXVI is $C_{1-6}$alkyl. In other embodiments, $R_{10}$ of Formula LXVI is methyl. In other embodiments, $R_{10}$ of Formula LXVI is ethyl.

In yet other embodiments, the compounds of Formula (I) are represented by compounds of Formula LXVII (LXVII)

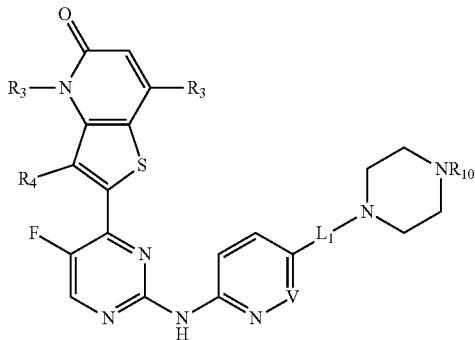

or a pharmaceutically acceptable salt thereof, wherein
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, $R_{10}$ of Formula LXVII is H. In some embodiments, $R_{10}$ of Formula LXVII is $C_{1-6}$alkyl. In other embodiments, $R_{10}$ of Formula LXVII is methyl. In other embodiments, $R_{10}$ of Formula LXVII is ethyl.

In yet other embodiments, the compounds of Formula (I) are represented by compounds of Formula c (LXVIII)

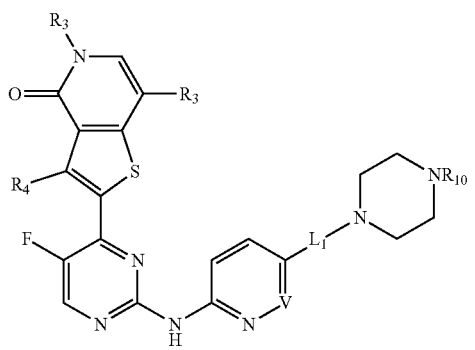

or a pharmaceutically acceptable salt thereof, wherein
$R_{10}$ is H, halogen (preferably fluoro), $C_{1-6}$alkyl, or $C_{1-6}$alkoxide; and
each $R_4$, $R_3$, V and $L_1$ is defined with respect to Formula (I).

In some embodiments, $R_{10}$ of Formula LXVIII is H. In some embodiments, $R_{10}$ of Formula LXVIII is $C_{1-6}$alkyl. In other embodiments, $R_{10}$ of Formula LXVIII is methyl. In other embodiments, $R_{10}$ of Formula LXVIII is ethyl.

In yet further embodiments, the compounds of Formula (I) are:
4-(3-Cyclopentyl-2,6-dimethyl-3H-thieno[2,3-d]imidazol-5-yl)-N-(5-(4-ethylpiperazin-1-yl)pyridin-2-yl)-5-fluoropyrimidin-2-amine;
N-(5-(4-Ethylpiperazin-1-yl)pyridin-2-yl)-5-fluoro-4-(3-isopropyl-2,6-dimethyl-3H-thieno[2,3-d]imidazol-5-yl)pyrimidin-2-amine;
N-(5-((4-Ethylpiperazin-1-yl)methyl)pyridin-2-yl)-5-fluoro-4-(3-isopropyl-2,6-dimethyl-3H-thieno[2,3-d]imidazol-5-yl)pyrimidin-2-amine;
4-(3-Cyclobutyl-2,6-dimethylthieno[2,3-d]imidazol-5-yl)-N-[5-(4-ethylpiperazin-1-yl)pyridin-2-yl]-5-fluoropyrimidin-2-amine;
4-(3-Cyclopentyl-2,6-dimethyl-3H-thieno[2,3-d]imidazol-5-yl)-N-(5-(1-ethylpiperidin-4-yl)pyridin-2-yl)-5-fluoropyrimidin-2-amine;
4-(3-Cyclopentyl-2,6-dimethyl-3H-thieno[2,3-d]imidazol-5-yl)-5-fluoro-N-(5-(1-methylpiperidin-4-yl)pyridin-2-yl)pyrimidin-2-amine;
4-(3-Cyclopentyl-2,6-dimethyl-3H-thieno[2,3-d]imidazol-5-yl)-5-fluoro-N-(5-(4-methylpiperazin-1-yl)pyridin-2-yl)pyrimidin-2-amine;
4-(3-Cyclobutyl-2,6-dimethyl-3H-thieno[2,3-d]imidazol-5-yl)-N-(5-(1-ethylpiperidin-4-yl)pyridin-2-yl)-5-fluoropyrimidin-2-amine;
5-Fluoro-4-(3-isopropyl-2,6-dimethyl-3H-thieno[2,3-d]imidazol-5-yl)-N-(5-(4-methylpiperazin-1-yl)pyridin-2-yl)pyrimidin-2-amine;
4-(3-Cyclobutyl-2,6-dimethylthieno[2,3-d]imidazol-5-yl)-N-[5-[(4-ethylpiperazin-1-yl)methyl]pyridin-2-yl]-5-fluoropyrimidin-2-amine;
4-(3-Cyclopentyl-2,6-dimethyl-3H-thieno[2,3-d]imidazol-5-yl)-N-(5-(3,3-difluoropyrrolidin-1-yl)pyridin-2-yl)-5-fluoropyrimidin-2-amine;
4-(3-Cyclopentyl-2,6-dimethyl-3H-thieno[2,3-d]imidazol-5-yl)-N-(5-((4-ethylpiperazin-1-yl)methyl)pyridin-2-yl)-5-fluoropyrimidin-2-amine;
4-(3-Cyclopentyl-2-methyl-3H-thieno[2,3-d]imidazol-5-yl)-5-fluoro-N-(5-(4-methylpiperazin-1-yl)pyridin-2-yl)pyrimidin-2-amine;
N-[5-(4-Ethylpiperazin-1-yl)pyridin-2-yl]-5-fluoro-4-(7-propan-2-ylthieno[3,2-b]pyridin-2-yl)pyrimidin-2-amine;
4-(7-Cyclopentylthieno[3,2-b]pyridin-2-yl)-N-[5-(6-ethyl-2,6-diazaspiro[3.3]heptan-2-yl)pyridin-2-yl]-5-fluoropyrimidin-2-amine;
4-(3-Chloro-7-cyclopentylthieno[3,2-b]pyridin-2-yl)-N-[5-(4-ethylpiperazin-1-yl)pyridin-2-yl]-5-fluoropyrimidin-2-amine;
2-[2-[2-[[5-(4-Ethylpiperazin-1-yl)pyridin-2-yl]amino]-5-fluoropyrimidin-4-yl]thieno[3,2-b]pyridin-7-yl]propan-2-ol;
2-[2-[2-[[5-(6-Ethyl-2,6-diazaspiro[3.3]heptan-2-yl)pyridin-2-yl]amino]-5-fluoropyrimidin-4-yl]thieno[3,2-b]pyridin-7-yl]-1,1,1-trifluoropropan-2-ol;
N-[5-[(4-Ethylpiperazin-1-yl)methyl]pyridin-2-yl]-5-fluoro-4-(7-propan-2-ylthieno[3,2-b]pyridin-2-yl)pyrimidin-2-amine;
4-(3-Chloro-7-cyclopentylthieno[3,2-b]pyridin-2-yl)-N-[5-(1-ethylpiperidin-4-yl)pyridin-2-yl]-5-fluoropyrimidin-2-amine;
2-[2-[2-[[5-(6-Ethyl-2,6-diazaspiro[3.3]heptan-2-yl)pyridin-2-yl]amino]-5-fluoropyrimidin-4-yl]thieno[3,2-b]pyridin-7-yl]propan-2-ol;
4-(7-Cyclopentyl-3-methylthieno[3,2-b]pyridin-2-yl)-N-(5-((4-ethylpiperazin-1-yl)methyl)pyridin-2-yl)-5-fluoropyrimidin-2-amine;
N-[5-(6-Ethyl-2,6-diazaspiro[3.3]heptan-2-yl)pyridin-2-yl]-5-fluoro-4-(7-propan-2-ylthieno[3,2-b]pyridin-2-yl)pyrimidin-2-amine;
4-(7-Cyclopentylthieno[3,2-b]pyridin-2-yl)-N-[5-(4-ethylpiperazin-1-yl)pyridin-2-yl]-5-fluoropyrimidin-2-amine;
2-[2-[2-[[5-[(4-Ethylpiperazin-1-yl)methyl]pyridin-2-yl]amino]-5-fluoropyrimidin-4-yl]thieno[3,2-b]pyridin-7-yl]-1,1,1-trifluoropropan-2-ol;

4-(7-Cyclopentyl-3-methylthieno[3,2-b]pyridin-2-yl)-5-fluoro-N-(5-(1-methylpiperidin-4-yl)pyridin-2-yl)pyrimidin-2-amine;

2-[2-[2-[[5-[(4-Ethylpiperazin-1-yl)methyl]pyridin-2-yl]amino]-5-fluoropyrimidin-4-yl]thieno[3,2-b]pyridin-7-yl]propan-2-ol;

4-(7-Cyclopentyl-3-methylthieno[3,2-b]pyridin-2-yl)-5-fluoro-N-(5-(4-methylpiperazin-1-yl)pyridin-2-yl)pyrimidin-2-amine;

2-[2-[2-[[5-(4-Ethylpiperazin-1-yl)pyridin-2-yl]amino]-5-fluoropyrimidin-4-yl]thieno[3,2-b]pyridin-7-yl]-1,1,1-trifluoropropan-2-ol;

4-(3-Chloro-7-cyclopentylthieno[3,2-b]pyridin-2-yl)-N-[5-[(4-ethylpiperazin-1-yl)methyl]pyridin-2-yl]-5-fluoropyrimidin-2-amine;

4-(7-Cyclopentyl-3-methylthieno[3,2-b]pyridin-2-yl)-N-(5-(4-ethylpiperazin-1-yl)pyridin-2-yl)-5-fluoropyrimidin-2-amine;

N-(5-(2,6-Diazaspiro[3.3]heptan-2-yl)pyridin-2-yl)-4-(7-cyclopentyl-3-methylthieno[3,2-b]pyridin-2-yl)-5-fluoropyrimidin-2-amine;

4-(7-Cyclopentylthieno[3,2-b]pyridin-2-yl)-N-[5-[(4-ethylpiperazin-1-yl)methyl]pyridin-2-yl]-5-fluoropyrimidin-2-amine;

4-(7-Cyclopentylthieno[3,2-b]pyridin-2-yl)-5-fluoro-N-(5-(1-methylpiperidin-4-yl)pyridin-2-yl)pyrimidin-2-amine;

4-(7-Cyclopentyl-3-methylthieno[3,2-b]pyridin-2-yl)-5-fluoro-N-(5-(piperazin-1-yl)pyridin-2-yl)pyrimidin-2-amine;

4-(7-Cyclopentylthieno[3,2-b]pyridin-2-yl)-5-fluoro-N-(5-piperazin-1-ylpyridin-2-yl)pyrimidin-2-amine;

4-(7-Cyclopentylthieno[3,2-b]pyridin-2-yl)-5-fluoro-N-[5-(4-methylpiperazin-1-yl)pyridin-2-yl]pyrimidin-2-amine;

4-(7-Cyclopentyl-3-methylthieno[3,2-b]pyridin-2-yl)-5-fluoro-N-(5-morpholinopyridin-2-yl)pyrimidin-2-amine;

4-(7-Cyclopentylthieno[3,2-b]pyridin-2-yl)-5-fluoro-N-[5-(4-methoxypiperidin-1-yl)pyridin-2-yl]pyrimidin-2-amine;

4-(7-Cyclopentylthieno[3,2-b]pyridin-2-yl)-5-fluoro-N-(5-morpholinopyridin-2-yl)pyrimidin-2-amine;

4-(7-Cyclopentylthieno[3,2-b]pyridin-2-yl)-N-[5-(3,3-difluoropyrrolidin-1-yl)pyridin-2-yl]-5-fluoropyrimidin-2-amine;

4-(4-Cyclopentylthieno[2,3-b]pyridin-2-yl)-5-fluoro-N-(5-morpholin-4-ylpyridin-2-yl)pyrimidin-2-amine;

4-(4-Cyclopentylthieno[2,3-b]pyridin-2-yl)-5-fluoro-N-(5-(1-methylpiperidin-4-yl)pyridin-2-yl)pyrimidin-2-amine;

4-(4-Cyclopentylthieno[2,3-b]pyridin-2-yl)-N-[5-(4-ethylpiperazin-1-yl)pyridin-2-yl]-5-fluoropyrimidin-2-amine;

4-(4-Cyclopentylthieno[2,3-b]pyridin-2-yl)-5-fluoro-N-[5-(4-methylpiperazin-1-yl)pyridin-2-yl]pyrimidin-2-amine;

4-(4-Cyclopentylthieno[2,3-b]pyridin-2-yl)-5-fluoro-N-(5-piperazin-1-ylpyridin-2-yl)pyrimidin-2-amine;

4-(4-Cyclopentylthieno[2,3-b]pyridin-2-yl)-N-[5-(6-ethyl-2,6-diazaspiro[3.3]heptan-2-yl)pyridin-2-yl]-5-fluoropyrimidin-2-amine;

4-(7-Cyclopentyl-3-methylthieno[3,2-c]pyridin-2-yl)-5-fluoro-N-(5-(4-methylpiperazin-1-yl)pyridin-2-yl)pyrimidin-2-amine;

4-(4-Cyclopentyl-7-methylthieno[3,2-d]pyrimidin-6-yl)-5-fluoro-N-(5-(1-methylpiperidin-4-yl)pyridin-2-yl)pyrimidin-2-amine;

N-[5-(4-Ethylpiperazin-1-yl)pyridin-2-yl]-5-fluoro-4-(4-oxido-7-propan-2-ylthieno[3,2-b]pyridin-4-ium-2-yl)pyrimidin-2-amine;

2-[5-Fluoro-2-[[5-(4-methylpiperazin-1-yl)pyridin-2-yl]amino]pyrimidin-4-yl]-3,5-dimethyl-7-propan-2-ylthieno[3,2-c]pyridin-4-one;

4-(2,6-Dimethyl-3-propan-2-ylthieno[2,3-d]imidazol-5-yl)-N-[5-(6-ethyl-2,6-diazaspiro [3.3]heptan-2-yl)pyridin-2-yl]-5-fluoropyrimidin-2-amine;

6-(6-Ethyl-2,6-diazaspiro[3.3]heptan-2-yl)-N-(5-fluoro-4-(3-isopropyl-2,6-dimethyl-3H-thieno[2,3-d]imidazol-5-yl)pyrimidin-2-yl)pyridazin-3-amine;

(4-Ethylpiperazin-1-yl)-[6-[[5-fluoro-4-(2-methyl-3-propan-2-ylthieno[2,3-d]imidazol-5-yl)pyrimidin-2-yl]amino]pyridin-3-yl]methanone;

4-(2,6-Dimethyl-3-propan-2-ylthieno[3,2-c]pyrazol-5-yl)-N-[5-(6-ethyl-2,6-diazaspiro[3.3]heptan-2-yl)pyridin-2-yl]-5-fluoropyrimidin-2-amine;

2-(5-Fluoro-2-((5-(1-methylpiperidin-4-yl)pyridin-2-yl)amino)pyrimidin-4-yl)-7-isopropyl-3,5-dimethylthieno[3,2-c]pyridin-4(5H)-one;

2-(2-((5-(6-Ethyl-2,6-diazaspiro[3.3]heptan-2-yl)pyridin-2-yl)amino)-5-fluoropyrimidin-4-yl)-7-isopropyl-3,5-dimethylthieno[3,2-c]pyridin-4(5H)-one;

2-(2-((5-(6-Ethyl-3,6-diazabicyclo[3.1.1]heptan-3-yl)pyridin-2-yl)amino)-5-fluoropyrimidin-4-yl)-7-isopropyl-5-methylthieno[3,2-c]pyridin-4(5H)-one;

2-(2-((5-(4-Ethylpiperazine-1-carbonyl)pyridin-2-yl)amino)-5-fluoropyrimidin-4-yl)-7-isopropyl-5-methylthieno[3,2-c]pyridin-4(5H)-one;

2-(5-Fluoro-2-((5-(1-methylpiperidin-4-yl)pyridin-2-yl)amino)pyrimidin-4-yl)-7-isopropyl-3-methylthieno[3,2-c]pyridin-4(5H)-one;

2-(5-Fluoro-2-((5-(6-methyl-2,6-diazaspiro[3.4]octan-2-yl)pyridin-2-yl)amino)pyrimidin-4-yl)-7-isopropyl-3,5-dimethylthieno[3,2-c]pyridin-4(5H)-one;

6-(2-((5-(6-Ethyl-2,6-diazaspiro[3.3]heptan-2-yl)pyridin-2-yl)amino)-5-fluoropyrimidin-4-yl)-1-isopropyl-5-methylthieno[2,3-d]pyrimidin-4(1H)-one;

2-(2-((5-(6-Ethyl-2,6-diazaspiro[3.3]heptan-2-yl)pyridin-2-yl)amino)-5-fluoropyrimidin-4-yl)-7-isopropyl-3,5-dimethylthieno[2,3-d]pyridazin-4(5H)-one;

or a pharmaceutically acceptable salt thereof.

In yet further embodiments, the compounds of Formula (I) are:

N-[5-[[4-(2,2-Difluoroethyl)piperazin-1-yl]methyl]pyridin-2-yl]-5-fluoro-4-(2-methyl-3-propan-2-ylthieno[2,3-d]imidazol-5-yl) pyrimidin-2-amine;

1-[[6-[[5-Fluoro-4-(2-methyl-3-propan-2-ylthieno[2,3-d]imidazol-5-yl)pyrimidin-2-yl]amino]pyridin-3-yl]methyl]-N,N-dimethylpyrrolidine-3-carboxamide;

4-(2,6-Dimethyl-3-propan-2-ylthieno[2,3-d]imidazol-5-yl)-5-fluoro-N-pyridin-2-ylpyrimidin-2-amine;

4-(2,6-Dimethyl-3-propan-2-ylthieno[2,3-d]imidazol-5-yl)-5-fluoro-N-[5-(1-methyl-1,6-diazaspiro[3.3]heptan-6-yl)pyridin-2-yl]pyrimidin-2-amine;

4-(2,6-Dimethyl-3-propan-2-ylthieno[2,3-d]imidazol-5-yl)-N-[5-(4-ethyl-6,6-difluoro-1,4-diazepan-1-yl)pyridin-2-yl]-5-fluoropyrimidin-2-amine;

4-(2,6-Dimethyl-3-propan-2-ylthieno[2,3-d]imidazol-5-yl)-5-fluoro-N-[5-[2,2,3,3,5,5,6,6-octadeuterio-4-(trideuteriomethyl)piperazin-1-yl]pyridin-2-yl]pyrimidin-2-amine;

N-[5-(5,5-Difluoro-7-methyl-2,7-diazaspiro[3.4]octan-2-yl)pyridin-2-yl]-4-(2,6-dimethyl-3-propan-2-ylthieno[2,3-d]imidazol-5-yl)-5-fluoropyrimidin-2-amine;

(6-Dthyl-2,6-diazaspiro[3.3]heptan-2-yl)-[6-[[5-fluoro-4-(2-methyl-3-propan-2-ylthieno[2,3-d] imidazol-5-yl)pyrimidin-2-yl]amino]pyridin-3-yl]methanone;

N-[5-[3-(Dimethylamino) azetidin-1-yl]pyridin-2-yl]-5-fluoro-4-(2-methyl-3-propan-2-ylthieno[2,3-d]imidazol-5-yl)pyrimidin-2-amine;

N-[5-[3-(Dimethylamino) pyrrolidin-1-yl]pyridin-2-yl]-4-(2,6-dimethyl-3-propan-2-ylthieno[2,3-d]imidazol-5-yl)-5-fluoropyrimidin-2-amine;

N-[5-(6-ethyl-3,6-Diazabicyclo[3.1.1]heptan-3-yl)pyridin-2-yl]-5-fluoro-4-(2-methyl-3-propan-2-ylthieno[2,3-d]imidazol-5-yl)pyrimidin-2-amine;

1-[6-[[4-(2,6-Dimethyl-3-propan-2-ylthieno[2,3-d]imidazol-5-yl)-5-fluoropyrimidin-2-yl]amino]pyridin-3-yl]-4-methylpiperazin-2-one;

2-(5-Fluoro-2-((5-(7-methyl-2,7-diazaspiro[4.4]nonan-2-yl)pyridin-2-yl)amino) pyrimidin-4-yl)-7-isopropyl-3,5-dimethylthieno[3,2-c]pyridin-4(5H)-one;

2-(5-Fluoro-2-((5-(7-methyl-2,7-diazaspiro[3.5]nonan-2-yl)pyridin-2-yl)amino) pyrimidin-4-yl)-7-isopropyl-3,5-dimethylthieno[3,2-c]pyridin-4(5H)-one;

2-(5-Fluoro-2-((5-((3aR,6aS)-5-methylhexahydropyrrolo[3,4-c]pyrrol-2(1H)-yl)pyridin-2-yl)amino)pyrimidin-4-yl)-7-isopropyl-3,5-dimethylthieno [3,2-c]pyridin-4(5H)-one;

2-(5-Fluoro-2-((5-((3aS,6aS)-5-methylhexahydropyrrolo[3,4-c]pyrrol-2(1H)-yl)pyridin-2-yl)amino)pyrimidin-4-yl)-7-isopropyl-3,5-dimethylthieno [3,2-c]pyridin-4(5H)-one;

2-(5-Fluoro-2-((5-(4-(2,2,2-trifluoroethyl)piperazin-1-yl)pyridin-2-yl)amino) pyrimidin-4-yl)-7-isopropyl-3,5-dimethylthieno [3,2-c]pyridin-4(5H)-one;

2-(2-((5-(5-Ethyl-2,5-diazabicyclo[2.2.1]heptan-2-yl)pyridin-2-yl)amino)-5-fluoropyrimidin-4-yl)-7-isopropyl-5-methylthieno [3,2-c]pyridin-4(5H)-one;

2-(5-Fluoro-2-((5-(1-(methyl-d3)piperidin-4-yl)pyridin-2-yl)amino) pyrimidin-4-yl)-7-isopropyl-3,5-dimethylthieno[3,2-c]pyridin-4(5H)-one;

2-(2-((5-(1,4-Diazabicyclo[3.2.2]nonan-4-yl)pyridin-2-yl)amino)-5-fluoropyrimidin-4-yl)-7-isopropyl-3,5-dimethylthieno [3,2-c]pyridin-4(5H)-one;

2-(5-Fluoro-2-((5-(1-(tetrahydrofuran-3-yl)piperidin-4-yl)pyridin-2-yl)amino)pyrimidin-4-yl)-7-isopropyl-3,5-dimethylthieno [3,2-c]pyridin-4(5H)-one;

2-(5-Fluoro-2-((5-(1-methylpiperidin-4-yl)pyridin-2-yl)amino) pyrimidin-4-yl)-7-isopropyl-3-methyl-5-(methyl-d3)thieno[3,2-c]pyridin-4(5H)-one;

2-(5-Fluoro-2-((5-(1-methylpiperidin-4-yl)pyridin-2-yl)amino) pyrimidin-4-yl)-7-isopropyl-5-methylthieno[3,2-c]pyridin-4(5H)-one;

2-(2-((5-(1-Ethylpiperidin-4-yl)pyridin-2-yl)amino)-5-fluoropyrimidin-4-yl)-7-isopropyl-3,5-dimethylthieno[3,2-c]pyridin-4(5H)-one;

2-(5-Fluoro-2-((5-(1-methylpiperidin-3-yl)pyridin-2-yl)amino) pyrimidin-4-yl)-7-isopropyl-3,5-dimethylthieno[3,2-c]pyridin-4(5H)-one;

2-(5-Fluoro-2-((5-(4-isopropylpiperazin-1-yl)pyridin-2-yl)amino) pyrimidin-4-yl)-7-isopropyl-3,5-dimethylthieno[3,2-c]pyridin-4(5H)-one;

2-(2-((5-((4-Ethylpiperazin-1-yl)methyl)pyridin-2-yl)amino)-5-fluoropyrimidin-4-yl)-7-isopropyl-3,5-dimethylthieno[3,2-c]pyridin-4(5H)-one;

2-(5-Fluoro-2-((5-(2-methyl-2,7-diazaspiro[3.5]nonan-7-yl)pyridin-2-yl)amino) pyrimidin-4-yl)-7-isopropyl-3,5-dimethylthieno[3,2-c]pyridin-4(5H)-one;

2-(5-Fluoro-2-((5-(6-isopropyl-2,6-diazaspiro[3.3]heptan-2-yl)pyridin-2-yl)amino) pyrimidin-4-yl)-7-isopropyl-3,5-dimethylthieno[3,2-c]pyridin-4(5H)-one;

2-(5-Fluoro-2-((6-(1-methylpiperidin-4-yl)pyridazin-3-yl)amino)pyrimidin-4-yl)-7-isopropyl-3,5-dimethylthieno[3,2-c]pyridin-4(5H)-one;

2-(5-Fluoro-2-((5-(piperidin-4-yl)pyridin-2-yl)amino) pyrimidin-4-yl)-7-isopropyl-3,5-dimethylthieno [3,2-c]pyridin-4(5H)-one;

2-(5-Fluoro-2-((5-(1-isopropylpyrrolidin-3-yl)pyridin-2-yl)amino)pyrimidin-4-yl)-7-isopropyl-3,5-dimethylthieno[3,2-c]pyridin-4(5H)-one;

7-Isopropyl-5-methyl-2-(2-((5-(1-methylpiperidin-4-yl)pyridine-2-yl)amino) pyrimidin-4-yl)thieno[3,2-c]pyridin-4(5H)-one;

7-Isopropyl-5-methyl-2-(5-methyl-2-((5-(1-methylpiperidin-4-yl)pyridin-2-yl)amino)pyrimidin-4-yl)thieno [3,2-c]pyridin-4(5H)-one;

4-(6-((5-Fluoro-4-(7-isopropyl-3,5-dimethyl-4-oxo-4,5-dihydrothieno[3,2-c]pyridin-2-yl)pyrimidin-2-yl)amino) pyridin-3-yl)-1-methylpiperidine 1-oxide;

5-Fluoro-4-(3-isopropyl-2-methyl-2H-thieno[3,2-c]pyrazol-5-yl)-N-(5-(1-methylpiperidin-4-yl)pyridin-2-yl)pyrimidin-2-amine;

N-(5-((4-Ethylpiperazin-1-yl)methyl)pyridin-2-yl)-5-fluoro-4-(3-isopropyl-6-methyl-2H-thieno[3,2-c]pyrazol-5-yl)pyrimidin-2-amine;

4-(3-Cyclopropyl-2,6-dimethyl-2H-thieno[3,2-c]pyrazol-5-yl)-N-(5-(6-ethyl-2,6-diazaspiro[3.3]heptan-2-yl)pyridin-2-yl)-5-fluoropyrimidin-2-amine;

2-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)-1,1,1-trifluoropropan-2-ol;

1-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)ethan-1-one;

1-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)ethan-1-ol;

N-(5-(6-Ethyl-2,6-diazaspiro[3.3]heptan-2-yl)pyridin-2-yl)-5-fluoro-4-(3-(2-methoxypropan-2-yl)-2,6-dimethyl-2H-thieno[3,2-c]pyrazol-5-yl)pyrimidin-2-amine;

4-(1,6-dimethyl-3-propan-2-ylthieno[3,2-c]pyrazol-5-yl)-N-[5-(4-ethylpiperazin-1-yl) pyridin-2-yl]-5-fluoropyrimidin-2-amine;

N-(5-Fluoro-4-(3-isopropyl-2-methyl-3H-thieno[2,3-d]imidazol-5-yl)pyrimidin-2-yl)pyridazin-3-amine;

5-Fluoro-4-(3-isopropyl-2,6-dimethyl-3H-thieno[2,3-d]imidazol-5-yl)-N-(5-(1-methylazetidin-3-yl)pyridin-2-yl)pyrimidin-2-amine;

tert-Butyl 3-(2-(2-((5-(6-ethyl-2,6-diazaspiro[3.3]heptan-2-yl)pyridin-2-yl)amino)-5-fluoropyrimidin-4-yl)-5-methyl-4-oxo-4,5-dihydrothieno[2,3-d]pyridazin-7-yl)azetidine-1-carboxylate;

2-(5-Fluoro-2-((5-(1-methylpiperidin-4-yl)pyridin-2-yl)amino)pyrimidin-4-yl)-7-(3-fluorobicyclo[1.1.1]pentan-1-yl)-5-methylthieno[2,3-d]pyridazin-4(5H)-one;

5-(2-((5-(6-Ethyl-2,6-diazaspiro[3.3]heptan-2-yl)pyridin-2-yl)amino)-5-fluoropyrimidin-4-yl)-3-isopropyl-N,N,6-trimethyl-3H-thieno[2,3-d]imidazol-2-amine;

N-(5-(2-Ethyl-2-azaspiro [3.3]heptan-6-yl)pyridin-2-yl)-5-fluoro-4-(3-isopropyl-2-methyl-3H-thieno[2,3-d]imidazol-5-yl)pyrimidin-2-amine;

4-(2,6-Dimethyl-3-propan-2-ylthieno[2,3-d]imidazol-5-yl)-N-[6-(4-ethylpiperazin-1-yl) pyridin-2-yl]-5-fluoropyrimidin-2-amine;

5-Fluoro-4-(2-methyl-3-propan-2-ylthieno[2,3-d]imidazol-5-yl)-N-[5-(1-methylpyrrolidin-3-yl)oxypyridin-2-yl]pyrimidin-2-amine;

5-Fluoro-4-(3-isopropyl-2,6-dimethyl-3H-thieno[2,3-d]imidazol-5-yl)-N-(5-(4-methylmorpholin-2-yl)pyridin-2-yl) pyrimidin-2-amine;

N-[5-[1-(4-Ethylpiperazin-1-yl)ethyl]pyridin-2-yl]-5-fluoro-4-(2-methyl-3-propan-2-ylthieno[2,3-d]imidazol-5-yl) pyrimidin-2-amine;

3-[6-[[5-Fluoro-4-(2-methyl-3-propan-2-ylthieno[2,3-d]imidazol-5-yl)pyrimidin-2-yl]amino]pyridin-3-yl]-1,4-dimethylpiperazin-2-one;

((8aS)-6-(6-(((5-Fluoro-4-(3-isopropyl-2,6-dimethyl-3H-thieno[2,3-d]imidazol-5-yl) pyrimidin-2-yl)amino)pyridin-3-yl)-2-methylhexahydropyrrolo [1,2-a]pyrazin-3(4H)-one;

4-(2,6-Dimethyl-3-propan-2-ylthieno[2,3-d]imidazol-5-yl)-N-[4-(4-ethylpiperazin-1-yl) pyridin-2-yl]-5-fluoropyrimidin-2-amine;

4-(3-Isopropyl-2-methyl-3H-thieno[2,3-d]imidazol-5-yl)-N-(5-(1-methylpiperidin-4-yl) pyridin-2-yl)-5-(trifluoromethyl) pyrimidin-2-amine;

N-[5-(4-Ethylpiperazin-1-yl)pyridin-2-yl]-5-fluoro-4-[7-propan-2-yl-3-(trifluoromethyl) thieno[3,2-b]pyridin-2-yl]pyrimidin-2-amine;

2-(2-((5-(4-Ethylpiperazin-1-yl) pyridin-2-yl)amino)-5-fluoropyrimidin-4-yl)-7-isopropylthieno[3,2-b]pyridine-3-carbonitrile;

5-Fluoro-N-[5-(1-methylpiperidin-4-yl)pyridin-2-yl]-4-(3-methyl-7-propan-2-ylthieno[3,2-c]pyridin-2-yl) pyrimidin-2-amine;

N-[5-[(4-Ethylpiperazin-1-yl)methyl]pyridin-2-yl]-5-fluoro-4-(6-methyl-3-propan-2-ylthieno[2,3-d]imidazol-5-yl)pyrimidin-2-amine;

5-Fluoro-N-[5-[-1-methylpiperidin-3-yl]pyridin-2-yl]-4-(6-methyl-3-propan-2-ylthieno[2,3-d]imidazol-5-yl) pyrimidin-2-amine (isomer 1);

5-Fluoro-N-[5-[-1-methylpiperidin-3-yl]pyridin-2-yl]-4-(6-methyl-3-propan-2-ylthieno[2,3-d]imidazol-5-yl)pyrimidin-2-amine (isomer 2);

4-(3-Isopropyl-2-methyl-3H-thieno[2,3-d]imidazol-5-yl)-5-methoxy-N-(5-(1-methylpiperidin-4-yl)pyridin-2-yl)pyrimidin-2-amine;

N-(5-(1-Ethylpiperidin-4-yl)pyridin-2-yl)-5-fluoro-4-(3-isopropyl-6-methyl-3H-thieno[2,3-d]imidazol-5-yl) pyrimidin-2-amine;

N-(5-(6-ethyl-2,6-diazaspiro[3.3]heptan-2-yl) pyridin-2-yl)-5-fluoro-4-(3-isopropyl-3H-thieno[2,3-d] imidazol-5-yl) pyrimidin-2-amine;

5-Chloro-4-(3-isopropyl-6-methyl-3H-thieno[2,3-d]imidazol-5-yl)-N-(5-(1-methylpiperidin-3-yl)pyridin-2-yl)pyrimidin-2-amine;

2-(5-Fluoro-2-((5-(1-methylpiperidin-4-yl)pyridin-2-yl)amino)pyrimidin-4-yl)-7-isopropyl-3-methylthieno[3,2-c] pyridine 5-oxide;

or a pharmaceutically acceptable salt thereof.

It will be apparent that the compounds of Formula I, including all subgenera described herein, may have multiple stereogenic centers. As a result, there exist multiple stereoisomers (enantiomers and diastereomers) of the compounds of Formula I (and subgenera described herein). The present disclosure contemplates and encompasses each stereoisomer of any compound of Formula I (and subgenera described herein), as well as mixtures of said stereoisomers.

Pharmaceutically acceptable salts and solvates of the compounds of Formula I (including all subgenera described herein) are also within the scope of the disclosure.

Isotopic variants of the compounds of Formula I (including all subgenera described herein) are also contemplated by the present disclosure.

Pharmaceutical Compositions and Methods of Administration

In some embodiments, the disclosure is directed to pharmaceutical compositions comprising compounds of Formula I, or a pharmaceutically acceptable salt or solvate thereof.

The subject pharmaceutical compositions are typically formulated to provide a therapeutically effective amount of a compound of the present disclosure as the active ingredient, or a pharmaceutically acceptable salt, ester, prodrug, solvate, hydrate or derivative thereof. Where desired, the pharmaceutical compositions contain pharmaceutically acceptable salt and/or coordination complex thereof, and one or more pharmaceutically acceptable excipients, carriers, including inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the one or more compounds of the invention and other agent(s) may be mixed into a preparation or both components may be formulated into separate preparations to use them in combination separately or at the same time.

In some embodiments, the concentration of one or more compounds provided in the pharmaceutical compositions of the present invention is less than 100%, 90%, 80%, 70%, 60%, 50%, 40%, 30%, 20%, 19%, 18%, 17%, 16%, 15%, 14%, 13%, 12%, 11%, 10%, 9%, 8%, 7%, 6%, 5%, 4%, 3%, 2%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v or v/v.

In some embodiments, the concentration of one or more compounds of the invention is greater than 90%, 80%, 70%, 60%, 50%, 40%, 30%, 20%, 19.75%, 19.50%, 19.25%, 19%, 18.75%, 18.50%, 18.25% 18%, 17.75%, 17.50%, 17.25% 17%, 16.75%, 16.50%, 16.25%, 16%, 15.75%, 15.50%, 15.25% 15%, 14.75%, 14.50%, 14.25% 14%, 13.75%, 13.50%, 13.25%, 13%, 12.75%, 12.50%, 12.25%, 12%, 11.75%, 11.50%, 11.25% 11%, 10.75%, 10.50%, 10.25% 10%, 9.75%, 9.50%, 9.25%, 9%, 8.75%, 8.50%, 8.25% 8%, 7.75%, 7.50%, 7.25%, 7%, 6.75%, 6.50%, 6.25%, 6%, 5.75%, 5.50%, 5.25%, 5%, 4.75%, 4.50%, 4.25%, 4%, 3.75%, 3.50%, 3.25%, 3%, 2.75%, 2.50%, 2.25%, 2%, 1.75%, 1.50%, 1.25%, 1%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, 0.01%, 0.009%, 0.008%, 0.007%, 0.006%, 0.005%, 0.004%, 0.003%, 0.002%, 0.001%, 0.0009%, 0.0008%, 0.0007%, 0.0006%, 0.0005%, 0.0004%, 0.0003%, 0.0002%, or 0.0001% (or a number in the range defined by and including any two numbers above) w/w, w/v, or v/v.

In some embodiments, the concentration of one or more compounds of the invention is in the range from approximately 0.0001% to approximately 50%, approximately 0.001% to approximately 40%, approximately 0.01% to approximately 30%, approximately 0.02% to approximately 29%, approximately 0.03% to approximately 28%, approximately 0.04% to approximately 27%, approximately 0.05% to approximately 26%, approximately 0.06% to approximately 25%, approximately 0.07% to approximately 24%, approximately 0.08% to approximately 23%, approximately 0.09% to approximately 22%, approximately 0.1% to approximately 21%, approximately 0.2% to approximately 20%, approximately 0.3% to approximately 19%, approximately 0.4% to approximately 18%, approximately 0.5% to approximately 17%, approximately 0.6% to approximately 16%, approximately 0.7% to approximately 15%, approximately 0.8% to approximately 14%, approximately 0.9% to approximately 12%, approximately 1% to approximately 10% w/w, w/v or v/v.

In some embodiments, the concentration of one or more compounds of the invention is in the range from approximately 0.001% to approximately 10%, approximately 0.01% to approximately 5%, approximately 0.02% to approximately 4.5%, approximately 0.03% to approximately 4%, approximately 0.04% to approximately 3.5%, approximately 0.05% to approximately 3%, approximately 0.06% to approximately 2.5%, approximately 0.07% to approximately 2%, approximately 0.08% to approximately 1.5%, approximately 0.09% to approximately 1%, approximately 0.1% to approximately 0.9% w/w, w/v or v/v.

In some embodiments, the amount of one or more compounds of the invention is equal to or less than 10 g, 9.5 g, 9.0 g, 8.5 g, 8.0 g, 7.5 g, 7.0 g, 6.5 g, 6.0 g, 5.5 g, 5.0 g, 4.5 g, 4.0 g, 3.5 g, 3.0 g, 2.5 g, 2.0 g, 1.5 g, 1.0 g, 0.95 g, 0.9 g, 0.85 g, 0.8 g, 0.75 g, 0.7 g, 0.65 g, 0.6 g, 0.55 g, 0.5 g, 0.45 g, 0.4 g, 0.35 g, 0.3 g, 0.25 g, 0.2 g, 0.15 g, 0.1 g, 0.09 g, 0.08 g, 0.07 g, 0.06 g, 0.05 g, 0.04 g, 0.03 g, 0.02 g, 0.01 g, 0.009 g, 0.008 g, 0.007 g, 0.006 g, 0.005 g, 0.004 g, 0.003 g, 0.002 g, 0.001 g, 0.0009 g, 0.0008 g, 0.0007 g, 0.0006 g, 0.0005 g, 0.0004 g, 0.0003 g, 0.0002 g, or 0.0001 g (or a number in the range defined by and including any two numbers above).

In some embodiments, the amount of one or more compounds of the invention is more than 0.0001 g, 0.0002 g, 0.0003 g, 0.0004 g, 0.0005 g, 0.0006 g, 0.0007 g, 0.0008 g, 0.0009 g, 0.001 g, 0.0015 g, 0.002 g, 0.0025 g, 0.003 g, 0.0035 g, 0.004 g, 0.0045 g, 0.005 g, 0.0055 g, 0.006 g, 0.0065 g, 0.007 g, 0.0075 g, 0.008 g, 0.0085 g, 0.009 g, 0.0095 g, 0.01 g, 0.015 g, 0.02 g, 0.025 g, 0.03 g, 0.035 g, 0.04 g, 0.045 g, 0.05 g, 0.055 g, 0.06 g, 0.065 g, 0.07 g, 0.075 g, 0.08 g, 0.085 g, 0.09 g, 0.095 g, 0.1 g, 0.15 g, 0.2 g, 0.25 g, 0.3 g, 0.35 g, 0.4 g, 0.45 g, 0.5 g, 0.55 g, 0.6 g, 0.65 g, 0.7 g, 0.75 g, 0.8 g, 0.85 g, 0.9 g, 0.95 g, 1 g, 1.5 g, 2 g, 2.5, 3 g, 3.5, 4 g, 4.5 g, 5 g, 5.5 g, 6 g, 6.5 g, 7 g, 7.5 g, 8 g, 8.5 g, 9 g, 9.5 g, or 10 g (or a number in the range defined by and including any two numbers above).

In some embodiments, the amount of one or more compounds of the invention is in the range of 0.0001-10 g, 0.0005-9 g, 0.001-8 g, 0.005-7 g, 0.01-6 g, 0.05-5 g, 0.1-4 g, 0.5-4 g, or 1-3 g.

The compounds according to the invention are effective over a wide dosage range. For example, in the treatment of adult humans, dosages from 0.01 to 1000 mg, from 0.5 to 100 mg, from 1 to 50 mg per day, and from 5 to 40 mg per day are examples of dosages that may be used. An exemplary dosage is 10 to 30 mg per day. The exact dosage will depend upon the route of administration, the form in which the compound is administered, the subject to be treated, the body weight of the subject to be treated, and the preference and experience of the attending physician.

A pharmaceutical composition of the invention typically contains an active ingredient (i.e., a compound of the disclosure) of the present invention or a pharmaceutically acceptable salt and/or coordination complex thereof, and one or more pharmaceutically acceptable excipients, carriers, including but not limited to inert solid diluents and fillers, diluents, sterile aqueous solution and various organic solvents, permeation enhancers, solubilizers and adjuvants.

Described below are non-limiting exemplary pharmaceutical compositions and methods for preparing the same.

Pharmaceutical Compositions for Oral Administration.

In some embodiments, the invention provides a pharmaceutical composition for oral administration containing a compound of the invention, and a pharmaceutical excipient suitable for oral administration.

In some embodiments, the invention provides a solid pharmaceutical composition for oral administration containing: (i) an effective amount of a compound of the invention; optionally (ii) an effective amount of a second agent; and (iii) a pharmaceutical excipient suitable for oral administration. In some embodiments, the composition further contains: (iv) an effective amount of a third agent.

In some embodiments, the pharmaceutical composition may be a liquid pharmaceutical composition suitable for oral consumption. Pharmaceutical compositions of the invention suitable for oral administration can be presented as discrete dosage forms, such as capsules, cachets, or tablets, or liquids or aerosol sprays each containing a predetermined amount of an active ingredient as a powder or in granules, a solution, or a suspension in an aqueous or non-aqueous liquid, an oil-in-water emulsion, or a water-in-oil liquid emulsion. Such dosage forms can be prepared by any of the methods of pharmacy, but all methods include the step of bringing the active ingredient into association with the carrier, which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet can be prepared by compression or molding, optionally with one or more accessory ingredients. Compressed tablets can be prepared by compressing in a suitable machine the active ingredient in a free-flowing form such as powder or granules, optionally mixed with an excipient such as, but not limited to, a binder, a lubricant, an inert diluent, and/or a surface active or dispersing agent. Molded tablets can be made by molding in a suitable machine a mixture of the powdered compound moistened with an inert liquid diluent.

This invention further encompasses anhydrous pharmaceutical compositions and dosage forms comprising an active ingredient, since water can facilitate the degradation of some compounds. For example, water may be added (e.g., 5%) in the pharmaceutical arts as a means of simulating long-term storage in order to determine characteristics such as shelf-life or the stability of formulations over time. Anhydrous pharmaceutical compositions and dosage forms of the invention can be prepared using anhydrous or low moisture containing ingredients and low moisture or low humidity conditions. Pharmaceutical compositions and dosage forms of the invention which contain lactose can be made anhydrous if substantial contact with moisture and/or humidity during manufacturing, packaging, and/or storage is expected. An anhydrous pharmaceutical composition may be prepared and stored such that its anhydrous nature is maintained. Accordingly, anhydrous compositions may be packaged using materials known to prevent exposure to water such that they can be included in suitable formulary kits. Examples of suitable packaging include, but are not limited to, hermetically sealed foils, plastic or the like, unit dose containers, blister packs, and strip packs.

An active ingredient can be combined in an intimate admixture with a pharmaceutical carrier according to conventional pharmaceutical compounding techniques. The carrier can take a wide variety of forms depending on the form of preparation desired for administration. In preparing the compositions for an oral dosage form, any of the usual pharmaceutical media can be employed as carriers, such as, for example, water, glycols, oils, alcohols, flavoring agents, preservatives, coloring agents, and the like in the case of oral liquid preparations (such as suspensions, solutions, and elixirs) or aerosols; or carriers such as starches, sugars, micro-crystalline cellulose, diluents, granulating agents, lubricants, binders, and disintegrating agents can be used in the case of oral solid preparations, in some embodiments without employing the use of lactose. For example, suitable carriers include powders, capsules, and tablets, with the solid oral preparations. If desired, tablets can be coated by standard aqueous or nonaqueous techniques.

Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, microcrystalline cellulose, and mixtures thereof.

Examples of suitable fillers for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof.

Disintegrants may be used in the compositions of the invention to provide tablets that disintegrate when exposed to an aqueous environment. Too much of a disintegrant may produce tablets which may disintegrate in the bottle. Too little may be insufficient for disintegration to occur and may thus alter the rate and extent of release of the active ingredient(s) from the dosage form. Thus, a sufficient amount of disintegrant that is neither too little nor too much to detrimentally alter the release of the active ingredient(s) may be used to form the dosage forms of the compounds disclosed herein. The amount of disintegrant used may vary based upon the type of formulation and mode of administration, and may be readily discernible to those of ordinary skill in the art. About 0.5 to about 15 weight percent of disintegrant, or about 1 to about 5 weight percent of disintegrant, may be used in the pharmaceutical composition. Disintegrants that can be used to form pharmaceutical compositions and dosage forms of the invention include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums or mixtures thereof.

Lubricants which can be used to form pharmaceutical compositions and dosage forms of the invention include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, or mixtures thereof. Additional lubricants include, for example, a syloid silica gel, a coagulated aerosol of synthetic silica, or mixtures thereof. A lubricant can optionally be added, in an amount of less than about 1 weight percent of the pharmaceutical composition.

When aqueous suspensions and/or elixirs are desired for oral administration, the active ingredient therein may be combined with various sweetening or flavoring agents, coloring matter or dyes and, if so desired, emulsifying and/or suspending agents, together with such diluents as water, ethanol, propylene glycol, glycerin and various combinations thereof.

The tablets can be uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Surfactant which can be used to form pharmaceutical compositions and dosage forms of the invention include, but are not limited to, hydrophilic surfactants, lipophilic surfactants, and mixtures thereof. That is, a mixture of hydrophilic surfactants may be employed, a mixture of lipophilic surfactants may be employed, or a mixture of at least one hydrophilic surfactant and at least one lipophilic surfactant may be employed.

A suitable hydrophilic surfactant may generally have an HLB value of at least 10, while suitable lipophilic surfactants may generally have an HLB value of or less than about 10. An empirical parameter used to characterize the relative hydrophilicity and hydrophobicity of non-ionic amphiphilic compounds is the hydrophilic-lipophilic balance ("HLB" value). Surfactants with lower HLB values are more lipophilic or hydrophobic, and have greater solubility in oils, while surfactants with higher HLB values are more hydrophilic, and have greater solubility in aqueous solutions.

Hydrophilic surfactants are generally considered to be those compounds having an HLB value greater than about 10, as well as anionic, cationic, or zwitterionic compounds for which the HLB scale is not generally applicable. Similarly, lipophilic (i.e., hydrophobic) surfactants are compounds having an HLB value equal to or less than about 10. However, HLB value of a surfactant is merely a rough guide generally used to enable formulation of industrial, pharmaceutical and cosmetic emulsions.

Hydrophilic surfactants may be either ionic or non-ionic. Suitable ionic surfactants include, but are not limited to, alkylammonium salts; fusidic acid salts; fatty acid derivatives of amino acids, oligopeptides, and polypeptides; glyceride derivatives of amino acids, oligopeptides, and polypeptides; lecithins and hydrogenated lecithins; lysolecithins and hydrogenated lysolecithins; phospholipids and derivatives thereof; lysophospholipids and derivatives thereof; carnitine fatty acid ester salts; salts of alkylsulfates; fatty acid salts; sodium docusate; acyl lactylates; mono- and di-acetylated tartaric acid esters of mono- and di-glycerides; succinylated mono- and di-glycerides; citric acid esters of mono- and di-glycerides; and mixtures thereof.

Within the aforementioned group, ionic surfactants include, by way of example: lecithins, lysolecithin, phospholipids, lysophospholipids and derivatives thereof; carnitine fatty acid ester salts; salts of alkylsulfates; fatty acid salts; sodium docusate; acylactylates; mono- and di-acetylated tartaric acid esters of mono- and di-glycerides; succinylated mono- and di-glycerides; citric acid esters of mono- and di-glycerides; and mixtures thereof.

Ionic surfactants may be the ionized forms of lecithin, lysolecithin, phosphatidylcholine, phosphatidylethanolamine, phosphatidylglycerol, phosphatidic acid, phosphatidylserine, lysophosphatidylcholine, lysophosphatidylethanolamine, lysophosphatidylglycerol, lysophosphatidic acid, lysophosphatidylserine, PEG-phosphatidylethanolamine, PVP-phosphatidylethanolamine, lactylic esters of fatty acids, stearoyl-2-lactylate, stearoyl lactylate, succinylated monoglycerides, mono/diacetylated tartaric acid esters of mono/diglycerides, citric acid esters of mono/diglycerides, cholylsarcosine, caproate, caprylate, caprate, laurate, myristate, palmitate, oleate, ricinoleate, linoleate, linolenate, stearate, lauryl sulfate, teracecyl sulfate, docusate, lauroyl carnitines, palmitoyl carnitines, myristoyl carnitines, and salts and mixtures thereof.

Hydrophilic non-ionic surfactants may include, but are not limited to, alkylglucosides; alkylmaltosides; alkylthioglucosides; lauryl macrogolglycerides; polyoxyalkylene alkyl ethers such as polyethylene glycol alkyl ethers; polyoxyalkylene alkylphenols such as polyethylene glycol alkyl phenols; polyoxyalkylene alkyl phenol fatty acid esters such as polyethylene glycol fatty acids monoesters and polyethylene glycol fatty acids diesters; polyethylene glycol glycerol fatty acid esters; polyglycerol fatty acid esters; polyoxyalkylene sorbitan fatty acid esters such as polyethylene glycol sorbitan fatty acid esters; hydrophilic transesterification products of a polyol with at least one member of the group consisting of glycerides, vegetable oils, hydrogenated vegetable oils, fatty acids, and sterols; polyoxyethylene sterols, derivatives, and analogues thereof; polyoxyethylated vitamins and derivatives thereof; polyoxyethylene-polyoxypropylene block copolymers; and mixtures thereof; polyethylene glycol sorbitan fatty acid esters and hydrophilic transesterification products of a polyol with at least one member of the group consisting of triglycerides, vegetable oils, and hydrogenated vegetable oils. The polyol may be glycerol, ethylene glycol, polyethylene glycol, sorbitol, propylene glycol, pentaerythritol, or a saccharide.

Other hydrophilic-non-ionic surfactants include, without limitation, PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-lOoleate, Tween 40, Tween 60, sucrose monostearate, sucrose mono laurate, sucrose monopalmitate, PEG 10-100 nonyl phenol series, PEG 15-100 octyl phenol series, and poloxamers.

Suitable lipophilic surfactants include, by way of example only: fatty alcohols; glycerol fatty acid esters; acetylated glycerol fatty acid esters; lower alcohol fatty acids esters; propylene glycol fatty acid esters; sorbitan fatty acid esters; polyethylene glycol sorbitan fatty acid esters; sterols and sterol derivatives; polyoxyethylated sterols and sterol derivatives; polyethylene glycol alkyl ethers; sugar esters; sugar ethers; lactic acid derivatives of mono- and di-glycerides; hydrophobic transesterification products of a polyol with at least one member of the group consisting of glycerides, vegetable oils, hydrogenated vegetable oils, fatty acids and sterols; oil-soluble vitamins/vitamin derivatives; and mixtures thereof. Within this group, preferred lipophilic surfactants include glycerol fatty acid esters, propylene glycol fatty acid esters, and mixtures thereof, or are hydrophobic transesterification products of a polyol with at least one member of the group consisting of vegetable oils, hydrogenated vegetable oils, and triglycerides.

In one embodiment, the composition may include a solubilizer to ensure good solubilization and/or dissolution of the compound of the present invention and to minimize precipitation of the compound of the present invention. This can be especially important for compositions for non-oral use, e.g., compositions for injection. A solubilizer may also be added to increase the solubility of the hydrophilic drug and/or other components, such as surfactants, or to maintain the composition as a stable or homogeneous solution or dispersion.

Examples of suitable solubilizers include, but are not limited to, the following: alcohols and polyols, such as ethanol, isopropanol, butanol, benzyl alcohol, ethylene glycol, propylene glycol, butanediols and isomers thereof, glycerol, pentaerythritol, sorbitol, mannitol, transcutol, dimethyl isosorbide, polyethylene glycol, polypropylene glycol, polyvinylalcohol, hydroxypropyl methylcellulose and other cellulose derivatives, cyclodextrins and cyclodextrin derivatives; ethers of polyethylene glycols having an average molecular weight of about 200 to about 6000, such as tetrahydrofurfuryl alcohol PEG ether (glycofurol) or methoxy PEG; amides and other nitrogen-containing compounds such as 2-pyrrolidone, 2-piperidone, F-caprolactam, N-alkylpyrrolidone, N-hydroxyalkylpyrrolidone, N-alkylpiperidone, N-alkylcaprolactam, dimethylacetamide and polyvinylpyrrolidone; esters such as ethyl propionate, tributylcitrate, acetyl triethylcitrate, acetyl tributyl citrate, triethylcitrate, ethyl oleate, ethyl caprylate, ethyl butyrate, triacetin, propylene glycol monoacetate, propylene glycol diacetate, F-caprolactone and isomers thereof, S-valerolactone and isomers thereof, β-butyrolactone and isomers thereof, and other solubilizers known in the art, such as dimethyl acetamide, dimethyl isosorbide, N-methyl pyrrolidones, monooctanoin, diethylene glycol monoethyl ether, and water.

Mixtures of solubilizers may also be used. Examples include, but not limited to, triacetin, triethylcitrate, ethyl oleate, ethyl caprylate, dimethylacetamide, N-methylpyrrolidone, N-hydroxyethylpyrrolidone, polyvinylpyrrolidone, hydroxypropyl methylcellulose, hydroxypropyl cyclodextrins, ethanol, polyethylene glycol 200-100, glycofurol, transcutol, propylene glycol, and dimethyl isosorbide. Particularly preferred solubilizers include sorbitol, glycerol, triacetin, ethyl alcohol, PEG-400, glycofurol and propylene glycol.

The amount of solubilizer that can be included is not particularly limited. The amount of a given solubilizer may be limited to a bioacceptable amount, which may be readily determined by one of skill in the art. In some circumstances, it may be advantageous to include amounts of solubilizers far in excess of bioacceptable amounts, for example to maximize the concentration of the drug, with excess solubilizer removed prior to providing the composition to a subject using conventional techniques, such as distillation or evaporation. Thus, if present, the solubilizer can be in a weight ratio of 10%, 25% o, 50%), 100% o, or up to about 200%> by weight, based on the combined weight of the drug, and other excipients. If desired, very small amounts of solubilizer may also be used, such as 5%>, 2%>, 1%) or even less. Typically, the solubilizer may be present in an amount of about 1%> to about 100%, more typically about 5%> to about 25%> by weight.

The composition can further include one or more pharmaceutically acceptable additives and excipients. Such additives and excipients include, without limitation, detackifiers, anti-foaming agents, buffering agents, polymers, antioxidants, preservatives, chelating agents, viscomodulators, tonicifiers, flavorants, colorants, odorants, opacifiers, suspending agents, binders, fillers, plasticizers, lubricants, and mixtures thereof.

In addition, an acid or a base may be incorporated into the composition to facilitate processing, to enhance stability, or for other reasons. Examples of pharmaceutically acceptable bases include amino acids, amino acid esters, ammonium hydroxide, potassium hydroxide, sodium hydroxide, sodium hydrogen carbonate, aluminum hydroxide, calcium carbonate, magnesium hydroxide, magnesium aluminum silicate, synthetic aluminum silicate, synthetic hydrocalcite, magnesium aluminum hydroxide, diisopropylethylamine, ethanolamine, ethylenediamine, triethanolamine, triethylamine, triisopropanolamine, trimethylamine, tris(hydroxymethyl) aminomethane (TRIS) and the like. Also suitable are bases that are salts of a pharmaceutically acceptable acid, such as acetic acid, acrylic acid, adipic acid, alginic acid, alkanesulfonic acid, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid, and the like. Salts of polyprotic acids, such as sodium phosphate, disodium hydrogen phosphate, and sodium dihydrogen phosphate can also be used. When the base is a salt, the cation can be any convenient and pharmaceutically acceptable cation, such as ammonium, alkali metals, alkaline earth metals, and the like. Example may include, but not limited to, sodium, potassium, lithium, magnesium, calcium and ammonium.

Suitable acids are pharmaceutically acceptable organic or inorganic acids. Examples of suitable inorganic acids include hydrochloric acid, hydrobromic acid, hydriodic acid, sulfuric acid, nitric acid, boric acid, phosphoric acid, and the like. Examples of suitable organic acids include acetic acid, acrylic acid, adipic acid, alginic acid, alkanesulfonic acids, amino acids, ascorbic acid, benzoic acid, boric acid, butyric acid, carbonic acid, citric acid, fatty acids, formic acid, fumaric acid, gluconic acid, hydroquinosulfonic acid, isoascorbic acid, lactic acid, maleic acid, methanesulfonic acid, oxalic acid, para-bromophenylsulfonic acid, propionic acid, p-toluenesulfonic acid, salicylic acid, stearic acid, succinic acid, tannic acid, tartaric acid, thioglycolic acid, toluenesulfonic acid, uric acid and the like.

Pharmaceutical Compositions for Injection.

In some embodiments, the invention provides a pharmaceutical composition for injection containing a compound of the present invention and a pharmaceutical excipient suitable for injection. Components and amounts of agents in the compositions are as described herein.

The forms in which the novel compositions of the present invention may be incorporated for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles.

Aqueous solutions in saline are also conventionally used for injection. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, for the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the compound of the present invention in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, certain desirable methods of preparation are vacuum-drying and freeze-drying techniques which yield a powder of the active ingredient plus any additional desired ingredient from a previously sterile-filtered solution thereof.

Pharmaceutical Compositions for Topical (e.g. Transdermal) Delivery.

In some embodiments, the invention provides a pharmaceutical composition for transdermal delivery containing a compound of the present invention and a pharmaceutical excipient suitable for transdermal delivery.

Compositions of the present invention can be formulated into preparations in solid, semisolid, or liquid forms suitable for local or topical administration, such as gels, water soluble jellies, creams, lotions, suspensions, foams, powders, slurries, ointments, solutions, oils, pastes, suppositories, sprays, emulsions, saline solutions, dimethylsulfoxide (DMSO)-based solutions. In general, carriers with higher densities are capable of providing an area with a prolonged exposure to the active ingredients. In contrast, a solution formulation may provide more immediate exposure of the active ingredient to the chosen area.

The pharmaceutical compositions also may comprise suitable solid or gel phase carriers or excipients, which are compounds that allow increased penetration of, or assist in the delivery of, therapeutic molecules across the stratum corneum permeability barrier of the skin. There are many of these penetration-enhancing molecules known to those trained in the art of topical formulation.

Examples of such carriers and excipients include, but are not limited to, humectants (e.g., urea), glycols (e.g., propylene glycol), alcohols (e.g., ethanol), fatty acids (e.g., oleic acid), surfactants (e.g., isopropyl myristate and sodium lauryl sulfate), pyrrolidones, glycerol monolaurate, sulfoxides, terpenes (e.g., menthol), amines, amides, alkanes, alkanols, water, calcium carbonate, calcium phosphate, various sugars, starches, cellulose derivatives, gelatin, and polymers such as polyethylene glycols.

Another exemplary formulation for use in the methods of the present invention employs transdermal delivery devices ("patches"). Such transdermal patches may be used to provide continuous or discontinuous infusion of a compound of the present invention in controlled amounts, either with or without another agent.

The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

Pharmaceutical Compositions for Inhalation.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices that deliver the formulation in an appropriate manner.

Other Pharmaceutical Compositions.

Pharmaceutical compositions may also be prepared from compositions described herein and one or more pharmaceutically acceptable excipients suitable for sublingual, buccal, rectal, intraosseous, intraocular, intranasal, epidural, or intraspinal administration. Preparations for such pharmaceutical compositions are well-known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 20037ybg; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999); all of which are incorporated by reference herein in their entirety.

Administration of the compounds or pharmaceutical composition of the present invention can be effected by any method that enables delivery of the compounds to the site of action. These methods include oral routes, intraduodenal routes, parenteral injection (including intravenous, intraarterial, subcutaneous, intramuscular, intravascular, intraperitoneal or infusion), topical (e.g. transdermal application), rectal administration, via local delivery by catheter or stent or through inhalation. Compounds can also be administered intraadiposally or intrathecally.

The amount of the compound administered will be dependent on the subject being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose.

Typically, such administration will be by injection, e.g., intravenous injection, in order to introduce the agent quickly. However, other routes may be used as appropriate. A single dose of a compound of the invention may also be used for treatment of an acute condition.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the compounds of the invention may continue as long as necessary. In some embodiments, a compound of the invention is administered for more than 1, 2, 3, 4, 5, 6, 7, 14, or 28 days. In some embodiments, a compound of the invention is administered for less than 28, 14, 7, 6, 5, 4, 3, 2, or 1 day. In some embodiments, a compound of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intra-arterial injection, intravenously, intraperitoneally, parenterally, intramuscularly, subcutaneously, orally, topically, or as an inhalant.

The compositions of the invention may also be delivered via an impregnated or coated device such as a stent, for example, or an artery-inserted cylindrical polymer. Such a method of administration may, for example, aid in the prevention or amelioration of restenosis following procedures such as balloon angioplasty. Without being bound by theory, compounds of the invention may slow or inhibit the migration and proliferation of smooth muscle cells in the arterial wall which contribute to restenosis. A compound of the invention may be administered, for example, by local delivery from the struts of a stent, from a stent graft, from grafts, or from the cover or sheath of a stent. In some embodiments, a compound of the invention is admixed with a matrix. Such a matrix may be a polymeric matrix, and may serve to bond the compound to the stent. Polymeric matrices suitable for such use, include, for example, lactone-based polyesters or copolyesters such as polylactide, polycaprolactonglycolide, polyorthoesters, polyanhydrides, polyaminoacids, polysaccharides, polyphosphazenes, poly (etherester) copolymers (e.g. PEO-PLLA); polydimethylsiloxane, poly(ethylene-vinylacetate), acrylate-based polymers or copolymers (e.g. polyhydroxyethyl methylmethacrylate, polyvinyl pyrrolidinone), fluorinated polymers such as polytetrafluoroethylene and cellulose esters. Suitable matrices may be nondegrading or may degrade with time, releasing the compound or compounds. Compounds of the invention may be applied to the surface of the stent by various methods such as dip/spin coating, spray coating, dip-coating, and/or brush-coating. The compounds may be applied in a solvent and the solvent may be allowed to evaporate, thus forming a layer of compound onto the stent. Alternatively, the compound may be located in the body of the stent or graft, for example in microchannels or micropores. When implanted, the compound diffuses out of the body of the stent to contact the arterial wall. Such stents may be prepared by dipping a stent manufactured to contain such micropores or microchannels into a solution of the compound of the invention in a suitable solvent, followed by evaporation of the solvent. Excess drug on the surface of the stent may be removed via an additional brief solvent wash. In yet other embodiments, compounds of the invention may be covalently linked to a stent or graft. A covalent linker may be used which degrades in vivo, leading to the release of the compound of the invention. Any bio-labile linkage may be used for such a purpose, such as ester, amide or anhydride linkages. Compounds of the invention may additionally be administered intravascularly from a balloon used during angioplasty. Extravascular administration of the compounds via the pericard or via advential application of formulations of the invention may also be performed to decrease restenosis.

A variety of stent devices which may be used as described are disclosed, for example, in the following references, all of which are hereby incorporated by reference: U.S. Pat. Nos. 5,451,233; 5,040,548; 5,061,273; 5,496,346; 5,292,331; 5,674,278; 3,657,744; 4,739,762; 5,195,984; 5,292,331; U.S. Pat. Nos. 5,674,278; 5,879,382; 6,344,053.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention is administered in a composition that comprises one or more agents, and the agent has a shorter half-life than the compound of the invention unit dose forms of the agent and the compound of the invention may be adjusted accordingly.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, adjuvants, etc.

Exemplary parenteral administration forms include solutions or suspensions of active compound in sterile aqueous solutions, for example, aqueous propylene glycol or dextrose solutions. Such dosage forms can be suitably buffered, if desired.

Methods of Use

The method typically comprises administering to a subject a therapeutically effective amount of a compound of the invention. The therapeutically effective amount of the subject combination of compounds may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g., reduction of proliferation or downregulation of activity of a target protein. The specific dose will vary depending on the particular compounds chosen, the dosing regimen to be followed, whether it is administered in combination with other compounds, timing of administration, the tissue to which it is administered, and the physical delivery system in which it is carried.

As used herein, the term "$IC_{50}$" refers to the half maximal inhibitory concentration of an inhibitor in inhibiting biological or biochemical function. This quantitative measure indicates how much of a particular inhibitor is needed to inhibit a given biological process (or component of a process, i.e. an enzyme, cell, cell receptor or microorganism) by half. In other words, it is the half maximal (50%) inhibitory concentration (IC) of a substance (50% IC, or IC50). EC50 refers to the plasma concentration required for obtaining 50%> of a maximum effect in vivo.

In some embodiments, the subject methods utilize a CDK inhibitor with an IC50 value of about or less than a predetermined value, as ascertained in an in vitro assay. In some embodiments, the CDK inhibitor inhibits CDK a with an IC50 value of about 1 nM or less, 2 nM or less, 5 nM or less, 7 nM or less, 10 nM or less, 20 nM or less, 30 nM or less, 40 nM or less, 50 nM or less, 60 nM or less, 70 nM or less, 80 nM or less, 90 nM or less, 100 nM or less, 120 nM or less, 140 nM or less, 150 nM or less, 160 nM or less, 170 nM or less, 180 nM or less, 190 nM or less, 200 nM or less, 225 nM or less, 250 nM or less, 275 nM or less, 300 nM or less, 325 nM or less, 350 nM or less, 375 nM or less, 400 nM or less, 425 nM or less, 450 nM or less, 475 nM or less, 500 nM or less, 550 nM or less, 600 nM or less, 650 nM or less, 700 nM or less, 750 nM or less, 800 nM or less, 850 nM or less, 900 nM or less, 950 nM or less, 1 µM or less, 1.1 µM or less, 1.2 µM or less, 1.3 µM or less, 1.4 µM or less, 1.5 µM or less, 1.6 µM or less, 1.7 µM or less, 1.8 µM or less, 1.9 µM or less, 2 µM or less, 5 µM or less, 10 µM or less, 15 µM or less, 20 µM or less, 25 µM or less, 30 µM or less, 40 M or less, 50 µM, 60 µM, 70 µM, 80 µM, 90 µM, 100 µM, 200 µM, 300 µM, 400 µM, or 500 µM, or less, (or a number in the range defined by and including any two numbers above).

In some embodiments, the CDK inhibitor selectively inhibits CDK a with an IC50 value that is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two, or three other CDKs.

In some embodiments, the CDK inhibitor selectively inhibits CDK a with an IC50 value that is less than about 1 nM, 2 nM, 5 nM, 7 nM, 10 nM, 20 nM, 30 nM, 40 nM, 50 nM, 60 nM, 70 nM, 80 nM, 90 nM, 100 nM, 120 nM, 140 nM, 150 nM, 160 nM, 170 nM, 180 nM, 190 nM, 200 nM, 225 nM, 250 nM, 275 nM, 300 nM, 325 nM, 350 nM, 375 nM, 400 nM, 425 nM, 450 nM, 475 nM, 500 nM, 550 nM, 600 nM, 650 nM, 700 nM, 750 nM, 800 nM, 850 nM, 900 nM, 950 nM, 1 M, 1.1 µM, 1.2 µM, 1.3 µM, 1.4 µM, 1.5 µM, 1.6 µM, 1.7 µM, 1.8 µM, 1.9 µM, 2 µM, 5 µM, 10 M, 15 µM, 20 µM, 25 µM, 30 µM, 40 µM, 50 µM, 60 µM, 70 µM, 80 µM, 90 µM, 100 µM, 200 M, 300 µM, 400 µM, or 500 µM (or in the range defined by and including any two numbers above), and said IC50 value is at least 2, 3, 4, 5, 6, 7, 8, 9, 10, 15, 20, 25, 30, 35, 40, 45, 50, 100, or 1000 times less (or a number in the range defined by and including any two numbers above) than its IC50 value against one, two or three other CDKs.

The subject methods are useful for treating a disease condition associated with CDK. Any disease condition that results directly or indirectly from an abnormal activity or expression level of CDK can be an intended disease condition.

Different disease conditions associated with CDK have been reported. CDK has been implicated, for example, auto-immune diseases, neurodegeneration (such as Parkinson's disease, Alzheimer's disease and ischaemia), inflammatory diseases, viral infections and cancer such as, for example, colon cancer, breast cancer, small-cell lung cancer, non-small-cell lung cancer, bladder cancer, ovarian cancer, prostate cancer, chronic lymphoid leukemia, lymphoma, myeloma, acute myeloid leukemia, or pancreatic cancer.

Non-limiting examples of such conditions include but are not limited to Acanthoma, Acinic cell carcinoma, Acoustic neuroma, Acral lentiginous melanoma, Acrospiroma, Acute eosinophilic leukemia, Acute lymphoblastic leukemia, Acute lymphocytic leukemia, Acute megakaryoblastic leukemia, Acute monocytic leukemia, Acute myeloblasts leukemia with maturation, Acute myeloid dendritic cell leukemia, Acute myeloid leukemia, Acute myelogenous leukemia, Acute promyelocytic leukemia, Adamantinoma, Adenocarcinoma, Adenoid cystic carcinoma, Adenoma, Adenomatoid odontogenic tumor, Adrenocortical carcinoma, Adult T-cell leukemia, Aggressive NK-cell leukemia, AIDS-Related Cancers, AIDS-related lymphoma, Alveolar soft part sarcoma, Ameloblastic fibroma, Anal cancer, Anaplastic large cell lymphoma, Anaplastic thyroid cancer, Angioimmunoblastic T-cell lymphoma, Angiomyolipoma, Angiosarcoma, Appendix cancer, Astrocytoma, Atypical teratoid rhabdoid tumor, Basal cell carcinoma, Basal-like carcinoma, B-cell leukemia, B-cell lymphoma, Bellini duct carcinoma, Biliary tract cancer, Bladder cancer, Blastoma, Bone Cancer, Bone tumor, Brain Stem Glioma, Brain Tumor, Breast Cancer, Brenner tumor, Bronchial Tumor, Bronchioloalveolar carcinoma, Brown tumor, Burkitt's lymphoma, Cancer of Unknown Primary Site, Carcinoid Tumor, Carcinoma, Carcinoma in situ, Carcinoma of the penis, Carcinoma of Unknown Primary Site, Carcinosarcoma, Castleman's Disease, Central Nervous System Embryonal Tumor, Cerebellar Astrocytoma, Cerebral Astrocytoma, Cervical Cancer, Cholangiocarcinoma, Chondroma, Chondrosarcoma, Chordoma, Choriocarcinoma, Choroid plexus papilloma, Chronic Lymphocytic Leukemia, Chronic monocytic leukemia, Chronic myelogenous leukemia, Chronic Myeloproliferative Disorder, Chronic neutrophilic leukemia, Clear-cell tumor, Colon Cancer, Colorectal cancer, Craniopharyngioma, Cutaneous T-cell lymphoma, Degos disease, Dermatofibrosarcoma protuberans, Dermoid cyst, Desmoplastic small round cell tumor, Diffuse large B cell lymphoma, Dysembryoplastic neuroepithelial tumor, Embryonal carcinoma, Endodermal sinus tumor, Endometrial cancer, Endometrial Uterine Cancer, Endometrioid tumor, Enteropathy-associated T-cell lymphoma, Ependymoblastoma, Ependymoma, Epidermoid cancer, Epithelioid sarcoma, Erythroleukemia, Esophageal cancer, Esthesioneuroblastoma, Ewing Family of Tumor, Ewing Family Sarcoma, Ewing's sarcoma, Extracranial Germ Cell Tumor, Extragonadal Germ Cell Tumor, Extrahepatic Bile Duct Cancer, Extramammary Paget's disease, Fallopian tube cancer, Fetus in fetu, Fibroma, Fibrosarcoma, Follicular lymphoma, Follicular thyroid cancer, Gallbladder Cancer, Gallbladder cancer, Ganglioglioma, Ganglioneuroma, Gastric Cancer, Gastric lymphoma, Gastrointestinal cancer, Gastrointestinal Carcinoid Tumor, Gastrointestinal Stromal Tumor, Gastrointestinal stromal tumor, Germ cell tumor, Germinoma, Gestational choriocarcinoma, Gestational Trophoblastic Tumor, Giant cell tumor of bone, Glioblastoma multiforme, Glioma, Gliomatosis cerebri, Glomus tumor, Glucagonoma, Gonadoblastoma, Granulosa cell tumor, Hairy Cell Leukemia, Head and Neck Cancer, Head and neck cancer, Heart cancer, Hemoglobinopathies such as b-thalassemia and sickle cell disease (SCD), Hemangioblastoma, Hemangiopericytoma, Hemangiosarcoma, Hematological malignancy, Hepatocellular carcinoma, Hepatosplenic T-cell lymphoma, Hereditary breast-ovarian cancer syndrome, Hodgkin Lymphoma, Hodgkin's lymphoma, Hypopharyngeal Cancer, Hypothalamic Glioma, Inflammatory breast cancer, Intraocular Melanoma, Islet cell carcinoma, Islet Cell Tumor, Juvenile myelomonocytic leukemia, Kaposi Sarcoma, Kaposi's sarcoma, Kidney Cancer, Klatskin tumor, Krukenberg tumor, Laryngeal Cancer, Laryngeal cancer, Lentigo maligna melanoma, Leukemia, Lip and Oral Cavity Cancer, Liposarcoma, Lung cancer, Luteoma, Lymphangioma, Lymphangiosarcoma, Lymphoepithelioma, Lymphoid leukemia, Lymphoma, Macroglobulinemia, Malignant Fibrous Histiocytoma, Malignant fibrous histiocytoma, Malignant Fibrous Histiocytoma of Bone, Malignant Glioma, Malignant Mesothelioma, Malignant peripheral nerve sheath tumor, Malignant rhabdoid tumor, Malignant triton tumor, MALT lymphoma, Mantle cell lymphoma, Mast cell leukemia, Mastocytosis, Mediastinal germ cell tumor, Mediastinal tumor, Medullary thyroid cancer, Medulloblastoma, Medulloblastoma, Medulloepithelioma, Melanoma, Melanoma, Meningioma, Merkel Cell Carcinoma, Mesothelioma, Mesothelioma, Metastatic Squamous Neck Cancer with Occult Primary, Metastatic urothelial carcinoma, Mixed Mullerian tumor, Monocytic leukemia, Mouth Cancer, Mucinous tumor, Multiple Endocrine Neoplasia Syndrome, Multiple Myeloma, Multiple myeloma, Mycosis Fungoides, Mycosis fungoides, Myelodysplasia Disease, Myelodysplasia Syndromes, Myeloid leukemia, Myeloid sarcoma, Myeloproliferative Disease, Myxoma, Nasal Cavity Cancer, Nasopharyngeal Cancer, Nasopharyngeal carcinoma, Neoplasm, Neurinoma, Neuroblastoma, Neuroblastoma, Neurofibroma, Neuroma, Nodular melanoma, Non-Hodgkin Lymphoma, Non-Hodgkin lymphoma, Nonmelanoma Skin Cancer, Non-Small Cell Lung Cancer, Ocular oncology, Oligoastrocytoma, Oligodendroglioma, Oncocytoma, Optic nerve sheath meningioma, Oral Cancer, Oral cancer, Oropharyngeal Cancer, Osteosarcoma, Osteosarcoma, Ovarian Cancer, Ovarian cancer, Ovarian Epithelial Cancer, Ovarian Germ Cell Tumor, Ovarian Low Malignant Potential Tumor, Paget's disease of the breast, Pancoast tumor, Pancreatic Cancer, Pancreatic cancer, Papillary thyroid cancer, Papillomatosis, Paraganglioma, Paranasal Sinus Cancer, Parathyroid Cancer, Penile Cancer, Perivascular epithelioid cell tumor, Pharyngeal Cancer, Pheochromocytoma, Pineal Parenchymal Tumor of Intermediate Differentiation, Pineoblastoma, Pituicytoma, Pituitary adenoma, Pituitary tumor, Plasma Cell Neoplasm, Pleuropulmonary blastoma, Polyembryoma, Precursor T-lymphoblastic lymphoma, Primary central nervous system lymphoma, Primary effusion lymphoma, Primary Hepatocellular Cancer, Primary Liver Cancer, Primary peritoneal cancer, Primitive neuroectodermal tumor, Prostate cancer, Pseudomyxoma peritonei, Rectal Cancer, Renal cell carcinoma, Respiratory Tract Carcinoma Involving the NUT Gene onChromosome 15, Retinoblastoma, Rhabdomyoma, Rhabdomyosarcoma, Richter's transformation, Sacrococcygeal teratoma, Salivary Gland Cancer, Sarcoma, Schwannomatosis, Sebaceous gland carcinoma, Secondary neoplasm, Seminoma, Serous tumor, Sertoli-Leydig cell tumor, Sex cord-stromal tumor, Sezary Syndrome, Signet ring cell carcinoma, Skin Cancer, Small blue round cell tumor, Small cell carcinoma, Small Cell Lung Cancer, Small cell lymphoma, Small intestine cancer, Soft tissue sarcoma, Somatostatinoma, Soot wart, Spinal Cord Tumor, Spinal tumor, Splenic marginal zone lymphoma, Squamous cell carcinoma, Stomach cancer, Superficial spreading melanoma, Supratentorial Primitive Neuroectodermal Tumor, Surface epithelial-stromal tumor, Synovial sarcoma, T-cell acute lymphoblastic leukemia, T-cell large granular lymphocyte leukemia, T-cell leukemia, T-cell lymphoma, T-cell prolymphocytic leukemia, Teratoma, Terminal lymphatic cancer, Testicular cancer, Thecoma, Throat Cancer, Thymic Carcinoma, Thymoma, Thyroid cancer, Transitional Cell Cancer of Renal Pelvis and Ureter, Transitional cell carcinoma, Urachal cancer, Urethral cancer, Urogenital neoplasm, Uterine sarcoma, Uveal melanoma, Vaginal Cancer, Verner Morrison syndrome, Verrucous carcinoma, Visual Pathway Glioma, Vulvar Cancer, Waldenstrom's macroglobulinemia, Warthin's tumor, Wilms' tumor, or any combination thereof.

In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

In other embodiments, said method is for treating a disease selected from breast cancer, lung cancer, pancreatic cancer, prostate cancer, colon cancer, ovarian cancer, uterine cancer, or cervical cancer.

In other embodiments, said method is for treating a disease selected from leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), myelodysplastic syndrome (MDS) or epidermoid cancer.

Compounds of the disclosure, as well as pharmaceutical compositions comprising them, can be administered to treat any of the described diseases, alone or in combination with a medical therapy. Medical therapies include, for example, surgery and radiotherapy (e.g., gamma-radiation, neutron beam radiotherapy, electron beam radiotherapy, proton therapy, brachytherapy, systemic radioactive isotopes).

In other aspects, compounds of the disclosure, as well as pharmaceutical compositions comprising them, can be administered to treat any of the described diseases, alone or in combination with one or more other agents.

In other methods, the compounds of the disclosure, as well as pharmaceutical compositions comprising them, can be administered in combination with agonists of nuclear receptors agents.

In other methods, the compounds of the disclosure, as well as pharmaceutical compositions comprising them, can be administered in combination with antagonists of nuclear receptors agents.

In other methods, the compounds of the disclosure, as well as pharmaceutical compositions comprising them, can be administered in combination with an anti-proliferative agent.

In some embodiments, the disclosure is directed to methods for treating a CDK4-mediated and a CDK6-mediated disorder in a patient in need thereof, comprising administering to said patient a compound of Formula I, including all subgenera described herein, or a pharmaceutically acceptable salt thereof, or a pharmaceutical composition comprising the compound of Formula I, including all subgenera described herein.

In some embodiments, the CDK4-mediated and CDK6-mediated disorder is a cancer. In some embodiments, the cancer is breast cancer, malignant brain tumors, colon cancer, small-cell lung cancer, non-small-cell lung cancer, bladder cancer, ovarian cancer, prostate cancer, chronic lymphoid leukemia, lymphoma, myeloma, acute myeloid leukemia, secondary pancreatic cancer or secondary brain metastases.

In some embodiments, the cancer is breast cancer. In some embodiments, the cancer is malignant brain tumors. In some embodiments, the cancer is colon cancer. In some embodiments, the cancer is small-cell lung cancer. In some embodiments, the cancer is non-small-cell lung cancer. In some embodiments, the cancer is bladder cancer. In some embodiments, the cancer is ovarian cancer.

In some embodiments, the cancer is prostate cancer. In some embodiments, the cancer is chronic lymphoid leukemia. In some embodiments, the cancer is lymphoma. In some embodiments, the cancer is myeloma. In some embodiments, the cancer is acute myeloid leukemia. In some embodiments, the cancer is secondary pancreatic cancer. In some embodiments, the cancer is secondary brain metastases.

In some embodiments, the breast cancer is HR+/HER2– or HR+/HER2+ advanced or metastatic breast cancer. In some embodiments, the breast cancer is HR+/IER2– advanced breast cancer. In some embodiments, the breast cancer is HR+/IER2– metastatic breast cancer. In some embodiments, the breast cancer is HR+/HER2+ advanced breast cancer. In some embodiments, the breast cancer is HR+/IER2+ metastatic breast cancer.

In some embodiments, the malignant brain tumors are glioblastoma, astrocytoma, or pontine glioma. In some embodiments, the malignant brain tumors are a glioblastoma. In some embodiments, the malignant brain tumors are an astrocytoma. In some embodiments, the malignant brain tumors are a pontine glioma.

In some embodiments, the patient is administered a pharmaceutical composition comprising a compound of Formula I, including all subgenera described herein, or a pharmaceutically acceptable salt thereof. In some embodiments, the administration is oral administration.

Combination Therapies

For treating cancer and other proliferative diseases, the compounds of the invention can be used in combination with chemotherapeutic agents, agonists or antagonists of nuclear receptors, or other anti-proliferative agents. The compounds of the invention can also be used in combination with a medical therapy such as surgery or radiotherapy, e.g., gamma-radiation, neutron beam radiotherapy, electron beam radiotherapy, proton therapy, brachytherapy, and systemic radioactive isotopes. Examples of suitable chemotherapeutic agents include any of: abarelix, aldesleukin, alemtuzumab, alitretinoin, allopurinol, all-trans retinoic acid, altretamine, anastrozole, arsenic trioxide, asparaginase, azacitidine, bendamustine, bevacizumab, bexarotene, bleomycin, bortezombi, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, mechlorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panobinostat, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinstat and zoledronate.

In some embodiments, the compounds of the invention can be used in combination with a therapeutic agent that targets an epigenetic regulator. Examples of epigenetic regulators include bromodomain inhibitors, the histone lysine methyltransferase inhibitors, histone arginine methyl transferase inhibitors, histone demethylase inhibitors, histone deacetylase inhibitors, histone acetylase inhibitors, and DNA methyltransferase inhibitors. Histone deacetylase inhibitors include, e.g., vorinostat. Histone arginine methyl transferase inhibitors include inhibitors of protein arginine methyltransferases (PRMTs) such as PRMT5, PRMT1 and PRMT4. DNA methyltransferase inhibitors include inhibitors of DNMT1 and DNMT3.

For treating cancer and other proliferative diseases, the compounds of the invention can be used in combination with targeted therapies, including JAK kinase inhibitors (e.g. Ruxolitinib), PI3 kinase inhibitors including PI3K-delta selective and broad spectrum PI3K inhibitors, MEK inhibitors, Cyclin Dependent kinase inhibitors, including CDK4/6 inhibitors and CDK9 inhibitors, BRAF inhibitors, mTOR inhibitors, proteasome inhibitors (e.g. Bortezomib, Carfilzomib), HDAC inhibitors (e.g. panobinostat, vorinostat), DNA methyl transferase inhibitors, dexamethasone, bromo and extra terminal family member (BET) inhibitors, BTK inhibitors (e.g. ibrutinib, acalabrutinib), BCL2 inhibitors (e.g. venetoclax), dual BCL2 family inhibitors (e.g. BCL2/BCLxL), PARP inhibitors, FLT3 inhibitors, or LSD1 inhibitors.

In some embodiments, the inhibitor of an immune checkpoint molecule is an inhibitor of PD-1, e.g., an anti-PD-1 monoclonal antibody. In some embodiments, the anti-PD-1 monoclonal antibody is nivolumab, pembrolizumab (also known as MK-3475), or PDR001. In some embodiments, the anti-PD-1 monoclonal antibody is nivolumab or pembrolizumab. In some embodiments, the anti-PD1 antibody is pembrolizumab. In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, durvalumab, or BMS-935559. In some embodiments, the inhibitor of an immune checkpoint molecule is an inhibitor of CTLA-4, e.g., an anti-CTLA-4 antibody. In some embodiments, the anti-CTLA-4 antibody is ipilimumab.

In some embodiments, the agent is an alkylating agent, a proteasome inhibitor, a corticosteroid, or an immunomodulatory agent. Examples of an alkylating agent include cyclophosphamide (CY), melphalan (MEL), and bendamustine.

In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM).

For treating autoimmune or inflammatory conditions, the compound of the invention can be administered in combination with a corticosteroid such as triamcinolone, dexamethasone, fluocinolone, cortisone, prednisolone, or flumetholone.

For treating autoimmune or inflammatory conditions, the compound of the invention can be administered in combination with an immune suppressant such as fluocinolone acetonide (Retisert®), rimexolone (AL-2178, Vexol, Alcon), or cyclosporine (Restasis®).

In some embodiments, the disclosure is directed to methods described herein, further comprising administering an additional therapeutic agent to the patient. In some embodiments, the additional therapeutic agent is a PRMT5 inhibitor, a HER2 kinase inhibitor, an aromatase inhibitor, an estrogen receptor antagonist or an alkylating agent.

In some embodiments, the additional therapeutic agent is a PRMT5 inhibitor. In some embodiments, the additional therapeutic agent is a HER2 kinase inhibitor. In other embodiments, the additional therapeutic agent is an aromatase inhibitor. In other embodiments, the additional therapeutic agent is an estrogen receptor antagonist. In yet other embodiments, the additional therapeutic agent is an alkylating agent.

In some embodiments, the aromatase inhibitor is letrozole. In some embodiments, the estrogen receptor antagonist is fulvestrant. In other embodiments, the alkylating agent is temozolomide.

In yet other embodiments, the PRMT5 inhibitor is a compound disclosed in US Published Patent Application No. 2020/0148692 (filed Jan. 16, 2020); US Published Patent Application No. 2019/0284193 (filed Apr. 5, 2019); and US Published Patent Application No. 2019/0048014 (filed Aug. 9, 2018); each of which is hereby incorporated herein in its entirety.

In some embodiments, the PRMT5 inhibitor is:
(2R,3R,4S,5S)-2-(4-amino-7H-pyrrolo[2,3-d]pyrimidin-7-yl)-5-((R)-6-chloroisochroman-1-yl)tetrahydrofuran-3,4-diol, or a pharmaceutically acceptable salt or solvate thereof;
(2R,3R,4S,5S)-2-(4-amino-7H-pyrrolo[2,3-d]pyrimidin-7-yl)-5-((R)-7-chloroisochroman-1-yl)tetrahydrofuran-3,4-diol, or a pharmaceutically acceptable salt or solvate thereof;
(2R,3R,4S,5S)-2-(4-amino-7H-pyrrolo[2,3-d]pyrimidin-7-yl)-5-((R)-5-chloroisochroman-1-yl)tetrahydrofuran-3,4-diol, or a pharmaceutically acceptable salt or solvate thereof,
(2R,3R,4S,5S)-2-(4-amino-7H-pyrrolo[2,3-d]pyrimidin-7-yl)-5-((R)-6,7-difluoroisochroman-1-yl)tetrahydrofuran-3,4-diol, or a pharmaceutically acceptable salt or solvate thereof,
(2R,3R,4S,5S)-2-(4-amino-7H-pyrrolo[2,3-d]pyrimidin-7-yl)-5-((R)-5,6-difluoroisochroman-1-yl)tetrahydrofuran-3,4-diol, or a pharmaceutically acceptable salt or solvate thereof,
(2R,3R,4S,5S)-2-(4-amino-7H-pyrrolo[2,3-d]pyrimidin-7-yl)-5-((R)-6-chloro-5-fluoroisochroman-1-yl)tetrahydrofuran-3,4-diol, or a pharmaceutically acceptable salt or solvate thereof, (2R,3R,4S,5S)-2-(4-amino-5-fluoro-7H-pyrrolo[2,3-d]pyrimidin-7-yl)-5-((R)-6-chloroisochroman-1-yl)tetrahydrofuran-3,4-diol, or a pharmaceutically acceptable salt or solvate thereof, (2R,3R,4S,5S)-2-(4-amino-7H-pyrrolo[2,3-d]pyrimidin-7-yl)-5-((R)-6,7-dichloroisochroman-1-yl)tetrahydrofuran-3,4-diol, or a pharmaceutically acceptable salt or solvate thereof, (2S,3S,4R,5R)-2-((R)-6-chloroisochroman-1-yl)-5-(4-methyl-7H-pyrrolo[2,3-d]pyrimidin-7-yl)tetrahydrofuran-3,4-diol, or a pharmaceutically acceptable salt or solvate thereof;

(2S,3S,4R,5R)-2-((R)-6,7-difluoroisochroman-1-yl)-5-(4-methyl-7H-pyrrolo[2,3-d]pyrimidin-7-yl)tetrahydrofuran-3,4-diol, or a pharmaceutically acceptable salt or solvate thereof, (2S,3S,4R,5R)-2-((R)-5,6-difluoroisochroman-1-yl)-5-(4-methyl-7H-pyrrolo[2,3-d]pyrimidin-7-yl)tetrahydrofuran-3,4-diol, or a pharmaceutically acceptable salt or solvate thereof, (2S,3S,4R,5R)-2-((R)-6-chloroisochroman-1-yl)-5-(5-fluoro-4-methyl-7H-pyrrolo[2,3-d]pyrimidin-7-yl)tetrahydrofuran-3,4-diol, or a pharmaceutically acceptable salt or solvate thereof, (2S,3S,4R,5R)-2-((R)-6,7-dichloroisochroman-1-yl)-5-(4-methyl-7H-pyrrolo[2,3-d]pyrimidin-7-yl)tetrahydrofuran-3,4-diol, or a pharmaceutically acceptable salt or solvate thereof.

In some embodiments, the PRMT5 inhibitor is (2S,3S,4R,5R)-2-((R)-6-chloroisochroman-1-yl)-5-(4-methyl-7H-pyrrolo[2,3-d]pyrimidin-7-yl)tetrahydrofuran-3,4-diol, or a pharmaceutically acceptable salt or solvate thereof.

Synthesis

Compounds of the invention, including salts thereof, can be prepared using known organic synthesis techniques and can be synthesized according to any of numerous possible synthetic routes.

The reactions for preparing compounds of the invention can be carried out in suitable solvents which can be readily selected by one of skill in the art of organic synthesis. Suitable solvents can be substantially nonreactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd. Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1H$ or $^{13}C$), infrared spectroscopy, spectrophotometry (e.g., UV-visible), or mass spectrometry, or by chromatography such as high performance liquid chromatography (HPLC) or thin layer chromatography.

The expressions, "ambient temperature," "room temperature," and "r.t." as used herein, are understood in the art, and refer generally to a temperature, e.g. a reaction temperature, that is about the temperature of the room in which the reaction is carried out, for example, a temperature from about 20° C. to about 30° C.

Compounds of the invention can be prepared using numerous preparatory reactions known in the literature. The Schemes below provide general guidance in connection with preparing the compounds of the invention. One skilled in the art would understand that the preparations shown in the Schemes can be modified or optimized using general knowledge of organic chemistry to prepare various compounds of the invention. Example synthetic methods for preparing compounds of the invention are provided in the Schemes below.

The following Examples are provided to illustrate some of the concepts described within this disclosure. While the Examples are considered to provide an embodiment, it should not be considered to limit the more general embodiments described herein.

EXAMPLES

General Synthetic Procedures

Compounds of Formula (I) can be prepared from optionally protected 1-1 where $W^1$ is halogen (e.g., Cl, Br, or I) or pseudohalogen (e.g., OTf or OMs) as shown in Scheme I. Compounds 1-1 can be coupled with compounds 1-2 where $M^1$ is a boronic acid, boronate ester, potassium trifluoroborate, or an appropriately substituted metal, such as $Sn(Bu)_3$ or ZnCl under standard Suzuki conditions (e.g., in the presence of a palladium catalyst, such as [1,1'-bis(diphenylphosphino)ferrocene]dichloropalladium(II) and a base, such as $K_3PO_4$) or standard Stille conditions (e.g., in the presence of a palladium(0) catalyst, such as tetrakis(triphenyl-phosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloropalladium(II)), to give compounds 1-3 where $W^2$ is halogen (e.g., Cl, Br, or I) or pseudohalogen (e.g., OTf or OMs). Coupling of compounds 1-3 with amines 1-4 under standard Buchwald-Hartwig amination conditions (e.g., in the presence of a palladium catalyst, such as XPhos Pd G2, and a base, such as $K_3PO_4$) can provide compounds of Formula (I).

Alternatively, compounds 1-1 can be converted to the appropriate compounds 1-5 (e.g., $M^2$ is $B(OH)_2$, Bpin, $BF_3K$, $Sn(Me)_3$, $Sn(Bu)_3$, or ZnCl) and then coupled to 1-6 where $W^3$ is halogen (e.g., Cl, Br, or I) or pseudohalogen (e.g., OTf or OMs) under standard Suzuki conditions (e.g., in the presence of a palladium catalyst, such as [1,1'-bis(diphenylphosphino)ferrocene]dichloro-palladium(II), and a base, such as $K_3PO_4$) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis(triphenylphosphine) palladium(0) or [1,1'-bis(diphenylphosphino)ferrocene]dichloropalladium(II)) to give compounds 1-3, which can be used to synthesize compound of Formula (I).

Scheme I

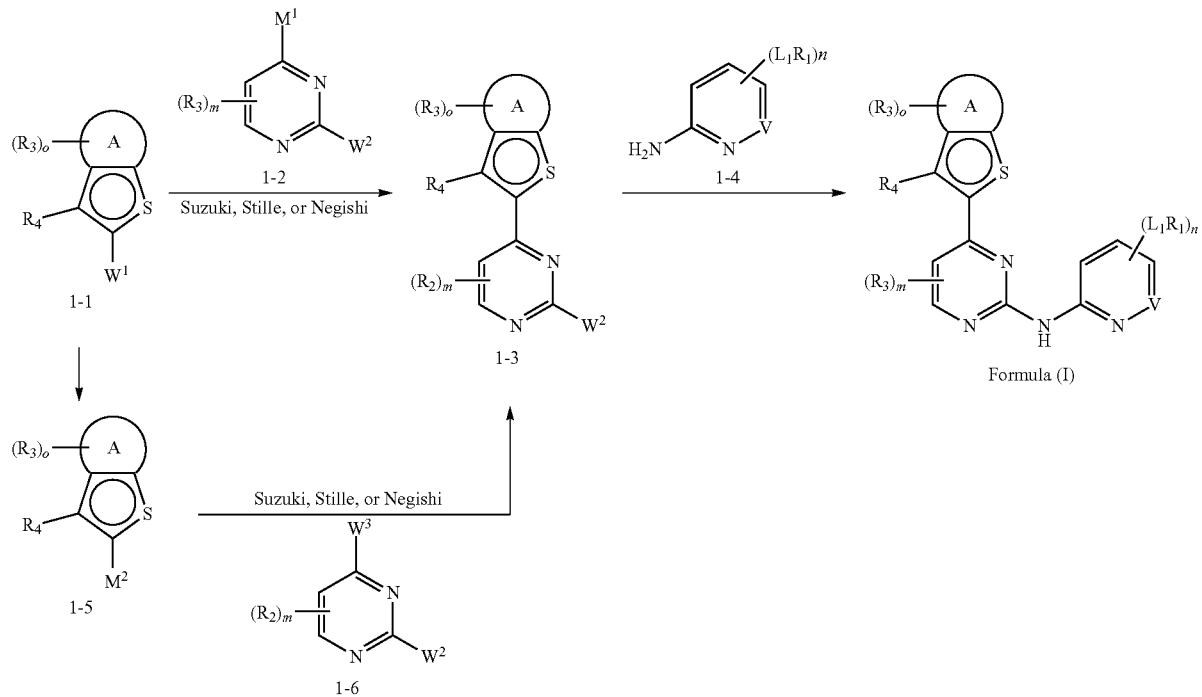

Intermediates for the synthesis of compounds of Formula (I) can be prepared as described in Scheme II. Compounds 2-1 can be halogenated with suitable reagents, such as N-bromo-succinimide or N-iodosuccinimide, to provide compounds 1-1. Alternatively, compounds 2-1 can be metalated in the presence of a strong base, such as lithium diisopropylamide or butyllithium, and an appropriate reagent (e.g., 2-isopropoxy-4,4,5,5-tetramethyl-1,3,2-dioxaborolane, hexamethylditin, trimethyltin chloride, or zinc chloride) to afford compounds 1-5.

Scheme II

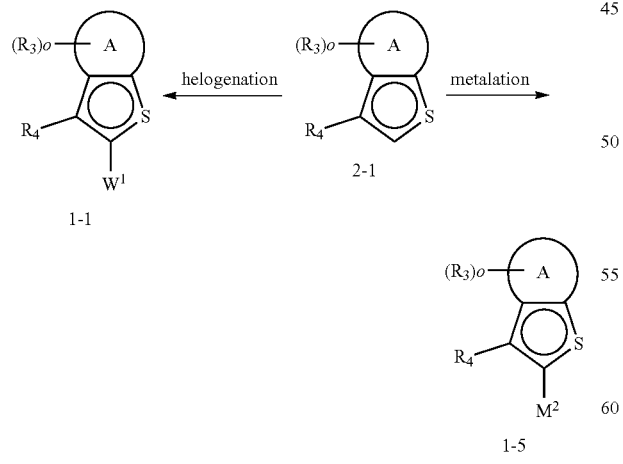

Intermediates for the synthesis of compounds of Formula (I) can be prepared as described in Scheme III. Coupling of compounds 3-1 where $W^4$ is halogen (e.g., $C_1$, Br, or I) or pseudohalogen (e.g., OTf or OMs) with amines 3-2 under either standard Buchwald-Hartwig amination conditions (e.g., in the presence of a palladium catalyst, such as XPhos Pd G2, and a base, such as $K_3PO_4$) or standard conditions for nucleophilic aromatic substitution optionally in the presence of a base (e.g., diisopropylethylamine) can provide compounds 3-3. Nitro compounds 3-3 can be reduced to amino compounds 3-4 under standard reductive conditions such as, but not limited to, $H_2$ in the presence of a transition metal catalyst (e.g., palladium on charcoal) in MeOH, Fe/$NH_4Cl$ in MeOH/$H_2O$, or sodium dithionite in EtOH/$H_2O$. Compounds 3-4 can be employed in Scheme I to afford compounds of Formula (I).

Scheme III

Intermediates for the synthesis of compounds of Formula (I) can be prepared as described in Scheme IV from compounds 4-1 where $M^3$ is a boronic acid, boronate ester, potassium trifluoroborate, or an appropriately substituted metal, such as Sn(Bu)₃ or ZnCl; $R^x$, $R^y$, and $R^z$ are independently H, D, $C_1$-$C_5$ alkyl, 5-7 membered aryl, 5-7 membered heteroaryl, cycloalkyl, or 4-, 5-, 6- or 7-membered heterocycloalkyl wherein said $C_1$-$C_5$ alkyl groups, 5-7 membered aryl, 5-7 membered heteroaryl, cycloalkyl, or 4-, 5-, 6- or 7-membered heterocycloalkyl may be optionally substituted; and optionally $R^x$ and $R^z$, together with alkene to which they are both attached, may form a cycloalkenyl or heterocycloalkenyl group. Compounds 4-1 can be coupled with compounds 4-2 where $Y^1$ is halogen (e.g., $C_1$, Br, or I) or pseudohalogen (e.g., OTf or OMs) under standard Suzuki conditions (e.g., in the presence of a palladium catalyst, such as [1,1'-bis(diphenyl-phosphino)ferrocene]dichloropalladium(II) and a base, such as $K_3PO_4$) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine)palladium(0) or [1,1'-bis(diphenylphosphino)ferrocene]dichloro-palladium(II)), to give compounds 4-3. Alkenes 4-3 can be converted to compounds 4-4 under reductive conditions such as, but not limited to, $H_2$ in the presence of a transition metal catalyst (e.g., palladium on charcoal) in alcohol solvent (e.g., MeOH or EtOH).

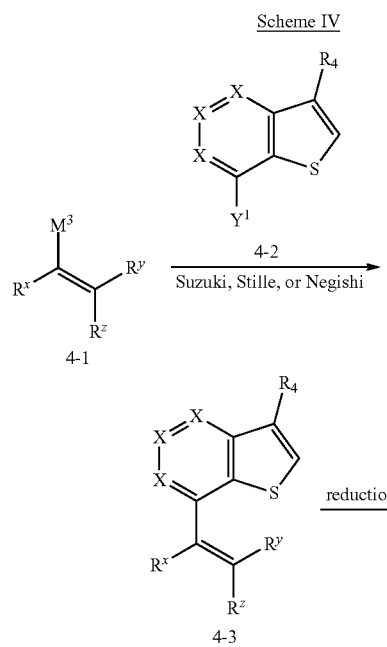

Scheme IV

Intermediates for the synthesis of compounds of Formula (I) can be prepared as described in Scheme V from compounds 5-1 where $R^v$ and $R^w$ are independently H, D, $C_1$-$C_5$ alkyl, 5-7 membered aryl, 5-7 membered heteroaryl, cycloalkyl, or 4-, 5-, 6- or 7-membered heterocycloalkyl wherein said $C_1$-$C_5$ alkyl, 5-7 membered aryl, 5-7 membered heteroaryl, cycloalkyl, or 4-, 5-, 6- or 7-membered heterocycloalkyl may be optionally substituted, and optionally $R^v$ and $R^w$, together with carbon to which they are both attached, may form a cyclic ketone. Reaction with amines 5-2 where $R^q$ is a $C_1$-$C_6$ alkyl group under standard conditions for reductive amination (e.g., in the presence of a reducing agent such as sodium triacetoxyborohydride and optionally an acid, such as acetic acid) can provide compounds 5-3. Hydrolysis of esters 5-3 under standard conditions (e.g., in the presence of a base, such as NaOH, or an acid, such as HCl) can provide carboxylic acids 5-4. Amines 5-4 can be coupled to compounds 5-5 where $Y^1$ is Cl when compound 5-5 is an acid chloride or —OC(=O)$R^s$ where $R^s$ is a $C_1$-$C_6$ alkyl when compound 5-5 is an acid anhydride under appropriate conditions (e.g., in the presence of a base such as triethylamine and optionally a catalyst such as 4-(dimethylamino)pyridine) to afford amides 5-6. Curtius rearrangement of compounds 5-6 under standard conditions, such as in the presence of diphenyl phosphoryl azide, and base, such as triethylamine, and subsequent exposure to aqueous conditions (e.g., dioxane/water) can afford compounds 5-7. Cyclization of 5-7 under appropriate conditions such as in the presence of a dehydrating agent (e.g., phosphorous oxychloride) can provide compounds 5-8.

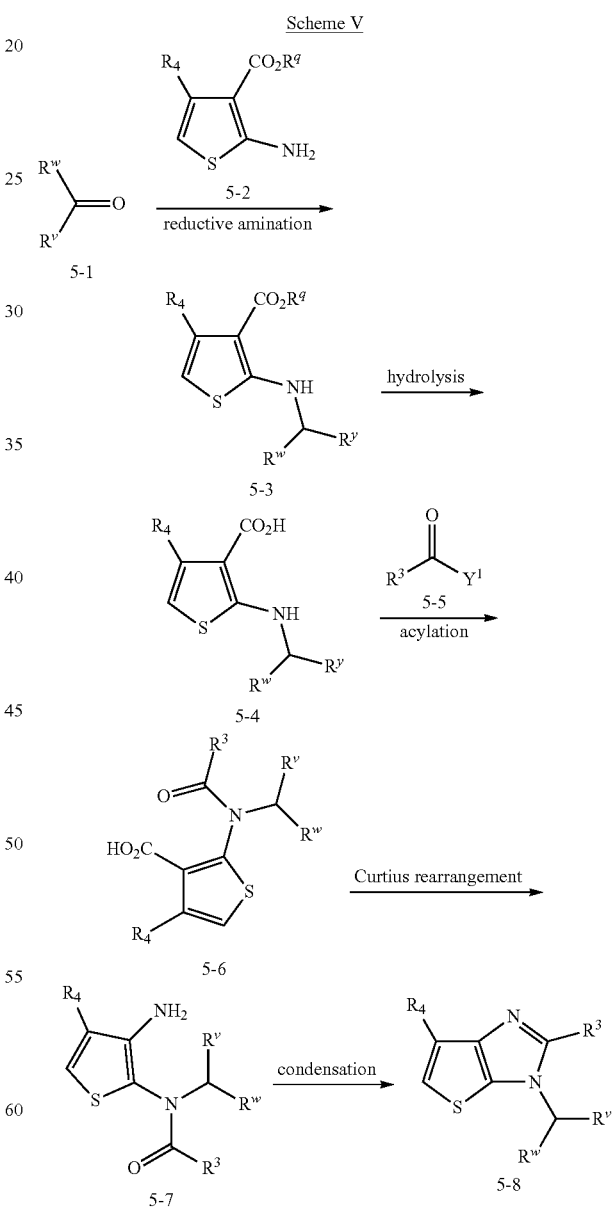

Scheme V

Intermediates for the synthesis of compounds of Formula (I) can be prepared as described in Scheme VI. Carboxylic acids 6-1 can be converted the appropriate acid chlorides 6-2 under standard conditions (e.g., in the presence of a reagent such as oxalyl chloride or thionyl chloride and optionally a catalyst such as N,N-dimethylformamide). Reaction with hydroxyl amine or its salts (e.g., NH$_2$OH.HCl) under appropriate conditions (e.g., in the presence of a base, such as sodium hydroxide) can afford hydroxamic acids 6-3. Compound 6-3 can be acylated with acid chlorides 6-4 where RP is a $C_1$-$C_6$ alkyl group under appropriate conditions (e.g., in the presence of a base, such as triethylamine) to afford compounds 6-5. Compounds 6-5 can be coupled with compounds 6-6 where $R^g$ and $R^h$ are each independently $R^3$ under standard transition-metal-catalyzed C—H activation conditions (e.g., in the presence of a rhodium catalyst, such as pentamethylcyclopentadienyl-rhodium(III) chloride dimer, and a base, such as cesium acetate) to afford compounds 6-8. Alternatively, compounds 6-5 can be coupled with compounds 6-6 where $R^g$ and $R^h$ are each independently $R^3$ under standard transition-metal-catalyzed C—H activation conditions (e.g., in the presence of a rhodium catalyst, such as pentamethylcyclopentadienyl-rhodium(III) chloride dimer, and a base, such as cesium acetate) to afford compounds 6-8 where $R^g$ and $R^h$ are each H. Dehydrative halogenation of compounds 6-8 (e.g., by treating with a reagent such as POCl$_3$ or POBr$_3$) can afford compounds 6-9 where $Y^2$ is halogen (e.g., Cl or Br).

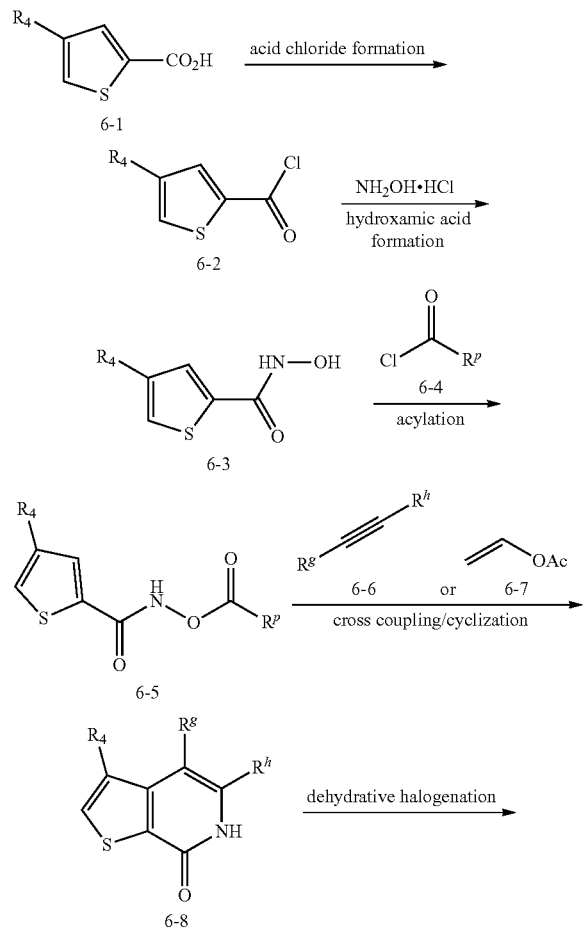

Scheme VI

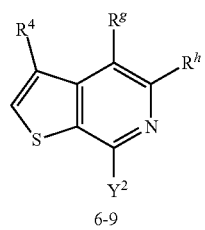

6-9

Intermediates for the synthesis of compounds of Formula (I) can be prepared as described in Scheme VII. Carbonyl compound 7-1 where $R^1$ is $C_1$-$C_5$ alkyl, 5-7 membered aryl, 5-7 membered heteroaryl, cycloalkyl, or 4-, 5-, 6- or 7-membered heterocycloalkyl wherein said $C_1$-$C_5$ alkyl groups, 5-7 membered aryl, 5-7 membered heteroaryl, cycloalkyl, or 4-, 5-, 6- or 7-membered heterocycloalkyl may be optionally substituted can be reacted with an organometallic reagent 7-2 where $M^4$ is an appropriate metal (e.g., Li, MgCl, MgBr, ZnCl, or ZnR$^j$) and R$^j$ is $C_1$-$C_5$ alkyl, 5-7 membered aryl, 5-7 membered heteroaryl, cycloalkyl, or 4-, 5-, 6- or 7-membered heterocycloalkyl wherein said $C_1$-$C_5$ alkyl groups, 5-7 membered aryl, 5-7 membered heteroaryl, cycloalkyl, or 4-, 5-, 6- or 7-membered heterocycloalkyl may be optionally substituted to afford alcohols 7-3. Alternatively, compounds 7-1 can be converted to alcohols 7-5 where $Z^1$ is a fluoroalkyl group (e.g., CF$_3$ or CF$_2$H) upon reaction with silane 7-4 where $Y^3$ is a halogen (e.g., F or Br) or H under standard conditions (e.g., in the presence of tetrabutylammonium fluoride or triphenyl phosphine and N,N'-dimethylpropylene urea).

Scheme VII

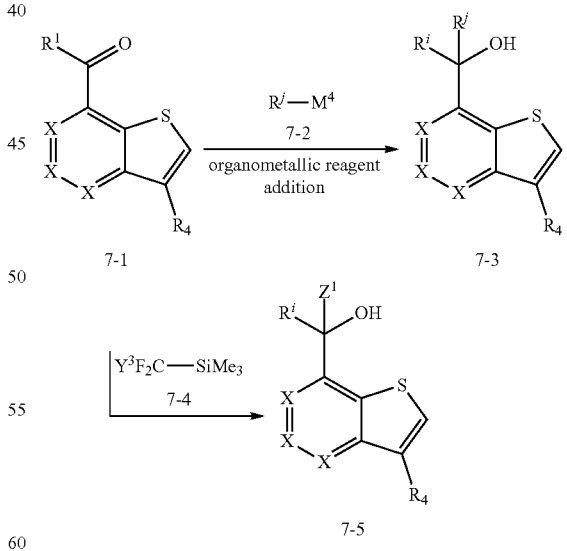

Intermediates for the synthesis of compounds of Formula (I) can be prepared as described in Scheme VIII. Oxidation of compounds 8-1 under standard conditions, such as in the presence of a peroxyacid (e.g., mCPBA) or a peroxide (e.g., urea-hydrogen peroxide adduct), can afford N-oxides 8-2.

Scheme VIII

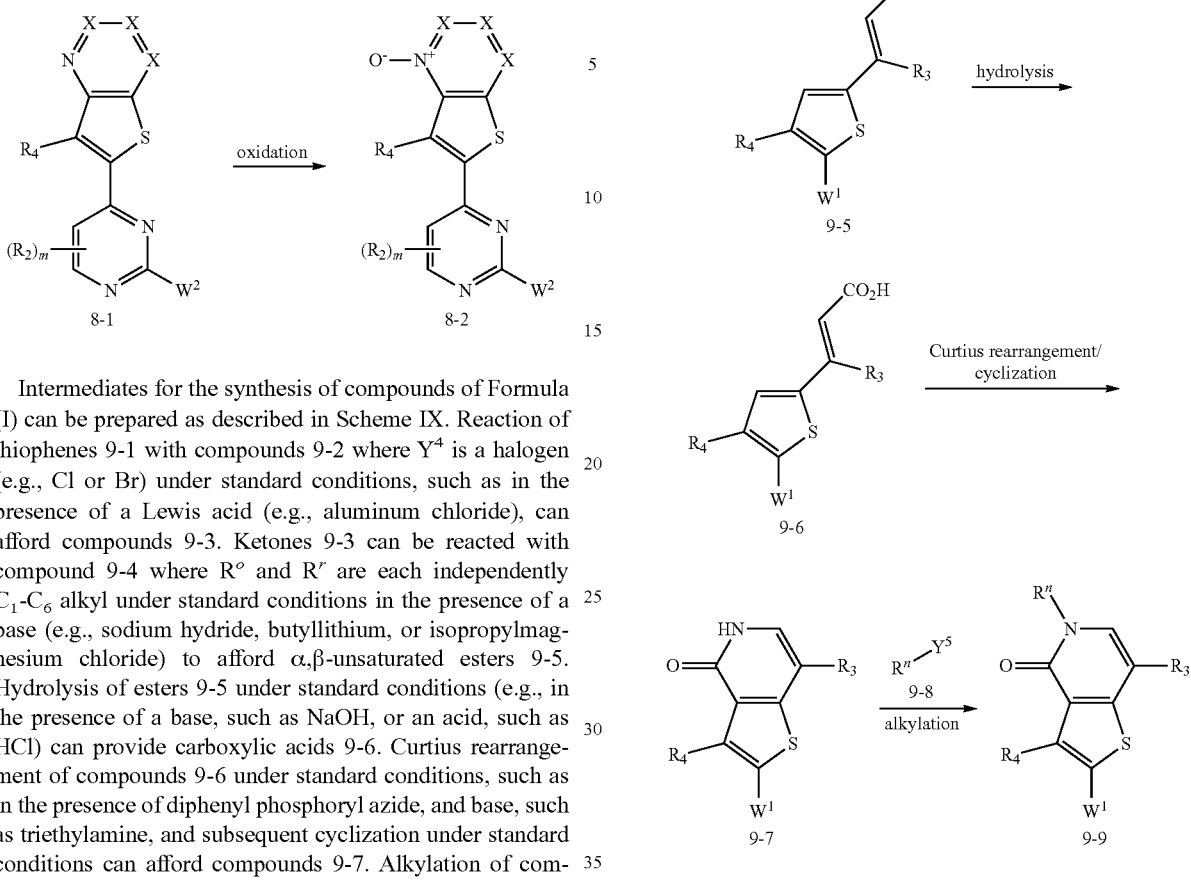

Intermediates for the synthesis of compounds of Formula (I) can be prepared as described in Scheme IX. Reaction of thiophenes 9-1 with compounds 9-2 where $Y^4$ is a halogen (e.g., Cl or Br) under standard conditions, such as in the presence of a Lewis acid (e.g., aluminum chloride), can afford compounds 9-3. Ketones 9-3 can be reacted with compound 9-4 where $R^o$ and $R^r$ are each independently $C_1$-$C_6$ alkyl under standard conditions in the presence of a base (e.g., sodium hydride, butyllithium, or isopropylmagnesium chloride) to afford α,β-unsaturated esters 9-5. Hydrolysis of esters 9-5 under standard conditions (e.g., in the presence of a base, such as NaOH, or an acid, such as HCl) can provide carboxylic acids 9-6. Curtius rearrangement of compounds 9-6 under standard conditions, such as in the presence of diphenyl phosphoryl azide, and base, such as triethylamine, and subsequent cyclization under standard conditions can afford compounds 9-7. Alkylation of compounds 9-7 with halides 9-8 where $Y^5$ is a halide (e.g., Cl, Br, or I) and $R^n$ is a —$C_1$-$C_6$alkyl, —$C_2$-$C_6$alkenyl, —$C_2$-$C_6$alkynyl, $C_1$alk-aryl, $C_1$alk-heteroaryl, cycloalkyl, cycloalkenyl, heterocycloalkyl, or heterocycloalkenyl group can provide compounds 9-9.

Scheme IX

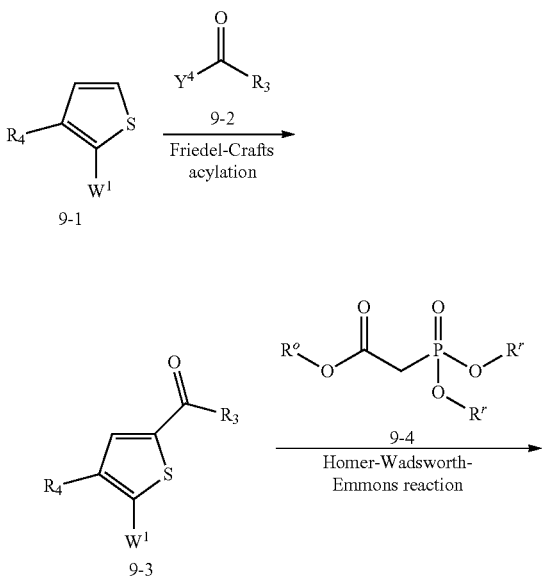

Intermediates for the synthesis of compounds of Formula (I) can be prepared as described in Scheme X. Coupling of compounds 3-1 with compounds 10-1 where x and y are independently 0, 1, 2, or 3; where $Q^1$ is H or a protecting group, such as Boc, Cbz, Bn, PMB, Trt, acetamido, or trifluoracetamido; and where $M^5$ is a boronic acid, boronate ester, potassium trifluoroborate, or an appropriately substituted metal, such as $Sn(Bu)_3$ or ZnCl, under standard Suzuki conditions (e.g., in the presence of a palladium catalyst, such as [1,1'-bis(diphenylphosphino)ferrocene]dichloropalladium(II) and a base, such as $K_3PO_4$ or $K_2CO_3$) or standard Stille conditions (e.g., in the presence of a palladium(0) catalyst, such as tetrakis(triphenylphosphine)palladium(0)) or standard Negishi conditions (e.g., in the presence of a palladium catalyst, such as tetrakis(triphenylphosphine) palladium(0) or [1,1'-bis(diphenylphosphino)ferrocene]dichloropalladium(II)), and then optional deprotection can provide compounds 10-2. Alkylation of amines 10-2 with halides 10-3 where $Y^6$ is a halide (e.g., Cl, Br, or I) or pseudohalide (e.g., OTf, OTs, or OMs) and $R^a$ is a —$C_1$-$C_6$alkyl, —$C_2$-$C_6$alkenyl, —$C_2$-$C_6$alkynyl, $C_1$alk-aryl, $C_1$alk-heteroaryl, cycloalkyl, cycloalkenyl, heterocycloalkyl, or heterocycloalkenyl group can provide compounds 10-4. Compounds 10-4 can be reduced to amines 10-5 under standard reductive conditions such as, but not limited to, $H_2$ in the presence of a transition metal catalyst (e.g., palladium on charcoal or platinum(IV) oxide).

Alternatively, reaction of amines 10-2 under standard conditions for reductive amination (e.g., in the presence of a reducing agent such as sodium triacetoxyborohydride or sodium cyanoborohydride and optionally an acid, such as acetic acid) with compounds 10-6 where $R^b$ and $R^c$ are each independently H, D, $C_1$-$C_6$ alkyl, 5-7 membered aryl, 5-7 membered heteroaryl, cycloalkyl, or 4-, 5-, 6- or 7-membered heterocycloalkyl wherein said $C_1$-$C_5$ alkyl, 5-7 membered aryl, 5-7 membered heteroaryl, cycloalkyl, or 4-, 5-, 6- or 7-membered heterocycloalkyl may be optionally substituted and optionally $R^b$ and $R^c$, together with carbon to which they are both attached, may form a cyclic ketone can provide compounds 10-7. Compounds 10-7 can be reduced to amines 10-8 under standard reductive conditions such as, but not limited to, $H_2$ in the presence of a transition metal catalyst (e.g., palladium on charcoal or platinum(IV) oxide).

Scheme XI

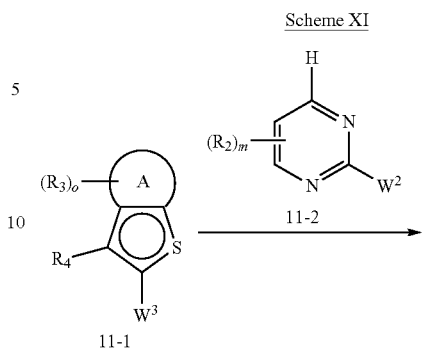

Scheme X

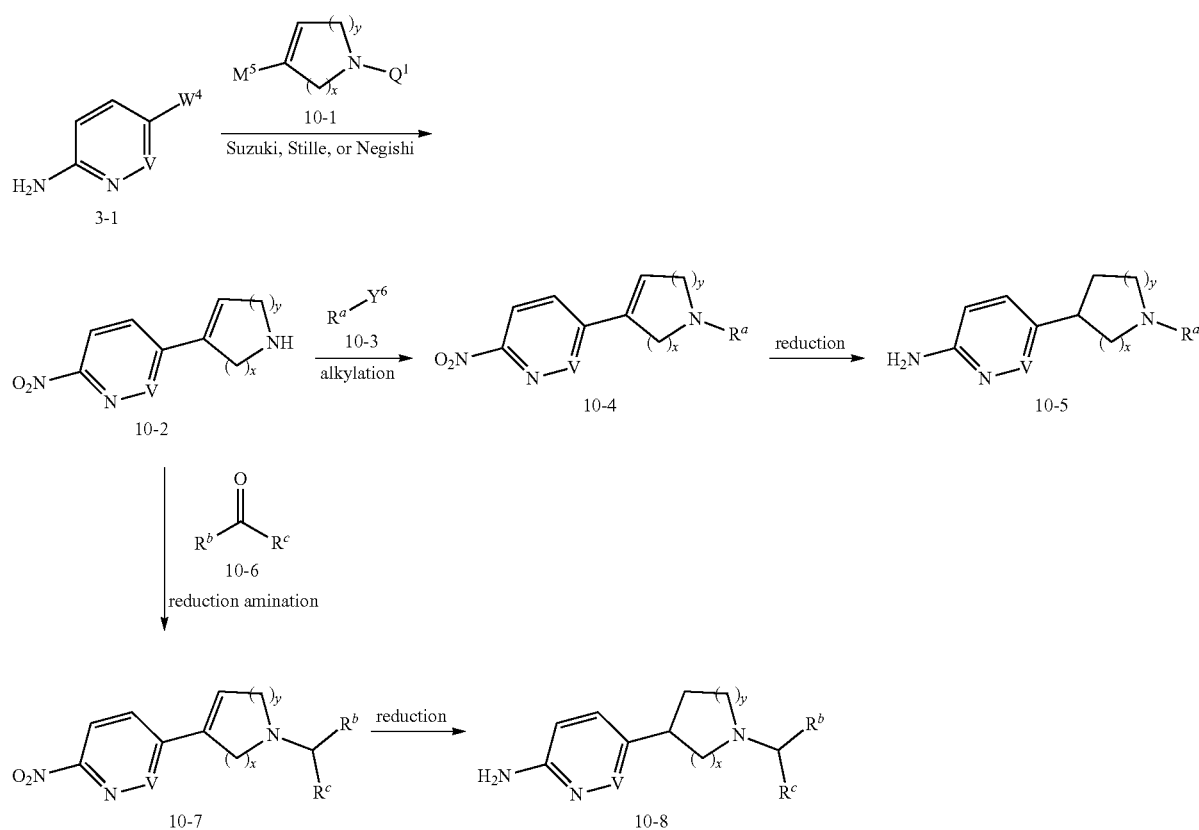

Intermediates for the synthesis of compounds of Formula (I) can be prepared as described in Scheme XI. Metalation of halides 11-1 where $W^3$ is a halogen (e.g., Br or I) under standard metal-halogen exchange conditions (e.g., in the presence of magnesium metal, Grignard reagents (e.g., isopropylmagnesium bromide) or alkyllithium reagents, such as butyllithium) and subsequent addition to pyrimidines 11-2 where $W^2$ is halogen (e.g., Cl, Br, or I) or pseudohalogen (e.g., OTf or OMs) can provide compounds 11-3. Compounds 11-3 can be oxidized to heteroaromatic compounds 1-3 under standard oxidative conditions such as, but not limited to, in the presence of 2,3-dichloro-5,6-dicyano-p-benzoquinone.

-continued

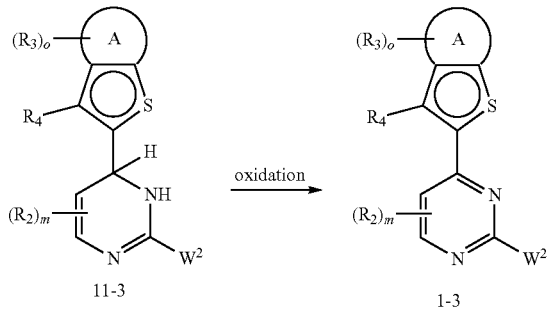

Compounds of Formula (I) can be prepared from compounds 1-3 as shown in Scheme XII. Compounds 1-3 can reacted under standard nucleophilic aromatic substitution conditions (e.g., in the presence of anhydrous $NH_3$ or $NH_4OH$ (aq.)) or standard Buchwald-Hartwig amination conditions (e.g., in the presence of an ammonia surrogate such as benzophenone imine, lithium bis(trimethylsilyl) amide, or tert-butyl carbamate; a palladium catalyst, such as $Pd_2(dba)_3$; a ligand, such as XPhos or XantPhos; and optionally base, such as $Cs_2CO_3$) or standard Ullman coupling conditions (e.g., in the presence of an ammonia source, such as $NH_3$ or ammonium bicarbonate, and a copper catalyst, such as CuO, $CuSO_4$, or CuI) to provide amino pyrimidines 12-1. Coupling of compounds 12-1 with halides 12-2 where $W^5$ is halogen (e.g., Cl, Br, or I) or pseudohalogen (e.g., OTf or OMs) under standard Buchwald-Hartwig amination conditions (e.g., in the presence of a palladium catalyst, such as XPhos Pd G2 or BrettPhos Pd G3, and a base, such as sodium tert-butoxide or $K_3PO_4$) can provide compounds of Formula (I).

pounds 13-2 with anhydrides 13-3 where $R^t$ is a $C_1$-$C_6$ alkyl group under standard conditions (e.g., in the presence of potassium acetate) and subsequent nitrosation/cyclization under standard conditions, such as in the presence of an alkyl nitrite (e.g., isoamyl nitrite), can afford compounds 13-4. Hydrolysis of acyl thienopyrazoles 13-4 under standard conditions (e.g., in the presence of a base, such as NaOH, or an acid, such as HCl) can provide thienopyrazoles 13-5. Compounds 13-5 can be halogenated with suitable reagents, such as iodine, bromine, or N-bromosuccinimide, optionally in the presence of a base (e.g., potassium carbonate or sodium hydroxide) to afford the compounds 13-6 where $W^6$ is a halogen (e.g., Br or I). Alkylation of thienopyrazoles 13-6 with electrophiles 13-7 where $Y^8$ is a halogen (e.g., Cl, Br, or I) or pseudohalogen (e.g., OTf, OTs, or OMs) or other leaving group (e.g., dimethyloxonium) and $R^u$ is a —$C_1$-$C_6$alkyl, —$C_2$-$C_6$alkenyl, —$C_2$-$C_6$alkynyl, $C_1$alkaryl, $C_1$alk-heteroaryl, cycloalkyl, cycloalkenyl, heterocycloalkyl, or heterocycloalkenyl group can provide compounds 13-8. Heteroaryl halides 13-8 can be coupled with the appropriate compounds 13-9 (e.g., $M^6$ is $B(OH)_2$, Bpin, $BF_3K$, $Sn(Me)_3$, $Sn(Bu)_3$, or ZnCl) under standard Suzuki conditions (e.g., in the presence of a palladium catalyst, such as [1,1'-bis(diphenylphosphino)ferrocene]dichloropalladium(II), and a base, such as $K_3PO_4$) or standard Stille conditions (e.g., in the presence of a palladium(0) catalyst, such as tetrakis(triphenylphosphine)palladium(0)) or standard Negishi conditions (e.g., in the presence of a palladium (0) catalyst, such as tetrakis(triphenylphosphine)palladium (0) or [1,1'-bis(diphenylphosphino)ferrocene] dichloropalladium(II)) to give compounds 13-10.

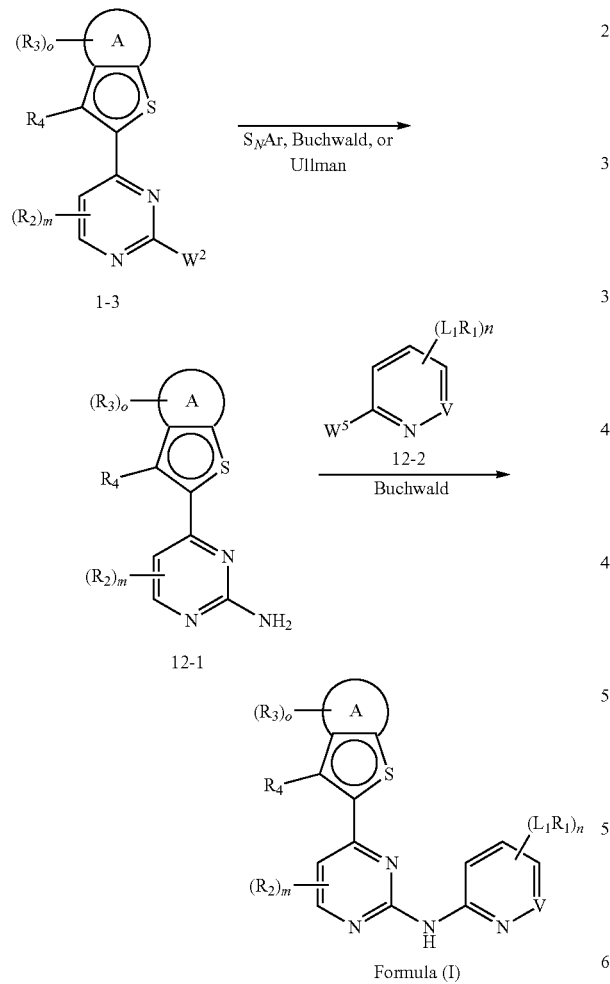

Scheme XII

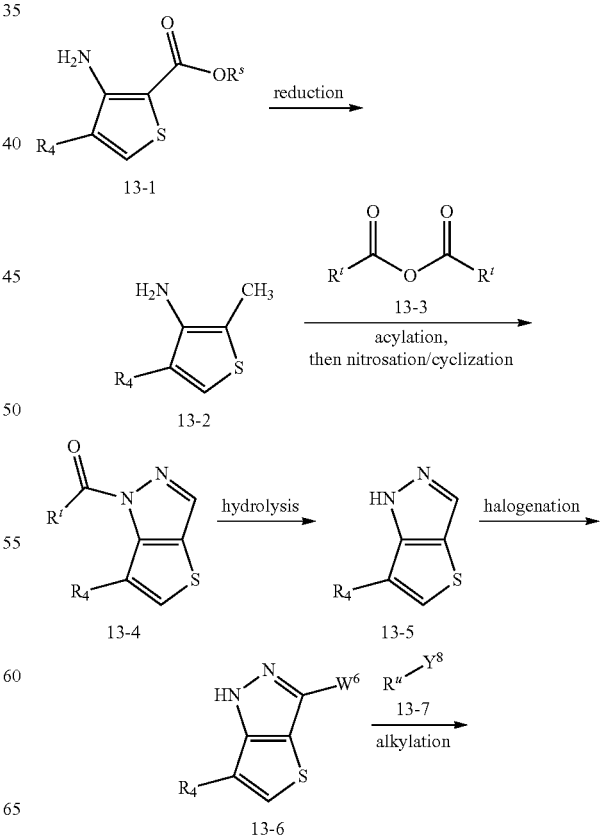

Scheme XIII

Intermediates for the synthesis of compounds Formula (I) can be prepared as described in Scheme XIII. Reduction of esters 13-1 where $R^s$ is a —$C_1$-$C_6$ alkyl group under standard conditions (e.g., in the presence of lithium aluminum hydride) can provide compounds 13-2. Acylation of com-

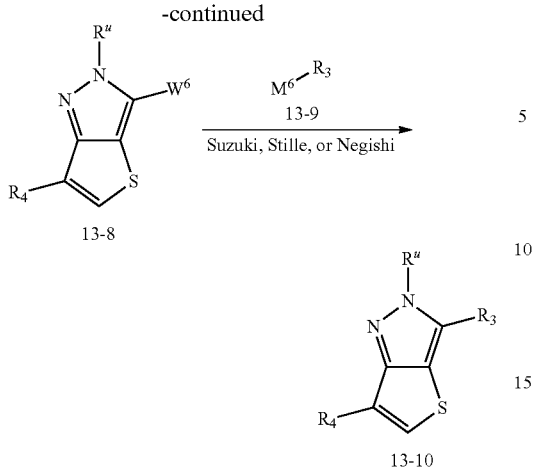

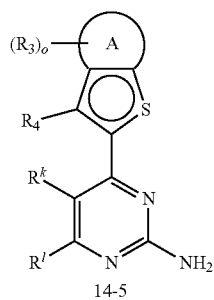

Intermediates for the synthesis of compounds of Formula (I) can be prepared as described in Scheme XIV. Friedel-Crafts acylation of compounds 2-1 with acid halides 14-1 where $R^k$ is H, D, F, $C_1$-$C_8$ alkoxide, $C_1$-$C_8$ alkyl, fluoroalkyl, or CN and $Y^9$ is a halogen (e.g., Cl or Br) under standard conditions, such as in the presence of a Lewis acid (e.g., $AlCl_3$), can afford ketones 14-2. Condensation of compounds 14-2 with acetal 14-3 where $R^1$ is H, D, —$C_1$-$C_8$ alkoxide, —$C_1$-$C_8$ alkyl, fluoroalkyl, or CN can afford compounds 14-4. Subsequent condensation of compounds 14-4 with guanidine or one of its salts (e.g., guanidine hydrochloride) optionally in the presence of a base (e.g., $K_2CO_3$) can afford amino pyrimidines 14-5.

Intermediates for the synthesis of compounds of Formula (I) can be prepared as described in Scheme XV. Compounds 13-8 can be coupled with compounds 4-1 under standard Suzuki conditions (e.g., in the presence of a palladium catalyst, such as [1,1'-bis(diphenylphosphino) ferrocene] dichloropalladium(II), and a base, such as $K_3PO_4$) or standard Stille conditions (e.g., in the presence of a palladium(0) catalyst, such as tetrakis(triphenylphosphine)palladium(0)) or standard Negishi conditions (e.g., in the presence of a palladium(0) catalyst, such as tetrakis (triphenylphosphine) palladium(0) or [1,1'-bis(diphenylphosphino)ferrocene]dichloropalladium(II)) to give compounds 15-1. Alkenes 15-1 can be converted to compounds 15-2 under reductive conditions such as, but not limited to, $H_2$ in the presence of a transition metal catalyst (e.g., palladium on charcoal) in alcohol solvent (e.g., MeOH or EtOH).

Scheme XIV

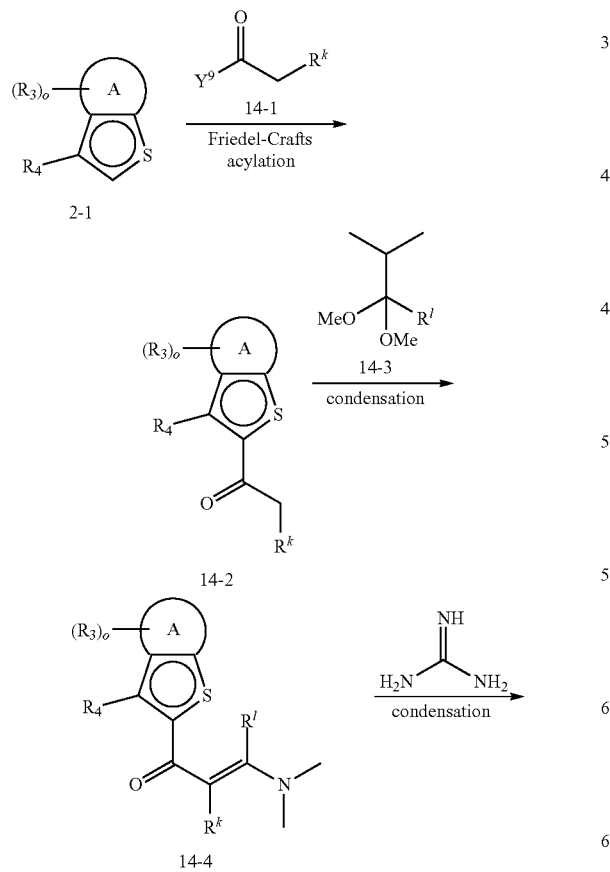

Scheme XV

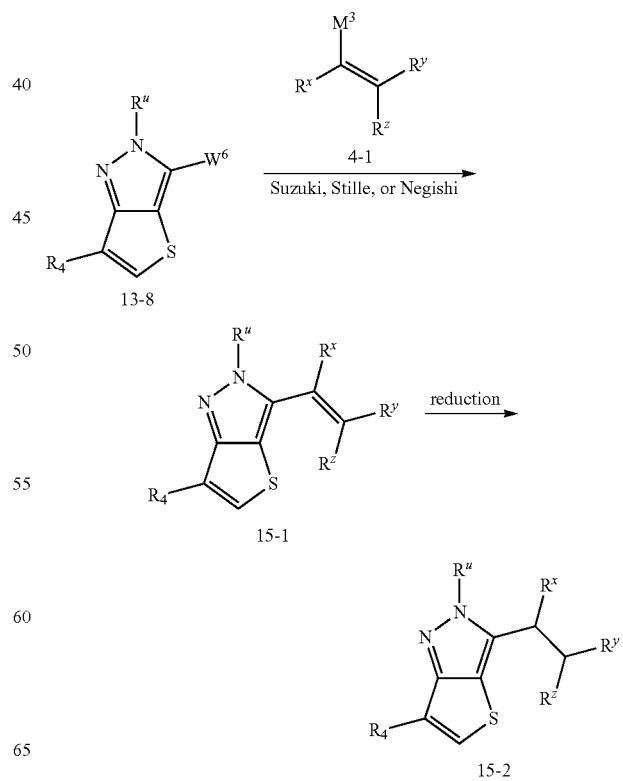

Example 1. 4-(3-Cyclopentyl-2,6-dimethyl-3H-thieno[2,3-d]imidazol-5-yl)-N-(5-(4-ethylpiperazin-1-yl)pyridin-2-yl)-5-fluoropyrimidin-2-amine

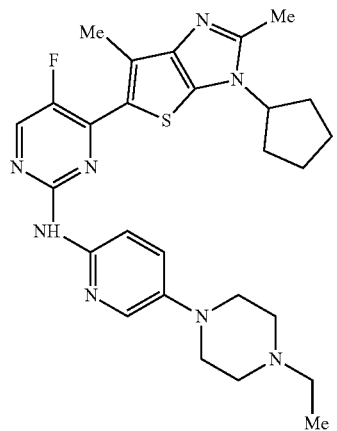 [SMILES: CCN1CCN(c2ccc(Nc3ncc(F)c(-c4sc5c(nc(C)n5C5CCCC5)c4C)n3)nc2)CC1]

Step 1: Methyl 2-(cyclopentylamino)-4-methylthiophene-3-carboxylate

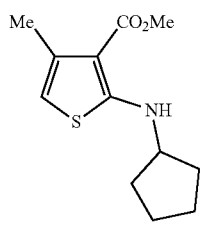

NaBH(OAc)$_3$ (18.382 g, 86.7 mmol, 2.50 equiv.) was added portionwise to a solution of methyl 2-amino-4-methylthiophene-3-carboxylate (5.940 g, 34.7 mmol, 1.00 equiv.), cyclo-pentanone (7.556 g, 86.7 mmol, 2.50 equiv.), and acetic acid (5.209 g, 86.7 mmol, 2.50 equiv.) in DCE (120 mL). The resulting suspension was stirred at ambient temperature for 18 h. The reaction mixture was slowly poured over 10% Na$_2$CO$_3$ solution (200 mL) and stirred until gas evolution ceased. The organic layer was separated, and the aqueous layer extracted with DCM (50 mL×3). The combined organic phase was washed with H$_2$O (50 mL) and brine (50 mL), dried over Na$_2$SO$_4$, filtered, and concentrated under reduced pressure. The residue was purified by flash chromatography on silica gel (80 g) (0-5% MTBE in heptanes) to give the title compound (5.221 g, 21.8 mmol, 62.9% yield) as colorless oil. R$_f$=0.6 (10% MTBE in heptanes). LCMS calc. for C$_{12}$H$_{18}$NO$_2$S [M+H]$^+$: m/z=240.1; Found: 240.0.

Step 2. 2-(Cyclopentylamino)-4-methylthiophene-3-carboxylic Acid

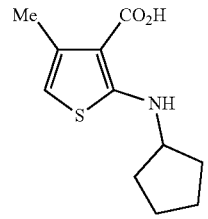 [SMILES: Cc1csc(NC2CCCC2)c1C(=O)O]

Powder NaOH (8.276 g, 218.2 mmol, 10.0 equiv.) was dissolved in H$_2$O (30 mL) and the resulting aqueous solution was slowly added to the solution of methyl 2-(cyclopentylamino)-4-methylthiophene-3-carboxylate (5.221 g, 21.8 mmol, 1.00 equiv.) in MeOH (30 mL) at ambient temperature. The reaction mixture was heated at 80° C. for 18 h. The organic solvent was evaporated under reduced pressure. The remaining aqueous solution was diluted with H$_2$O (30 mL), acidified with 4 N HCl solution (to pH 3-4), and extracted with MTBE (50 mL×3). The combined organic phase was washed with H$_2$O (50 mL) and brine (50 mL), dried over Na$_2$SO$_4$, filtered, and evaporated in vacuo to give the title compound (4.175 g, 18.5 mmol, 85.0% yield) as an amber solid. R$_f$=0.3 (30% MTBE in heptanes). LCMS calc. for C$_{11}$H$_{16}$NO$_2$S [M+H]$^+$: m/z=226.1; Found: 226.0.

Step 3. 2-(N-Cyclopentylacetamido)-4-methylthiophene-3-carboxylic Acid

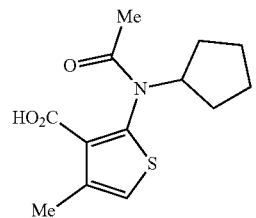 [SMILES: CC(=O)N(c1scc(C)c1C(=O)O)C1CCCC1]

Acetic anhydride (4.729 g, 46.3 mmol, 2.50 equiv.) was added dropwise into the solution of 2-(cyclopentylamino)-4-methylthiophene-3-carboxylic acid (4.175 g, 18.5 mmol, 1.00 equiv.), Et3N (5.625, 55.6 mmol, 3.00 equiv.), and DMAP (226 mg, 1.85 mmol, 0.10 equiv.) in DCM (50 mL). The resulting mixture was stirred at room temperature for 18 h. The reaction mixture was poured over cold saturated NH4Cl solution (100 mL). The organic layer was separated and the aqueous layer extracted twice with DCM (50 mL). The combined organic phase was washed with H2O (50 mL) and brine (50 mL), dried over Na$_2$SO$_4$, filtered, and evaporated in vacuo. The crude product was purified by flash chromatography on silica gel (0-50% EtOAc in heptanes as eluent) to give the title compound (3.897 g, 14.6 mmol, 78.8% yield) as a yellow viscous oil. R$_f$=0.2 (50% EtOAc in heptanes). LCMS calc. for C$_{13}$H$_{18}$NO$_3$S [M+H]$^+$: m/z=268.1; Found: 268.0.

Step 4. N-(3-Amino-4-methylthiophen-2-yl)-N-cyclopentylacetamide

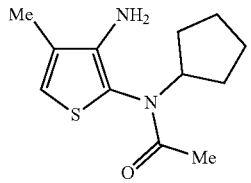

To the solution of 2-[acetyl(cyclopentyl)amino]thiophene-3-carboxylic acid (3.897 g, 14.6 mmol) and Et₃N (7.375 g, 72.9 mmol, 5.00 equiv.) in 1,4-dioxane (40 mL), DPPA (10.029 g, 36.4 mmol, 2.50 equiv.) was added dropwise. The reaction mixture was stirred at room temperature for 1 h. H2O (40 mL) was added and the reaction was heated to reflux for 18 h. The reaction mixture was cooled to room temperature and 2 M NaOH solution (20 mL) was added and the resulting mixture was further stirred at room temperature for 30 min. The reaction mixture was poured over saturated NH₄Cl solution (30 mL) and extracted with DCM (50 mL×3). The combined organic phase was washed with H₂O (50 mL) and brine (50 mL), dried over Na₂SO₄, filtered, and concentrated under reduced pressure. The crude product was used in the next step without further purification.

Step 5. 3-Cyclopentyl-2,6-dimethyl-3H-thieno[2,3-d]imidazole

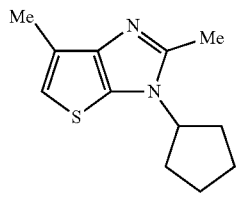 [SMILES: Cc1csc2c1nc(C)n2C1CCCC1]

To the solution of N-(3-amino-4-methylthiophen-2-yl)-N-cyclopentylacetamide (crude, from previous step, 4.118 g, 17.3 mmol, 1.00 equiv.) in toluene (40 mL), POCl3 (2.782 g, 18.1 mmol, 1.05 mmol) was added dropwise at ambient temperature. The resulting solution was heated at 100° C. for 18 h. The reaction mixture was cooled to room temperature and poured over 10% Na2CO3 solution. The organic layer was separated, and the aqueous layer extracted with EtOAc (3 mL×3). The combined organic phase was washed with brine (15 mL), dried over Na₂SO₄, filtered, and concentrated under reduced pressure. The residue was purified by flash chromatography on silica gel column (0%-75% EtOAc and 0.1% Et3N in heptanes) to give the title compound (1.547 g, 7.02 mmol, 40.6% yield) as amber oil. $R_f$=0.2 (50% EtOAc in heptanes). LCMS calc. for $C_{12}H_{17}N_2S$ [M+H]⁺: m/z=221.1; Found: 221.0.

Step 6. 3-Cyclopentyl-2,6-dimethyl-5-(4,4,5,5-tetramethyl-1,3,2-dioxaborolan-2-yl)-3H-thieno[2,3-d]imidazole

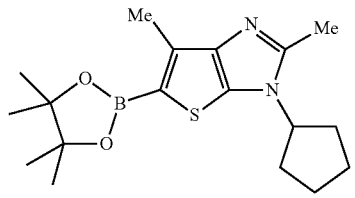 [SMILES: Cc1c(B2OC(C)(C)C(C)(C)O2)sc2c1nc(C)n2C1CCCC1]

The solution of LDA (1.29 mL, 9.74 mmol, 5.00 equiv.) in THF and hexanes (1.40 M) was added dropwise to the solution of 3-cyclopentyl-2,6-dimethylthieno[2,3-d]imidazole (429 mg, 1.95 mmol, 1.00 equiv.) and 4,4,5,5-tetramethyl-2-propan-2-yloxy-1,3,2-dioxaborolane (725 mg, 3.89 mmol, 2.00 equiv.) in THF (10 mL) at −78° C. The reaction mixture was stirred at −78° C. and monitored with LCMS. When LCMS analysis indicated the complete consumption of the starting material (~1 h), the reaction was quenched by the dropwise addition of saturated NH4Cl (15 mL). The resulting mixture was extracted with CHCl₃/iPrOH (1:1, 20 mL x 3). The combined organic phase was washed with H₂O (10 mL) and brine (10 mL), dried over anhydrous Na₂SO₄, filtered, and evaporated in vacuo. The residue was used in the next step without further purification. LCMS calc. for $C_{18}H_{28}BN_2O_2S$ [M+H]⁺: m/z=347.2; Found: 347.1.

Step 7. 5-(2-Chloro-5-fluoropyrimidin-4-yl)-3-cyclopentyl-2,6-dimethyl-3H-thieno[2,3-d]imidazole

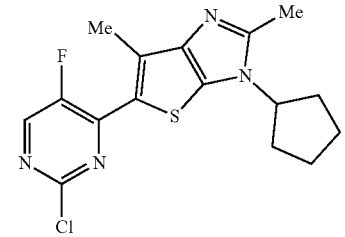 [SMILES: Cc1c(-c2nc(Cl)ncc2F)sc2c1nc(C)n2C1CCCC1]

To the crude boronate ester in 1,4-dioxane (8 mL) was added 2,6-dichloro-5-fluororacil (285 mg, 1.71 mmol, 1.00 equiv.), Pd(dppf)Cl₂ (62 mg, 0.09 mmol, 0.05 equiv.), K₃PO₄ (1.449 g, 6.83 mmol, 4.00 equiv.), and H₂O (2 mL). The resulting mixture was stirred at 100° C. under a nitrogen atmosphere for 6 h, when TLC analysis showed the disappearance of the starting material. The reaction mixture was cooled to ambient temperature and partitioned between H₂O (15 mL) and EtOAc (15 mL). The organic layer was separated and the aqueous phase was extracted with EtOAc (15 mL×3). The combined organic phase was washed with brine (15 mL), dried over anhydrous Na2SO4, filtered, and evaporated in vacuo. The residue was purified by flash column chromatography (0-50% EtOAc in heptanes) to give the title compound (120 mg, 0.34 mmol, 20.0% yield) as yellow solid. $R_f$=0.25 (50% EtOAc in heptanes). LCMS calc. for $C_{16}H_{17}ClFN_4S$ [M+H]⁺ m/z=351.1; Found: 351.0.

Step 8. 4-(3-Cyclopentyl-2,6-dimethyl-3H-thieno[2,3-d]imidazol-5-yl)-N-(5-(4-ethyl-piperazin-1-yl)pyridin-2-yl)-5-fluoropyrimidin-2-amine The suspension of 5-(2-chloro-5-fluoropyrimidin-4-yl)-3-cyclopentyl-2,6-dimethylthieno[2,3-d]imidazole (70.0 mg, 0.20 mmol, 1.00 equiv.), 5-(4-ethylpiperazin-1-yl)pyridin-2-amine (41.0 mg, 0.20 mmol, 1.00 equiv.), XPhos Pd G2 (7.9 mg, 0.01 mmol, 0.05 equiv.), and $K_3PO_4$ (169.0 mg, 0.80 mmol, 4.00 equiv.) in 1,4-dioxane (2 mL) was heated at 100° C. under $N_2$ atmosphere for 18 h. The reaction mixture was cooled to room temperature and TFA (2 drops) was added. The inorganic salts were filtered off and the filtrate was purified by Prep-HPLC on a $C_{18}$ column (6%-80% MeCN in $H_2O$) to give the title compound as its HCl salt (46.2 mg, 0.09 mmol, 43.6% yield), light yellow solid. $^1$H NMR (300 MHz, $CD_3OD$) δ 8.81 (d, J=3.0 Hz, 1H), 8.28 (dd, J=9.7, 2.8 Hz, 1H), 7.95 (d, J=2.7 Hz, 1H), 7.59 (d, J=9.6 Hz, 1H), 5.15-5.02 (m, 1H), 3.97 (t, J=10.8 Hz, 2H), 3.74 (t, J=10.6 Hz, 2H), 3.40-3.33 (m, 2H), 3.28-3.24 (m, 2H), 2.89 (s, 3H), 2.74 (d, J=3.1 Hz, 3H), 2.46-2.33 (m, 2H), 2.27-1.78 (m, 7H), 1.44 (t, J=7.3 Hz, 3H). LCMS calc. for $C_{27}H_{34}FN_8S$ $[M+H]^+$: m/z=521.3; Found: 520.9.

Examples listed in Tables 1-1 and 1-2 are synthesized according to procedures analogous to Example 1.

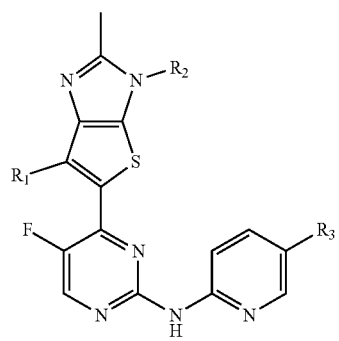

TABLE 1-1

Examples 2-13

| Example | $R_1$ | $R_2$ | $R_3$ | LCMS $[M + H]^+$ |
|---|---|---|---|---|
| 2 | Me | iso-propyl | piperazine-N-ethyl | 495.1 |
| 3 | Me | iso-propyl | CH2-piperazine-N-ethyl | 509.3 |
| 4 | Me | cyclo-butyl | piperazine-N-ethyl | 507.2 |
| 5 | Me | cyclo-pentyl | piperidine-N-ethyl (4-linked) | 520.1 |
| 6 | Me | cyclo-pentyl | piperidine-N-methyl (4-linked) | 506.1 |
| 7 | Me | cyclo-pentyl | piperazine-N-methyl | 507.2 |
| 8 | Me | cyclo-butyl | piperidine-N-ethyl (4-linked) | 506.2 |
| 9 | Me | iso-propyl | piperazine-N-methyl | 481.1 |
| 10 | Me | cyclo-butyl | CH2-piperazine-N-ethyl | 521.2 |
| 11 | Me | cyclo-pentyl | 3,3-difluoropyrrolidine | 513.8 |
| 12 | Me | cyclo-pentyl | CH2-piperazine-N-ethyl | 535.0 |
| 13 | H | cyclo-pentyl | piperazine-N-methyl | 493.1 |

TABLE 1-2

Examples 2-13

| Example | Compound name | NMR |
|---|---|---|
| 2 | N-(5-(4-Ethylpiperazin-1-yl)pyridin-2-yl)-5-fluoro-4-(3-isopropyl-2,6-dimethyl-3H-thieno[2,3-d]imidazol-5-yl)pyrimidin-2-amine | $^1$H NMR (300 MHz, CD$_3$OD) δ 8.78 (d, J = 3.1 Hz, 1H), 8.25 (dd, J = 9.7, 2.9 Hz, 1H), 7.95 (d, J = 2.7 Hz, 1H), 7.63 (d, J = 9.6 Hz, 1H), 5.01-4.92 (m, 1H), 3.97-3.91 (m, 2H), 3.77-3.71 (m, 2H), 3.43-3.13 (m, 6H), 2.86 (s, 3H), 2.75 (d, J = 3.0 Hz, 3H), 1.68 (d, J = 6.7 Hz, 6H), 1.44 (t, J = 7.3 Hz, 3H). |
| 3 | N-(5-((4-Ethylpiperazin-1-yl)methyl)pyridin-2-yl)-5-fluoro-4-(3-isopropyl-2,6-dimethyl-3H-thieno[2,3-d]imidazol-5-yl)pyrimidin-2-amine | $^1$H NMR (300 MHz, CD$_3$OD) δ 8.81 (d, J = 3.0 Hz, 1H), 8.37-8.31 (m, 2H), 7.70-7.63 (m, 1H), 5.01-4.92 (m, 1H), 3.77 (s, 2H), 3.32-3.04 (m, 9H), 2.88 (d, J = 2.9 Hz, 3H), 2.75 (d, J = 3.0 Hz, 3H), 2.04 (s, 2H), 1.68 (d, J = 6.7 Hz, 6H), 1.36 (t, J = 7.3 Hz, 3H). |
| 4 | 4-(3-Cyclobutyl-2,6-dimethylthieno[2,3-d]imidazol-5-yl)-N-[5-(4-ethylpiperazin-1-yl)-pyridin-2-yl]-5-fluoro-pyrimidin-2-amine | $^1$H NMR (300 MHz, CD$_3$OD) δ 8.76 (d, J = 3.1 Hz, 1H), 8.24 (dd, J = 9.7, 2.9 Hz, 1H), 7.93 (d, J = 2.7 Hz, 1H), 7.62 (d, J = 9.6 Hz, 1H), 5.25-5.02 (m, 1H), 4.14-3.37 (m, 8H), 3.28-3.20 (m, 2H), 2.79 (s, 3H), 2.74 (d, J = 3.0 Hz, 3H), 2.71-2.61 (m, 4H), 2.11-2.03 (m, 2H), 1.42 (t, J = 7.3 Hz, 3H). |
| 5 | 4-(3-Cyclopentyl-2,6-dimethyl-3H-thieno[2,3-d]imidazol-5-yl)-N-(5-(1-ethylpiperidin-4-yl)pyridin-2-yl)-5-fluoro-pyrimidin-2-amine | $^1$H NMR (300 MHz, CD$_3$OD) δ 8.55 (d, J = 3.1 Hz, 1H), 8.16-8.02 (m, 2H), 7.46 (d, J = 9.7 Hz, 1H), 4.85-4.80 (m, 1H), 3.58-3.49 (m, 1H), 3.02 (q, J = 7.4 Hz, 2H), 2.97-2.86 (m, 3H), 2.62 (d, J = 6.6 Hz, 3H), 2.53 (d, J = 3.1 Hz, 3H), 2.45 (d, J = 3.3 Hz, 1H), 2.21-2.01 (m, 4H), 1.91-1.79 (m, 6H), 1.71-1.64 (m, 2H), 1.19 (t, J = 7.3 Hz, 3H). |
| 6 | 4-(3-Cyclopentyl-2,6-dimethyl-3H-thieno[2,3-d]imidazol-5-yl)-5-fluoro-N-(5-(1-methylpiperidin-4-yl)pyridin-2-yl)pyrimidin-2-amine | — |
| 7 | 4-(3-Cyclopentyl-2,6-dimethyl-3H-thieno[2,3-d]imidazol-5-yl)-5-fluoro-N-(5-(4-methyl-piperazin-1-yl)pyridin-2-yl)pyrimidin-2-amine | $^1$H NMR (300 MHz, CD$_3$OD) δ 8.44 (d, J = 3.3 Hz, 1H), 7.88 (dd, J = 9.6, 2.9 Hz, 1H), 7.71 (s, 1H), 7.49 (d, J = 9.6 Hz, 1H), 5.01-4.92 (m, 1H), 3.39-3.17 (m, 4H), 2.99-2.84 (m, 4H), 2.79 (s, 3H), 2.53 (s, 3H), 2.51 (d, J = 3.0 Hz, 3H), 2.20-2.03 (m, 2H), 1.90-1.64 (m, 6H). |
| 8 | 4-(3-Cyclobutyl-2,6-dimethyl-3H-thieno[2,3-d]imidazol-5-yl)-N-(5-(1-ethylpiperidin-4-yl)pyridin-2-yl)-5-fluoro-pyrimidin-2-amine | $^1$H NMR (300 MHz, CD$_3$OD) δ 8.81 (d, J = 3.0 Hz, 1H), 8.47-8.25 (m, 2H), 7.67 (s, 1H), 5.20 (q, J = 8.8 Hz, 1H), 3.75 (d, J = 12.7 Hz, 2H), 3.31-3.08 (m, 6H), 2.80 (d, J = 1.9 Hz, 3H), 2.75 (t, J = 2.5 Hz, 4H), 2.71-2.61 (m, 3H), 2.25 (d, J = 14.3 Hz, 2H), 2.08 (td, J = 10.3, 4.1 Hz, 4H), 1.41 (t, J = 7.3 Hz, 3H). |
| 9 | 5-Fluoro-4-(3-isopropyl-2,6-dimethyl-3H-thieno[2,3-d]imidazol-5-yl)-N-(5-(4-methylpiperazin-1-yl)pyridin-2-yl)pyrimidin-2-amine, HCl salt | 1H NMR (300 MHz, CD$_3$OD) δ 8.78 (d, J = 3.1 Hz, 1H), 8.25 (dd, J = 9.7, 2.9 Hz, 1H), 7.95 (d, J = 2.7 Hz, 1H), 7.63 (d, J = 9.6 Hz, 1H), 5.01-4.92 (m, 1H), 3.99-3.82 (m, 2H), 3.75-3.60 (m, 2H), 3.45-3.30 (m, 4H), 3.02 (s, 3H), 2.86 (s, 3H), 2.75 (d, J = 3.0 Hz, 3H), 1.68 (d, J = 6.7 Hz, 6H). |
| 10 | 4-(3-Cyclobutyl-2,6-dimethylthieno[2,3-d]imidazol-5-yl)-N-[5-[(4-ethylpiperazin-1-yl)methyl]pyridin-2-yl]-5-fluoropyrimidin-2-amine, HCl salt | $^1$H NMR (300 MHz, CD$_3$OD) δ 8.88 (d, J = 2.9 Hz, 1H), 8.56 (s, 1H), 8.50 (d, J = 9.1 Hz, 1H), 7.68 (d, J = 9.1 Hz, 1H), 5.25-5.15 (m, 1H), 4.22 (s, 2H), 4.14-3.37 (m, 8H), 3.23-3.09 (m, 2H), 2.84 (d, J = 7.6 Hz, 3H), 2.77 (d, J = 3.0 Hz, 3H), 2.69 (m, 4H), 2.14-2.05 (m, 2H), 1.41 (t, J = 7.3 Hz, 3H). |
| 11 | 4-(3-Cyclopentyl-2,6-dimethyl-3H-thieno[2,3-d]imidazol-5-yl)-N-(5-(3,3-difluoropyrrolidin-1-yl)pyridin-2-yl)-5-fluoro-pyrimidin-2-amine | $^{1H}$ NMR (300 MHz, CD$_3$OD) δ 8.72 (d, J = 3.2 Hz, 1H), 7.86 (dd, J = 9.5, 2.9 Hz, 1H), 7.54 (t, J = 6.0 Hz, 2H), 5.06 (dt, J = 15.4, 7.7 Hz, 1H), 3.78-3.57 (m, 4H), 2.83 (s, 3H), 2.73 (d, J = 3.1 Hz, 3H), 2.67-2.55 (m, 2H), 2.43-2.31 (m, 2H), 2.17-1.86 (m, 6H). |

TABLE 1-2-continued

Examples 2-13

| Example | Compound name | NMR |
|---|---|---|
| 12 | 4-(3-Cyclopentyl-2,6-dimethyl-3H-thieno[2,3-d]imidazol-5-yl)-N-(5-((4-ethylpiperazin-1-yl)methyl)pyridin-2-yl)-5-fluoropyrimidin-2-amine | — |
| 13 | 4-(3-Cyclopentyl-2-methyl-3H-thieno[2,3-d]imidazol-5-yl)-5-fluoro-N-(5-(4-methylpiperazin-1-yl)pyridin-2-yl)pyrimidin-2-amine, HCl salt | $^1$H NMR (300 MHz, CD$_3$OD) δ 8.78 (d, J = 2.8 Hz, 1H), 8.27 (d, J = 8.5 Hz, 1H), 8.15 (s, 1H), 7.95 (s, 1H), 7.56 (d, J = 9.5 Hz, 1H), 5.13 (dd, J = 14.3, 7.2 Hz, 1H), 4.11-3.52 (m, 4H), 3.49-3.33 (m, 2H), 3.28-3.06 (m, 2H), 3.00 (s, 3H), 2.88 (s, 3H), 2.57-2.34 (m, 2H), 2.18-2.00 (m, 4H), 1.98-1.85 (m, 2H). |

Example 14. N-[5-(4-Ethylpiperazin-1-yl)pyridin-2-yl]-5-fluoro-4-(7-propan-2-ylthieno[3,2-b]pyridin-2-yl)pyrimidin-2-amine

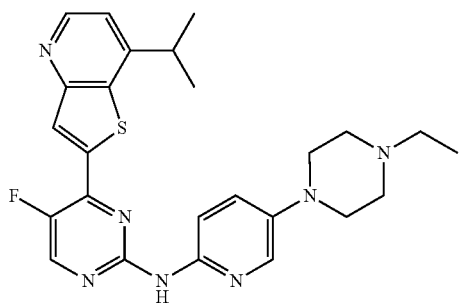 [SMILES: CCN1CCN(c2ccc(Nc3ncc(F)c(-c4cc5nccc(C(C)C)c5s4)n3)nc2)CC1]

Step 1: 7-Prop-1-en-2-ylthieno[3,2-b]pyridine

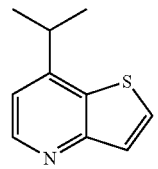

A mixture of 7-chlorothieno[3,2-b]pyridine (2.0 g, 11.79 mmol), 2-isopropenyl-4,4,5,5-tetramethyl-1,3,2-dioxaborolane (3.0 g, 17.69 mmol), K$_3$PO$_4$ (7.5 g, 35.37 mmol) and [1,1'-bis(diphenylphosphino)ferrocene]dichloropalladium (II) (862.7 mg, 1.18 mmol) in 1,4-dioxane (20 mL) and water (6 mL) was bubbled with N$_2$ for 5 min and stirred at 100° C. overnight. LCMS showed the starting material was consumed. The solid was removed by filtration and the filtrate was concentrated to dryness. The residue was dissolved in EtOAc (50 mL), washed with water (30 mL) and brine (30 mL), dried over Na$_2$SO$_4$, filtered, and concentrated under reduced pressure. The residue was purified by flash chromatography on a silica gel column using EtOAc/heptanes (0-25%) to afford the title compound (1.71 g, 82.8% yield). LCMS calc. for C$_{10}$H$_{10}$NS [M+H]$^+$: m/z=176.1; Found: 175.9.

Step 2: 7-Isopropylthieno[3,2-b]pyridine

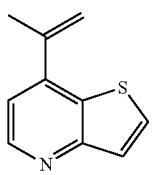

A mixture of 7-prop-1-en-2-ylthieno[3,2-b]pyridine (1.8 g, 10.15 mmol) and Pd/C (180.0 mg, 0.17 mmol) in methanol (20 mL) was stirred under a H$_2$ atmosphere overnight. LCMS showed the starting material was consumed. The solid was removed by filtration and the solvent was removed under reduced pressure. The residue was purified by flash chromatography on a silica gel column using EtOAc/heptanes (0-25%) to afford the title compound (1.53 g, 84.0% yield). LCMS calc. for C$_{10}$H$_{12}$NS [M+H]+: m/z=178.1/179.1; Found: 178.2/179.4.

Step 3: (7-Propan-2-ylthieno[3,2-b]pyridin-2-yl)boronic Acid

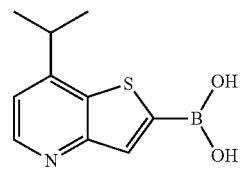

To a solution of 7-propan-2-ylthieno[3,2-b]pyridine (300.0 mg, 1.69 mmol) in THF (5 mL) at −78° C. was added n-BuLi (0.81 mL, 2.03 mmol) dropwise. The reaction mixture was stirred at −78° C. for 1 h. Then 4,4,5,5-tetramethyl-2-propan-2-yloxy-1,3,2-dioxaborolane (629.7 mg, 3.38 mmol) was added dropwise. The resulting mixture was stirred from −78° C. to rt overnight. LCMS showed the starting material was consumed. The reaction was quenched with saturated NH$_4$Cl solution (5 mL) and extracted with IPA/CHCl$_3$ (1:3, 5 mL x 3). The combined organic layers were dried over Na$_2$SO$_4$, filtered, and concentrated under reduced pressure to yield the title compound as a crude mixture (330 mg), which was used for the next reaction without further purification.

Step 4: 2-(2-Chloro-5-fluoropyrimidin-4-yl)-7-propan-2-ylthieno[3,2-b]pyridine

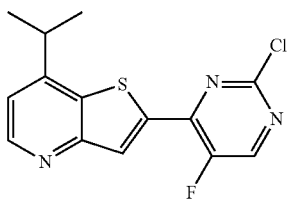 [SMILES: CC(C)c1ccnc2cc(-c3nc(Cl)ncc3F)sc12]

A mixture of (7-propan-2-ylthieno[3,2-b]pyridin-2-yl)boronic acid (330.0 mg, 1.49 mmol), 2,6-dichloro-5-fluororacil (373.8 mg, 2.24 mmol), K₃PO₄ (950.5 mg, 4.48 mmol) and [1,1'-bis(diphenylphosphino)ferrocene]dichloropalladium (II) (109.2 mg, 0.15 mmol) in 1,4-dioxane (3 mL) and water (1 mL) was bubbled with N₂ for 5 min and stirred at 100° C. overnight. LCMS showed the starting material was consumed. The solvent was removed under reduced pressure. The residue was dissolved in EtOAc (10 mL), washed with water (10 mL) and brine (10 mL), dried over Na₂SO₄, filtered, and concentrated under reduced pressure. The residue was purified by flash chromatography on a silica gel column using EtOAc/heptanes (5-60%) to afford the title compound (180.0 mg, 39.2% yield). LCMS calc. For $C_{14}H_{11}ClFN_3S$ [M+H]⁺: m/z=308.0; Found: 307.9.

Step 5: N-[5-(4-Ethylpiperazin-1-yl)pyridin-2-yl]-5-fluoro-4-(7-propan-2-ylthieno[3,2-b]pyridin-2-yl)pyrimidin-2-amine A mixture of 2-(2-chloro-5-fluoropyrimidin-4-yl)-7-propan-2-ylthieno[3,2-b]pyridine (18.0 mg, 0.06 mmol), 5-(4-ethylpiperazin-1-yl)pyridin-2-amine (18.1 mg, 0.09 mmol), K₃PO₄ (37.2 mg, 0.18 mmol) and XPhos Pd G2 (4.6 mg, 0.01 mmol) in 1,4-dioxane (1 mL) was bubbled with N₂ for 5 min and stirred at 100° C. overnight. LCMS showed the starting material was consumed. The solvent was removed under reduced pressure. The residue was purified by prep-HPLC on a C₁₈ column eluting with MeCN/H₂O (5-100%) with 0.1% TFA to yield title compound as its TFA salt (8.2 mg, 27.2% yield). ¹H NMR (300 MHz, CD₃OD) δ 8.82 (d, J=2.8 Hz, 1H), 8.74 (dd, J=5.1, 2.1 Hz, 1H), 8.48 (t, J=2.0 Hz, 1H), 8.20 (dd, J=9.7, 2.6 Hz, 1H), 7.95 (s, 1H), 7.69 (d, J=9.5 Hz, 1H), 7.52 (dd, J=5.1, 2.0 Hz, 1H), 3.35 (d, J=1.8 Hz, 1H), 3.33-3.32 (m, 8H), 3.31 (s, 2H), 1.52 (d, J=2.1 Hz, 3H), 1.50 (d, J=2.3 Hz, 3H), 1.47-1.40 (m, 3H). LCMS calc. for $C_{25}H_{29}FN_7S$ [M+H]⁺: m/z=478.2/479.2; Found: 477.9/479.3.

Example 15. 4-(7-Cyclopentylthieno[3,2-b]pyridin-2-yl)-N-[5-(6-ethyl-2,6-diazaspiro[3.3]heptan-2-yl)pyridin-2-yl]-5-fluoropyrimidin-2-amine

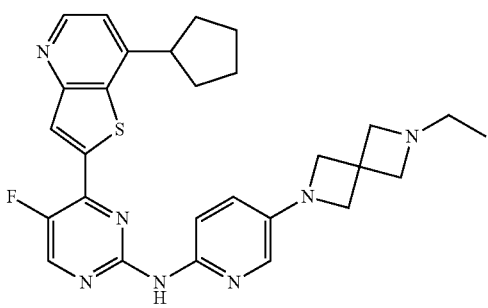 [SMILES: CCN1CC2(C1)CN(c1ccc(Nc3ncc(F)c(-c4cc5nccc(C6CCCC6)c5s4)n3)nc1)C2]

Step 1: 2-(6-Nitropyridin-3-yl)-2,6-diazaspiro[3.3]heptane

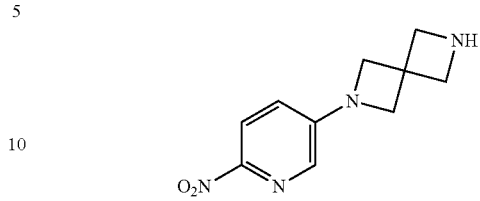

A mixture of tert-butyl 6-(6-nitropyridin-3-yl)-2,6-diazaspiro[3.3]heptane-2-carboxylate (500.0 mg, 1.56 mmol) and TFA (5.0 mL, 65.34 mmol) in DCM (10 mL) was stirred at room temperature for 2 h. The solvent was removed under reduced pressure. The residue 2-(6-nitropyridin-3-yl)-2,6-diazaspiro[3.3]heptane (300 mg, 87.3% yield) was used in the next step without further purification. LC-MS calc. for $C_{10}H_{13}N_4O_2$ [M+H]⁺: m/z=221.2; Found 220.9.

Step 2: 6-Ethyl-2-(6-nitropyridin-3-yl)-2,6-diazaspiro[3.3]heptane

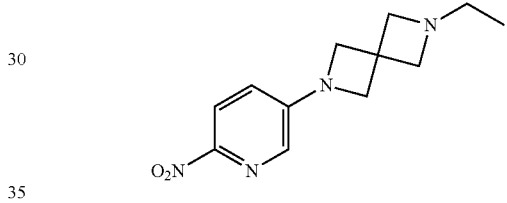

A mixture of 2-(6-nitropyridin-3-yl)-2,6-diazaspiro[3.3]heptane (500.0 mg, 2.27 mmol), triethylamine (0.63 mL, 4.54 mmol), acetic acid (0.01 mL, 0.23 mmol), acetaldehyde (500.1 mg, 11.35 mmol), and NaBH₃CN (713.4 mg, 11.35 mmol) in methanol (5 mL) was stirred at room temperature overnight. The solvent was removed under reduced pressure. To the resulting material was added HCl (1 N, 10 mL), and the aqueous mixture was extracted with ethyl acetate (10 mL×3). The combined organic layers were dried over Na₂SO₄, filtered, and concentrated under reduced pressure to provide the title compound (300 mg, 53.2% yield), which was directly used in the next step without further purification. LC-MS calc. for $C_{12}H_{17}N_4O_2$ [M+H]⁺: m/z=249.3; Found 249.0.

Step 3: 5-(6-Ethyl-2,6-diazaspiro[3.3]heptan-2-yl)pyridin-2-amine

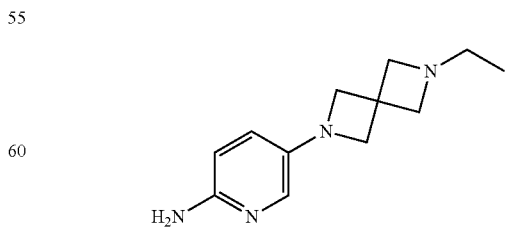

A mixture of 6-ethyl-2-(6-nitropyridin-3-yl)-2,6-diazaspiro[3.3]heptane (500.0 mg, 2.01 mmol) and Pd/C (60% H₂O, 50 mg) in ethanol (10 mL) was stirred under a H₂ atmosphere overnight. The reaction mixture was filtered through Celite. The filtrate was concentrated under reduced pressure. The residue was purified by prep-HPLC on a $C_{18}$ column (30×250 mm, 10 m) using mobile phase 0 to 10% MeCN/H$_2$O ($t_R$=15 min) to afford the title compound (240 mg, 54.6% yield). LC-MS calc. for $C_{12}H_{19}N_4[M+H]^+$: m/z=219.2; Found 218.9.

Step 4: 4-(7-Cyclopentylthieno[3,2-b]pyridin-2-yl)-N-[5-(6-ethyl-2,6-diazaspiro[3.3]heptan-2-yl)pyridin-2-yl]-5-fluoropyrimidin-2-amine The title compound is synthesized by procedures analogous to those outlined in Example 14, Steps 1-5. $^1$H NMR (300 MHz, DMSO-d$_6$) δ 10.24 (s, 1H), 8.78 (d, J=3.0 Hz, 1H), 8.71 (d, J=4.8 Hz, 1H), 8.30 (s, 1H), 7.96 (d, J=9.0 Hz, 1H), 7.64 (d, J=2.5 Hz, 1H), 7.43 (d, J=4.7 Hz, 1H), 7.21 (d, J=8.9 Hz, 1H), 4.41-4.31 (m, 2H), 4.27-4.19 (m, 2H), 4.13 (s, 2H), 4.03 (s, 2H), 2.20 (m, 3H), 2.05-1.95 (m, 2H), 1.84 (m, 6H). LC-MS calc. for $C_{28}H_{31}FN_7S$ [M+H]$^+$: m/z=516.2/517.2; Found 516.2/517.2.

Example 16. 4-(3-Chloro-7-cyclopentylthieno[3,2-b]pyridin-2-yl)-N-[5-(4-ethylpiperazin-1-yl)pyridin-2-yl]-5-fluoropyrimidin-2-amine

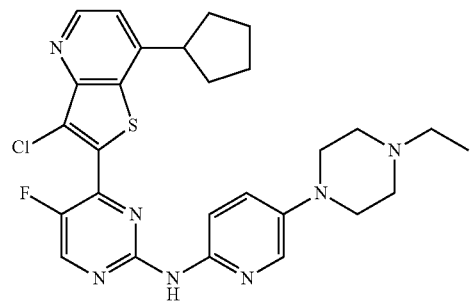 [SMILES: CCN1CCN(c2ccc(Nc3ncc(F)c(-c4sc5c(C6CCCC6)ccnc5c4Cl)n3)nc2)CC1]

Step 1: 7-(Cyclopenten-1-yl)thieno[3,2-b]pyridine

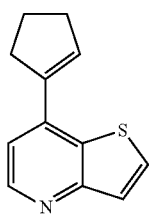 [SMILES: C1=C(c2ccnc3ccsc23)CCC1]

A mixture of 7-chlorothieno[3,2-b]pyridine (1.02 g, 6.01 mmol), 2-(cyclopenten-1-yl)-4,4,5,5-tetramethyl-1,3,2-dioxaborolane (1.75 g, 9.02 mmol), K$_3$PO$_4$ (3.83 g, 18.04 mmol), and [1,1'-bis(diphenylphosphino)ferrocene]dichloropalladium(II) (439.98 mg, 0.60 mmol) in 1,4-dioxane (9 mL) and water (3 mL) was bubbled with N$_2$ for 5 min and stirred at 100° C. overnight. LCMS showed the starting material was consumed. The solvent was removed under reduced pressure. The residue was dissolved in EtOAc (20 mL), washed with water (20 mL) and brine (20 mL), dried over Na$_2$SO$_4$, filtered, and concentrated under reduced pressure. The residue was purified by flash chromatography on a silica gel column using EtOAc/heptanes (0-20%) to afford the title compound (1.1 g, 91% yield) as a colorless oil. LC-MS calc. for $C_{12}H_{12}NS$ [M+H]$^+$: m/z=202.0; Found 201.9.

Step 2: 7-Cyclopentylthieno[3,2-b]pyridine

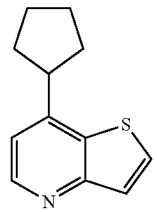 [SMILES: c1cc(C2CCCC2)c2sccc2n1]

A mixture of 7-(cyclopenten-1-yl)thieno[3,2-b]pyridine (1.1 g, 5.46 mmol) and Pd/C (10 wt % Pd, 200.0 mg, 0.19 mmol) in methanol (20 mL) was stirred under a H$_2$ atmosphere overnight. LCMS showed the starting material was consumed. The solid was removed by filtration, and the filtrate was concentrated under reduced pressure. The residue was purified by flash chromatography on a silica gel column using EtOAc/heptanes (0-20%) to afford the title compound (1.0 g, 90.0% yield) as a colorless oil. LC-MS calc. for $C_{12}H_{14}NS$ [M+H]$^+$: m/z=204.0; Found 203.9.

Step 3: 3-Chloro-7-cyclopentylthieno[3,2-b]pyridine

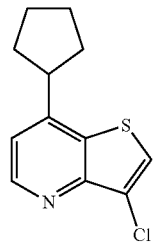 [SMILES: Clc1csc2c(C3CCCC3)ccnc12]

A mixture of 7-cyclopentylthieno[3,2-b]pyridine (300.0 mg, 1.48 mmol) and 1-chloropyrrolidine-2,5-dione (236.46 mg, 1.77 mmol) in trifluoromethanesulfonic acid (1.0 mL, 11.33 mmol) was stirred at room temperature overnight. LCMS showed the starting material was consumed. The mixture was poured into cold NaHCO$_3$ solution (10 mL) and extracted with EtOAc (10 mL×3). The combined organic layers were dried over Na$_2$SO$_4$, filtered, and concentrated under reduced pressure. The residue was purified by flash chromatography on a silica gel column using EtOAc/heptanes (0-20%) to afford the title compound as a mixture with the dichloro compound (276 mg, 78.7% yield, 3:1 ratio by HPLC). LCMS calc. for $C_{12}H_{13}ClNS$ [M+H]$^+$: m/z=238.05/240.04; Found: 238.3/240.0.

Step 4: 4-(3-Chloro-7-cyclopentylthieno[3,2-b]pyridin-2-yl)-N-[5-(4-ethylpiperazin-1-yl)pyridin-2-yl]-5-fluoropyrimidin-2-amine The title compound is synthesized by procedures analogous to those outlined in Example 14, Steps 3-5. $^1$H NMR (300 MHz, CD$_3$OD) δ 8.93 (d, J=2.2 Hz, 1H), 8.78 (d, J=4.9 Hz, 1H), 8.32-8.22 (m, 1H), 7.94 (s, 1H), 7.64-7.54 (m, 2H), 3.96 (d, J=9.4 Hz, 2H), 3.75 (s, 2H), 3.50-3.43 (m, 1H), 3.32 (m, 6H), 2.30 (d, J=8.8 Hz, 2H), 2.01-1.81 (m, 6H), 1.44 (t, J=7.2 Hz, 3H). LCMS calc. for $C_{27}H_{30}ClFN_7S$ [M+H]: m/z=538.2/540.2; Found: 538.1/540.3.

Example 17. 2-[2-[2-[[5-(4-Ethylpiperazin-1-yl)pyridin-2-yl]amino]-5-fluoropyrimidin-4-yl]thieno[3,2-b]pyridin-7-yl]propan-2-ol

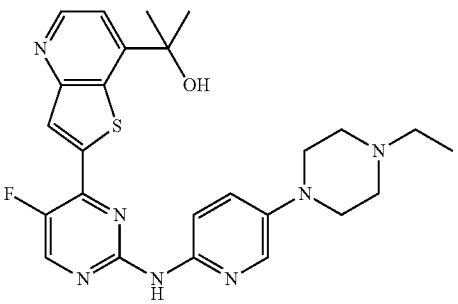 [SMILES: CCN1CCN(c2ccc(Nc3ncc(F)c(-c4cc5nccc(C(C)(C)O)c5s4)n3)nc2)CC1]

Step 1: 1-Thieno[3,2-b]pyridin-7-ylethanone

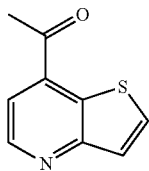

A mixture of 7-chlorothieno[3,2-b]pyridine (1.21 g, 7.13 mmol), tributyl(1-ethoxyvinyl)tin (3.61 mL, 10.7 mmol), and tetrakis(triphenylphosphine)palladium(0) (824 mg, 0.713 mmol) in 1,4-dioxane (25 mL) was stirred at 100° C. for 16 h. The reaction mixture was cooled to room temperature, and 2N HCl (aq.) (10 mL) was added. The mixture was further stirred overnight. The mixture was neutralized with sat. NaHCO₃ (aq.) (10 mL) and extracted with EtOAc (25 mL×3). The combined organic layers were washed with water (25 mL) and brine (25 mL), dried over Na₂SO₄, filtered, and concentrated. The residue was purified by silica gel chromatography (0-50% EtOAc/heptane) to give the title compound (601 mg, 3.39 mmol, 47.5% yield) as a white solid. LCMS calc. for $C_9H_8NOS$ [M+H]⁺: m/z=178.0; Found: 178.1.

Step 2: 2-Thieno[3,2-b]pyridin-7-ylpropan-2-ol

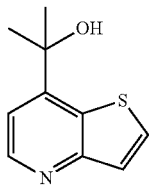

A mixture of methylmagnesium chloride solution (0.86 mL, 2.59 mmol) and 1-thieno[3,2-b]pyridin-7-ylethanone (153.0 mg, 0.86 mmol) in THF (2 mL) was stirred at room temperature for 2 h. LCMS showed the starting material was consumed. The reaction was quenched with saturated NH₄Cl solution (5 mL) and extracted with EtOAc (5 mL×3). The combined organic layers were dried over Na₂SO₄, filtered, and concentrated under reduced pressure. The residue was purified by flash chromatography on a silica gel column using EtOAc/heptanes (5-50%) to afford the title compound (112.0 mg, 67.1% yield). LCMS calc. for $C_{10}H_{12}NOS$ [M+H]" m/z=194.0; Found: 193.9.

Step 3: 2-[2-[2-[[5-(4-Ethylpiperazin-1-yl)pyridin-2-yl]amino]-5-fluoropyrimidin-4-yl]thieno[3,2-b]pyridin-7-yl]propan-2-ol The title compound is synthesized by procedures analogous to those outlined in Example 14, Steps 3-5. LCMS calc. for $C_{25}H_{29}FN_7OS$ [M+H]⁺: m/z=494.2/495.2; Found: 494.0/495.4.

Example 18. 2-[2-[2-[[5-(6-Ethyl-2,6-diazaspiro[3.3]heptan-2-yl)pyridin-2-yl]amino]-5-fluoropyrimidin-4-yl]thieno[3,2-b]pyridin-7-yl]-1,1,1-trifluoropropan-2-ol

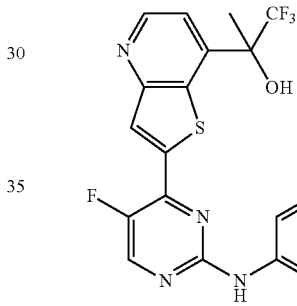

Step 1: 1,1,1-Trifluoro-2-thieno[3,2-b]pyridin-7-ylpropan-2-ol

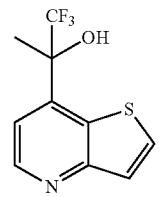 [SMILES: CC(O)(c1ccnc2ccsc12)C(F)(F)F]

To a solution of 1-thieno[3,2-b]pyridin-7-ylethanone (88.0 mg, 0.50 mmol) in THF (2 mL) was added tetrabutylammonium fluoride solution (0.1 mL, 0.10 mmol), followed by the addition of trimethyl(trifluoromethyl)silane (91.8 mg, 0.65 mmol) dropwise at 0° C. The reaction mixture was stirred at 0° C. for 5 min and room temperature for 2 h. The mixture was cooled to 0° C. and tetrabutylammonium fluoride solution (0.1 mL, 0.10 mmol) and water (0.1 mL, 5.55 mmol) were added. The resulting mixture was stirred at room temperature for 30 min. LCMS showed the starting material was consumed. The reaction was quenched with brine (5 mL) and extracted with EtOAc (5 mL×3). The combined organic layers were dried over Na₂SO₄, filtered, and concentrated under reduced pressure. The residue was purified by flash chromatography on a silica gel column using EtOAc/heptanes (5-50%) to afford the title compound (80.0 mg, 65.2% yield). LCMS calc. for $C_{10}H_9F_3NOS$ [M+H]⁺: m/z=248.04/249.04; Found: 248.1/249.3.

Step 2: 2-[2-[2-[[5-(6-Ethyl-2,6-diazaspiro[3.3]heptan-2-yl)pyridin-2-yl]amino]-5-fluoropyrimidin-4-yl]thieno[3,2-b]pyridin-7-yl]-1,1,1-trifluoropropan-2-ol The title compound is synthesized by procedures analogous to those outlined in Example 14, Steps 3-5. ¹H NMR (300 MHz, CD₃OD) δ 8.75 (t, J=4.2 Hz, 2H), 8.41 (d, J=1.8 Hz, 1H), 7.64 (dd, J=9.4, 2.8 Hz, 1H), 7.58-7.51 (m, 2H), 7.47 (d, J=2.7 Hz, 1H), 4.51 (d, J=11.2 Hz, 2H), 4.30 (d, J=14.6 Hz, 4H), 4.18 (s, 2H), 3.25 (d, J=7.1 Hz, 2H), 1.94 (s, 3H), 1.23 (t, J=7.2 Hz, 3H). LCMS calc. for $C_{26}H_{26}F_4N_7OS$ [M+H]⁺: m/z=560.2/561.2; Found: 560.0/561.3.

Examples listed in Table 2-1 and 2-2 are synthesized according to procedures analogous to Example 14 (Method 1), Example 15 (Method 2), Example 16 (Method 3), Example 17 (Method 4), or Example 18 (Method 5).

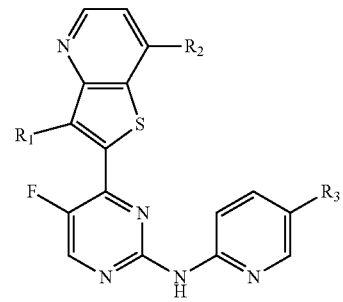

TABLE 2-1

Examples 19-41

| Example | R₁ | R₂ | R₃ | LCMS [M + H]⁺ | Method |
|---------|----|----|----|---------------|--------|
| 19 | H | isopropyl | piperazine-N-ethyl | 491.9 | 1 |
| 20 | Cl | cyclopentyl | piperidine-N-ethyl | 537.1 | 3 |
| 21 | H | C(CH₃)₂OH | 2,6-diazaspiro[3.3]heptane-N-ethyl | 560.0 | 4 |
| 22 | Me | cyclopentyl | piperazine-N-ethyl | 532.3 | 1 |
| 23 | H | isopropyl | 2,6-diazaspiro[3.3]heptane-N-ethyl | 490.0 | 2 |
| 24 | H | cyclopentyl | piperazine-N-ethyl | 504.2 | 1 |
| 25 | H | C(CF₃)(CH₃)OH | piperazine-CH₂-N-ethyl | 562.0 | 5 |

TABLE 2-1-continued

Examples 19-41

| Example | R₁ | R₂ | R₃ | LCMS [M + H]⁺ | Method |
|---|---|---|---|---|---|
| 26 | Me | cyclopentyl | N-methylpiperidin-4-yl | 502.9 | 1 |
| 27 | H | C(CH₃)₂OH | 4-ethylpiperazin-1-ylmethyl | 507.9 | 4 |
| 28 | Me | cyclopentyl | 4-methylpiperazin-1-yl | 503.9 | 1 |
| 29 | H | C(CF₃)(CH₃)OH | 4-ethylpiperazin-1-yl | 547.9 | 5 |
| 30 | Cl | cyclopentyl | 4-ethylpiperazin-1-ylmethyl | 552.2 | 3 |
| 31 | Me | cyclopentyl | 4-ethylpiperazin-1-yl | 518.0 | 1 |
| 32 | Me | cyclopentyl | 2,6-diazaspiro[3.3]heptan-2-yl | 501.9 | 2 |
| 33 | H | cyclopentyl | 4-ethylpiperazin-1-ylmethyl | 518.2 | 1 |
| 34 | H | cyclopentyl | N-methylpiperidin-4-yl | 489.0 | 1 |
| 35 | Me | cyclopentyl | piperazin-1-yl | 489.8 | 1 |
| 36 | H | cyclopentyl | piperazin-1-yl | 476.1 | 1 |

TABLE 2-1-continued

Examples 19-41

| Example | R₁ | R₂ | R₃ | LCMS [M + H]⁺ | Method |
|---|---|---|---|---|---|
| 37 | H | cyclopentyl | 4-methylpiperazin-1-yl | 490.1 | 1 |
| 38 | Me | cyclopentyl | morpholin-4-yl | 490.9 | 1 |
| 39 | H | cyclopentyl | 4-methoxypiperidin-1-yl | 504.9 | 1 |
| 40 | H | cyclopentyl | morpholin-4-yl | 476.9 | 1 |
| 41 | H | cyclopentyl | 3,3-difluoropyrrolidin-1-yl | 496.9 | 1 |

TABLE 2-2

Examples 19-41

| Example | Compound name | NMR |
|---|---|---|
| 19 | N-[5-[(4-Ethylpiperazin-1-yl)methyl]pyridin-2-yl]-5-fluoro-4-(7-propan-2-ylthieno[3,2-b]pyridin-2-yl)pyrimidin-2-amine | ¹H NMR (300 MHz, CD₃OD) δ 8.89 (d, J = 3.0 Hz, 1H), 8.79 (d, J = 5.2 Hz, 1H), 8.51 (d, J = 1.5 Hz, 1H), 8.35 (dd, J = 7.0, 2.2 Hz, 2H), 7.68 (d, J = 9.6 Hz, 1H), 7.60 (d, J = 5.2 Hz, 1H), 3.78 (s, 2H), 3.46-3.40 (m, 1H), 3.31 (m, 8H), 3.24 (dd, J = 7.4, 1.7 Hz, 2H), 1.52 (dd, J = 7.0, 1.8 Hz, 6H), 1.37 (t, J = 7.3 Hz, 3H). |
| 20 | 4-(3-Chloro-7-cyclopentylthieno[3,2-b]pyridin-2-yl)-N-[5-(1-ethylpiperidin-4-yl)pyridin-2-yl]-5-fluoropyrimidin-2-amine | ¹H NMR (300 MHz, Methanol-d₄) δ 8.99 (t, J = 1.8 Hz, 1H), 8.80 (d, J = 5.0 Hz, 1H), 8.44-8.30 (m, 2H), 7.68-7.55 (m, 2H), 3.75 (d, J = 12.5 Hz, 2H), 3.49 (t, J = 7.4 Hz, 1H), 3.27 (d, J = 7.5 Hz, 2H), 3.16 (s, 2H), 2.34-1.81 (m, 13H), 1.43 (t, J = 7.3 Hz, 3H) |
| 21 | 2-[2-[2-[[5-(6-Ethyl-2,6-diazaspiro[3.3]heptan-2-yl)pyridin-2-yl]amino]-5-fluoropyrimidin-4-yl]thieno[3,2-b]pyridin-7-yl]propan-2-ol | ¹H NMR (300 MHz, CD₃OD) δ 8.78 (d, J = 3.1 Hz, 1H), 8.71 (d, J = 5.1 Hz, 1H), 8.43 (d, J = 1.8 Hz, 1H), 7.67 (dd, J = 9.4, 2.8 Hz, 1H), 7.55-7.47 (m, 3H), 4.51 (d, J = 11.2 Hz, 2H), 4.31 (d, J = 12.3 Hz, 4H), 4.19 (s, 2H), 3.27 (d, J = 7.3 Hz, 2H), 1.72 (s, 6H), 1.23 (t, J = 7.2 Hz, 3H). |
| 22 | 4-(7-Cyclopentyl-3-methylthieno[3,2-b]pyridin-2-yl)-N-(5-((4-ethylpiperazin-1-yl)methyl)pyridin-2-yl)-5-fluoropyrimidin-2-amine | ¹H NMR (300 MHz, CD₃OD) δ 8.89 (d, J = 2.4 Hz, 1H), 8.74 (d, J = 5.2 Hz, 1H), 8.32 (d, J = 6.7 Hz, 1H), 7.60 (dd, J = 19.4, 7.4 Hz, 2H), 3.74 (s, 2H), 3.59-3.32 (m, 4H), 3.21 (dd, J = 14.7, 7.3 Hz, 4H), 2.75 (d, J = 3.0 Hz, 3H), 2.36-2.22 (m, 2H), 2.00-1.78 (m, 6H), 1.34 (t, J = 7.3 Hz, 3H). |

TABLE 2-2-continued

Examples 19-41

| Example | Compound name | NMR |
|---|---|---|
| 23 | N-[5-(6-Ethyl-2,6-diazaspiro[3.3]heptan-2-yl)pyridin-2-yl]-5-fluoro-4-(7-propan-2-ylthieno[3,2-b]pyridin-2-yl)pyrimidin-2-amine | $^1$H NMR (300 MHz, CD$_3$OD) δ 8.83 (d, J = 3.0 Hz, 1H), 8.77 (d, J = 5.1 Hz, 1H), 8.48 (d, J = 1.5 Hz, 1H), 7.71 (dd, J = 9.5, 2.8 Hz, 1H), 7.60-7.52 (m, 2H), 7.53-7.49 (m, 1H), 4.53 (d, J = 11.4 Hz, 2H), 4.33 (d, J = 12.0 Hz, 4H), 4.21 (s, 2H), 3.41 (t, J = 6.9 Hz, 1H), 3.30-3.24 (m, 2H), 1.54 (s, 3H), 1.51 (s, 3H), 1.25 (t, J = 7.2 Hz, 3H). |
| 24 | 4-(7-Cyclopentylthieno[3,2-b]pyridin-2-yl)-N-[5-(4-ethylpiperazin-1-yl)pyridin-2-yl]-5-fluoropyrimidin-2-amine | $^1$H NMR (300 MHz, DMSO-d$_6$) δ 10.57 (s, 1H), 8.80 (d, J = 2.9 Hz, 1H), 8.69 (d, J = 4.6 Hz, 1H), 8.29 (s, 1H), 8.07 (s, 1H), 7.99 (d, J = 9.2 Hz, 1H), 7.78 (d, J = 9.3 Hz, 1H), 7.41 (d, J = 4.7 Hz, 1H), 3.86 (d, J = 11.9 Hz, 2H), 3.62 (d, J = 10.9 Hz, 2H), 3.27-2.99 (m, 7H), 2.17 (s, 2H), 1.80 (d, J = 5.1 Hz, 6H), 1.24 (dd, J = 14.8, 7.6 Hz, 3H). |
| 25 | 2-[2-[2-[[5-[(4-Ethylpiperazin-1-yl)methyl]pyridin-2-yl]amino]-5-fluoropyrimidin-4-yl]thieno[3,2-b]pyridin-7-yl]-1,1,1-trifluoropropan-2-ol | $^1$H NMR (300 MHz, CD$_3$OD) δ 8.85 (d, J = 3.0 Hz, 1H), 8.77 (d, J = 5.0 Hz, 1H), 8.45 (d, J = 1.8 Hz, 1H), 8.36-8.29 (m, 2H), 7.66 (d, J = 9.6 Hz, 1H), 7.58 (d, J = 4.9 Hz, 1H), 3.75 (s, 2H), 3.55 (s, 2H), 3.34-3.31 (m, 6H), 3.24 (d, J = 7.3 Hz, 2H), 1.95 (s, 3H), 1.36 (t, J = 7.3 Hz, 3H). |
| 26 | 4-(7-Cyclopentyl-3-methylthieno[3,2-b]pyridin-2-yl)-5-fluoro-N-(5-(1-methylpiperidin-4-yl)pyridin-2-yl)pyrimidin-2-amine | — |
| 27 | 2-[2-[2-[[5-[(4-Ethylpiperazin-1-yl)methyl]pyridin-2-yl]amino]-5-fluoropyrimidin-4-yl]thieno[3,2-b]pyridin-7-yl]propan-2-ol | $^1$H NMR (300 MHz, CD$_3$OD) δ 8.87-8.83 (m, 1H), 8.75-8.71 (m, 1H), 8.45 (d, J = 1.8 Hz, 1H), 8.36-8.29 (m, 2H), 7.70-7.64 (m, 1H), 7.54 (dd, J = 5.2, 1.8 Hz, 1H), 3.75 (s, 2H), 3.30 (m, 8H), 3.25-3.20 (m, 2H), 1.73 (s, 6H), 1.38-1.32 (m, 3H). |
| 28 | 4-(7-Cyclopentyl-3-methylthieno[3,2-b]pyridin-2-yl)-5-fluoro-N-(5-(4-methylpiperazin-1-yl)pyridin-2-yl)pyrimidin-2-amine | $^1$H NMR (300 MHz, CD$_3$OD) δ 8.84 (d, J = 2.5 Hz, 1H), 8.74 (d, J = 5.2 Hz, 1H), 8.22 (dd, J = 9.7, 2.9 Hz, 1H), 7.90 (d, J = 2.8 Hz, 1H), 7.58 (dd, J = 7.4, 4.7 Hz, 2H), 4.08-3.30 (m, 8H), 3.24-3.20 (m, 1H), 2.98 (s, 3H), 2.74 (d, J = 3.0 Hz, 3H), 2.38-2.21 (m, 2H), 1.99-1.74 (m, 6H). |
| 29 | 2-[2-[2-[[5-(4-Ethylpiperazin-1-yl)pyridin-2-yl]amino]-5-fluoropyrimidin-4-yl]thieno[3,2-b]pyridin-7-yl]-1,1,1-trifluoropropan-2-ol | $^1$H NMR (300 MHz, CD$_3$OD) δ 8.81 (d, J = 3.2 Hz, 1H), 8.76 (d, J = 5.0 Hz, 1H), 8.43 (d, J = 1.8 Hz, 1H), 8.22 (dd, J = 9.6, 2.9 Hz, 1H), 7.91 (d, J = 2.9 Hz, 1H), 7.62 (d, J = 9.6 Hz, 1H), 7.57 (d, J = 5.1 Hz, 1H), 3.67 (d, J = 1.3 Hz, 2H), 3.37-3.31 (m, 8H), 1.94 (s, 3H), 1.43 (t, J = 7.4 Hz, 3H). |
| 30 | 4-(3-Chloro-7-cyclopentylthieno[3,2-b]pyridin-2-yl)-N-[5-[(4-ethylpiperazin-1-yl)methyl]pyridin-2-yl]-5-fluoropyrimidin-2-amine | — |
| 31 | 4-(7-Cyclopentyl-3-methylthieno[3,2-b]pyridin-2-yl)-N-(5-(4-ethylpiperazin-1-yl)pyridin-2-yl)-5-fluoropyrimidin-2-amine | $^1$H NMR (300 MHz, CD$_3$OD) δ 8.84 (d, J = 2.0 Hz, 1H), 8.72 (d, J = 5.1 Hz, 1H), 8.22 (dd, J = 9.6, 2.3 Hz, 1H), 7.91 (s, 1H), 7.56 (dd, J = 13.8, 7.4 Hz, 2H), 4.15-3.10 (m, 11H), 2.73 (d, J = 2.8 Hz, 3H), 2.31-2.21 (m, 2H), 1.94-1.81 (m, 6H), 1.39 (t, J = 7.3 Hz, 3H). |
| 32 | N-(5-(2,6-Diazaspiro[3.3]heptan-2-yl)pyridin-2-yl)-4-(7-cyclopentyl-3-methylthieno[3,2-b]pyridin-2-yl)-5-fluoropyrimidin-2-amine | $^1$H NMR (300 MHz, CD$_3$OD) δ 8.60 (d, J = 2.5 Hz, 1H), 8.50 (d, J = 5.0 Hz, 1H), 7.46 (dd, J = 9.4, 2.7 Hz, 1H), 7.32 (s, 1H), 7.28 (s, 2H), 4.13 (s, 4H), 4.01 (s, 4H), 3.26-3.21 (m, 1H), 2.53 (d, J = 2.9 Hz, 3H), 2.15-2.00 (m, 2H), 1.79-1.63 (m, 6H). |
| 33 | 4-(7-Cyclopentylthieno[3,2-b]pyridin-2-yl)-N-[5-[(4-ethylpiperazin-1-yl)methyl]pyridin-2-yl]-5-fluoropyrimidin-2-amine | $^1$H NMR (300 MHz, DMSO-d$_6$) δ 10.83 (s, 1H), 8.85 (d, J = 3.0 Hz, 1H), 8.70 (d, J = 4.9 Hz, 1H), 8.38 (s, 1H), 8.30 (s, 1H), 8.20 (d, J = 8.7 Hz, 1H), 7.98 (dd, J = 8.8, 1.9 Hz, 1H), 7.42 (d, J = 4.9 Hz, 1H), 4.06 (s, 2H), 3.70-2.75 (m 11H), 2.26-2.10 (m, 2H), 1.90-1.69 (m, 6H), 1.20 (t, J = 7.2 Hz, 3H). |

TABLE 2-2-continued

Examples 19-41

| Example | Compound name | NMR |
|---|---|---|
| 34 | 4-(7-Cyclopentylthieno[3,2-b]pyridin-2-yl)-5-fluoro-N-(5-(1-methylpiperidin-4-yl)pyridin-2-yl)pyrimidin-2-amine | $^1$H NMR (300 MHz, DMSO-$d_6$) δ 10.41 (s, 1H), 9.49 (s, 1H), 8.83 (d, J = 3.0 Hz, 1H), 8.70 (d, J = 4.8 Hz, 1H), 8.30 (d, J = 1.6 Hz, 1H), 8.24 (d, J = 2.0 Hz, 1H), 8.18 (d, J = 8.7 Hz, 1H), 7.78 (dd, J = 8.7, 2.2 Hz, 1H), 7.42 (d, J = 4.8 Hz, 1H), 3.09 (dd, J = 22.5, 10.3 Hz, 4H), 2.97-2.78 (m, 5H), 2.30-2.13 (m, 2H), 2.13-2.00 (m, 2H), 1.97-1.69 (m, 8H). |
| 35 | 4-(7-Cyclopentyl-3-methylthieno[3,2-b]pyridin-2-yl)-5-fluoro-N-(5-(piperazin-1-yl)pyridin-2-yl)pyrimidin-2-amine | $^1$H NMR (300 MHz, CD$_3$OD) δ 8.83 (s, 1H), 8.71 (d, J = 5.1 Hz, 1H), 8.22 (d, J = 9.7 Hz, 1H), 7.90 (s, 1H), 7.59 (d, J = 9.4 Hz, 1H), 7.52 (d, J = 5.1 Hz, 1H), 3.55-3.42 (m, 8H), 3.24-3.15 (m, 1H), 2.73 (d, J = 2.7 Hz, 3H), 2.38-2.22 (m, 2H), 2.00-1.78 (m, 6H). |
| 36 | 4-(7-Cyclopentylthieno[3,2-b]pyridin-2-yl)-5-fluoro-N-(5-piperazin-1-ylpyridin-2-yl)pyrimidin-2-amine | $^1$H NMR (300 MHz, DMSO-$d_6$) δ 10.65 (s, 1H), 8.84 (d, J = 2.9 Hz, 1H), 8.73 (d, J = 4.8 Hz, 1H), 8.33 (s, 1H), 8.06 (d, J = 2.7 Hz, 1H), 8.00 (d, J = 9.2 Hz, 1H), 7.81 (d, J = 9.3 Hz, 1H), 7.45 (d, J = 4.8 Hz, 1H), 3.43-3.26 (m, 9H), 2.20 (s, 2H), 1.83 (m, 6H). |
| 37 | 4-(7-Cyclopentylthieno[3,2-b]pyridin-2-yl)-5-fluoro-N-[5-(4-methylpiperazin-1-yl)pyridin-2-yl]pyrimidin-2-amine | $^1$H NMR (300 MHz, DMSO-$d_6$) δ 10.69 (s, 1H), 8.81 (d, J = 3.0 Hz, 1H), 8.70 (d, J = 4.8 Hz, 1H), 8.30 (s, 1H), 8.05 (d, J = 2.7 Hz, 1H), 7.96 (d, J = 9.3 Hz, 1H), 7.81 (dd, J = 9.3, 2.7 Hz, 1H), 7.42 (d, J = 4.9 Hz, 1H), 3.85 (d, J = 11.4 Hz, 2H), 3.54 (s, 2H), 3.45-3.30 (m, 1H), 3.20 (s, 2H), 3.05 (d, J = 11.9 Hz, 2H), 2.87 (s, 3H), 2.19 (d, J = 8.3 Hz, 2H), 1.92-1.68 (m, 6H). |
| 38 | 4-(7-Cyclopentyl-3-methylthieno[3,2-b]pyridin-2-yl)-5-fluoro-N-(5-morpholinopyridin-2-yl)pyrimidin-2-amine | $^1$H NMR (300 MHz, CD$_3$OD) δ 8.65 (d, J = 2.4 Hz, 1H), 8.54 (d, J = 5.2 Hz, 1H), 7.99 (dd, J = 92, 2.8 Hz, 1H), 7.58 (d, J = 2.3 Hz, 1H), 7.39 (d, J = 5.2 Hz, 1H), 7.32 (d, J = 9.7 Hz, 1H), 3.66 (t, 4H), 3.35-3.24 (m, 1H), 3.03 (t, 4H), 2.55 (d, J = 3.0 Hz, 3H), 2.14-2.04 (m, 2H), 1.78-1.63 (m, 6H). |
| 39 | 4-(7-Cyclopentylthieno[3,2-b]pyridin-2-yl)-5-fluoro-N-[5-(4-methoxypiperidin-1-yl)pyridin-2-yl]pyrimidin-2-amine | — |
| 40 | 4-(7-Cyclopentylthieno[3,2-b]pyridin-2-yl)-5-fluoro-N-(5-morpholinopyridin-2-yl)pyrimidin-2-amine | $^1$H NMR (300 MHz, CDCl3) δ 12.55 (s, 1H), 9.05 (s, 1H), 8.91 (d, J = 9.8 Hz, 1H), 8.79 (d, J = 5.7 Hz, 1H), 8.70 (d, J = 2.3 Hz, 1H), 8.16 (dd, J = 10.0, 2.5 Hz, 1H), 7.66 (d, J = 2.9 Hz, 1H), 7.59 (d, J = 5.6 Hz, 1H), 3.97-3.89 (m, 4H), 3.59 (d, J = 8.1 Hz, 1H), 3.29-3.17 (m, 4H), 2.40 (s, 2H), 2.14-1.78 (m, 6H). |
| 41 | 4-(7-Cyclopentylthieno[3,2-b]pyridin-2-yl)-N-[5-(3,3-difluoropyrrolidin-1-yl)pyridin-2-yl]-5-fluoropyrimidin-2-amine | — |

Example 42. 4-(4-Cyclopentylthieno[2,3-b]pyridin-2-yl)-5-fluoro-N-(5-morpholin-4-ylpyridin-2-yl)pyrimidin-2-amine

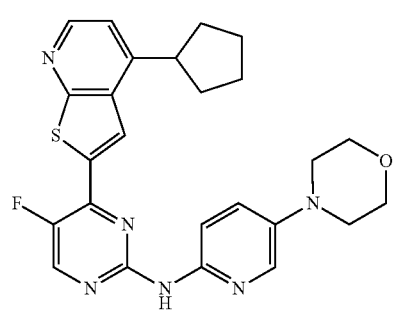 [SMILES: Fc1cnc(Nc2ccc(N3CCOCC3)cn2)nc1-c1cc2c(C3CCCC3)ccnc2s1]

Step 1: 4-(Cyclopenten-1-yl)thieno[2,3-b]Pyridine

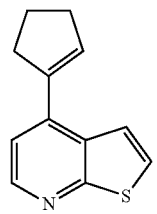 [SMILES: C1=C(c2ccnc3sccc23)CCC1]

A mixture of 4-chlorothieno[2,3-b]pyridine (696.0 mg, 4.10 mmol), 2-(cyclopenten-1-yl)-4,4,5,5-tetramethyl-1,3,2-dioxaborolane (1194.5 mg, 6.15 mmol), K$_3$PO$_4$ (2612.8 mg, 12.31 mmol) and 1,1'-[bis(diphenylphosphino)ferrocene]dichloropalladium(II) (300.2 mg, 0.41 mmol) in 1,4-dioxane (8 mL) and H$_2$O (2 mL) was bubbled with N$_2$ for 5 min and stirred at 100° C. for 6 h. LCMS showed the starting material was consumed. The solvent was removed under reduced pressure. The residue was dissolved in EtOAc (20 mL), washed with water (20 mL) and brine (20 mL), dried over Na$_2$SO$_4$, filtered, and concentrated under reduced pressure. The residue was purified by flash chromatography on a silica gel column using EtOAc/heptanes (0-20%) to afford the title compound (775.0 mg, 93.8% yield). LCMS calc. for C$_{12}$H$_{12}$NS [M+H]$^+$: m/z=202.1; Found: 201.9.

Step 2: 4-Cyclopentylthieno[2,3-b]pyridine

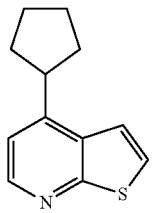 [SMILES: c1cc(C2CCCC2)c2ccsc2n1]

A mixture of 4-(cyclopenten-1-yl)thieno[2,3-b]pyridine (930.0 mg, 4.62 mmol) and Pd/C (10 wt % Pd, 180.0 mg, 0.17 mmol) in methanol (30 mL) and acetic acid (3 mL) was stirred under a H$_2$ atmosphere for 24 h. The reaction mixture was filtered, and the filtrate was concentrated under reduced pressure. The residue was dissolved in EtOAc (20 mL), washed with saturated NaHCO$_3$ solution (20 mL) and brine (20 mL), dried over Na$_2$SO$_4$, filtered, and concentrated under reduced pressure. The residue was purified by flash chromatography on a silica gel column using EtOAc/heptanes (0-15%) to afford the title compound (565.0 mg, 60.2% yield). LCMS calc. for C$_{12}$H$_{14}$NS [M+H]$^+$: m/z=204.1; Found: 203.9.

Step 3: 4-(4-Cyclopentylthieno[2,3-b]pyridin-2-yl)-5-fluoro-N-(5-morpholin-4-ylpyridin-2-yl)pyrimidin-2-amine The title compound is synthesized by procedures analogous to those outlined in Example 14, Steps 3-5. $^1$H NMR (300 MHz, CD$_3$OD) δ 8.77 (d, J=3.3 Hz, 1H), 8.57 (d, J=5.0 Hz, 1H), 8.45 (s, 1H), 8.18 (dd, J=9.7, 2.9 Hz, 1H), 7.79 (d, J=2.7 Hz, 1H), 7.54 (d, J=9.6 Hz, 1H), 7.44 (d, J=5.0 Hz, 1H), 3.94-3.84 (m, 4H), 3.73-3.63 (m, 1H), 3.27-3.22 (m, 4H), 2.33-2.18 (m, 2H), 1.98-1.78 (m, 6H). LCMS calc. for C$_{25}$H$_{26}$FN$_6$OS [M+H]$^+$: m/z=477.2/478.2; Found: 477.0/478.3.

Examples listed in Table 3-1 and 3-2 are synthesized according to procedures analogous to Example 42.

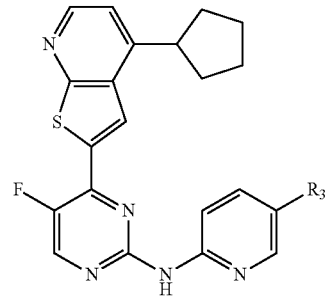

TABLE 3-1

Examples 43-47

| Example | R$_3$ | LCMS [M + H]$^+$ |
|---|---|---|
| 43 | *N-methylpiperidin-4-yl* | 489.0 |
| 44 | *4-ethylpiperazin-1-yl* | 504.0 |
| 45 | *4-methylpiperazin-1-yl (via N)* | 490.0 |
| 46 | *piperazin-1-yl* | 476.0 |
| 47 | *2-ethyl-2,6-diazaspiro[3.3]heptan-6-yl* | 516.0 |

TABLE 3-2

Examples 43-47

| Example | Compound name | NMR |
|---|---|---|
| 43 | 4-(4-Cyclopentylthieno[2,3-b]pyridin-2-yl)-5-fluoro-N-(5-(1-methylpiperidin-4-yl)pyridin-2-yl)pyrimidin-2-amine | $^1$H NMR (300 MHz, CD$_3$OD) δ 8.77 (dd, J = 14.1, 3.2 Hz, 1H), 8.59 (dd, J = 5.0, 2.6 Hz, 1H), 8.47 (d, J = 11.0 Hz, 1H), 8.28 (d, J = 4.4 Hz, 1H), 8.24-8.05 (m, 1H), 7.83 (d, J = 9.0 Hz, 1H), 7.46 (dd, J = 5.0, 2.4 Hz, 1H), 3.70 (d, J = 10.3 Hz, 2H), 3.27 (s, 1H), 3.27-3.13 (m, 2H), 3.07 (s, 1H), 2.98 (s, 3H), 2.40-2.13 (m, 3H), 2.13-1.61 (m, 7H), 1.45-1.33 (m, 2H). |

TABLE 3-2-continued

Examples 43-47

| Example | Compound name | NMR |
|---|---|---|
| 44 | 4-(4-Cyclopentylthieno[2,3-b]pyridin-2-yl)-N-[5-(4-ethylpiperazin-1-yl)pyridin-2-yl]-5-fluoropyrimidin-2-amine | $^1$H NMR (300 MHz, CD$_3$OD) δ 8.74 (d, J = 3.2 Hz, 1H), 8.55 (d, J = 5.0 Hz, 1H), 8.42 (s, 1H), 8.23-8.15 (m, 1H), 7.93 (d, J = 2.4 Hz, 1H), 7.61 (d, J = 9.6 Hz, 1H), 7.42 (d, J = 5.0 Hz, 1H), 3.74-3.62 (m, 3H), 3.57 (s, 2H), 3.33-3.27 (m, 6H), 2.29-2.19 (m, 2H), 1.96-1.81 (m, 6H), 1.43 (t, J = 7.3 Hz, 3H). |
| 45 | 4-(4-Cyclopentylthieno[2,3-b]pyridin-2-yl)-5-fluoro-N-[5-(4-methylpiperazin-1-yl)pyridin-2-yl]pyrimidin-2-amine | $^1$H NMR (300 MHz, CD$_3$OD) δ 8.80 (d, J = 3.3 Hz, 1H), 8.58 (d, J = 5.0 Hz, 1H), 8.48 (s, 1H), 8.27 (dd, J = 9.7, 2.9 Hz, 1H), 7.94 (d, J = 2.7 Hz, 1H), 7.58 (d, J = 9.6 Hz, 1H), 7.46 (d, J = 5.0 Hz, 1H), 3.94 (s, 2H), 3.80-3.63 (m, 3H), 3.34 (m, 4H), 3.03 (s, 3H), 2.40-2.12 (m, 2H), 2.02-1.76 (m, 6H). |
| 46 | 4-(4-Cyclopentylthieno[2,3-b]pyridin-2-yl)-5-fluoro-N-(5-piperazin-1-ylpyridin-2-yl)pyrimidin-2-amine | $^1$H NMR (300 MHz, CD$_3$OD) δ 8.77 (d, J = 3.2 Hz, 1H), 8.57 (d, J = 5.0 Hz, 1H), 8.45 (s, 1H), 8.26 (dd, J = 9.7, 2.9 Hz, 1H), 7.92 (d, J = 2.7 Hz, 1H), 7.56 (d, J = 9.6 Hz, 1H), 7.44 (d, J = 5.1 Hz, 1H), 3.72-3.64 (m, 1H), 3.58-3.52 (m, 4H), 3.50-3.45 (m, 4H), 2.33-2.19 (m, 2H), 1.96-1.76 (m, 6H). |
| 47 | 4-(4-Cyclopentylthieno[2,3-b]pyridin-2-yl)-N-[5-(6-ethyl-2,6-diazaspiro[3.3]heptan-2-yl)pyridin-2-yl]-5-fluoropyrimidin-2-amine | $^1$H NMR (300 MHz, DMSO-d$_6$) δ 10.24 (s, 1H), 8.78 (d, J = 3.0 Hz, 1H), 8.71 (d, J = 4.8 Hz, 1H), 8.30 (s, 1H), 7.96 (d, J = 9.0 Hz, 1H), 7.64 (d, J = 2.5 Hz, 1H), 7.43 (d, J = 4.7 Hz, 1H), 7.21 (d, J = 8.9 Hz, 1H), 4.41-4.31 (m, 2H), 4.27-4.19 (m, 2H), 4.13 (s, 2H), 4.03 (s, 2H), 2.20 (m, 3H), 2.05-1.95 (m, 2H), 1.84 (m, 6H). |

Example 48. 4-(7-Cyclopentyl-3-methylthieno[2,3-c]pyridin-2-yl)-5-fluoro-N-(5-(4-methylpiperazin-1-yl)pyridin-2-yl)pyrimidin-2-amine

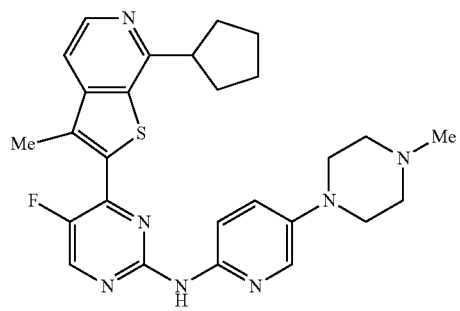 [SMILES: Cc1c(-c2nc(Nc3ccc(N4CCN(C)CC4)cn3)ncc2F)sc2c(C3CCCC3)nccc12]

Step 1. 4-Methylthiophene-2-carbonyl Chloride

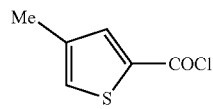

Oxalyl chloride (2.631 g, 1.778 mL, 20.7 mmol, 1.25 equiv.) was added dropwise into the solution of 4-methylthiophene-2-carboxylic acid (2.358 g, 16.6 mmol, 1.00 equiv.) in DMF (61 mg, 64 μL, 0.83 mmol, 0.05 equiv.) at 0° C. The resulting light green solution was allowed to warm to ambient temperature and stirred for 4 h, when LC-MS analysis (quenched with morpholine) indicated the complete consumption of the carboxylic acid. The reaction mixture was concentrated under reduced pressure and dried under high vacuum. The crude acid chloride was used directly without further purification.

Step 2.
N-Hydroxy-4-methylthiophene-2-carboxamide

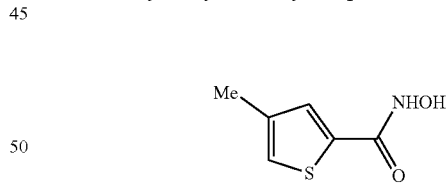

The solution of crude 4-methylthiophene-2-carbonyl chloride from Step 1 in THF (10 mL) was added dropwise into the suspension of NH$_2$OH·HCl (4.615 g, 66.4 mmol, 4.00 equiv.) and NaOH (3.320 g, 83.0 mmol, 5.00 equiv.) in THF (10 mL) and H$_2$O (20 mL) at 0° C. The resulting mixture was slowly warmed to ambient temperature and stirred for another 2 h. The reaction mixture was acidified with 2 N HCl (pH 3) and extracted with EtOAc (30 mL×3). The combined organic layer was washed with saturated NaHCO$_3$ solution (30 mL), H$_2$O (30 mL) and brine (30 mL), dried over anhydrous Na$_2$SO$_4$, filtered, and evaporated in vacuo. The crude product obtained as yellow solid, was used in the next step without further purification. LCMS calc. for C$_6$H$_8$NO$_2$S [M+H]$^+$: m/z=158.0; Found: 158.1.

Step 3. 4-Methyl-N-(pivaloyloxy)thiophene-2-carboxamide

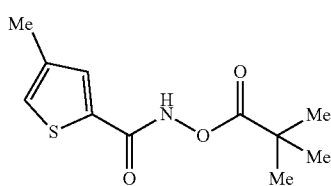 [SMILES: Cc1csc(C(=O)NOC(=O)C(C)(C)C)c1]

Trimethylacetyl chloride (1.951 g, 16.6 mmol, 1.00 equiv.) was added dropwise into the solution of crude N-hydroxy-4-methylthiophene-2-carboxamide (from Step 2) and Et$_3$N (2.016 g, 2.777 mL, 19.9 mmol, 1.20 equiv.) in THF (25 mL) at 0° C. The resulting orange suspension was warmed to ambient temperature and stirred for 18 h. The light-yellow milky reaction mixture was concentrated to ⅓ of its original volume and partitioned between H$_2$O (30 mL) and EtOAc (30 mL). The organic phase was separated and the aqueous phase extracted with EtOAc (20 mL×3). The combined organic phase was washed with H$_2$O (30 mL) and brine (30 mL), dried over Na$_2$SO$_4$, filtered, and concentrated in vacuo. The residue was purified by flash column chromatography on silica gel (5%-20% EtOAc, 10% DCM in heptanes) to give the title compound (3.732 g, 15.5 mmol, 93.2% yield for three steps) as white solid. R$_f$=0.4 (30% EtOAc in heptanes). LCMS calc. for C$_{11}$H$_{16}$NO$_3$S [M+H]$^+$: m/z=242.1; Found: 242.0.

Step 4. 3-Methylthieno[2,3-c]pyridin-7(6H)-one

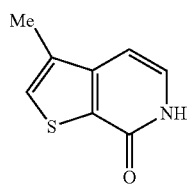 [SMILES: Cc1csc2c(=O)[nH]ccc12]

The suspension of [(4-methylthiophene-2-carbonyl)amino] 2,2-dimethylpropanoate (1.316 g, 5.45 mmol, 1.00 equiv.), CsOAc (1.050 g, 5.45 mmol, 1.00 equiv.), [Cp*RhCl$_2$]$_2$ (101 mg, 0.16 mmol, 0.03 equiv.), and vinyl acetate (704 mg, 8.18 mmol, 1.50 equiv.) in anhydrous MeOH (15 mL) was stirred at 45° C. under a N$_2$ atmosphere for 18 h. The reaction was diluted with H$_2$O (30 mL) and extracted with EtOAc (20 mL×3). The combined organic phase was washed with H$_2$O (20 mL) and brine (20 mL), dried over Na$_2$SO$_4$, filtered, and evaporated under reduced pressure. The residue was purified by flash chromatography on silica gel column (0-50% EtOAc in heptanes containing 0.1% Et$_3$N) to give the title compound (527 mg, 3.19 mmol, 58.5% yield) as salmon solid. R$_f$=0.25 (50% EtOAc in heptanes). LCMS calc. for C$_8$H$_8$NOS [M+H]$^+$: m/z=166.0; Found: 166.1.

Step 5. 7-Chloro-3-methylthieno[2,3-c]pyridine

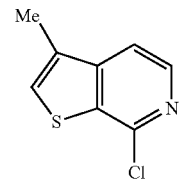

The mixture of 3-methyl-6H-thieno[2,3-c]pyridin-7-one (527 mg, 3.19 mmol, 1.00 equiv.) and POCl$_3$ (2.935 mg, 19.1 mmol, 6.00 equiv.) was heated at 100° C. for 3 h, when LCMS indicated the complete consumption of the starting material. The excess POCl$_3$ was evaporated under reduced pressure and the residue was partitioned between 10% Na$_2$CO$_3$ (20 mL) solution and EtOAc (10 mL). The organic layer was separated, and the aqueous layer extracted with EtOAc (10 mL×3). The combined organic phase was washed with 10% Na$_2$CO$_3$ solution (10 mL), H$_2$O (10 mL) and brine (10 mL), dried over Na$_2$SO$_4$, filtered and evaporated under reduced pressure. The oily residue was purified by flash chromatography on a silica gel column (0-50% EtOAc in heptanes) to give the title compound (332 mg, 1.81 mmol, 56.7% yield) as a yellow solid. R$_f$=0.3 (50% EtOAc in heptanes). LCMS calc. for C$_8$H$_7$ClNS [M+H]$^+$: m/z=184.0; Found: 184.1.

Step 6. 7-(Cyclopent-1-en-1-yl)-3-methylthieno[2,3-c]pyridine

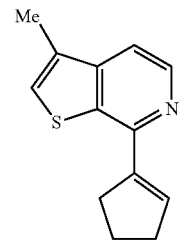

The suspension of 7-chloro-3-methylthieno[2,3-c]pyridine (332 mg, 1.81 mmol, 1.00 equiv.), 2-(cyclopenten-1-yl)-4,4,5,5-tetramethyl-1,3,2-dioxaborolane (526 mg, 2.71 mmol, 1.50 equiv.), Pd(dppf)Cl$_2$ (66 mg, 0.09 mmol, 0.05 equiv.), and K$_3$PO$_4$ (1.535 g, 7.23 mmol, 4.00 equiv.) in 1,4-dioxane (8 mL) and H$_2$O (2 mL) was stirred at 100° C. under nitrogen atmosphere for 18 h. The reaction mixture was cooled to ambient temperature and then partitioned between H$_2$O (30 mL) and EtOAc (15 mL). The organic layer was separated, and the aqueous layer was extracted with EtOAc (15 mL×3). The combined organic phase was dried over anhydrous Na$_2$SO$_4$, filtered, and evaporated in vacuo. The residue was purified by flash chromatography on silica gel column (0-25% MTBE in heptanes) to give the title compound (308 mg, 1.43 mmol, 79.0% yield) as colorless oil. R$_f$=0.4 (30% MTBE in heptanes). LCMS calc. for C$_{13}$H$_{14}$NS [M+H]$^+$: m/z=216.1; Found: 216.0.

Step 7. 7-Cyclopentyl-3-methylthieno[2,3-c]pyridine

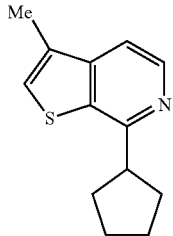 [SMILES: Cc1csc2c(C3CCCC3)nccc12]

The solution of 7-(cyclopenten-1-yl)-3-methylthieno[2,3-c]pyridine (308 mg, 1.43 mmol) in MeOH (5 mL) was cooled at 0° C. Pd/C (10 wt % Pd, 31 mg, 0.29 mmol) was added and the reaction flask was evacuated and flushed with hydrogen gas. The reaction mixture was allowed to warm to room temperature and stirred for 4 h. The solid materials were filtered off through a pad of Celite and the filter cake was washed with MeOH (5 mL×2). The combined filtrate was concentrated under reduced pressure and the residue was purified by flash chromatography on silica gel column (0-25% MTBE in heptanes) to give the title compound (305 mg, 1.40 mmol, 98.1% yield) as light yellow solid. $R_f$=0.3 (25% MTBE in heptanes). LCMS calc. for $C_{13}H_{16}NS$ $[M+H]^+$: m/z=218.1; Found: 218.0.

Step 8. 4-(7-Cyclopentyl-3-methylthieno[2,3-c]pyridin-2-yl)-5-fluoro-N-(5-(4-methylpiperazin-1-yl)pyridin-2-yl)pyrimidin-2-amine The title compound is synthesized by procedures analogous to those outlined in Example 14, Steps 3-5. LCMS calc. for $C_{27}H_{31}FN_7S$ $[M+H]^+$: m/z=504.2; Found: 504.0.

Example 49. 4-(4-Cyclopentyl-7-methylthieno[3,2-d]pyrimidin-6-yl)-5-fluoro-N-(5-(1-methylpiperidin-4-yl)pyridin-2-yl)pyrimidin-2-amine

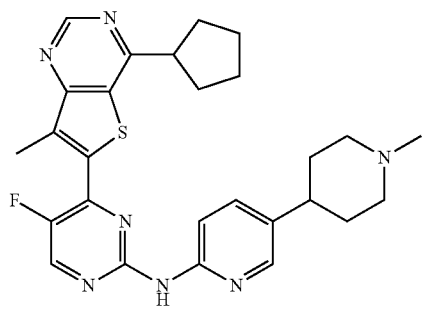 [SMILES: Cc1c(-c2nc(Nc3ccc(C4CCN(C)CC4)cn3)ncc2F)sc2c(C3CCCC3)ncnc12]

Step 1: 4-(Cyclopent-1-en-1-yl)-7-methylthieno[3,2-d]pyrimidine

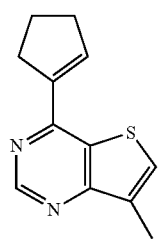

4-chloro-7-methylthieno[3,2-d]pyrimidine (800 mg, 4.33 mmol), 2-(cyclopenten-1-yl)-4,4,5,5-tetramethyl-1,3,2-dioxaborolane (1.37 mL, 6.5 mmol), Pd(dppf)Cl₂ (169 mg, 0.26 mmol), and K₃PO₄ (3679 mg, 17.33 mmol) were weighed into a 40-mL vial. Then 1,4-dioxane (8 mL) and water (2 mL) was added. The mixture was purged with N₂ for 2 mins. Then it was heated overnight. The mixture was diluted with water and extracted by ethyl acetate twice. The combined organic layer was dried over Na₂SO₄. The solution was concentrated to dryness and the residue was purified by auto flash column chromatography system on a pre-packed silica gel column (40 g) using EtOAc/heptanes (5-70%) to give the title compound (840 mg, 3.88 mmol, 89.6% yield) as a white solid. LC-MS calc. for $C_{12}H_{13}N_2S$ $[M+H]^+$: m/z=217.08; Found 217.04.

Step 2: 4-Cyclopentyl-7-methylthieno[3,2-d]pyrimidine

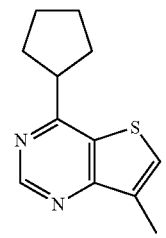

To a suspension of 4-(cyclopenten-1-yl)-7-methylthieno[3,2-d]pyrimidine (800.0 mg, 3.7 mmol) and Pd/C (5 wt % Pd, 100.0 mg, 0.94 mmol) in methanol (20 mL), 3 drops of AcOH was added. The mixture was stirred overnight under a H₂ atmosphere. The solvent was removed under vacuum. The residue was purified by flash chromatography on a silica gel column (0-30% EtOAc/heptane with 0.1% Et₃N) to afford the title compound (720 mg, 3.30 mmol, 89.2% yield) as a white solid. LC-MS calc. for $C_{12}H_{15}N_2S$ $[M+H]^+$: m/z=219.10; Found 219.08.

Step 3: 4-(4-Cyclopentyl-7-methylthieno[3,2-d]pyrimidin-6-yl)-5-fluoro-N-(5-(1-methylpiperidin-4-yl)pyridin-2-yl)pyrimidin-2-amine The title compound is synthesized by procedures analogous to those outlined in Example 14, Steps 3-5. ¹H NMR (300 MHz, methanol-d₄) δ 9.50-9.05 (m, 1H), 9.04-8.91 (m, 1H), 8.46-8.30 (m, 2H), 7.68-7.55 (m, 1H), 3.67 (d, J=12.1 Hz, 2H), 3.35 (s, 3H), 3.22 (d, J=12.9 Hz, 2H), 2.94 (s, 3H), 2.75 (dd, J=14.4, 3.1 Hz, 2H), 2.44-1.78 (m, 12H). LC-MS calc. for $C_{27}H_{30}FN_7S$ $[M+H]^+$: m/z=504.23; Found 504.03.

Example 50. N-[5-(4-Ethylpiperazin-1-yl)pyridin-2-yl]-5-fluoro-4-(4-oxido-7-propan-2-ylthieno[3,2-b]pyridin-4-ium-2-yl)pyrimidin-2-amine

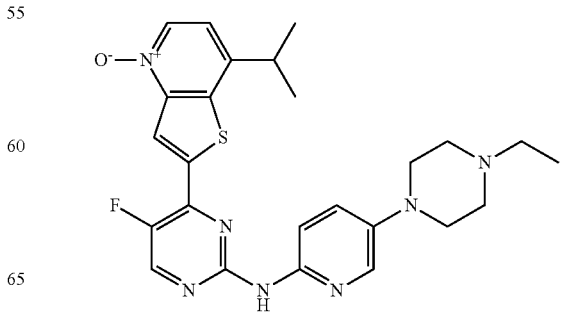

Step 1: 2-(2-Chloro-5-fluoropyrimidin-4-yl)-4-oxido-7-propan-2-ylthieno[3,2-b]pyridin-4-ium

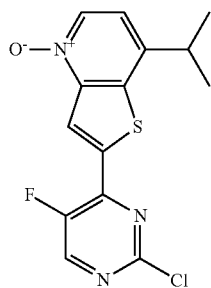 [SMILES: CC(C)c1cc[n+]([O-])c2cc(-c3nc(Cl)ncc3F)sc12]

A mixture of 2-(2-chloro-5-fluoropyrimidin-4-yl)-7-propan-2-ylthieno[3,2-b]pyridine (20.0 mg, 0.06 mmol) and mCPBA (16.82 mg, 0.10 mmol) in DCM (3 mL) was stirred at r.t. for 1 h. The reaction was quenched with H$_2$O (2 mL) and extracted with DCM (2 mL×3). The combined organic layers were concentrated and purified by prep-HPLC on C$_{18}$ column using mobile phase 20% to 100% MeCN/H$_2$O (t$_R$=15 min) to afford the title compound (9.1 mg, 43%) as a bright yellow solid. $^1$H NMR (300 MHz, CDCl$_3$) δ 8.72 (d, J=1.7 Hz, 1H), 8.63 (d, J=2.4 Hz, 1H), 8.32 (d, J=6.5 Hz, 1H), 7.20 (d, J=6.5 Hz, 1H), 3.33-3.17 (m, 1H), 1.45 (d, J=6.9 Hz, 6H).

Step 2: N-[5-(4-Ethylpiperazin-1-yl)pyridin-2-yl]-5-fluoro-4-(4-oxido-7-propan-2-ylthieno[3,2-b]pyridin-4-ium-2-yl)pyrimidin-2-amine The title compound is synthesized by procedures analogous to those outlined in Example 14, Step 5. $^1$H NMR (300 MHz, CD$_3$OD) δ 8.85 (d, J=3.0 Hz, 1H), 8.61 (d, J=0.9 Hz, 1H), 8.48 (d, J=6.5 Hz, 1H), 8.24 (dd, J=9.6, 2.9 Hz, 1H), 7.94 (d, J=2.7 Hz, 1H), 7.59 (d, J=9.6 Hz, 1H), 7.53 (d, J=6.5 Hz, 1H), 4.05-3.86 (m, 2H), 3.85-3.64 (m, 2H), 3.40-3.24 (m, 7H), 1.49 (d, J=6.9 Hz, 6H), 1.43 (t, J=7.3 Hz, 3H). LC-MS calc. for C$_{25}$H$_{29}$FN$_7$OS [M+H]$^+$: m/z=494.2/495.2; Found 494.1/495.3.

Example 51. 2-[5-Fluoro-2-[[5-(4-methylpiperazin-1-yl)pyridin-2-yl]amino]pyrimidin-4-yl]-3,5-dimethyl-7-propan-2-ylthieno[3,2-c]pyridin-4-one

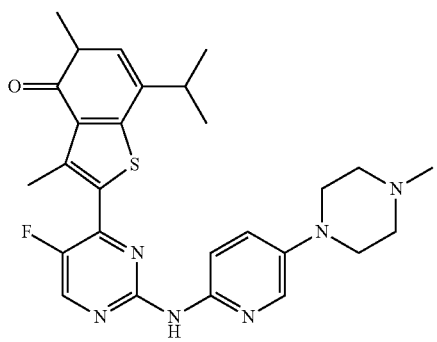 [SMILES: Cc1c(-c2nc(Nc3ccc(N4CCN(C)CC4)cn3)ncc2F)sc2c1C(=O)C(C)C=C2C(C)C]

Step 1: 1-(5-Bromo-4-methylthiophen-2-yl)-2-methylpropan-1-one

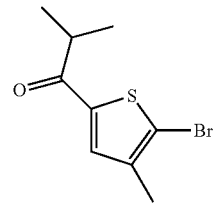

To a suspension of aluminum chloride (1.66 g, 12.43 mmol) in DCM (20 mL) at 0° C. was added isobutyryl chloride (1.32 g, 12.43 mmol) dropwise, next 2-bromo-3-methylthiophene (2.0 g, 11.3 mmol) was added slowly at 0° C. The resulting mixture was stirred at rt overnight. The reaction was quenched with water (20 mL) and extracted with DCM (20 mL×3). The combined organic layers were dried over Na$_2$SO$_4$, filtered, and concentrated under reduced pressure. The residue was purified by flash chromatography on a silica gel column using EtOAc/heptanes (0-10%) to afford the title compound (2.11 g, 75.2%). $^1$H NMR (300 MHz, CDCl$_3$) δ 7.39 (s, 1H), 3.35-3.19 (m, 1H), 2.22 (s, 3H), 1.21 (d, J=6.9 Hz, 6H).

Step 2: Ethyl (E)-3-(5-bromo-4-methylthiophen-2-yl)-4-methylpent-2-enoate

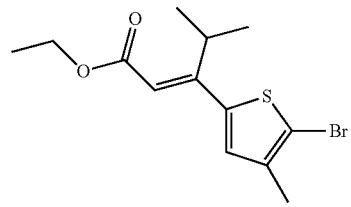 [SMILES: CCOC(=O)/C=C(/c1cc(C)c(Br)s1)C(C)C]

To a suspension of sodium hydride (407.8 mg, 10.2 mmol) in THF (20 mL) at 0° C. was added triethyl phosphonoacetate (2.11 g, 9.4 mmol) dropwise at 0° C. The reaction mixture was stirred at 0° C. for 30 min and then stirred at rt for 30 min. A solution of 1-(5-bromo-4-methylthiophen-2-yl)-2-methylpropan-1-one (2.1 g, 8.5 mmol) in THF (5 mL) was added dropwise. The reaction mixture was stirred at rt for 2 days. The reaction was quenched with water (20 mL) and extracted with EtOAc (20 mL×3). The combined organic layers were dried over Na$_2$SO$_4$, filtered and concentrated under reduced pressure to yield the title compound (2.01 g), which was used for the next reaction without further purification.

Step 3: (E)-3-(5-Bromo-4-methylthiophen-2-yl)-4-methylpent-2-enoic Acid

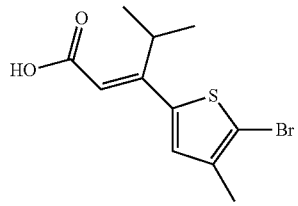

To a solution of ethyl (E)-3-(5-bromo-4-methylthiophen-2-yl)-4-methylpent-2-enoate (2.01 g, 6.3 mmol) in methanol (10 mL) was added a solution of sodium hydroxide (1.26 g, 31.52 mmol) in water (10 mL) dropwise. The reaction mixture was stirred at 65° C. for 1 h. The solvent was removed under reduced pressure. The residue was dissolved in EtOAc (20 mL) and acidify with 2N HCl solution (20 mL). The layer was separated, and the aqueous layer was extracted with EtOAc (20 mL×3). The combined organic layers were washed with brine (30 mL), dried over Na$_2$SO$_4$, filtered and concentrated under reduced pressure to yield the title compound (1.30 g), which was used for the next reaction without further purification.

Step 4: 2-Bromo-3-methyl-7-propan-2-yl-5H-thieno[3,2-c]pyridin-4-one

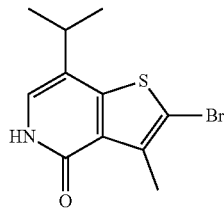

To a solution of (E)-3-(5-bromo-4-methylthiophen-2-yl)-4-methylpent-2-enoic acid (1.30 g, 4.50 mmol) and triethyamine (1.93 g, 13.49 mmol) in diphenyl ether (10 mL) was added diphenyl phosphoryl azide (1.86 g, 6.74 mmol) dropwise. The reaction mixture was stirred at rt for 30 min and heated at 180° C. for 30 min. The reaction was quenched with 1 N NaOH solution (10 mL) and stirred at rt for 30 min. The reaction was extracted with EtOAc (20 mL×3). The combined organic layers were washed with brine (20 mL), dried over Na$_2$SO$_4$, filtered and concentrated under reduced pressure. The residue was purified by flash chromatography on a silica gel column using EtOAc/heptanes (5-90%) to afford the title compound (0.45 g, 35.0%). $^1$H NMR (300 MHz, CDCl$_3$) δ 10.75 (s, 1H), 6.95 (s, 1H), 3.00-2.76 (m, 1H), 2.64 (s, 3H), 1.31 (d, J=6.9 Hz, 6H).

Step 5: 2-Bromo-3,5-dimethyl-7-propan-2-ylthieno[3,2-c]pyridin-4-one

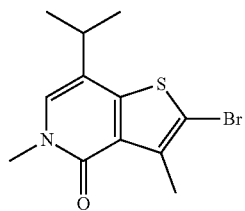 [SMILES: Cc1c(Br)sc2c(C(C)C)cn(C)c(=O)c12]

To a solution of 2-bromo-3-methyl-7-propan-2-yl-5H-thieno[3,2-c]pyridin-4-one (105.0 mg, 0.37 mmol) in DMF (1 mL) was added cesium carbonate (239.1 mg, 0.73 mmol), followed by the addition of iodomethane (104.2 mg, 0.73 mmol). The reaction mixture was stirred at rt for 1 h. The reaction was quenched with water (2 mL) and extracted with EtOAc (2 mL×3). The combined organic layers were dried over Na$_2$SO$_4$, filtered and concentrated under reduced pressure. The residue was purified by flash chromatography on a silica gel column using EtOAc/heptanes (5-70%) to afford the title compound (75.0 mg, 68.1% yield). $^1$H NMR (300 MHz, CDCl$_3$) δ 7.03 (s, 1H), 3.71 (s, 3H), 3.00-2.78 (m, 1H), 2.60 (s, 3H), 1.34 (d, J=6.9 Hz, 6H).

Step 6: 2-(2-Chloro-5-fluoropyrimidin-4-yl)-3,5-dimethyl-7-propan-2-ylthieno[3,2-c]pyridin-4-one

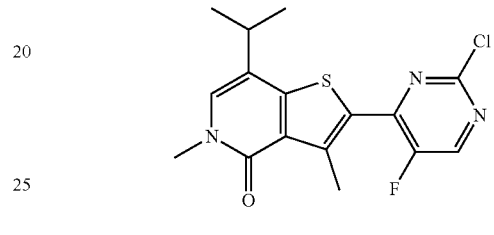

To a solution of 2-bromo-3,5-dimethyl-7-propan-2-ylthieno[3,2-c]pyridin-4-one (130.0 mg, 0.43 mmol) and bis(pinacolato)diboron (164.9 mg, 0.65 mmol) in 1,4-dioxane (3 mL) was added KOAc (127.5 mg, 1.3 mmol) and 1,1'-bis(diphenylphosphino)ferrocene-dichloropalladium (1:1) (31.7 mg, 0.04 mmol). The reaction mixture was purged with N$_2$ for 5 min and stirred at 100° C. for 1 h. LCMS showed the starting material was consumed. The reaction was cooled to rt and a solution of K$_3$PO$_4$ (275.8 mg, 1.3 mmol) in water (1 mL) was added. The resulting mixture was stirred at rt for 30 min. Next 2,6-dichloro-5-fluororacil (108.4 mg, 0.65 mmol) and 1,1'-[bis(diphenylphosphino)ferrocene]dichloropalladium(II) (31.7 mg, 0.04 mmol) was added. The reaction mixture was purged with N$_2$ for 5 min and stirred at 100° C. overnight. LCMS showed the starting material was consumed. The solvent was removed under reduced pressure. The residue was purified by prep-HPLC on a C18 column eluting with MeCN/H$_2$O (20-100%) to yield the title compound (14.1 mg, 9.2% yield). LCMS calc. for C$_{16}$H$_{16}$ClFN$_3$OS [M+H]$^+$: m/z=352.07/354.07; Found: 352.0/353.9.

Step 7: 2-[5-Fluoro-2-[[5-(4-methylpiperazin-1-yl)pyridin-2-yl]amino]pyrimidin-4-yl]-3,5-dimethyl-7-propan-2-ylthieno[3,2-c]pyridin-4-one The title compound is synthesized by procedures analogous to those outlined in Example 14, Step 5. $^1$H NMR (300 MHz, CD$_3$OD) δ 8.77 (d, J=2.7 Hz, 1H), 8.23 (dd, J=9.6, 3.0 Hz, 1H), 7.91 (d, J=2.9 Hz, 1H), 7.59 (d, J=9.6 Hz, 1H), 7.46 (s, 1H), 3.63 (s, 3H), 4.00-3.10 (m, 8H), 3.05-2.93 (m, 4H), 2.85 (s, 3H), 1.40 (d, J=7.0 Hz, 6H). LCMS calc. for C$_{26}$H$_{31}$FN$_7$OS [M+H]$^+$: m/z=508.2/509.2; Found: 508.2/509.4.

Example 52: 4-(2,6-Dimethyl-3-propan-2-ylthieno[2,3-d]imidazol-5-yl)-N-[5-(6-ethyl-2,6-diazaspiro[3.3]heptan-2-yl)pyridin-2-yl]-5-fluoropyrimidin-2-amine

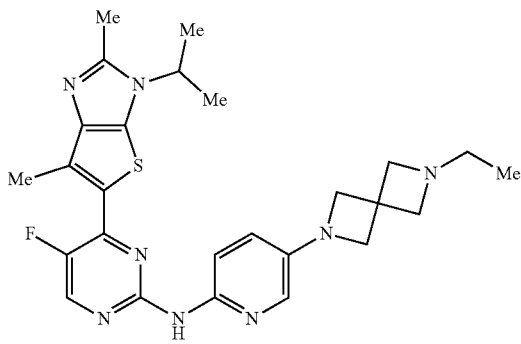 [SMILES: CCN1CC2(C1)CN(c1ccc(Nc3ncc(F)c(-c4sc5c(nc(C)n5C(C)C)c4C)n3)nc1)C2]

Step 1. Methyl 2-(isopropylamino)-4-methylthiophene-3-carboxylate

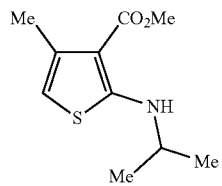 [SMILES: COC(=O)c1c(C)csc1NC(C)C]

Sodium triacetoxyborohydride (13.5 g, 63.7 mmol) was added in portions to a mixture of methyl 2-amino-4-methylthiophene-3-carboxylate (7.27 g, 42.5 mmol), 2-methoxyprop-1-ene (4.6 g, 63.7 mmol), and acetic acid (3.64 mL, 63.7 mmol) in DCE (140 mL). The resulting mixture was stirred for 4 h. The reaction mixture was slowly poured into 10% Na$_2$CO$_3$ (aq) and stirred until gas evolution ceased (30 min). The organic layer was separated, and the aqueous layer extracted with DCM (60 mL×3). The combined organic layers were washed with 10% Na$_2$CO$_3$ (aq) (60 mL), water (60 mL), and brine (60 mL); dried over Na$_2$SO$_4$; filtered; and concentrated. The crude product was purified by silica gel chromatography (0-10% MTBE/heptanes) to give the title compound (7.81 g, 36.6 mmol, 86.1% yield) as colorless oil. LCMS calc. for C$_{10}$H$_{16}$NO$_2$S [M+H]$^+$: m/z=214.1; Found: 214.2.

Step 2. 2-(Isopropylamino)-4-methylthiophene-3-carboxylic Acid

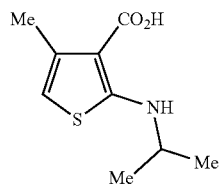 [SMILES: Cc1csc(NC(C)C)c1C(=O)O]

A solution of NaOH (8.78 g, 220 mmol) in water (70 mL) was added to a solution of methyl 2-(isopropylamino)-4-methylthiophene-3-carboxylate (7.81 g, 36.6 mmol) in methanol (70 mL). The reaction mixture was heated at 70° C. for 18 h. The organic solvent was removed under reduced pressure. The remaining aqueous mixture was diluted with water (20 mL), acidified to pH 3 with 2 N HCl, and extracted with MTBE (30 mL×3). The combined organic layers were washed with water (30 mL) and brine (30 mL), dried over Na$_2$SO$_4$, filtered, and concentrated in vacuo to afford the title compound (6.26 g, 31.4 mmol, 85.8% yield) as an amber solid, which was used in the next step without further purification. LCMS calc. for C$_9$H$_{14}$NO$_2$S [M+H]$^+$: m/z=200.1; Found: 200.1.

Step 3. 2-(N-Isopropylacetamido)-4-methylthiophene-3-carboxylic Acid

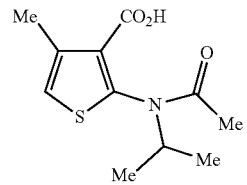

Acetic anhydride (7.43 mL, 78.6 mmol) was added dropwise to a mixture of 2-(isopropylamino)-4-methylthiophene-3-carboxylic acid (6.26 g, 31.4 mmol), triethylamine (13.1 mL, 94.3 mmol) and 4-(dimethylamino)pyridine (0.38 g, 3.14 mmol) in DCM (60 mL) at room temperature. The resulting light amber solution was stirred for 18 h. The reaction mixture was poured into water (80 mL) and extracted with DCM (30 mL×3). The combined organic layers were washed sequentially with water (30 mL) and brine (30 mL), dried over Na$_2$SO$_4$, filtered, and concentrated. The residue was purified by silica gel chromatography (0-50% EtOAc/heptanes) to give the title compound (4.71 g, 19.5 mmol, 62.1% yield) as yellow viscous oil. LCMS calc. for C$_{11}$H$_{16}$NO$_3$S [M+H]$^+$: m/z=242.1; Found: 242.1.

Step 4. N-(3-Amino-4-methylthiophen-2-yl)-N-isopropylacetamide

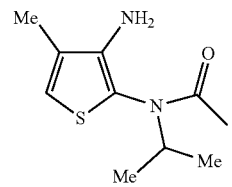

To mixture of 2-(N-isopropylacetamido)-4-methylthiophene-3-carboxylic acid (4.71 g, 19.5 mmol) and triethylamine (8.15 mL, 58.5 mmol) in 1,4-dioxane (25 mL), was added diphenyl phosphoryl azide (8.05 g, 29.2 mmol) dropwise over 30 min. The resulting mixture was stirred for 1 h. Water (25 mL) was added, and the reaction mixture was heated at 100° C. for 18 h. After cooling to room temperature, 2 N NaOH (aq) (10 mL) was added. The resulting mixture was stirred for 15 min and then extracted with DCM (50 mL×3). The combined organic layers were washed with brine (50 mL), dried over Na₂SO₄, filtered, and concentrated to afford the title compound, which was used in the subsequent step without further purification. LCMS calc. for $C_{10}H_{17}N_2OS$ [M+H]⁺: m/z=213.1; Found: 213.1.

Step 5. 3-Isopropyl-2,6-dimethyl-3H-thieno[2,3-d]imidazole

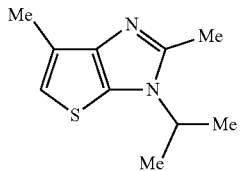

To the solution of crude N-(3-amino-4-methylthiophen-2-yl)-N-isopropylacetamide (from Step 4) in toluene (40 mL) was added POCl₃ (3.29 mg, 21.5 mmol) slowly at room temperature, and then the mixture was heated at 100° C. for 18 h. The reaction mixture was poured onto ice-cold 10% Na₂CO₃ (aq) with vigorous stirring. The organic layer was separated, and the aqueous layer was extracted with EtOAc (40 mL×3). The combined organic layers were washed with 10% Na₂CO₃ (aq) (40 mL) and brine (40 mL), dried over Na₂SO₄, filtered, and concentrated. The residue was purified by silica gel chromatography (0-75% EtOAc/heptanes with 0.1% NEt₃) to give the title compound (2.88 g, 14.8 mmol, 75.9% yield over two steps) as a red oil. LCMS calc. for $C_{10}H_{15}N_2S$ [M+H]⁺: m/z=195.1; Found: 195.1.

Step 6. 3-Isopropyl-2,6-dimethyl-5-(4,4,5,5-tetramethyl-1,3,2-dioxaborolan-2-yl)-3H-thieno[2,3-d]imidazole

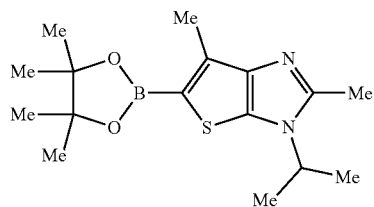 [SMILES: Cc1c(B2OC(C)(C)C(C)(C)O2)sc2c1nc(C)n2C(C)C]

A solution of lithium diisopropylamide (5.43 mL, 41.0 mmol) (2.0 M in THF/ethylbenzene/hexanes) was added dropwise to a mixture of 3-isopropyl-2,6-dimethyl-3H-thieno[2,3-d]imidazole (1.60 g, 8.21 mmol) and 2-isopropoxy-4,4,5,5-tetramethyl-1,3,2-dioxaborolane (4.19 mL, 20.5 mmol) in THF (50 mL) at −78° C. The mixture was stirred at −78° C. After 4 h, the reaction was quenched by the dropwise addition of sat. NH₄Cl (aq) (75 mL) at 0° C. The mixture was extracted with EtOAc (75 mL×3) and 1:1 CHCl₃/iPrOH (75 mL×3). The combined organic layers were dried over sodium sulfate, filtered, and concentrated to afford the title compound, which was used in the next step without further purification. LCMS calc. for $C_{16}H_{26}BN_2O_2S$ [M+H]⁺: m/z=321.2; Found: 321.1.

Step 7. 5-(2-Chloro-5-fluoropyrimidin-4-yl)-3-isopropyl-2,6-dimethyl-3H-thieno[2,3-d]imidazole A suspension of 2,6-dichloro-5-fluororacil (1.77 g, 10.6 mmol), 3-isopropyl-2,6-dimethyl-5-(4,4,5,5-tetramethyl-1,3,2-dioxaborolan-2-yl)-3H-thieno[2,3-d]imidazole (from Step 6), [1,1'-bis(diphenylphosphino)ferrocene]dichloropalladium(II) (323 mg, 0.44 mmol), and K₃PO₄ (7.50 g, 35.4 mmol) in 1,4-dioxane (16 mL) and water (4 mL) was heated at 100° C. under a nitrogen atmosphere for 18 h. The reaction mixture was cooled to room temperature and partitioned between EtOAc (20 mL) and water (20 mL). The organic layer was separated, and the aqueous layer was extracted with EtOAc (15 mL×3). The combined organic layers were washed with water (15 mL) and brine (15 mL), dried over Na₂SO₄, filtered, and concentrated. The residue was purified by silica gel chromatography (0-75% EtOAc/heptanes containing 0.1% NEt₃) and then repurified via prep-HPLC on a C18 column (15-60% MeCN/H₂O containing 0.1% TFA) to afford the title compound as its TFA salt (1.57 g, 3.58 mmol, 43.7% yield for two steps) as yellow solid. LCMS calc. for $C_{14}H_{15}ClFN_4S$ [M+H]⁺: m/z=325.1; Found: 325.0.

Step 8. 4-(2,6-Dimethyl-3-propan-2-ylthieno[2,3-d]imidazol-5-yl)-N-[5-(6-ethyl-2,6-diazaspiro[3.3]heptan-2-yl)pyridin-2-yl]-5-fluoropyrimidin-2-amine A suspension of 5-(2-chloro-5-fluoropyrimidin-4-yl)-3-isopropyl-2,6-dimethyl-3H-thieno[2,3-d]imidazole, TFA salt (500 mg, 1.14 mmol), XPhos Pd G2 (121 mg, 0.15 mmol), K₃PO₄ (980 mg, 4.62 mmol) and 5-(6-ethyl-2,6-diazaspiro[3.3]heptan-2-yl)pyridin-2-amine (437 mg, 2.0 mmol) in 1,4-dioxane (10 mL) and DMSO (1 mL) was heated at 100° C. under a nitrogen atmosphere for 5 h. The reaction mixture was cooled to room temperature, diluted with MeOH (5 mL), filtered, and purified by prep-HPLC on C18 column (5-40% MeCN/H₂O containing 0.1% TFA) to afford title compound as its TFA salt (701 mg, 0.955 mmol, 62.0% yield). ¹H NMR (300 MHz, methanol-d₄) δ 8.47 (d, J=3.5 Hz, 1H), 7.95 (d, J=9.0 Hz, 1H), 7.58 (d, J=2.8 Hz, 1H), 7.22 (dd, J=9.1, 2.9 Hz, 1H), 4.81-4.76 (m, 1H), 4.41 (s, 4H), 4.16 (s, 4H), 3.30 (q, J=7.3 Hz, 2H), 2.65 (s, 3H), 2.64 (s, 3H), 1.62 (d, J=6.7 Hz, 6H), 1.26 (t, J=7.2 Hz, 3H). LC-MS calc. for $C_{26}H_{32}FN_8S$ [M+H]⁺: m/z=507.2; Found 506.9.

Example 53: 6-(6-Ethyl-2,6-diazaspiro[3.3]heptan-2-yl)-N-(5-fluoro-4-(3-isopropyl-2,6-dimethyl-3H-thieno[2,3-d]imidazol-5-yl)pyrimidin-2-yl)pyridazin-3-amine

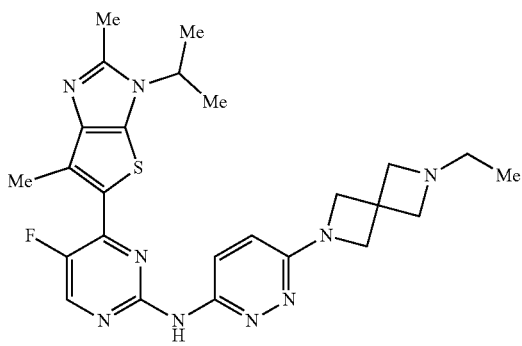 [SMILES: CCN1CC2(C1)CN(c1ccc(Nc3ncc(F)c(-c4sc5c(nc(C)n5C(C)C)c4C)n3)nn1)C2]

Step 1. 5-Fluoro-4-(3-isopropyl-2,6-dimethyl-3H-thieno[2,3-d]imidazol-5-yl)pyrimidin-2-amine

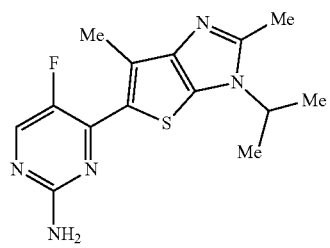 [SMILES: Cc1c(-c2nc(N)ncc2F)sc2c1nc(C)n2C(C)C]

To a suspension of 5-(2-chloro-5-fluoropyrimidin-4-yl)-3-isopropyl-2,6-dimethyl-3H-thieno[2,3-d]imidazole (138 mg, 0.426 mmol) in 2-propanol (2 mL) was added aqueous solution of NH$_4$OH (2.0 mL, 0.42 mmol, 33%). The resulting mixture was stirred at 100° C. in a sealed tube for 2 d. After cooling to room temperature, the volatiles were removed in vacuo. The residue was purified by prep-HPLC on a C18 column (15-60% MeCN/H$_2$O containing 0.1% TFA) to afford the title compound as its TFA salt (122 mg, 0.291 mmol, 68.4% yield) as yellow solid. LCMS calc. for C$_{14}$H$_{17}$FN$_5$S [M+H]$^+$: m/z=306.1; Found: 305.9.

Step 2. Tert-Butyl 6-(6-chloropyridazin-3-yl)-2,6-diazaspiro[3.3]heptane-2-carboxylate

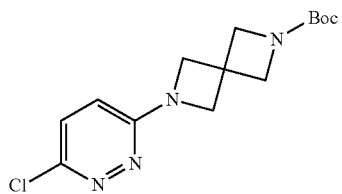 [SMILES: CC(C)(C)OC(=O)N1CC2(C1)CN(c1ccc(Cl)nn1)C2]

To a solution of 3,6-dichloropyridazine (500 mg, 3.36 mmol) in 1,4-dioxane (10 mL) was added tert-butyl 2,6-diazaspiro[3.3]heptane-2-carboxylate (665 mg, 3.36 mmol), K$_3$PO$_4$ (2.14 g, 10.1 mmol), and XPhos Pd G2 (264 mg, 0.34 mmol). The mixture was stirred at 100° C. under a N$_2$ atmosphere for 24 h. After cooling to room temperature, water was added (10 mL), and the mixture was extracted with EtOAc (10 mL×3). The combined organic layers were dried over Na$_2$SO$_4$, filtered, and concentrated under reduced pressure. The residue was purified by silica gel chromatography (10-90% EtOAc/heptanes) to afford the title compound (545 mg, 1.75 mmol, 52.1% yield). LCMS calc. for C$_{14}$H$_{20}$ClN$_4$O$_2$[M+H]$^+$: m/z=311.1, 313.1; Found 311.1, 313.0.

Step 3. 2-(6-Chloropyridazin-3-yl)-2,6-diazaspiro[3.3]heptane

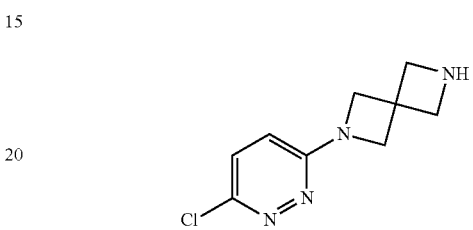

To a solution of tert-butyl 6-(6-chloropyridazin-3-yl)-2,6-diazaspiro[3.3]heptane-2-carboxylate (545 mg, 1.75 mmol) in DCM (5 mL) was added TFA (5.0 mL, 65 mmol). The mixture was stirred for 3 h and then concentrated under reduced pressure to provide the title compound (350 mg, 1.66 mmol, 94.9% yield). LCMS calc. for C$_9$H$_{12}$ClN$_4$ [M+H]$^+$: m/z=211.0; Found 211.1.

Step 4. 2-(6-Chloropyridazin-3-yl)-6-ethyl-2,6-diazaspiro[3.3]heptane

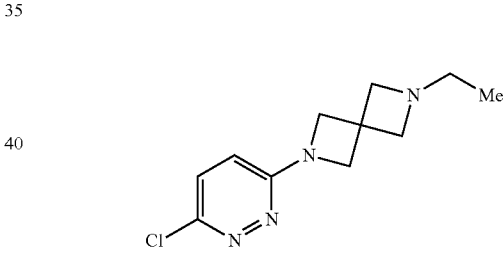

To a solution of 2-(6-chloropyridazin-3-yl)-2,6-diazaspiro[3.3]heptane (350 mg, 1.66 mmol) in MeOH (4 mL) was added triethylamine (0.46 mL, 3.32 mmol), acetaldehyde (365 mg, 8.31 mmol), acetic acid (100 mg, 1.66 mmol), and sodium cyanoborohydride (1.04 g, 16.6 mmol). The mixture was stirred at room temperature overnight. Water (10 mL) was added, and the resulting mixture was extracted with ethyl acetate (5 mL×3). The combined organic layers were dried over Na$_2$SO$_4$, filtered, and concentrated under reduced pressure to afford the title compound (300 mg, 1.26 mmol, 75.9% yield). LCMS calc. for C$_{11}$H$_{16}$ClN$_4$ [M+H]+: m/z=239.1; Found 239.2.

Step 5. 6-(6-Ethyl-2,6-diazaspiro[3.3]heptan-2-yl)-N-(5-fluoro-4-(3-isopropyl-2,6-dimethyl-3H-thieno[2,3-d]imidazol-5-yl)pyrimidin-2-yl)pyridazin-3-amine A suspension of 5-fluoro-4-(3-isopropyl-2,6-dimethyl-3H-thieno[2,3-d]imidazol-5-yl)pyrimidin-2-amine (53 mg, 0.17 mmol), 2-(6-chloropyridazin-3-yl)-6-ethyl-2,6-diazaspiro[3.3]heptane (38 mg, 0.16 mmol), sodium tert-butoxide (61 mg, 0.63 mmol), and BrettPhos Pd G3 (7.2 mg, 0.010 mmol, CAS: 1470372-59-8) in 1,4-dioxane (1 mL) was heated at 100° C. for 18 h. The reaction mixture was cooled to room temperature and diluted with MeOH (2 mL). The solid salts were removed by filtration, and the filtrate was purified by prep-HPLC on C-18 column (6-80% MeCN/H$_2$O containing 0.1% TFA) to afford the title compound as a TFA salt (25 mg, 0.034 mmol, 21% yield) as yellow solid. $^1$H NMR (300 MHz, CD$_3$OD) δ 8.71 (d, J=3.0 Hz, 1H), 8.13 (d, J=9.8 Hz, 1H), 7.53 (d, J=9.9 Hz, 1H), 5.03-4.97 (m, 1H), 4.55-4.29 (m, 8H), 3.28-3.23 (m, 2H), 2.83 (s, 3H), 2.69 (d, J=3.1 Hz, 3H), 1.66 (d, J=6.6 Hz, 6H), 1.22 (t, J=7.2 Hz, 3H). LCMS calc. for C$_{25}$H$_{31}$FN$_9$S [M+H]$^+$: m/z=508.2; Found 508.0.

Example 54: (4-Ethylpiperazin-1-yl)-[6-[[5-fluoro-4-(2-methyl-3-propan-2-ylthieno[2,3-d]imidazol-5-yl)pyrimidin-2-yl]amino]pyridin-3-yl]methanone

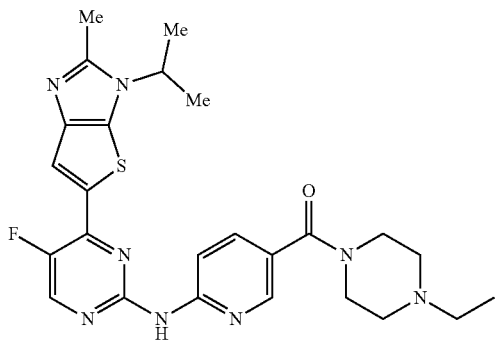 [SMILES: CCN1CCN(C(=O)c2ccc(Nc3ncc(F)c(-c4cc5nc(C)n(C(C)C)c5s4)n3)nc2)CC1]

Step 1. (6-Aminopyridin-3-yl)(4-ethylpiperazin-1-yl)methanone

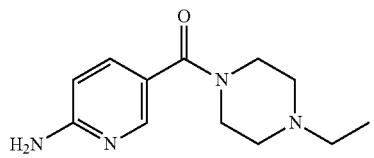 [SMILES: CCN1CCN(C(=O)c2ccc(N)nc2)CC1]

To a solution of 6-aminonicotinic acid (200 mg, 1.45 mmol) in 1,4-dioxane (10 mL) was added thionyl chloride (0.1 mL, 1 mmol). Upon stirring at room temperature for 3 h, 1-ethylpiperazine (0.19 mL, 1.5 mmol) was added. The mixture was stirred for an additional 24 h. Water (10 mL) and solid NaHCO$_3$ were added to adjust to pH>8. The solvent was removed under reduced pressure. The residue was purified by prep-HPLC on C$_{18}$ column (10-100% MeCN/H$_2$O) to afford the title compound (149 mg, 0.637 mmol, 43.9% yield). LCMS calc. for C$_{12}$H$_{19}$N$_4$O [M+H]$^+$: m/z=235.3; Found 235.2.

Step 2. (4-Ethylpiperazin-1-yl)-[6-[[5-fluoro-4-(2-methyl-3-propan-2-ylthieno[2,3-d]imidazol-5-yl)pyrimidin-2-yl]amino]pyridin-3-yl]methanone The TFA salt of the title compound is synthesized by procedures analogous to those outlined in Example 1, Step 8. $^1$H NMR (300 MHz, methanol-d$_4$) δ 8.69 (d, J=3.1 Hz, 1H), 8.53-8.49 (m, 1H), 8.19 (d, J=8.9 Hz, 1H), 8.12 (dd, J=8.9, 2.2 Hz, 1H), 8.09 (d, J=0.9 Hz, 1H), 5.10-4.91 (m, 1H), 3.88-3.34 (m, 6H), 3.30-3.15 (m, 4H), 2.87 (s, 3H), 1.71 (d, J=6.7 Hz, 6H), 1.40 (t, J=7.3 Hz, 3H). LCMS calc. for C$_{25}$H$_{30}$FN$_8$OS [M+H]$^+$: m/z=509.2; Found 509.0.

Example 55: 4-(2,6-Dimethyl-3-propan-2-ylthieno[3,2-c]pyrazol-5-yl)-N-[5-(6-ethyl-2,6-diazaspiro[3.3]heptan-2-yl)pyridin-2-yl]-5-fluoropyrimidin-2-amine

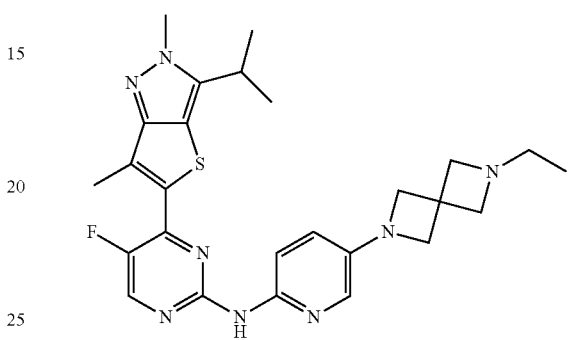

Step 1: 2,4-Dimethylthiophen-3-amine

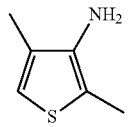

A solution of methyl 3-amino-4-methylthiophene-2-carboxylate (30.0 g, 175 mmol) in dioxane (20 mL) was added over 10 min to a stirred solution of lithium aluminum hydride (13.3 g, 350 mmol) in 1,4-dioxane (250 mL) at 80° C. The resulting mixture was stirred at 100° C. for 30 min. The reaction mixture was cooled to room temperature and diluted with MTBE (300 mL). The reaction was quenched by sequential addition of water (60 mL), 15% NaOH (aq) (60 mL), and water (180 mL). After stirring for 30 min, the reaction mixture was extracted with EtOAc (200 mL×2), and the combined organic layers were washed with brine, dried over MgSO$_4$, filtered, and concentrated to afford the title compound (23.0 g, 181 mmol) as an orange oil. This material was used in next step without further purification. LC-MS: [M+H]$^+$ calc. for C$_6$H$_{10}$NS: 128.1; Found: 128.0.

Step 2. 1-(6-Methylthieno[3,2-c]pyrazol-1-yl)ethanone

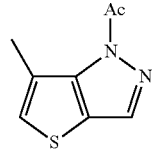

To a solution of 2,4-dimethylthiophen-3-amine (23.0 g, 181 mmol) in toluene (250 mL) was added KOAc (17.74 g, 180.8 mmol) and dropwise acetic anhydride (34.18 mL, 361.6 mmol). Upon heating to 80° C., isoamyl nitrite (36.15 mL, 271.2 mmol) was added dropwise over 10 min. The mixture was then heated at 95° C. for 1 h. The reaction was quenched by addition of saturated NaHCO₃ (aq) (50 mL). The reaction mixture was extracted with EtOAc (50 mL×3). The combined organic layers were dried over sodium sulfate, filtered, and concentrated. The crude product was purified by silica gel chromatography (5-30% EtOAc/heptane) to afford the title compound (31.9 g, 177 mmol, 97.8% yield) as an orange solid. LCMS (C18 column; 0.8 mL/min; MeCN/H₂O with 0.1% formic acid; 5% 1 min, 5-95% 4 min, 95% 2 min) $t_R$=3.57 min. LCMS calc. for $C_6H_7N_2S[M+H—COCH_3]^+$: m/z=139.0; Found: 138.9.

Step 3. 6-Methyl-1H-thieno[3,2-c]pyrazole

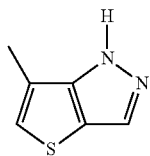

To a solution of 1-(6-methylthieno[3,2-c]pyrazol-1-yl)ethanone (31 g, 0.17 mol) in ethanol (120 mL) and water (120 mL) was added conc. HCl (143 mL, 1.72 mol). The resulting mixture was stirred at 60° C. for 2 h. The reaction mixture was diluted with water (50 mL), and the reaction quenched with NaHCO₃ to reach pH 8-9. The reaction mixture was extracted with DCM (50 mL×3). The combined organic layers were dried over sodium sulfate, filtered, and concentrated. The crude product was purified by silica gel chromatography (3-30% EtOAc/heptanes) to afford the title compound (23 g, 0.16 mol, 95% yield) as a sticky brown solid. LCMS (C18 column; 0.8 mL/min; MeCN/H₂O with 0.1% formic acid; 5% 1 min, 5-95% 4 min, 95% 2 min) $t_R$=3.32 min. LCMS calc. for $C_6H_7N_2S$ [M+H]⁺: m/z=139.0; Found: 138.9.

Step 4. 3-Iodo-6-methyl-1H-thieno[3,2-c]pyrazole

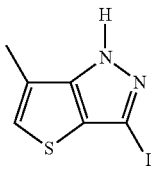

To a solution of 6-methyl-1H-thieno[3,2-c]pyrazole (22 g, 160 mmol) in methanol (200 mL) was added K₂CO₃ (48.4 g, 350 mmol) and iodine (44.5 g, 175 mmol). The resulting mixture was stirred at room temperature overnight. The reaction was quenched by the addition 10% Na₂S₂O₃ (aq) (50 mL), and the reaction mixture was extracted with EtOAc (50 mL×2). The combined organic layers were dried over sodium sulfate, filtered, and concentrated under reduced pressure. The crude product was purified by silica gel chromatography (0-30% EtOAc/heptanes) to afford the title compound (37 g, 140 mmol, 88% yield) as a red solid. LCMS calc. for $C_6H_6IN_2S$ [M+H]⁺: m/z=264.9; Found: 264.8.

Step 5. 3-Iodo-2,6-dimethylthieno[3,2-c]pyrazole

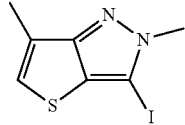

A suspension of 3-iodo-6-methyl-1H-thieno[3,2-c]pyrazole (30 g, 114 mmol) and NaHCO₃ (19.1 g, 227 mmol) in DCM (400 mL) was added to a vial charged with trimethyloxonium tetrafluoroborate (17.6 g, 119 mmol). After stirring at room temperature for 1 h, the reaction was quenched with water (200 mL). The reaction mixture was extracted with EtOAc (200 mL×3), and the combined organic phase was dried over Na₂SO₄, filtered, and. The residue was purified by silica gel chromatography (5-50% EtOAc/heptanes) to afford the title compound (29 g, 100 mmol, 92% yield). LCMS calc. for $C_7H_8IN_2S$ [M+H]⁺: m/z=278.9; Found: 278.8.

Step 6: 2,6-Dimethyl-3-prop-1-en-2-ylthieno[3,2-c]pyrazole

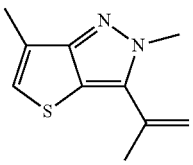

The title compound is synthesized by procedures analogous to those outlined in Example 14, Step 1. LCMS calc. for $C_{10}H_{13}N_2S$ [M+H]⁺: m/z=193.1; Found: 193.0.

Step 7. 2,6-Dimethyl-3-propan-2-ylthieno[3,2-c]pyrazole

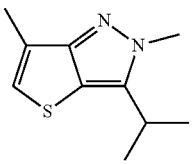

To a stirred solution of 2,6-dimethyl-3-prop-1-en-2-ylthieno[3,2-c]pyrazole (14 g, 73 mmol) in acetic acid (100 mL) was added 5% Pd/C (0.77 g, 7.3 mmol). The reaction vessel was charged with H₂, and the reaction mixture was stirred in a Parr shaker for 3 d. The reaction mixture was filtered through a pad of Celite, and the filtrate was concentrated. The residue was purified by silica gel chromatography (5-30% EtOAc/heptanes) to afford the title compound (11.8 g, 60.7 mmol, 83.1% yield). LCMS calc. for $C_{10}H_{15}N_2S$ [M+H]⁺: m/z=195.1; found 195.0.

Step 8. 2,6-Dimethyl-3-propan-2-yl-5-(4,4,5,5-tetramethyl-1,3,2-dioxaborolan-2-yl)thieno[3,2-c]pyrazole

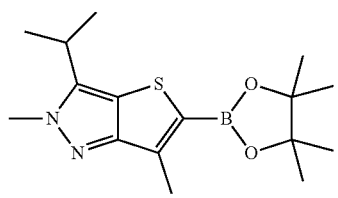

The title compound is synthesized by procedures analogous to those outlined in Example 52, Step 6. LCMS calc. for $C_{16}H_{26}BN_2O_2S$ [M+H]$^+$: m/z=321.2; Observed: 321.0.

Step 9. 5-(2-Chloro-5-fluoropyrimidin-4-yl)-2,6-dimethyl-3-propan-2-ylthieno[3,2-c]pyrazole

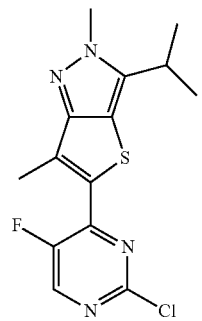 [SMILES: Cc1c(-c2nc(Cl)ncc2F)sc2c(C(C)C)n(C)nc12]

The title compound is synthesized by procedures analogous to those outlined in Example 52, Step 7. LCMS calc. for $C_{14}H_{15}ClFN_4S$ [M+H]$^+$: m/z=325.1, 327.1; Found: 324.8, 326.8.

Step 10. 4-(2,6-Dimethyl-3-propan-2-ylthieno[3,2-c]pyrazol-5-yl)-N-[5-(6-ethyl-2,6-diazaspiro[3.3]heptan-2-yl)pyridin-2-yl]-5-fluoropyrimidin-2-amine The title compound is synthesized by procedures analogous to those outlined in Example 1, Step 8. Purification via silica gel chromatography (1-10% MeOH/DCM) and recrystallizion in EtOAc afforded the title compound as a light yellow solid. $^1$H NMR (300 MHz, DMSO-d$_6$) δ 9.70 (s, 1H), 8.62 (d, J=2.8 Hz, 1H), 7.94 (d, J=8.9 Hz, 1H), 7.59 (d, J=2.9 Hz, 1H), 6.95 (dd, J=8.9, 3.0 Hz, 1H), 4.00 (s, 3H), 3.95 (s, 4H), 3.91 (s, 4H), 3.40-3.25 (m, 1H), 2.87 (q, J=7.2 Hz, 2H), 2.40 (d, J=3.4 Hz, 3H), 1.32 (d, J=6.8 Hz, 6H), 0.99 (t, J=7.1 Hz, 3H). LCMS calc. for $C_{26}H_{32}FN_8S$ [M+H]$^+$: m/z=507.2; Found 507.0.

Example 56: 2-(5-Fluoro-2-((5-(1-methylpiperidin-4-yl)pyridin-2-yl)amino)pyrimidin-4-yl)-7-isopropyl-3,5-dimethylthieno[3,2-c]pyridin-4(5H)-one

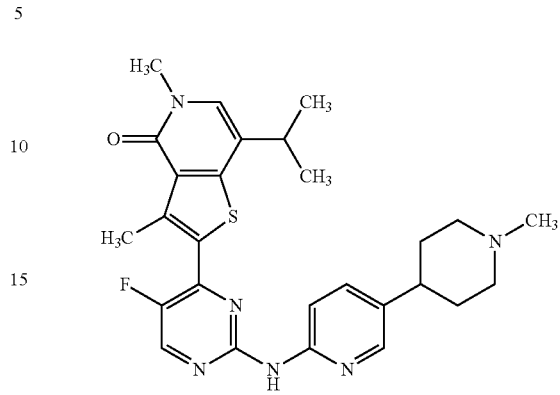

Step 1. tert-Butyl 6-nitro-3',6'-dihydro-[3,4'-bipyridine]-1'(2'H)-carboxylate

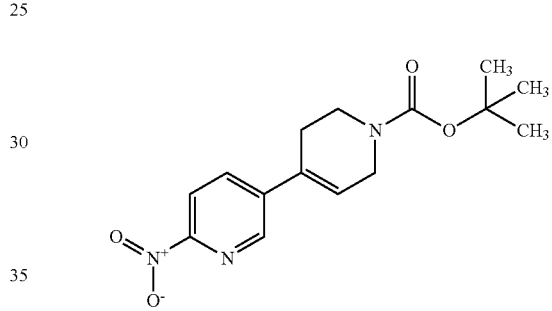

N-Boc-1,2,3,6-tetrahydropyridine-4-boronic acid pinacol ester (12.0 g, 38.8 mmol), 5-bromo-2-nitropyridine (7.80 g, 38.4 mmol), sodium carbonate (15.9 g, 115 mmol), and 1,1'-Bis(diphenylphosphino)ferrocene]dichloropalladium (II) (2.51 g, 3.84 mmol) were suspended in 1,4-dioxane (120 mL) and water (40.0 mL) under inert atmosphere. The reaction mixture was heated at 100° C. for 6 h. The reaction mixture was cooled to room temperature and diluted with water (100 mL). The mixture was extracted with EtOAc (100 mL×3). The organic layers were combined, washed with brine, dried over sodium sulfate, filtered, and concentrated. The crude residue was purified by silica gel chromatography using EtOAc in heptanes (10-60% with 0.1% Et$_3$N) to afford the title compound (9.20 g, 30.1 mmol, 78.4% yield) as a brown solid. LCMS calc. for $C_{15}H_{20}N_3O_4$ [M+H]$^+$: m/z=306.1; Found: 306.1.

Step 2. 6-Nitro-1',2',3',6'-tetrahydro-3,4'-bipyridine

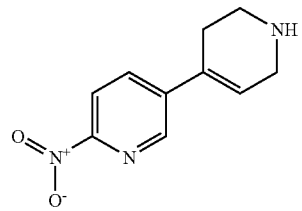 [SMILES: O=[N+]([O-])c1ccc(C2=CCNCC2)cn1]

tert-Butyl 6-nitro-3',6'-dihydro-[3,4'-bipyridine]-1'(2'H)-carboxylate (11.0 g, 36.0 mmol) was dissolved in DCM (30.0 mL) and cooled to 0° C. Trifluoroacetic acid (10.0 mL, 131 mmol) was added slowly at 0° C. The reaction mixture was warmed to room temperature and stirred for 5 h. The reaction mixture was concentrated under reduced pressure and then diluted with water (10.0 mL). The solution was lyophilized and used without further purification to afford the crude TFA salt of the title compound (18.6 g) as a yellow solid. LCMS calc. for $C_{10}H_{12}N_3O_2$ [M+H]$^+$: m/z=206.1; Found: 206.0.

Step 3. 1'-Methyl-6-nitro-1',2',3',6'-tetrahydro-3,4'-bipyridine

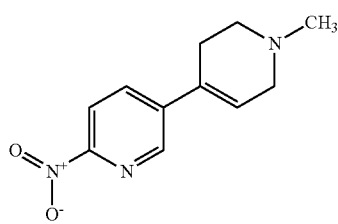 [SMILES: CN1CC=C(c2ccc([N+](=O)[O-])nc2)CC1]

Formaldehyde (24.9 mL, 335 mmol, 37 wt % in $H_2O$) and the crude TFA salt of 6-nitro-1',2',3',6'-tetrahydro-3,4'-bipyridine (18.6 g) were dissolved in DCM (60 mL) at room temperature. The mixture was stirred for 30 min, and the reaction was cooled to 0° C. Sodium triacetoxyborohydride (14.2 g, 66.9 mmol) was added portion-wise at 0° C. The resulting reaction mixture was allowed to warm to room temperature and stirred overnight. The reaction was quenched with sat. sodium bicarbonate (aq) (60.0 mL), and sodium carbonate was added until gas evolution was no longer observed. The organic phase was separated, and the aqueous layer was extracted with DCM (30.0 mL×2). The organic layers were combined, dried over sodium sulfate, filtered, and concentrated under reduced pressure. The reaction sequence in steps 2-3 was repeated with an additional portion of tert-butyl 6-nitro-3',6'-dihydro-[3,4'-bipyridine]-1'(2'H)-carboxylate (2.5 mmol in Step 2), and the crude material from both sequences was combined for purification. Purification by silica gel chromatography using MeOH in DCM (0-50%) afforded the freebase of the title compound (8.10 g, 36.9 mmol, quantitative yield over two steps) as a yellow solid. $^1$H NMR (300 MHz, DMSO-d$_6$) δ 8.74 (d, J=2.1 Hz, 1H), 8.29-8.16 (m, 2H), 6.57 (t, J=3.6 Hz, 1H), 3.09-3.03 (m, 2H), 2.60-2.52 (m, 4H), 2.27 (s, 3H). LCMS calc. for $C_{11}H_{14}N_3O_2$ [M+H]$^+$: m/z=220.1; Found: 220.0.

The freebase was dissolved in EtOAc (50.0 mL), DCM (5.00 mL), and MeOH (5.00 mL). Then a solution of HCl (37.0 mL, 74.0 mmol, 2N in iPrOAc) was added. The reaction mixture was stirred for 2 h at room temperature. The precipitate was collected by filtration and dried under reduced pressure to afford the HCl salt of the title compound (9.46 g, 32.4 mmol, 90.1% yield) as a white solid.

Step 4. 5-(1-Methylpiperidin-4-yl)pyridin-2-amine

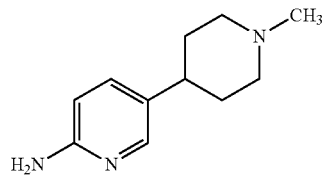

In a 500 mL reaction vessel, 1'-methyl-6-nitro-1',2',3',6'-tetrahydro-3,4'-bipyridine, HCl salt (9.46 g, 32.4 mmol) was dissolved in MeOH (150 mL). Palladium on carbon (0.875 g, 0.822 mmol, 10 wt %) and glacial acetic acid (1.00 mL, 17.5 mmol) were added sequentially at room temperature. The reaction vessel was sealed in a Parr shaker, and the vessel was charged with hydrogen (60 psi). The reaction mixture was mixed overnight. The atmosphere of hydrogen was removed, the mixture was filtered, and the filtrate was concentrated under reduced pressure. The dark residue was dissolved in DCM (30.0 mL) and neutralized with sodium hydroxide (3.39 g, 84.8 mmol). The organic layer was washed with water (30.0 mL×2), dried over sodium sulfate, filtered, and concentrated under reduced pressure. The crude residue was purified by silica gel chromatography using MeOH in DCM (0-50% with 0.1% Et$_3$N) to afford the title compound (6.10 g, 31.9 mmol, 98.5% yield) as an off-white solid. $^1$H NMR (300 MHz, DMSO-d$_6$) δ 7.74 (d, J=2.2 Hz, 1H), 7.23 (dd, J=8.5, 2.4 Hz, 1H), 6.36 (d, J=8.5 Hz, 1H), 5.62 (s, 2H), 2.81 (d, J=11.4 Hz, 2H), 2.40-2.16 (m, 1H), 2.15 (s, 3H), 2.00-1.75 (m, 2H), 1.64-1.47 (m, 4H). LCMS calc. for $C_{11}H_{18}N_3$[M+H]$^+$: m/z=192.1; Found: 192.1.

Step 5. 2-(2-Chloro-5-fluoropyrimidin-4-yl)-7-isopropyl-3,5-dimethylthieno[3,2-c]pyridin-4(5H)-one

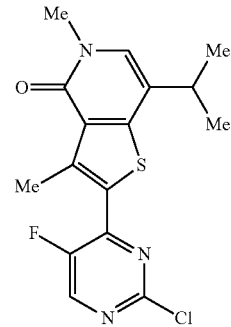 [SMILES: Cc1c(-c2nc(Cl)ncc2F)sc2c(C(C)C)cn(C)c(=O)c12]

Butyllithium (5.20 mL, 13.0 mmol, 2.5 M in hexanes) was added dropwise to a solution of 2-bromo-7-isopropyl-3,5-dimethylthieno[3,2-c]pyridin-4(5H)-one (2.60 g, 8.66 mmol, Example 51, Step 5) at −78° C. The reaction mixture was stirred for 20 min at −78° C. 2-Chloro-5-fluoropyrimidine (1.38 g, 10.4 mmol) was then added in a single portion. The reaction mixture stirred for 30 min at −78° C. The reaction was quenched with sat. NH$_4$Cl (aq) and diluted with DCM (30.0 mL). The mixture was allowed to warm to room temperature, and the two phases were separated. The organic layer was removed, and the aqueous layer was extracted with DCM (30.0 mL×2). The combined organic layers were washed with brine, dried over sodium sulfate, and concentrated.

To the crude residue in THF (30.0 mL) was added 2,3-dichloro-5,6-dicyano-p-benzoquinone (1.86 g, 8.20 mmol). The reaction mixture stirred for 30 min at room temperature. The reaction mixture was diluted with DCM (30.0 mL), washed with hot potassium carbonate (10 wt % aq.) (30.0 mL×2), dried over sodium sulfate, and concentrated. The crude residue was purified by prep-HPLC using a C18 column (20-100% MeCN/0.1% TFA (aq.)) to afford the title compound as the TFA salt (1.35 g, 2.90 mmol, 35.3% yield), an off-white solid. LCMS calc. for $C_{16}H_{16}ClFN_3OS$ $[M+H]^+$: m/z=352.1, 354.1; Found: 352.0, 353.9.

Step 6. 2-(5-Fluoro-2-((5-(1-methylpiperidin-4-yl)pyridin-2-yl)amino)pyrimidin-4-yl)-7-isopropyl-3,5-dimethylthieno[3,2-c]pyridin-4(5H)-one To a solution of 2-(2-chloro-5-fluoropyrimidin-4-yl)-7-isopropyl-3,5-dimethylthieno[3,2-c]pyridin-4(5H)-one, TFA salt (1.20 g, 2.58 mmol) and 5-(1-methylpiperidin-4-yl)pyridin-2-amine (0.783 g, 4.09 mmol) in 1,4-dioxane (24.0 mL) was added $K_3PO_4$ (2.17 g, 10.2 mmol) and XPhos Pd G2 (268 mg, 0.341 mmol, CAS 1310584-14-5). The reaction vessel was sealed, and the mixture was degassed with $N_2$ (3×). The reaction mixture was heated at 100° C. overnight. The reaction mixture was cooled to room temperature, filtered, and concentrated under reduced pressure. The dark residue was purified by prep-HPLC on a C18 column (10-50% MeCN/0.1% TFA (aq.)) to afford the title compound as the TFA salt. The TFA salt was neutralized with sat. $NaHCO_3$ (aq) (20.0 mL), and the aqueous layer was extracted with DCM (20.0 mL×3). The organic layers were combined, washed with brine, dried over sodium sulfate, filtered, and concentrated under reduced pressure. The residue was dissolved in 1N HCl (2.20 mL, 2.20 mmol, 1.05 equiv), and the solvent was removed by lyophilization to afford the HCl salt of the title compound (1.21 g, 2.23 mmol, 86.5% yield) as a yellow solid. $^1H$ NMR (300 MHz, DMSO-$d_6$) δ 10.46 (br s, 1H), 10.31 (br s, 1H), 8.75 (d, J=2.5 Hz, 1H), 8.21 (d, J=2.4 Hz, 1H), 8.12 (d, J=8.7 Hz, 1H), 7.71 (dd, J=8.8, 2.4 Hz, 1H), 7.55 (s, 1H), 3.52 (s, 3H), 3.46 (s, 2H), 3.20-2.97 (m, 2H), 2.95-2.84 (m, 2H), 2.77 (d, J=4.3 Hz, 3H), 2.69 (d, J=3.5 Hz, 3H), 2.06-1.93 (m, 4H), 1.31 (d, J=6.8 Hz, 6H). LCMS calc. for $C_{27}H_{32}FN_6OS$ $[M+H]^+$: m/z=507.2; Found: 507.2.

Examples 57-61

Examples listed in Table 4-1 are synthesized according to procedures analogous to Example 51 and Example 56.

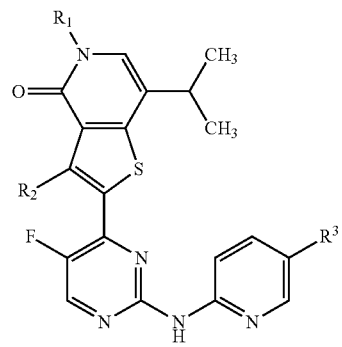

TABLE 4-1

Examples 57-61.

| Example | $R^1$ | $R^2$ | $R^3$ | LCMS $[M + H]^+$ |
|---|---|---|---|---|
| 57 | Me | Me | ![structure] diazaspiro with N-CH3 | 534.1 |
| 58 | Me | H | ![structure] bicyclic with N-CH3 | 519.9 |
| 59 | Me | H | ![structure] piperazinyl carbonyl with N-CH2CH3 | 536.3 |
| 60 | H | Me | ![structure] piperidinyl with N-CH3 | 493.0 |
| 61 | Me | Me | ![structure] spirocyclic with N-CH3 | 533.9 |

TABLE 4-2

Examples 57-61.

| Example | Compound name | NMR |
|---|---|---|
| 57 | 2-(2-((5-(6-Ethyl-2,6-diazaspiro[3.3]heptan-2-yl)pyridin-2-yl)amino)-5-fluoropyrimidin-4-yl)-7-isopropyl-3,5-dimethylthieno[3,2-c]pyridin-4(5H)-one, TFA salt | $^1H$ NMR (300 MHz, $CD_3OD$) δ 8.74 (d, J = 2.7 Hz, 1H), 7.68 (dd, J = 9.5, 2.8 Hz, 1H), 7.55-7.35 (m, 3H), 4.51 (d, J = 11.4 Hz, 2H), 4.40-4.22 (m, 4H), 4.18 (s, 2H), 3.63 (s, 3H), 3.26 (q, J = 7.3 Hz, 2H), 3.00 (p, J = 6.0 Hz, 1H), 2.84 (d, J = 3.3 Hz, 3H), 1.39 (d, J = 6.9 Hz, 6H), 1.23 (t, J = 7.2 Hz, 3H). |

TABLE 4-2-continued

Examples 57-61.

| Example | Compound name | NMR |
|---|---|---|
| 58 | 2-(2-((5-(6-Ethyl-3,6-diazabicyclo[3.1.1]heptan-3-yl)pyridin-2-yl)amino)-5-fluoropyrimidin-4-yl)-7-isopropyl-5-methylthieno[3,2-c]pyridin-4(5H)-one, TFA salt | $^1$H NMR (300 MHz, CD$_3$OD) δ 8.75 (d, J = 2.4 Hz, 1H), 8.56 (s, 1H), 8.07 (d, J = 9.5 Hz, 1H), 7.83 (s, 1H), 7.65 (d, J = 9.6 Hz, 1H), 7.55 (s, 1H), 4.75 (d, J = 6.0 Hz, 1H), 4.61 (d, J = 6.2 Hz, 1H), 4.10 (d, J = 12.0 Hz, 1H), 4.10-3.75 (m, 3H), 3.70 (s, 3H), 3.68-3.55 (m, 1H), 3.14-3.07 (m, 2H), 2.22 (dd, J = 15.7, 7.8 Hz, 2H), 1.46 (d, J = 6.9 Hz, 6H), 1.42-1.37 (m, 3H). |
| 59 | 2-(2-((5-(4-Ethylpiperazine-1-carbonyl)pyridin-2-yl)amino)-5-fluoro-pyrimidin-4-yl)-7-isopropyl-5-methylthieno[3,2-c]pyridin-4(5H)-one, TFA salt | $^1$H NMR (300 MHz, DMSO-d$_6$) δ 10.56 (s, 1H), 9.83 (s, 1H), 8.78 (d, J = 3.1 Hz, 1H), 8.45 (d, J = 2.3 Hz, 1H), 8.29 (d, J = 8.8 Hz, 1H), 8.21 (d, J = 1.7 Hz, 1H), 7.96 (dd, J = 8.7, 2.4 Hz, 1H), 7.60 (s, 1H), 3.54 (s, 3H), 3.52-3.02 (m, 10H), 2.96 (p, J = 6.9 Hz, 1H), 1.34 (d, J = 6.8 Hz, 6H), 1.23 (t, J = 7.2 Hz, 3H). |
| 60 | 2-(5-Fluoro-2-((5-(1-methylpiperidin-4-yl)pyridin-2-yl)amino)pyrimidin-4-yl)-7-isopropyl-3-methylthieno[3,2-c]pyridin-4(5H)-one, TFA salt | $^1$H NMR (300 MHz, CD$_3$OD) δ 8.80 (d, J = 2.6 Hz, 1H), 8.31 (dd, J = 9.1, 2.3 Hz, 1H), 8.27 (d, J = 2.1 Hz, 1H), 7.60 (d, J = 9.0 Hz, 1H), 7.18 (s, 1H), 3.68 (d, J = 13.0 Hz, 2H), 3.27-2.95 (m, 4H), 2.94 (s, 3H), 2.86 (d, J = 3.2, 3H), 2.23 (d, J = 14.2 Hz, 2H), 2.14-1.94 (m, 2H), 1.39 (d, J = 6.9 Hz, 6H). |
| 61 | 2-(5-Fluoro-2-((5-(6-methyl-2,6-diazaspiro[3.4]octan-2-yl)pyridin-2-yl)amino)pyrimidin-4-yl)-7-isopropyl-3,5-dimethylthieno[3,2-c]pyridin-4(5H)-one, TFA salt | $^1$H NMR (400 MHz, DMSO-d$_6$) δ 10.72 (s, 1H), 10.13 (s, 1H), 8.75 (d, J = 2.6 Hz, 1H), 7.79 (d, J = 9.1 Hz, 1H), 7.59 (d, J = 2.9 Hz, 1H), 7.56 (s, 1H), 7.34 (dd, J = 9.1, 3.0 Hz, 1H), 3.99-3.89 (m, 3H), 3.90-3.79 (m, 2H), 3.66-3.54 (m, 1H), 3.51 (s, 3H), 3.29 (dd, J = 12.0, 7.2 Hz, 1H), 3.20-3.04 (m, 1H), 2.90 (p, J = 6.8 Hz, 1H), 2.85 (d, J = 4.4 Hz, 3H), 2.70 (d, J = 3.4 Hz, 3H), 2.44 (td, J = 8.5, 4.2 Hz, 1H), 2.26 (dt, J = 13.6, 8.4 Hz, 1H), 1.31 (d, J = 6.8 Hz, 6H). |

Example 62: 6-(2-((5-(6-Ethyl-2,6-diazaspiro[3.3]heptan-2-yl)pyridin-2-yl)amino)-5-fluoropyrimidin-4-yl)-1-isopropyl-5-methylthieno[2,3-d]pyrimidin-4(1H)-one

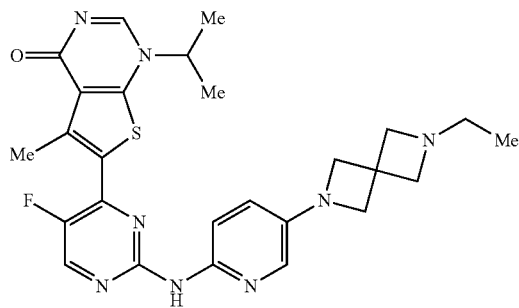 [SMILES: CCN1CC2(C1)CN(c1ccc(Nc3ncc(F)c(-c4sc5c(c4C)c(=O)ncn5C(C)C)n3)nc1)C2]

Step 1.
2-(Isopropylamino)-4-methylthiophene-3-carboxamide

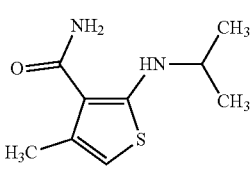

Sodium triacetoxyborohydride (4.24 g, 20.0 mmol) was added portionwise to a solution of 2-amino-4-methylthiophene-3-carboxamide (1.56 g, 10.0 mmol), 2-methoxyprop-1-ene (1.92 mL, 20.0 mmol), and acetic acid (1.14 mL, 20.0 mmol) in DCE (40.0 mL) at room temperature. The resulting suspension was stirred for 3 h. Additional sodium triacetoxyborohydride (1.70 g, 8.00 mmol) was added portionwise to the reaction mixture. The reaction suspension then stirred for 18 h. The reaction mixture was slowly poured over 10% sodium carbonate (aq) (100 mL) and stirred until gas evolution ceased. The organic layer was separated, and the aqueous layer extracted with DCM (50 mL) and EtOAc (50 mL). The combined organic layers were washed with water (50 mL) and brine (50 mL), dried over sodium sulfate, filtered, and concentrated. The residue was purified by flash chromatography on silica gel using EtOAc in hexanes (20%) to give the title compound (330 mg, 1.66 mmol, 16.6% yield) as an off-white solid. LCMS calc. for $C_9H_{15}N_2OS$ [M+H]$^+$: m/z=199.1; Found: 199.0.

Step 2. 1-Isopropyl-5-methylthieno[2,3-d]pyrimidin-4(1H)-one

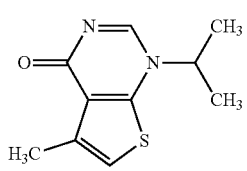

Formic acid (34.0 µL, 0.908 mmol) was added to a solution of 2-(isopropylamino)-4-methylthiophene-3-carboxamide (180 mg, 0.908 mmol) in trimethyl orthoformate (1.00 mL) at room temperature. The reaction mixture was heated to 85° C. for 1 h. The reaction mixture was cooled to room temperature and poured over 10% sodium bicarbonate (aq.). The organic layer was separated, and the aqueous layer extracted with EtOAc (20 mL×3). The combined organic layers were washed with brine, dried over sodium sulfate, filtered, and concentrated. The residue was purified by flash chromatography on silica gel using MeOH in DCM (10%) to give the title compound (72.0 mg, 0.346 mmol, 38.1% yield) as an off-white solid. LCMS calc. for $C_{10}H_{13}N_2OS$ [M+H]$^+$: m/z=209.1; Found: 209.0.

Step 3. 6-Bromo-1-isopropyl-5-methylthieno[2,3-d]pyrimidin-4(1H)-one

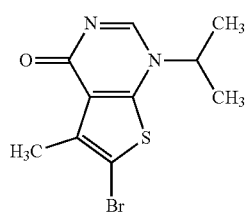

N-Bromosuccinimide (26.2 mg, 0.149 mmol) was added to a mixture of 1-isopropyl-5-methylthieno[2,3-d]pyrimidin-4(1H)-one (31.0 mg, 0.149 mmol) and indium(III) trifluoromethanesulfonate (8.4 mg, 0.015 mmol) in DCE (1.5 mL) at room temperature. The reaction mixture stirred for 30 min. The reaction mixture was diluted with water (20 mL), and the organic layer was separated. The aqueous layer was extracted with EtOAc (5 mL×3). The combined organic layers were washed with brine, dried over sodium sulfate, filtered, and concentrated. The residue was purified by flash chromatography on silica gel using MeOH in DCM (10%) to give the title compound (32.0 mg, 0.111 mmol, 74.9% yield) as a dark green solid. LCMS calc. for $C_{10}H_{12}BrN_2OS$ [M+H]$^+$: m/z=287.0, 289.0; Found: 287.0, 288.9.

Step 4. 6-(2-Chloro-5-fluoropyrimidin-4-yl)-1-isopropyl-5-methylthieno[2,3-d]pyrimidin-4(1H)-one

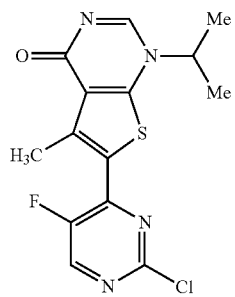 [SMILES: Cc1c(-c2nc(Cl)ncc2F)sc2c1c(=O)ncn2C(C)C]

A mixture of hexamethylditin (58.0 µL, 0.280 mmol), 6-bromo-1-isopropyl-5-methylthieno[2,3-d]pyrimidin-4(1H)-one (40.0 mg, 0.140 mmol), and tetrakis (triphenylphosphine)palladium(0) (24.1 mg, 0.0200 mmol) in 1,4-dioxane (5.00 mL) was heated at 100° C. for 1 h. The reaction mixture was cooled to room temperature, and 2,6-dichloro-5-fluoracil (69.8 mg, 0.420 mmol) was added to the mixture. The reaction mixture was then heated at 100° C. for 18 h. The reaction mixture was cooled to room temperature, and a solution of potassium fluoride (16.2 mg, 0.280 mmol) in water (2.0 mL) was added. The reaction mixture was stirred for 10 min. The mixture was filtered through a pad of Celite, and the organic layer was separated. The aqueous layer extracted with EtOAc (5 mL×2). The combined organic layers were washed with brine, dried over sodium sulfate, filtered, and concentrated. The residue was purified by flash chromatography on silica gel using MeOH in DCM (10%) to give the title compound (25.0 mg, 0.070 mmol, 53.0% yield) as an off-white solid. LCMS calc. for $C_{14}H_{13}ClFN_4OS$ [M+H]$^+$: m/z=339.0; Found: 338.9.

Step 5. 6-(2-((5-(6-Ethyl-2,6-diazaspiro[3.3]heptan-2-yl)pyridin-2-yl)amino)-5-fluoropyrimidin-4-yl)-1-isopropyl-5-methylthieno[2,3-d]pyrimidin-4(1H)-one A suspension of 6-(2-chloro-5-fluoropyrimidin-4-yl)-1-isopropyl-5-methylthieno[2,3-d]pyrimidin-4(1H)-one (20.0 mg, 0.060 mmol), 5-(6-ethyl-2,6-diazaspiro[3.3]heptan-2-yl)pyridine-2-amine (12.9 mg, 0.060 mmol), (2-dicyclohexylphosphino-2',4',6'-triisopropyl-1,1'-biphenyl)[2-(2'-amino-1,1'-biphenyl)]palladium(II) methanesulfonate (7.50 mg, 8.90 µmol), and cesium carbonate (38.5 mg, 0.12 mmol) in 1,4-dioxane (1.50 mL) was heated to 100° C. for 18 hours. Upon cooling to room temperature, TFA (27.1 µL, 0.350 mmol) was added. The inorganic salts were filtered off, and the filtrate was purified by prep-HPLC on C18 column (8-80% MeCN/0.1% TFA (aq.) to give the title compound as the TFA salt (6.60 mg, 8.80 µmol, 15% yield) as a yellow solid. $^1$H NMR (400 MHz, CD$_3$OD) δ 8.87-8.56 (m, 2H), 7.67 (dd, J=9.2, 2.7 Hz, 1H), 7.55-7.37 (m, 2H), 4.67 (p, J=6.7 Hz, 1H), 4.51 (d, J=11.3 Hz, 2H), 4.35-4.22 (m, 4H), 4.18 (s, 2H), 3.27 (q, J=7.4 Hz, 2H), 2.82 (d, J=3.2 Hz, 3H), 1.72 (d, J=6.6 Hz, 6H), 1.22 (t, J=7.2 Hz, 3H). LCMS calc. for $C_{26}H_{30}FN_8OS$ [M+H]$^+$: m/z=521.2; Found: 521.1.

Example 63 2-(2-((5-(6-Ethyl-2,6-diazaspiro[3.3]heptan-2-yl)pyridin-2-yl)amino)-5-fluoropyrimidin-4-yl)-7-isopropyl-3,5-dimethylthieno[2,3-d]pyridazin-4(5H)-one

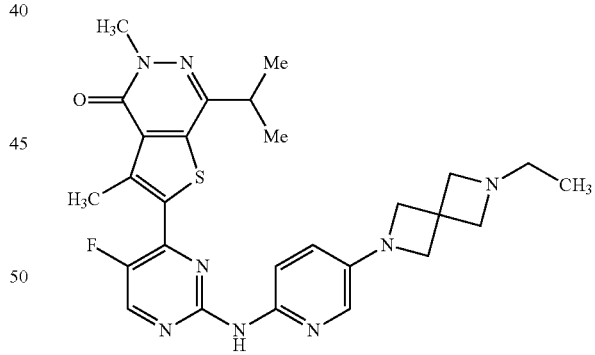

Step 1. 7-Isopropyl-3,5-dimethylthieno[2,3-d]pyridazin-4(5H)-one

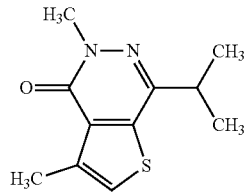

Lithium diisopropylamide (4.40 mL, 8.80 mmol, 2.0 M in THF/n-heptane/ethylbenzene) was added dropwise over 10 min to a solution of 4-methyl-3-thiophenecarboxylic acid (569 mg, 4.00 mmol) in THF (6.00 mL) at 0° C. To the reaction mixture was added a solution of N-methoxy-N,2-dimethylpropanamide (0.611 mL, 4.40 mmol) in THF (3.00 mL) dropwise over 10 min at 0° C. The reaction mixture was warmed to room temperature and was stirred for 2 h. The reaction mixture was poured into water (10 mL), and the organic layer was separated. The aqueous layer was washed with EtOAc (20 mL) and acidified with 1N HCl (5 mL). The aqueous layer was extracted again with EtOAc (20 mL×2). The combined organic layers were dried over sodium sulfate, filtered, and concentrated. The crude residue containing 2-isobutyryl-4-methylthiophene-3-carboxylic acid was used in the next step without further purification.

Methylhydrazine (0.150 mL, 2.93 mmol) was added to a solution of crude 2-isobutyryl-4-methylthiophene-3-carboxylic acid (415 mg) in ethanol (19.6 mL) at room temperature. The reaction mixture was at heated to 80° C. for 18 h. The reaction mixture was cooled to room temperature and concentrated under reduced pressure. The crude residue was purified by silica gel chromatography (0-30% EtOAc/hexanes) to give the title compound (362 mg, 1.63 mmol, 83.0% yield). $^1$H NMR (400 MHz, CDCl$_3$) δ 7.16 (s, 1H), 3.82 (s, 3H), 3.12 (p, J=8.0 Hz, 1H), 2.70 (s, 3H), 1.37 (d, J=8.0 Hz, 6H). LCMS calc. for C$_{11}$H$_{15}$N$_2$OS [M+H]$^+$: m/z=223.1; Found: 223.0.

Step 2. 2-Bromo-7-isopropyl-3,5-dimethylthieno[2,3-d]pyridazin-4(5H)-one

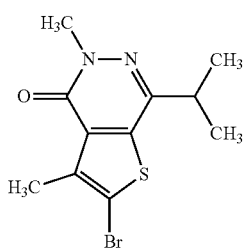 [SMILES: Cc1c(Br)sc2c(C(C)C)nn(C)c(=O)c12]

N-Bromosuccinimide (304 mg, 1.71 mmol) was added to a solution of 7-isopropyl-3,5-dimethylthieno[2,3-d]pyridazin-4(5H)-one (362 mg, 1.63 mmol) in acetonitrile (8.1 mL) at room temperature. The reaction mixture was stirred for 18 h. The reaction mixture was diluted with water (10 mL), and the organic layer was separated. The aqueous layer extracted with DCM (10 mL×3). The combined organic layers were washed with brine, dried over sodium sulfate, filtered, and concentrated. The residue was purified by flash chromatography on silica gel using EtOAc in hexanes (10%) to give title compound (350 mg, 1.16 mmol, 71.0% yield). LCMS calc. for C$_{11}$H$_{14}$BrN$_2$OS [M+H]$^+$: m/z=301.0, 303.0; Found: 300.9, 302.9.

Step 3. 2-(2-Chloro-5-fluoropyrimidin-4-yl)-7-isopropyl-3,5-dimethylthieno[2,3-d]pyridazin-4(5H)-one

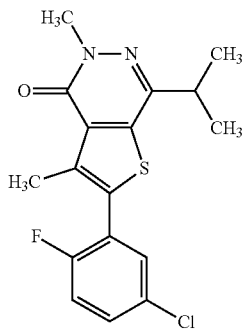 [SMILES: Cc1c(-c2cc(Cl)ccc2F)sc2c(C(C)C)nn(C)c(=O)c12]

The title compound is synthetized by a procedure analogous to that outline in Example 62, Step 4. LCMS calc. for C$_{15}$H$_{15}$ClFN$_4$OS [M+H]$^+$: m/z=353.1, 355.0; Found: 352.9, 355.0

Step 5. 2-(2-((5-(6-Ethyl-2,6-diazaspiro[3.3]heptan-2-yl)pyridin-2-yl)amino)-5-fluoropyrimidin-4-yl)-7-isopropyl-3,5-dimethylthieno[2,3-d]pyridazin-4(5H)-one The title is synthesized by a procedure analogous to that outline in Example 62, Step 5. Purification by prep-HPLC on a C18 column (20-40% MeCN/0.1% TFA (aq.)) afforded the title compound as the TFA salt (17.8 mg, 0.020 mmol, 26.0% yield), a yellow solid. $^1$H NMR (400 MHz, DMSO-d$_6$) δ 10.18 (s, 1H), 9.76 (s, 1H), 8.76 (d, J=2.4 Hz, 1H), 7.85 (d, J=9.0 Hz, 1H), 7.61 (d, J=2.9 Hz, 1H), 7.12 (dd, J=9.0, 2.9 Hz, 1H), 4.34 (dd, J=11.6, 6.3 Hz, 2H), 4.20 (dd, J=11.6, 6.0 Hz, 2H), 4.08 (s, 2H), 3.98 (s, 2H), 3.71 (s, 3H), 3.26-3.07 (m, 3H), 2.69 (d, J=3.1 Hz, 3H), 1.34 (d, J=6.9 Hz, 6H), 1.06 (s, 3H). LCMS calc. for C$_{27}$H$_{32}$FN$_8$OS [M+H]$^+$: m/z=535.2; Found: 535.1.

Examples 64-75

Examples listed in Tables 5-1 and 5-2 are synthesized according to procedures analogous to Example 1.

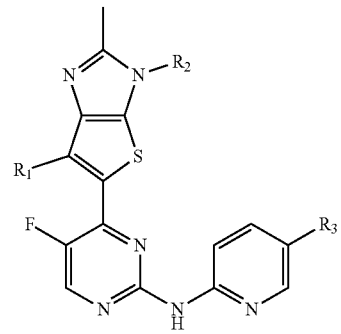

TABLE 5-1

Examples 64-75

| Example | R₁ | R₂ | R₃ | LCMS [M + H]⁺ |
|---|---|---|---|---|
| 64 | H | iso-propyl | piperazine-CH₂-CF₂H | 531.0 |
| 65 | H | iso-propyl | pyrrolidine-N,N-dimethylcarboxamide | 523.2 |
| 66 | Me | iso-propyl | H | 383.0 |
| 67 | Me | iso-propyl | N-methyl-diazaspiro[3.3]heptane | 492.9 |
| 68 | Me | iso-propyl | deuterated piperazine (D₂, CD₃) | 491.9 |
| 69 | Me | iso-propyl | 5,5-difluoro-1-ethyl-diazepane | 544.9 |
| 70 | Me | iso-propyl | difluoro diazaspiro | 542.8 |
| 71 | H | iso-propyl | N-ethyl-diazaspiro[3.3]heptane carbonyl | 520.9 |
| 72 | H | iso-propyl | azetidine-N,N-dimethyl | 466.8 |
| 73 | Me | iso-propyl | pyrrolidine-N,N-dimethyl | 494.7 |
| 74 | H | iso-propyl | N-ethyl-diazabicyclo | 493.0 |
| 75 | Me | iso-propyl | 4-methyl-piperazin-2-one | 495.0 |

TABLE 5-2

Examples 64-75

| Example | Compound name | NMR |
|---|---|---|
| 64 | N-[5-[[4-(2,2-Difluoroethyl)piperazin-1-yl]methyl]pyridin-2-yl]-5-fluoro-4-(2-methyl-3-propan-2-ylthieno[2,3-d]imidazol-5-yl)pyrimidin-2-amine, TFA salt | ¹H NMR (300 MHz, CD₃OD) δ 8.78 (d, J = 3.1 Hz, 1H), 8.53 (d, J = 2.0 Hz, 1H), 8.35 (dd, J = 9.0, 2.1 Hz, 1H), 8.17 (d, J = 1.0 Hz, 1H), 7.80 (d, J = 8.9 Hz, 1H), 6.07 (tt, J = 55.3, 4.0 Hz, 1H), 5.11-4.91 (m, 1H), 4.36 (s, 2H), 3.36-3.30 (m, 4H), 3.10-2.99 (m, 6H), 2.90 (s, 3H), 1.71 (d, J = 6.6 Hz, 6H). |
| 65 | 1-[[6-[[5-Fluoro-4-(2-methyl-3-propan-2-ylthieno[2,3-d]imidazol-5-yl)pyrimidin-2-yl]amino]pyridin-3-yl]methyl]-N,N-dimethylpyrrolidine-3-carboxamide, TFA salt | ¹H NMR (300 MHz, CD₃OD) δ 8.68 (d, J = 3.2 Hz, 1H), 8.53 (d, J = 2.2 Hz, 1H), 8.30 (d, J = 8.8 Hz, 1H), 8.16 (dd, J = 8.9, 2.3 Hz, 1H), 8.10 (d, J = 1.1 Hz, 1H), 5.02-4.98 (m, 1H), 4.55 (d, J = 8.2 Hz, 2H), 3.77 (s, 2H), 3.62-3.47 (m, 3H), 3.15 (s, |

TABLE 5-2-continued

Examples 64-75

| Example | Compound name | NMR |
|---|---|---|
| | | 3H), 3.01 (s, 3H), 2.86 (s, 3H), 2.23 (t, J = 7.6 Hz, 1H), 2.07 (d, J = 5.8 Hz, 1H), 1.73 (d, J = 6.6 Hz, 6H). |
| 66 | 4-(2,6-Dimethyl-3-propan-2-ylthieno[2,3-d]imidazol-5-yl)-5-fluoro-N-pyridin-2-ylpyrimidin-2-amine, TFA salt | $^1$H NMR (400 MHz, DMSO-d$_6$) δ 11.37 (s, 1H), 8.81 (d, J = 3.0 Hz, 1H), 8.40 (d, J = 5.7 Hz, 1H), 8.13 (t, J = 8.3 Hz, 1H), 7.90 (d, J = 8.7 Hz, 1H), 7.28 (t, J = 6.5 Hz, 1H), 4.85 (p, J = 6.8 Hz, 1H), 2.72 (s, 3H), 2.62 (d, J = 3.5 Hz, 3H), 1.54 (d, J = 6.6 Hz, 6H). |
| 67 | 4-(2,6-Dimethyl-3-propan-2-ylthieno[2,3-d]imidazol-5-yl)-5-fluoro-N-[5-(1-methyl-1,6-diazaspiro[3.3]heptan-6-yl)pyridin-2-yl]pyrimidin-2-amine, TFA salt | $^1$H NMR (300 MHz, CD$_3$OD) δ 8.73 (d, J = 3.1 Hz, 1H), 7.74 (dd, J = 9.2, 3.0 Hz, 1H), 7.61-7.56 (m, 2H), 5.01-4.92 (m, 1H), 4.59 (d, J = 8.6 Hz, 2H), 4.25 (d, J = 10.0 Hz, 2H), 4.09 (s, 2H), 3.07 (s, 3H), 2.88 (t, J = 6.1 Hz, 2H), 2.85 (s, 3H), 2.74 (d, J = 3.0 Hz, 3H), 1.67 (d, J = 6.7 Hz, 6H). |
| 68 | 4-(2,6-Dimethyl-3-propan-2-ylthieno[2,3-d]imidazol-5-yl)-N-[5-(4-ethyl-6,6-difluoro-1,4-diazepan-1-yl)pyridin-2-yl]-5-fluoropyrimidin-2-amine, TFA salt | $^1$H NMR (300 MHz, CD$_3$OD) δ 8.74 (d, J = 3.1 Hz, 1H), 8.13 (dd, J = 9.7, 3.0 Hz, 1H), 7.89 (d, J = 2.8 Hz, 1H), 7.58 (d, J = 9.7 Hz, 1H), 5.01-4.92 (m, 1H), 4.17 (t, J = 12.4 Hz, 2H), 3.86 (t, J = 5.6 Hz, 2H), 3.66 (t, J = 12.7 Hz, 2H), 3.52 (t, J = 5.4 Hz, 2H), 3.21 (q, J = 13.6, 6.4 Hz, 2H), 2.85 (s, 3H), 2.73 (d, J = 3.0 Hz, 3H), 1.67 (d, J = 6.7 Hz, 6H), 1.31 (t, J = 7.2 Hz, 3H). |
| 69 | 4-(2,6-Dimethyl-3-propan-2-ylthieno[2,3-d]imidazol-5-yl)-5-fluoro-N-[5-[2,2,3,3,5,5,6,6-octadeuterio-4-(trideuteriomethyl)piperazin-1-yl]pyridin-2-yl]pyrimidin-2-amine, TFA salt | $^1$H NMR (300 MHz, CD$_3$OD) δ 8.75 (d, J = 3.2 Hz, 1H), 8.22 (dd, J = 9.6, 3.0 Hz, 1H), 7.92 (d, J = 3.0 Hz, 1H), 7.63 (d, J = 9.6 Hz, 1H), 4.96 (dd, J = 8.3, 4.9 Hz, 1H), 2.85 (s, 3H), 2.74 (d, J = 3.0 Hz, 3H), 1.67 (d, J = 6.7 Hz, 6H). |
| 70 | N-[5-(5,5-Difluoro-7-methyl-2,7-diazaspiro[3.4]octan-2-yl)pyridin-2-yl]-4-(2,6-dimethyl-3-propan-2-ylthieno[2,3-d]imidazol-5-yl)-5-fluoropyrimidin-2-amine, TFA salt | $^1$H NMR (300 MHz, CD$_3$OD) δ 8.72 (d, J = 3.2 Hz, 1H), 7.73 (dd, J = 9.5, 2.7 Hz, 1H), 7.56 (dd, J = 6.1, 3.1 Hz, 2H), 5.01-4.89 (m, 1H), 4.33 (d, J = 8.2 Hz, 2H), 4.06 (d, J = 8.2 Hz, 2H), 3.98-3.86 (m, 4H), 2.98 (s, 3H), 2.83 (d, J = 1.6 Hz, 3H), 2.73 (d, J = 3.0 Hz, 3H), 1.67 (d, J = 6.7 Hz, 6H). |
| 71 | (6-Dthyl-2,6-diazaspiro[3.3]heptan-2-yl)-[6-[[5-fluoro-4-(2-methyl-3-propan-2-ylthieno[2,3-d]imidazol-5-yl)pyrimidin-2-yl]amino]pyridin-3-yl]methanone, TFA salt | $^1$H NMR (300 MHz, DMSO-d$_6$) δ 10.46 (s, 1H), 9.70 (s, 1H), 8.70 (d, J = 3.3 Hz, 1H), 8.54 (s, 1H), 8.28 (d, J = 8.8 Hz, 1H), 8.07 (dd, J = 8.8, 2.4 Hz, 1H), 7.97 (d, J = 1.3 Hz, 1H), 4.79 (hept, J = 6.4, 6.0 Hz, 1H), 4.58 (d, J = 27.4 Hz, 2H), 4.37-4.25 (m, 4H), 4.24-4.15 (m, 2H), 3.19-3.09 (m, 2H), 2.63 (s, 3H), 1.54 (d, J = 6.6 Hz, 6H), 1.04 (t, J = 7.1 Hz, 3H). |
| 72 | N-[5-[3-(Dimethylamino)azetidin-1-yl]pyridin-2-yl]-5-fluoro-4-(2-methyl-3-propan-2-ylthieno[2,3-d]imidazol-5-yl)pyrimidin-2-amine, TFA salt | $^1$H NMR (300 MHz, CD$_3$OD) δ 8.68 (d, J = 3.3 Hz, 1H), 8.11 (d, J = 1.2 Hz, 1H), 7.72 (dd, J = 9.2, 3.0 Hz, 1H), 7.59-7.53 (m, 2H), 4.96 (d, J = 6.5 Hz, 1H), 4.35 (dq, J = 10.3, 5.1, 3.6 Hz, 3H), 4.23 (dd, J = 7.8, 3.5 Hz, 2H), 2.98 (s, 6H), 2.81 (s, 3H), 1.68 (d, J = 6.7 Hz, 6H). |
| 73 | N-[5-[3-(Dimethylamino)pyrrolidin-1-yl]pyridin-2-yl]-4-(2,6-dimethyl-3-propan-2-ylthieno[2,3-d]imidazol-5-yl)-5-fluoropyrimidin-2-amine, TFA salt | $^1$H NMR (300 MHz, CD$_3$OD) δ 8.75 (d, J = 3.1 Hz, 1H), 7.91 (dd, J = 9.6, 3.0 Hz, 1H), 7.62 (d, J = 2.9 Hz, 1H), 7.56 (d, J = 9.5 Hz, 1H), 4.97 (t, J = 6.7 Hz, 1H), 4.13 (q, J = 7.2 Hz, 1H), 3.83 (dd, J = 10.6, 7.4 Hz, 1H), 3.75-3.66 (m, 2H), 3.52-3.42 (m, 1H), 3.02 (s, 6H), 2.86 (s, 3H), 2.74 (d, J = 3.0 Hz, 3H), 2.69-2.63 (m, 1H), 2.46-2.35 (m, 2H), 1.68 (d, J = 6.6 Hz, 6H). |
| 74 | N-[5-(6-ethyl-3,6-Diazabicyclo[3.1.1]heptan-3-yl)pyridin-2-yl]-5-fluoro-4-(2-methyl-3-propan-2-ylthieno[2,3-d]imidazol-5-yl)pyrimidin-2-amine, TFA salt | $^1$H NMR (300 MHz, CD$_3$OD) δ 8.71 (d, J = 3.3 Hz, 1H), 8.13 (d, J = 1.1 Hz, 1H), 8.06 (dt, J = 9.7, 3.0 Hz, 1H), 7.80 (d, J = 3.0 Hz, 1H), 7.62 (d, J = 9.6 Hz, 1H), 4.72 (d, J = 6.3 Hz, 1H), 4.58 (d, J = 6.4 Hz, 1H), 4.15-3.84 (m, 4H), 3.59 (q, J = 8.0, 7.5 Hz, 1H), 3.48-3.20 (m, 2H), 3.10 (p, |

TABLE 5-2-continued

Examples 64-75

| Example | Compound name | NMR |
|---|---|---|
| 75 | 1-[6-[[4-(2,6-Dimethyl-3-propan-2-ylthieno[2,3-d]imidazol-5-yl)-5-fluoropyrimidin-2-yl]amino]pyridin-3-yl]-4-methylpiperazin-2-one, TFA salt | J = 7.2 Hz, 1H), 2.82 (s, 3H), 2.28-2.11 (m, 1H), 1.68 (d, J = 6.6 Hz, 6H), 1.44-1.33 (m, 3H). $^1$H NMR (400 MHz, DMSO-d$_6$) δ 10.34 (s, 1H), 8.73 (d, J = 3.0 Hz, 1H), 8.30 (d, J = 2.7 Hz, 1H), 8.24 (d, J = 9.0 Hz, 1H), 7.79 (dd, J = 9.0, 2.7 Hz, 1H), 4.83 (p, J = 6.6 Hz, 1H), 4.17-4.03 (m, 2H), 3.94 (t, J = 5.6 Hz, 2H), 3.77-3.58 (m, 2H), 2.97 (s, 3H), 2.70 (s, 3H), 2.57 (d, J = 3.7 Hz, 3H), 1.54 (d, J = 6.6 Hz, 6H). |

Examples 76-92

Examples listed in Tables 6-1 and 6-2 are synthesized according to procedures analogous to Example 51 and Example 56.

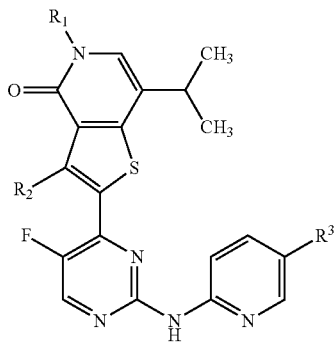

TABLE 6-1

Examples 76-92.

| Example | R$^1$ | R$^2$ | R$^3$ | LCMS [M + H]$^+$ |
|---|---|---|---|---|
| 76 | Me | Me | | 548.2 |
| 77 | Me | Me | | 548.1 |
| 78 | Me | Me | | 534.1 |
| 79 | Me | Me | | 534.2 |
| 80 | Me | Me | | 576.3 |
| 81 | Me | H | | 520.0 |
| 82 | Me | Me | | 510.0 |
| 83 | Me | Me | | 534.3 |
| 84 | Me | Me | | 563.2 |

TABLE 6-1-continued

Examples 76-92.

| Example | R¹ | R² | R³ | LCMS [M + H]⁺ |
|---|---|---|---|---|
| 85 | CD₃ | Me | 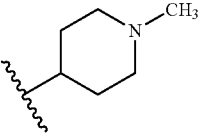 [SMILES: *C1CCN(C)CC1] | 510.2 |
| 86 | Me | H | 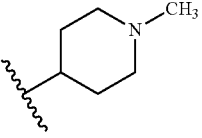 [SMILES: *C1CCN(C)CC1] | 493.0 |
| 87 | Me | Me | 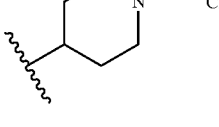 | 521.0 |
| 88 | Me | Me | 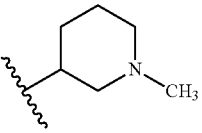 [SMILES: *C1CCCN(C)C1] | 507.0 |
| 89 | Me | Me | 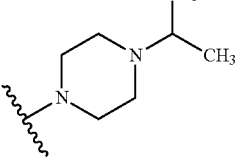 | 536.2 |
| 90 | Me | Me | 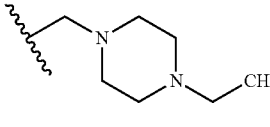 | 536.2 |
| 91 | Me | Me | 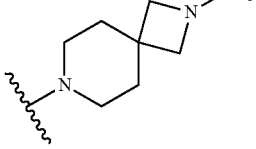 | 548.2 |
| 92 | Me | Me | 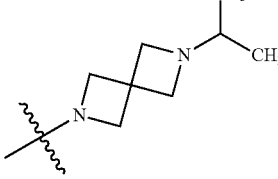 | 547.9 |

TABLE 6-2

Examples 76-92.

| Example | Compound name | NMR |
|---|---|---|
| 76 | 2-(5-Fluoro-2-((5-(7-methyl-2,7-diazaspiro[4.4]nonan-2-yl)pyridin-2-yl)amino)pyrimidin-4-yl)-7-isopropyl-3,5-dimethylthieno[3,2-c]pyridin-4(5H)-one, TFA salt | — |
| 77 | 2-(5-Fluoro-2-((5-(7-methyl-2,7-diazaspiro[3.5]nonan-2-yl)pyridin-2-yl)amino)pyrimidin-4-yl)-7-isopropyl-3,5-dimethylthieno[3,2-c]pyridin-4(5H)-one, TFA salt | ¹H NMR (400 MHz, DMSO-d₆) δ 8.74 (d, J = 2.7 Hz, 1H), 7.68 (dd, J = 9.5, 2.8 Hz, 1H), 7.53-7.42 (m, 3H), 3.91 (s, 2H), 3.81 (s, 2H), 3.63 (s, 3H), 3.58-3.42 (m, 2H), 3.20-2.95 (m, 3H), 2.91 (s, 3H), 2.84 (d, J = 3.2 Hz, 3H), 2.29 (d, J = 14.6 Hz, 2H), 2.15-1.98 (m, 2H), 1.40 (d, J = 6.9 Hz, 6H). |
| 78 | 2-(5-Fluoro-2-((5-((3aR,6aS)-5-methylhexahydropyrrolo[3,4-c]pyrrol-2(1H)-yl)pyridin-2-yl)amino)pyrimidin-4-yl)-7-isopropyl-3,5-dimethylthieno[3,2-c]pyridin-4(5H)-one, TFA salt | ¹H NMR (400 MHz, DMSO-d₆) δ 10.68 (d, J = 7.7 Hz, 1H), 10.05 (bs, 0.5H), 9.83 (bs, 0.5H), 8.76 (d, J = 2.5 Hz, 1H), 7.84 (d, J = 9.2 Hz, 1H), 7.76 (dd, J = 11.2, 2.9 Hz, 1H), 7.63-7.48 (m, 2H), 3.98-3.77 (m, 1H), 3.60-3.43 (m, 5H), 3.42-3.23 (m, 4H), 3.17-3.03 (m, 2H), 2.97-2.78 (m, 5H), 2.71 (d, J = 3.3 Hz, 3H), 1.31 (d, J = 6.8 Hz, 6H). |
| 79 | 2-(5-Fluoro-2-((5-((3aS,6aS)-5-methylhexahydropyrrolo[3,4-c]pyrrol-2(1H)-yl)pyridin-2-yl)amino)pyrimidin-4-yl)-7- | ¹H NMR (300 MHz, methanol-d₄) δ 8.73 (d, J = 2.6 Hz, 1H), 7.80 (dd, J = 9.6, 3.0 Hz, 1H), 7.54-7.41 (m, 3H), 4.06-3.91 (m, 1H), 3.75-3.34 (m, 5H), 3.63 (s, 3H), 3.14-2.86 (m, 3H), |

TABLE 6-2-continued

Examples 76-92.

| Example | Compound name | NMR |
|---|---|---|
| | isopropyl-3,5-dimethylthieno[3,2-c]pyridin-4(5H)-one, TFA salt | 3.07 (s, 3H), 2.83 (d, J = 3.2 Hz, 3H), 2.79-2.52 (m, 2H), 1.39 (d, J = 6.9 Hz, 6H). |
| 80 | 2-(5-Fluoro-2-((5-(4-(2,2,2-trifluoroethyl)piperazin-1-yl)pyridin-2-yl)amino)pyrimidin-4-yl)-7-isopropyl-3,5-dimethylthieno[3,2-c]pyridin-4(5H)-one, TFA salt | — |
| 81 | 2-(2-((5-(5-Ethyl-2,5-diazabicyclo[2.2.1]heptan-2-yl)pyridin-2-yl)amino)-5-fluoropyrimidin-4-yl)-7-isopropyl-5-methylthieno[3,2-c]pyridin-4(5H)-one, TFA salt | $^1$H NMR (300 MHz, methanol-d$_4$) δ 8.69 (d, J = 3.3 Hz, 1H), 8.50 (d, J = 1.7 Hz, 1H), 7.92 (dd, J = 9.6, 3.0 Hz, 1H), 7.66 (d, J = 2.9 Hz, 1H), 7.57-7.45 (m, 2H), 4.85-4.70 (m, 2H), 4.59 bs, 1H), 3.96-3.71 (m, 2H), 3.65 (s, 3H), 3.61-3.33 (m, 3H), 3.12-2.94 (m, 1H), 2.52-2.25 (m, 2H), 1.42 (d, J = 6.9 Hz, 6H), 1.36 (t, J = 7.2 Hz, 3H). |
| 82 | 2-(5-Fluoro-2-((5-(1-(methyl-d3)piperidin-4-yl)pyridin-2-yl)amino)pyrimidin-4-yl)-7-isopropyl-3,5-dimethylthieno[3,2-c]pyridin-4(5H)-one, TFA salt | $^1$H NMR (300 MHz, methanol-d$_4$) δ 8.81 (d, J = 2.7 Hz, 1H), 8.35-8.26 (m, 2H), 7.64 (d, J = 9.0 Hz, 1H), 7.47 (s, 1H), 3.75-3.65 (m, 2H), 3.64 (s, 3H), 3.30-2.98 (m, 4H), 2.86 (d, J = 3.3 Hz, 3H), 2.30-2.20 (m, 2H), 2.15-1.96 (m, 2H), 1.40 (d, J = 6.9 Hz, 6H). |
| 83 | 2-(2-((5-(1,4-Diazabicyclo[3.2.2]nonan-4-yl)pyridin-2-yl)amino)-5-fluoropyrimidin-4-yl)-7-isopropyl-3,5-dimethylthieno[3,2-c]pyridin-4(5H)-one, TFA salt | — |
| 84 | 2-(5-Fluoro-2-((5-(1-(tetrahydrofuran-3-yl)piperidin-4-yl)pyridin-2-yl)amino)pyrimidin-4-yl)-7-isopropyl-3,5-dimethylthieno[3,2-c]pyridin-4(5H)-one, TFA salt | $^1$H NMR (300 MHz, Methanol-d$_4$) δ 8.81 (d, J = 2.6 Hz, 1H), 8.55-8.10 (m, 2H), 7.61 (d, J = 9.0 Hz, 1H), 7.46 (s, 1H), 4.32-4.17 (m, 1H), 4.16-4.00 (m, 2H), 3.89 (dd, J = 11.0, 6.3 Hz, 1H), 3.83-3.56 (m, 6H), 3.31-3.07 (m, 3H), 3.00 (p, J = 6.9 Hz, 1H), 2.85 (d, J = 3.2 Hz, 3H), 2.57-2.36 (m, 1H), 2.34-2.20 (m, 3H), 2.19-2.00 (m, 2H), 1.39 (d, J = 6.9 Hz, 6H). |
| 85 | 2-(5-Fluoro-2-((5-(1-methylpiperidin-4-yl)pyridin-2-yl)amino)pyrimidin-4-yl)-7-isopropyl-3-methyl-5-(methyl-d3)thieno[3,2-c]pyridin-4(5H)-one, TFA salt | $^1$H NMR (300 MHz, methanol-d$_4$) δ 8.74 (d, J = 2.6 Hz, 1H), 8.27-8.20 (m, 2H), 7.58 (d, J = 8.9 Hz, 1H), 7.40 (s, 1H), 3.63 (d, J = 12.6 Hz, 2H), 3.20-3.07 (m, 3H), 2.98-2.92 (m, 1H), 2.89 (s, 3H), 2.80 (d, J = 3.2 Hz, 3H), 2.24-2.12 (m, 2H), 2.07-1.93 (m, 2H), 1.34 (d, J = 6.9 Hz, 6H). |
| 86 | 2-(5-Fluoro-2-((5-(1-methylpiperidin-4-yl)pyridin-2-yl)amino)pyrimidin-4-yl)-7-isopropyl-5-methylthieno[3,2-c]pyridin-4(5H)-one, TFA salt | $^1$H NMR (300 MHz, methanol-d$_4$) δ 8.77 (d, J = 3.2 Hz, 1H), 8.55 (d, J = 1.5 Hz, 1H), 8.36-8.26 (m, 2H), 7.61 (d, J = 9.0 Hz, 1H), 7.52 (s, 1H), 3.80-3.55 (m, 5H), 3.26-3.17 (m, 2H), 3.11-3.02 (m, 2H), 2.96 (s, 3H), 2.25 (d, J = 14.1 Hz, 2H), 2.15-1.95 (m, 2H), 1.43 (d, J = 6.9 Hz, 6H). |
| 87 | 2-(2-((5-(1-Ethylpiperidin-4-yl)pyridin-2-yl)amino)-5-fluoropyrimidin-4-yl)-7-isopropyl-3,5-dimethylthieno[3,2-c]pyridin-4(5H)-one, HCl salt | $^1$H NMR (300 MHz, DMSO-d$_6$) δ 10.09 (s, 2H), 8.73 (d, J = 2.5 Hz, 1H), 8.20 (s, 1H), 8.15 (d, J = 8.7 Hz, 1H), 7.65 (d, J = 8.4 Hz, 1H), 7.55 (s, 1H), 3.51 (s, 3H), 3.20-2.74 (m, 8H), 2.69 (d, J = 3.5 Hz, 3H), 2.20-1.80 (s, 4H), 1.31 (d, J = 6.8 Hz, 6H), 1.28-1.20 (m, 3H). |

TABLE 6-2-continued

Examples 76-92.

| Example | Compound name | NMR |
|---|---|---|
| 88 | 2-(5-Fluoro-2-((5-(1-methylpiperidin-3-yl)pyridin-2-yl)amino)pyrimidin-4-yl)-7-isopropyl-3,5-dimethylthieno[3,2-c]pyridin-4(5H)-one, TFA salt | $^1$H NMR (300 MHz, methanol-d$_4$) δ 8.76 (d, J = 2.6 Hz, 1H), 8.27 (d, J = 2.2 Hz, 1H), 8.19 (dd, J = 9.1, 2.1 Hz, 1H), 7.77 (d, J = 9.0 Hz, 1H), 7.45 (s, 1H), 3.71-3.55 (m, 5H), 3.23-3.14 (m, 2H), 3.08-2.97 (m, 2H), 2.94 (s, 3H), 2.83 (d, J = 3.3 Hz, 3H), 2.22-2.05 (m, 2H), 2.04-1.72 (m, 2H), 1.39 (d, J = 6.9 Hz, 6H). |
| 89 | 2-(5-Fluoro-2-((5-(4-isopropylpiperazin-1-yl)pyridin-2-yl)amino)pyrimidin-4-yl)-7-isopropyl-3,5-dimethylthieno[3,2-c]pyridin-4(5H)-one, HCl salt | $^1$H NMR (400 MHz, methanol-d$_4$) δ 8.79 (d, J = 2.6 Hz, 1H), 8.27 (dd, J = 9.7, 2.9 Hz, 1H), 7.92 (d, J = 2.8 Hz, 1H), 7.55 (d, J = 9.6 Hz, 1H), 7.45 (s, 1H), 3.97 (d, J = 12.1 Hz, 2H), 3.76-3.58 (m, 6H), 3.42-3.21 (m, 4H), 3.00 (sept, J = 6.9 Hz, 1H), 2.85 (d, J = 3.2 Hz, 3H), 1.46 (d, J = 6.7 Hz, 6H), 1.39 (d, J = 6.9 Hz, 6H). |
| 90 | 2-(2-((5-((4-Ethylpiperazin-1-yl)methyl)pyridin-2-yl)amino)-5-fluoropyrimidin-4-yl)-7-isopropyl-3,5-dimethylthieno[3,2-c]pyridin-4(5H)-one, TFA salt | $^1$H NMR (300 MHz, methanol-d$_4$) δ 8.81 (d, J = 2.6 Hz, 1H), 8.40-8.30 (m, 2H), 7.62 (d, J = 9.7 Hz, 1H), 7.47 (s, 1H), 3.76 (s, 2H), 3.64 (s, 3H), 3.32-2.95 (m, 11H), 2.86 (d, J = 3.2 Hz, 3H), 1.4-1.25 (m, 9H). |
| 91 | 2-(5-Fluoro-2-((5-(2-methyl-2,7-diazaspiro[3.5]nonan-7-yl)pyridin-2-yl)amino)pyrimidin-4-yl)-7-isopropyl-3,5-dimethylthieno[3,2-c]pyridin-4(5H)-one, TFA salt | $^1$H NMR (300 MHz, methanol-d$_4$) δ 8.74 (d, J = 2.6 Hz, 1H), 8.19 (dd, J = 9.7, 2.9 Hz, 1H), 7.79 (d, J = 2.8 Hz, 1H), 7.48 (d, J = 9.7 Hz, 1H), 7.44 (s, 1H), 4.19 (d, J = 11.2 Hz, 2H), 3.92 (d, J = 11.2 Hz, 2H), 3.62 (s, 3H), 3.28-3.15 (m, 3H), 3.09-2.91 (m, 5H), 2.83 (d, J = 3.2 Hz, 3H), 2.13-1.96 (m, 4H), 1.38 (d, J = 6.9 Hz, 6H). |
| 92 | 2-(5-Fluoro-2-((5-(6-isopropyl-2,6-diazaspiro[3.3]heptan-2-yl)pyridin-2-yl)amino)pyrimidin-4-yl)-7-isopropyl-3,5-dimethylthieno[3,2-c]pyridin-4(5H)-one, TFA salt | $^1$H NMR (300 MHz, DMSO-d$_6$) δ 10.53 (s, 1H), 10.36-10.07 (m, 1H), 8.73 (d, J = 2.6 Hz, 1H), 7.81 (d, J = 9.1 Hz, 1H), 7.66-7.46 (m, 2H), 7.29 (dd, J = 9.1, 2.7 Hz, 1H), 4.29 (d, J = 6.3 Hz, 4H), 4.12 (s, 2H), 3.98 (s, 2H), 3.52 (s, 3H), 3.48-3.31 (m, 1H), 2.89 (p, J = 6.8 Hz, 1H), 2.70 (d, J = 3.2 Hz, 3H), 1.31 (d, J = 6.8 Hz, 6H), 1.12 (d, J = 6.4 Hz, 6H). |

Example 93 2-(5-Fluoro-2-((6-(1-methylpiperidin-4-yl)pyridazin-3-yl)amino)pyrimidin-4-yl)-7-isopropyl-3,5-dimethylthieno[3,2-c]pyridin-4(5H)-one

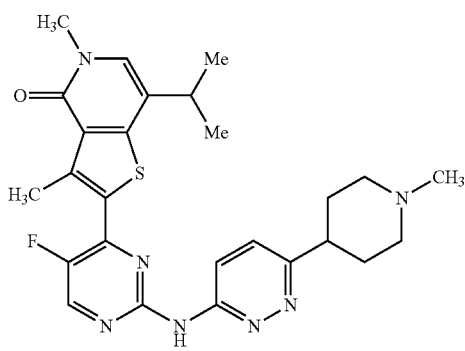 [SMILES: Cc1c(-c2nc(Nc3ccc(C4CCN(C)CC4)nn3)ncc2F)sc2c(C(C)C)cn(C)c(=O)c12]

Step 1. tert-Butyl 4-(6-aminopyridazin-3-yl)-3,6-dihydropyridine-1(2H)-carboxylate N-Boc-1,2,3,6-tetrahydropyridine-4-boronic acid pinacol ester (2.63 g, 8.49 mmol), 6-chloropyridazin-3-amine (1.00 g, 7.72 mmol), K$_3$PO$_4$ (4.92 g, 23.2 mmol), and [1,1'-bis(diphenylphosphino)ferrocene]dichloropalladium(II) (0.565 g, 0.772 mmol) were suspended in 1,4-dioxane (15.0 mL) and water (5.00 mL) under inert atmosphere. The reaction mixture was heated at 100° C. for 2 h. The reaction mixture was cooled to room temperature and diluted with water (30.0 mL). The mixture was extracted with EtOAc (30.0 mL×3). The organic layers were combined, dried over sodium sulfate, filtered, and concentrated. The crude material was suspended in DCM (20.0 mL), and the solid was collected by filtration to afford the title compound (1.65 g, 5.97 mmol, 77.4% yield) as a white solid. $^1$H NMR (300 MHz, CDCl$_3$) δ 7.39 (d, J=9.3 Hz, 1H), 6.73 (d, J=9.3 Hz, 1H), 6.32 (s, 1H), 4.69 (s, 2H), 4.12 (q, J=3.1 Hz, 2H), 3.64 (t, J=5.7 Hz, 2H), 2.76 (s, 2H), 1.49 (s, 9H).

Step 2. tert-Butyl 4-(6-aminopyridazin-3-yl)piperidine-1-carboxylate

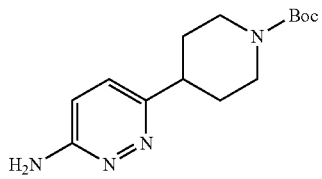

tert-Butyl 4-(6-aminopyridazin-3-yl)-3,6-dihydropyridine-1(2H)-carboxylate (1.60 g, 5.79 mmol) was dissolved in MeOH (30.0 mL). Palladium on carbon (0.800 g, 0.751 mmol, 10 wt %) and acetic acid (2.00 mL, 34.8 mmol) were added sequentially. The reaction vessel was sealed in a Parr shaker, and the vessel was charged with H$_2$ (60 psi). The reaction mixture was shaken overnight. The atmosphere of hydrogen was removed, the mixture was filtered, and the filtrate was concentrated under reduced pressure. The crude residue was purified by silica gel chromatography (50-100% EtOAc in heptanes, then 0-30% MeOH in EtOAc to afford the title compound (610 mg, 2.19 mmol, 37.8% yield). LCMS calc. for C$_{14}$H$_{23}$N$_4$O$_2$ [M+H]+: m/z=279.2; Found: 279.0.

Step 3. 6-(Piperidin-4-yl)pyridazin-3-amine

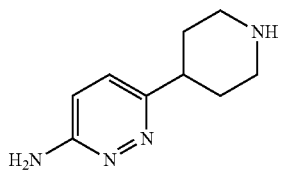

tert-Butyl 4-(6-aminopyridazin-3-yl)-3,6-dihydropyridine-1(2H)-carboxylate (610 mg, 2.19 mmol) was dissolved in DCM (6.00 mL), and trifluoroacetic acid (6.00 mL, 78.4 mmol) was added slowly at room temperature. The reaction mixture was stirred for 18 h. The reaction mixture was concentrated under reduced pressure, and crude residue was azeotroped with toluene (5.00 mL×3). The crude residue was used without further purification to afford the crude TFA salt of the title compound (1.10 g) as a pale-yellow oil. LCMS calc. for C$_9$H$_{15}$N$_4$[M+H]+: m/z=179.1; Found: 179.0.

Step 4. 6-(1-Methylpiperidin-4-yl)pyridazin-3-amine

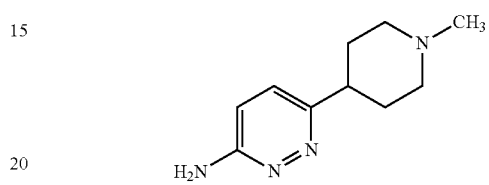

Formaldehyde (1.10 mL, 14.8 mmol, 37 wt % in H2O), acetic acid (0.845 mL, 14.8 mmol), and the crude TFA salt of 6-(piperidin-4-yl)pyridazin-3-amine (1.10 g) were dissolved in MeOH (20.0 mL) at room temperature. Sodium cyanoborohydride (0.928 g, 14.8 mmol) was added portionwise, and the reaction mixture was stirred overnight. The reaction was quenched with water (100 mL), and the reaction mixture diluted with EtOAc (100 mL). The organic phase was separated, and the aqueous layer was extracted with EtOAc (100 mL×3). The organic layers were combined, dried over sodium sulfate, filtered, and concentrated. The crude residue was purified by prep-HPLC using a C18 column (0-60% MeCN/0.1% TFA (aq.)) to afford a mixture of two compounds. The fractions were collected and partially concentrated under reduced pressure. TFA (0.50 mL) was added to the solution. The solution was concentrated to dryness under reduced pressure. The crude residue was further purified by prep-HPLC using a C18 column (0-60% MeCN/0.1% TFA (aq.)) to afford the TFA salt of the title compound (99.0 mg, 0.324 mmol, 14.8% yield) as a yellow oil. $^1$H NMR (300 MHz, Methanol-d$_4$) δ 7.87 (d, J=9.5 Hz, 1H), 7.53 (d, J=9.5 Hz, 1H), 3.68 (d, J=12.3 Hz, 2H), 3.27-3.05 (m, 3H), 2.95 (s, 3H), 2.30-2.22 (m, 2H), 2.06-1.95 (m, 2H).

Step 5. 2-(5-Fluoro-2-((6-(1-methylpiperidin-4-yl)pyridazin-3-yl)amino)pyrimidin-4-yl)-7-isopropyl-3,5-dimethylthieno[3,2-c]pyridin-4(5H)-one The title compound is synthesized by procedures analogous to those outlined in Example 1, Step 8. $^1$H NMR (300 MHz, Methanol-d$_4$) δ 8.84 (d, J=2.5 Hz, 1H), 8.25 (d, J=9.4 Hz, 1H), 8.09 (d, J=9.4 Hz, 1H), 7.50 (s, 1H), 3.74 (d, J=12.5 Hz, 2H), 3.67 (s, 3H), 3.33-3.20 (m, 3H), 3.08-3.01 (m, 1H), 2.99 (s, 3H), 2.87 (d, J=3.3 Hz, 3H), 2.50-2.30 (m, 2H), 2.25-2.11 (m, 2H), 1.43 (d, J=6.9 Hz, 6H). LCMS calc. for C$_{26}$H$_{31}$FN$_7$OS [M+H]+: m/z=508.2; Found: 507.9.

Example 94. 2-(5-Fluoro-2-((5-(piperidin-4-yl)pyridin-2-yl)amino)pyrimidin-4-yl)-7-isopropyl-3,5-dimethylthieno[3,2-c]pyridin-4(5H)-one

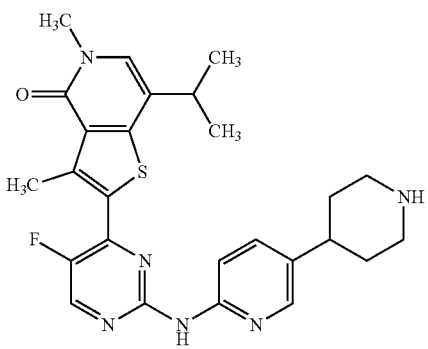 [SMILES: Cc1c(-c2nc(Nc3ccc(C4CCNCC4)cn3)ncc2F)sc2c(C(C)C)cn(C)c(=O)c12]

Step 1. tert-Butyl 4-(6-aminopyridin-3-yl)piperidine-1-carboxylate

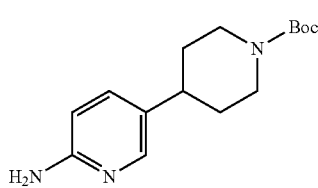

The title compound is synthesized by procedures analogous to those outlined in Example 93, Steps 1-2. LCMS calc. for $C_{15}H_{24}N_3O_2$ [M+H]+: m/z=278.2; Found: 278.0.

Step 2. 2-(5-Fluoro-2-((5-(piperidin-4-yl)pyridin-2-yl)amino)pyrimidin-4-yl)-7-isopropyl-3,5-dimethylthieno[3,2-c]pyridin-4(5H)-one To a solution of 2-(2-chloro-5-fluoropyrimidin-4-yl)-3,5-dimethyl-7-propan-2-ylthieno[3,2-c]pyridin-4-one, TFA salt (40.0 mg, 0.0860 mmol, Example 51, Step 6) and tert-butyl 4-(6-aminopyridin-3-yl)piperidine-1-carboxylate (37.8 mg, 0.136 mmol) in 1,4-dioxane (1.00 mL) was added K3PO4 (111 mg, 0.341 mmol) and XPhos Pd G2 (8.95 mg, 11.4 µmol, CAS 1310584-14-5). The reaction vessel was sealed, and the mixture was degassed with N2 (3×). The reaction mixture was heated at 100° C. overnight. The reaction mixture was cooled to room temperature and concentrated under reduced pressure. The residue was dissolved in DCM (20.0 mL) and washed with water (20.0 mL×2) and brine (20.0 mL×2). The organic layer was dried over sodium sulfate, filtered, and concentrated under reduced pressure. The crude material was dissolved in DCM (4.00 mL) and TFA (1.00 mL, 13.4 mmol) was added. The reaction was stirred at room temperature for 30 min. The reaction mixture was concentrated under reduced pressure and the dark residue was purified by prep-HPLC on a C18 column (0-60% MeCN/0.1% TFA (aq.)) afforded the TFA salt of the title compound (47.2 mg, 0.0779 mmol, 90.6% yield). $^1$H NMR (300 MHz, Methanol-d$_4$) δ 8.79 (d, J=2.6 Hz, 1H), 8.32-8.22 (m, 2H), 7.67 (d, J=9.7 Hz, 1H), 7.46 (s, 1H), 3.63 (s, 3H), 3.57 (d, J=13.0 Hz, 2H), 3.25-3.10 (m, 3H) 3.03-2.95 (m, 1H), 2.85 (d, J=3.2 Hz, 3H), 2.19 (d, J=12.8 Hz, 2H), 2.05-1.89 (m, 2H), 1.40 (d, J=6.9 Hz, 6H). LCMS calc. for $C_{26}H_{30}N_6OS$ [M+H]+: m/z=493.2; Found: 493.2.

Example 95. 2-(5-Fluoro-2-((5-(1-isopropylpyrrolidin-3-yl)pyridin-2-yl)amino)pyrimidin-4-yl)-7-isopropyl-3,5-dimethylthieno[3,2-c]pyridin-4(5H)-one

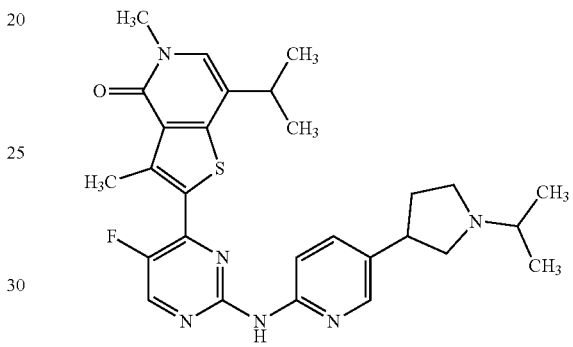

Step 1. 2-(5-Fluoro-2-((5-(pyrrolidin-3-yl)pyridin-2-yl)amino)pyrimidin-4-yl)-7-isopropyl-3,5-dimethylthieno[3,2-c]pyridin-4(5H)-one

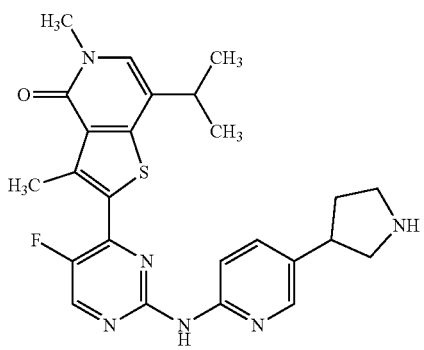 [SMILES: Cc1c(-c2nc(Nc3ccc(C4CCNC4)cn3)ncc2F)sc2c(C(C)C)cn(C)c(=O)c12]

The title compound is synthesized by procedures analogous to those outlined in Example 94). LCMS calc. for $C_{25}H_{28}FN_6OS$ [M+H]+: m/z=479.2; Found: 479.2.

Step 2. 2-(5-Fluoro-2-((5-(1-isopropylpyrrolidin-3-yl)pyridin-2-yl)amino)pyrimidin-4-yl)-7-isopropyl-3,5-dimethylthieno[3,2-c]pyridin-4(5H)-one To a solution of tert-butyl 3-(6-((5-fluoro-4-(7-isopropyl-3,5-dimethyl-4-oxo-4,5-dihydrothieno[3,2-c]pyridin-2-yl)

pyrimidin-2-yl)amino)pyridin-3-yl)pyrrolidine-1-carboxylate (50.0 mg, 0.104 mmol) and acetone (31.0 µL, 0.418 mmol) in methanol (0.800 mL) was added sodium cyanoborohydride (32.8 mg, 0.552 mmol) at room temperature. The reaction mixture was stirred at room temperature for 1 h. The reaction mixture was concentrated under reduced pressure and the residue was purified by prep-HPLC on a C18 column (5-95% MeCN/0.1% TFA (aq.)) afforded the TFA salt of the title compound (44.0 mg, 0.0694 mmol, 66.7% yield). $^1$H NMR (300 MHz, Methanol-$d_4$) δ 8.77 (d, J=2.6 Hz, 1H), 8.46-8.32 (m, 2H), 7.67 (d, J=8.8 Hz, 1H), 7.43 (s, 1H), 4.10-3.48 (m, 8H), 3.40-3.23 (m, 1H), 3.04-2.75 (m, 1H), 2.83 (d, J=3.0 Hz, 3H), 2.68-2.52 (m, 1H), 2.45-2.25 (m, 1H), 1.45 (d, J=6.5 Hz, 6H), 1.37 (d, J=6.9 Hz, 6H). LCMS calc. for $C_{28}H_{34}FN_6OS$ [M+H]+: m/z=521.3; Found: 521.2.

Example 96. 7-Isopropyl-5-methyl-2-(2-((5-(1-methylpiperidin-4-yl)pyridine-2-yl)amino)pyrimidin-4-yl)thieno[3,2-c]pyridin-4(5H)-one

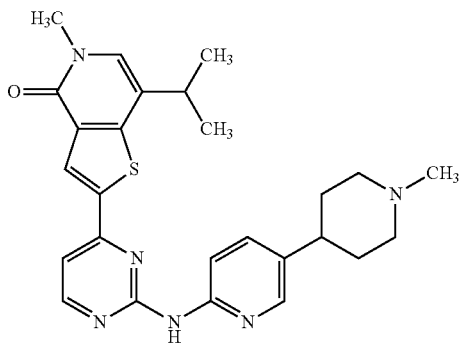 [SMILES: CC(C)c1cn(C)c(=O)c2cc(-c3ccnc(Nc4ccc(C5CCN(C)CC5)cn4)n3)sc12]

Step 1. 2-(2,5-Dichloropyrimidin-4-yl)-7-isopropyl-5-methylthieno[3,2-c]pyridin-4(5H)-one

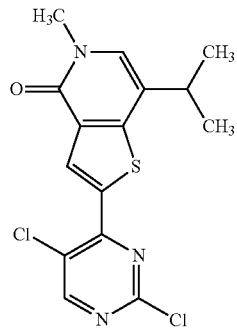 [SMILES: CC(C)c1cn(C)c(=O)c2cc(-c3nc(Cl)ncc3Cl)sc12]

The title compound is synthesized by a procedure analogous to that outline in Example 62, Step 4. LCMS calc. for $C_{15}H_{14}Cl_2N_3OS$ [M+H]+: m/z=354.0; Found: 353.9.

Step 2. 7-Isopropyl-5-methyl-2-(2-((5-(1-methylpiperidin-4-yl)pyridin-2-yl)amino) pyrimidin-4-yl)thieno[3,2-c]pyridin-4(5H)-one The title is synthesized by a procedure analogous to that outline in Example 56, Step 6. Purification by prep-HPLC on a C18 column (10-30% MeCN/0.1% TFA (aq.)) afforded the TFA salt of the title compound as a yellow solid. $^1$H NMR (300 MHz, Methanol-$d_4$) δ 8.75 (d, J=5.6 Hz, 1H), 8.48 (s, 1H), 8.38-8.28 (m, 2H), 7.84 (d, J=5.6 Hz, 1H), 7.57 (d, J=8.9 Hz, 1H), 7.48 (s, 1H), 3.75-3.55 (m, 2H), 3.65 (s, 3H), 3.30-2.96 (m, 4H), 2.95 (s, 3H), 2.40-2.00 (m, 4H), 1.41 (d, J=6.9 Hz, 6H). LCMS calc. for $C_{26}H_{31}N_6OS$ [M+H]+: m/z=475.2; Found: 475.3.

Example 97. 7-Isopropyl-5-methyl-2-(5-methyl-2-((5-(1-methylpiperidin-4-yl)pyridin-2-yl)amino)pyrimidin-4-yl)thieno[3,2-c]pyridin-4(5H)-one

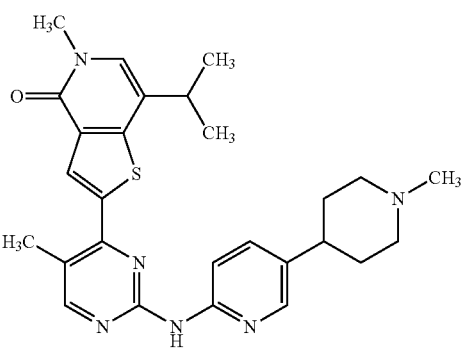 [SMILES: Cc1cnc(Nc2ccc(C3CCN(C)CC3)cn2)nc1-c1cc2c(=O)n(C)cc(C(C)C)c2s1]

Step 1. 2-(2-Chloro-5-methylpyrimidin-4-yl)-7-isopropyl-5-methylthieno[3,2-c]pyridin-4(5H)-one

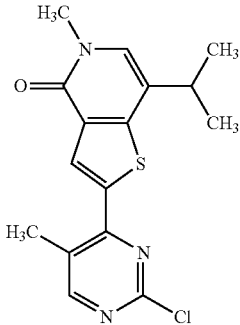 [SMILES: Cc1cnc(Cl)nc1-c1cc2c(=O)n(C)cc(C(C)C)c2s1]

The title compound is synthesized by a procedure analogous to that outline in Example 56, Step 5. LCMS calc. for $C_{16}H_{17}ClN_3OS$ [M+H]+: m/z=334.1; Found: 334.0.

Step 2. 7-Isopropyl-5-methyl-2-(5-methyl-2-((5-(1-methylpiperidin-4-yl)pyridin-2-yl)amino)pyrimidin-4-yl)thieno[3,2-c]pyridin-4(5H)-one The title is synthesized by a procedure analogous to that outline in Example 56, Step 6. Purification by prep-HPLC on a C18 column (2-40% MeCN/0.1% TFA (aq.)) afforded the title compound as the TFA salt, a yellow solid. $^1$H NMR (300 MHz, Methanol-$d_4$) δ 8.66 (s, 1H), 8.40 (s, 1H), 8.32-8.23 (m, 2H), 7.58 (d, J=9.8 Hz, 1H), 7.49 (s, 1H), 3.75-3.65 (m, 2H), 3.67 (s, 3H), 3.28-2.97 (m, 4H), 2.96 (s, 3H), 2.70 (s, 3H), 2.25 (d, J=14.1 Hz, 2H), 2.25-1.95 (m, 2H), 1.43 (d, J=6.9 Hz, 6H) LCMS calc. for $C_{27}H_{33}N_6OS$ [M+H]+: m/z=489.2; Found: 489.2.

Example 98. 4-(6-((5-Fluoro-4-(7-isopropyl-3,5-dimethyl-4-oxo-4,5-dihydrothieno[3,2-c]pyridin-2-yl)pyrimidin-2-yl)amino)pyridin-3-yl)-1-methylpiperidine 1-oxide

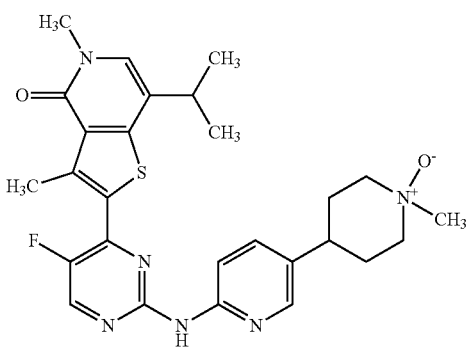 [SMILES: Cc1c(-c2nc(Nc3ccc(C4CC[N+](C)([O-])CC4)cn3)ncc2F)sc2c(C(C)C)cn(C)c(=O)c12]

To a solution of 2-(5-fluoro-2-((5-(1-methylpiperidin-4-yl)pyridin-2-yl)amino)pyrimidin-4-yl)-7-isopropyl-3,5-dimethylthieno[3,2-c]pyridin-4(5H)-one (18.0 mg, 0.036 mmol, Example 56) in DCM (2.00 mL) was added m-CPBA (12.9 mg, 0.0750 mmol) at room temperature. The mixture was heated to 100° C. for 3 h. The reaction mixture was cooled to room temperature and concentrated under reduced pressure. Purification by prep-HPLC on a C18 column (10-40% MeCN/0.1% TFA (aq.)) afforded the TFA salt of the title compound (12.0 mg, 0.019 mmol, 53.1% yield) as a yellow solid. $^1$H NMR (300 MHz, Methanol-$d_4$) δ 8.85 (d, J=2.6 Hz, 1H), 8.40-8.29 (m, 2H), 7.83 (d, J=8.9 Hz, 1H), 7.54 (s, 1H), 4.06-3.85 (m, 4H), 3.72 (s, 3H), 3.69 (s, 3H), 3.23-3.04 (m, 2H), 2.93 (d, J=3.3 Hz, 3H), 2.60-2.39 (m, 2H), 2.22 (d, J=14.1 Hz, 2H), 1.48 (d, J=6.9 Hz, 6H). LCMS calc. for $C_{27}H_{32}FN_6O_2S$ [M+H]$^+$: m/z=523.2; Found: 523.2.

Example 99. 5-Fluoro-4-(3-isopropyl-2-methyl-2H-thieno[3,2-c]pyrazol-5-yl)-N-(5-(1-methylpiperidin-4-yl)pyridin-2-yl)pyrimidin-2-amine

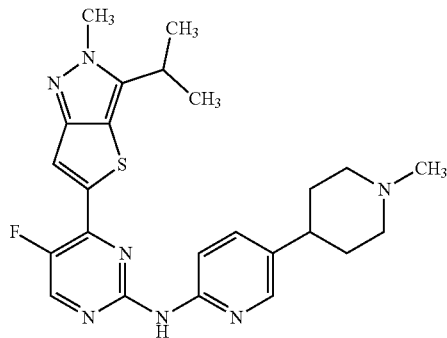 [SMILES: CC(C)c1c2sc(-c3nc(Nc4ccc(C5CCN(C)CC5)cn4)ncc3F)cc2nn1C]

The title compound is synthesized by procedures analogous to those outlined in Example 55. Purification by silica gel chromatography using MeOH in DCM (0-20%) afforded the free base of the title compound. The solvent was removed under reduced pressure and the residue was suspended in MeOH (10.0 mL) and water (10.0 mL) then 2N HCl (2.50 mL) was added. The mixture was concentrated under reduced pressure to afford the HCl salt of the title compound (1.33 g, 2.47 mmol, 61.4% yield) as a pale-yellow solid. $^1$H NMR (300 MHz, Methanol-$d_4$) δ 8.76 (d, J=3.3 Hz, 1H), 8.35 (dd, J=9.1, 2.3 Hz, 1H), 8.30 (d, J=2.1 Hz, 1H), 8.04 (d, J=1.5 Hz, 1H), 7.58 (d, J=9.1 Hz, 1H), 4.08 (s, 3H), 3.77-3.61 (m, 2H), 3.39 (p, J=6.8 Hz, 1H), 3.29-3.02 (m, 3H), 2.95 (s, 3H), 2.24 (d, J=14.3 Hz, 2H), 2.18-1.95 (m, 2H), 1.44 (d, J=6.8 Hz, 6H). LCMS calc. for $C_{24}H_{29}FN_7S$ [M+H]$^+$: m/z=466.2; Found: 466.0.

Example 100. N-(5-((4-Ethylpiperazin-1-yl)methyl)pyridin-2-yl)-5-fluoro-4-(3-isopropyl-6-methyl-2H-thieno[3,2-c]pyrazol-5-yl)pyrimidin-2-amine

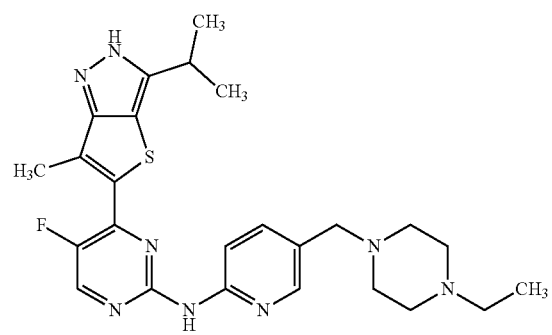 [SMILES: CCN1CCN(Cc2ccc(Nc3ncc(F)c(-c4sc5c(C(C)C)[nH]nc5c4C)n3)nc2)CC1]

Step 1. 3-Iodo-6-methyl-2-(tetrahydro-2H-pyran-2-yl)-2H-thieno[3,2-c]pyrazole and 3-iodo-6-methyl-1-(tetrahydro-2H-pyran-2-yl)-1H-thieno[3,2-c]pyrazole

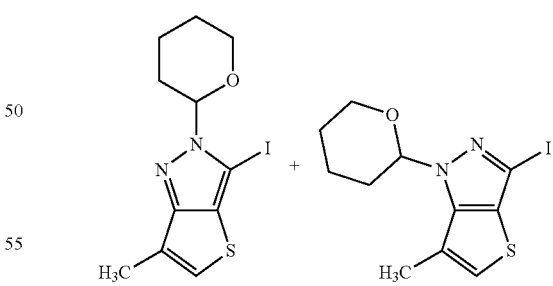

To a solution of 3-iodo-6-methyl-1H-thieno[3,2-c]pyrazole (1.17 mg, 4.43 mmol, Example 55, Step 4) in 3,4-dihydro-2H-pyran (5.00 mL, 54.8 mmol) was added TFA (0.339 mL, 4.43 mmol) at room temperature. The reaction was stirred at room temperature for 1 h. The crude reaction mixture was purified directly by silica gel chromatography using EtOAc in hexanes (0-15%) to afford a mixture of the title compounds (1.21 g, 3.46 mmol, 78.4% yield) as a colorless solid. Major isomer ¹H NMR (300 MHz, CDCl₃) δ 6.98 (d, J=1.2 Hz, 1H), 5.57 (dd, J=9.5, 2.6 Hz, 1H), 4.08-3.97 (m, 1H), 3.78-3.61 (m, 1H), 2.64-2.43 (m, 1H), 2.42 (d, J=1.2 Hz, 3H), 2.25-2.01 (m, 2H), 1.93-1.37 (m, 3H).

Step 2. 6-Methyl-3-(prop-1-en-2-yl)-2-(tetrahydro-2H-pyran-2-yl)-2H-thieno[3,2-c]pyrazole and 6-methyl-3-(prop-1-en-2-yl)-1-(tetrahydro-2H-pyran-2-yl)-1H-thieno[3,2-c]pyrazole

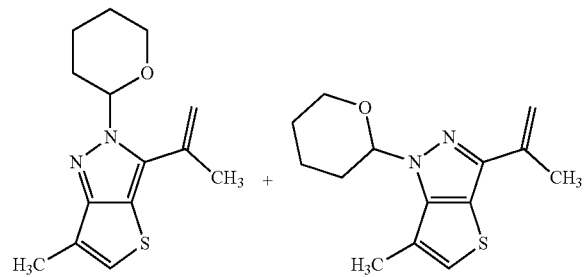 [SMILES: C=C(C)c1c2scc(C)c2nn1C1CCCCO1 ; C=C(C)c1nn(C2CCCCO2)c2c(C)csc12]

The title compound is synthesized by procedures analogous to those outlined in Example 14, Step 1. Major isomer ¹H NMR (300 MHz, CDCl₃) δ 6.97 (q, J=1.2 Hz, 1H), 5.62 (dd, J=9.4, 2.8 Hz, 1H), 5.40 (t, J=1.0 Hz, 1H), 5.30-5.22 (m, 1H), 4.12-3.96 (m, 1H), 3.81-3.57 (m, 1H), 2.65-2.47 (m, 1H), 2.45 (d, J=1.2 Hz, 3H), 2.24 (s, 3H), 2.23-2.01 (m, 2H), 1.82-1.54 (m, 3H).

Step 3. 3-Isopropyl-6-methyl-2-(tetrahydro-2H-pyran-2-yl)-2H-thieno[3,2-c]pyrazole and 3-isopropyl-6-methyl-1-(tetrahydro-2H-pyran-2-yl)-1H-thieno[3,2-c]pyrazole

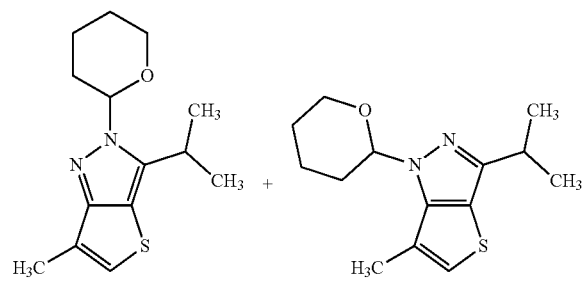 [SMILES: Cc1csc2c(C(C)C)n(C3CCCCO3)nc12 ; Cc1csc2c(C(C)C)nn(C3CCCCO3)c12]

In a 100 mL reaction vessel, a mixture of 3-isopropyl-6-methyl-2-(tetrahydro-2H-pyran-2-yl)-2H-thieno[3,2-c]pyrazole and 3-isopropyl-6-methyl-1-(tetrahydro-2H-pyran-2-yl)-1H-thieno[3,2-c]pyrazole (661 mg, 2.52 mmol) was dissolved in MeOH (20.0 mL), and palladium on carbon (100 mg, 0.094 mmol, 10 wt %) was added at room temperature. The reaction vessel was sealed in a Parr shaker, and the vessel was charged with hydrogen (50 psi). The reaction mixture was shaken for 4 d. The atmosphere of hydrogen was removed, the mixture was filtered, and the filtrate was concentrated under reduced pressure. The crude residue containing a mixture of the title compounds (536 mg) was used without further purification Step 4. 3-Isopropyl-6-methyl-2-(tetrahydro-2H-pyran-2-yl)-5-(tributylstannyl)-2H-thieno[3,2-c]pyrazole

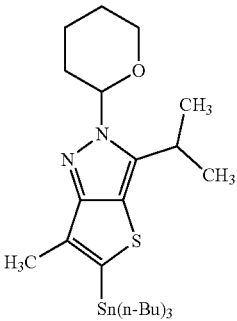

A solution of lithium diisopropylamide (3.84 mL, 7.68 mmol, 2.0 M in THF/heptane/ethylbenzene) was added to a mixture of 3-isopropyl-6-methyl-2-(tetrahydro-2H-pyran-2-yl)-2H-thieno[3,2-c]pyrazole and 3-isopropyl-6-methyl-1-(tetrahydro-2H-pyran-2-yl)-1H-thieno[3,2-c]pyrazole (406 mg) in THF (2.00 mL) at −78° C. After stirring at −78° C. for 30 min, tributyl(chloro)stannane (0.500 mL, 1.84 mmol) was added. The reaction mixture was warmed to room temperature and stirred for 30 min. The reaction was quenched with sat. aq. NH₄Cl solution (2.00 mL), and the reaction mixture was diluted with 3N aq. KF (2.00 mL). The mixture was stirred at room temperature for 1 h and then filtered. The organic layer was separated, and the aqueous layer was extracted with EtOAc (3.00 mL×2). The combined organic layers were dried over sodium sulfate, filtered, and concentrated. Purification by silica gel chromatography using EtOAc in hexanes (0-15%) afforded the title compound (401 mg, 0.725 mmol, 47.2% yield) as a colorless oil. ¹H NMR (300 MHz, CDCl₃) δ 5.55 (dd, J=10.0, 2.5 Hz, 1H), 4.19-4.02 (m, 1H), 3.77-3.60 (m, 1H), 3.13 (hept, J=7.0 Hz, 1H), 2.61-2.45 (m, 1H), 2.43 (s, 3H), 2.18-1.98 (m, 2H), 1.93-1.01 (m, 27H), 0.90 (t, J=7.3 Hz, 9H).

Step 5. 5-(2-Chloro-5-fluoropyrimidin-4-yl)-3-isopropyl-6-methyl-2-(tetrahydro-2H-pyran-2-yl)-2H-thieno[3,2-c]pyrazole

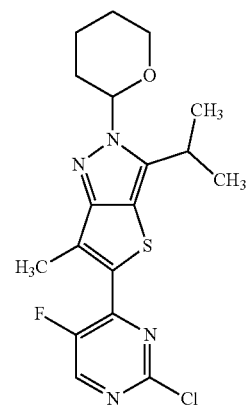 [SMILES: Cc1c(-c2nc(Cl)ncc2F)sc2c(C(C)C)n(C3CCCCO3)nc12]

To a solution of 3-isopropyl-6-methyl-2-(tetrahydro-2H-pyran-2-yl)-5-(tributylstannyl)-2H-thieno[3,2-c]pyrazole (401 mg, 0.724 mmol) in toluene (1.00 mL) was added 2,4-dichloro-5-fluoropyrimidine (252 mg, 1.45 mmol) and tetrakis(triphenylphosphine)palladium(0) (125 mg, 0.109 mmol). The reaction vessel was sealed, and the mixture was degassed with $N_2$ (3×). The reaction mixture was heated at 100° C. overnight. The reaction mixture was cooled to room temperature and purified by silica gel chromatography using EtOAc in heptanes (0-10%) to afford the title compound (142 mg, 0.359 mmol, 49.6% yield) as a colorless solid. $^1$H NMR (300 MHz, CDCl$_3$) δ 8.52 (d, J=2.4 Hz, 1H), 5.64 (dd, J=9.7, 2.5 Hz, 1H), 4.11-4.01 (m, 2H), 3.82-3.56 (m, 1H), 2.66 (d, J=3.0 Hz, 3H), 2.62-2.40 (m, 1H), 2.35-1.96 (m, 2H), 1.88-1.58 (m, 3H), 1.38 (d, J=3.4 Hz, 3H), 1.36 (d, J=3.4 Hz, 3H).

Step 6. N-(5-((4-Ethylpiperazin-1-yl)methyl)pyridin-2-yl)-5-fluoro-4-(3-isopropyl-6-methyl-2H-thieno[3,2-c]pyrazol-5-yl)pyrimidin-2-amine The title compound is synthesized by procedures analogous to those outlined in Example 1, Step 8. The crude residue was purified by prep-HPLC on a C18 column (2-50% MeCN/0.1% TFA (aq.)) to afford the TFA salt of the title compound as a yellow solid. $^1$H NMR (300 MHz, Methanol-d$_4$) δ 8.79 (d, J=2.9 Hz, 1H), 8.41-8.25 (m, 2H), 7.94-7.58 (m, 1H), 3.75 (s, 2H), 3.60-3.06 (m, 11H), 2.65 (d, J=3.0 Hz, 3H), 1.42 (d, J=7.0 Hz, 6H), 1.36 (t, J=7.4 Hz, 3H). LCMS calc. for $C_{25}H_{32}FN_8S$ [M+H]$^+$: m/z=495.2; Found: 494.9.

Example 101. 4-(3-Cyclopropyl-2,6-dimethyl-2H-thieno[3,2-c]pyrazol-5-yl)-N-(5-(6-ethyl-2,6-diazaspiro[3.3]heptan-2-yl)pyridin-2-yl)-5-fluoropyrimidin-2-amine

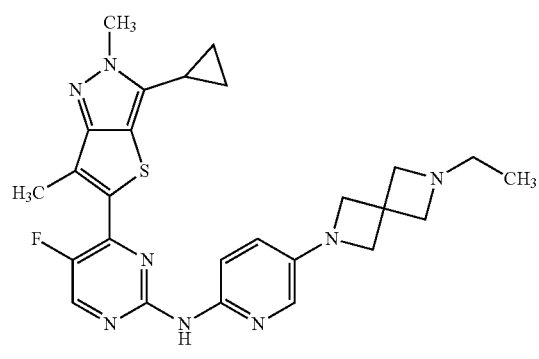 [SMILES: CCN1CC2(C1)CN(c1ccc(Nc3ncc(F)c(-c4sc5c(C6CC6)n(C)nc5c4C)n3)nc1)C2]

Step 1. 3-Cyclopropyl-2,6-dimethyl-2H-thieno[3,2-c]pyrazole

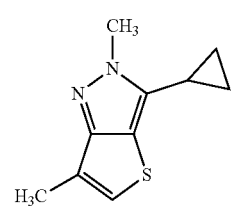

To a solution of 3-iodo-2,6-dimethylthieno[3,2-c]pyrazole (420 mg, 1.51 mmol, Example 55, Step 5) in toluene (6.00 mL) and water (0.600 mL) was added cyclopropylboronic acid (182 mg, 2.11 mmol), dichlorobis(tricyclohexylphosphine)palladium(II) (55.7 mg, 0.076 mmol), and $K_3PO_4$ (1.28 g, 6.04 mmol) at room temperature. The reaction vessel was sealed, and the mixture was degassed with $N_2$ (3×). The reaction mixture was heated at 100° C. overnight. The reaction mixture was cooled to room temperature and diluted with water and EtOAc. The organic layer was separated, and the aqueous layer was extracted with EtOAc (20.0 mL×2). The combined organic layers were washed with brine, dried over sodium sulfate, filtered, and concentrated. Purification by silica gel chromatography using EtOAc in heptane (10-60%) afforded the title compound (232 mg, 1.21 mmol, 79.9% yield) as a brown solid. LCMS calc. for $C_{10}H_{13}N_2S$ [M+H]$^+$: m/z=193.1; Found: 192.9.

Step 2. 4-(3-Cyclopropyl-2,6-dimethyl-2H-thieno[3,2-c]pyrazol-5-yl)-N-(5-(6-ethyl-2,6-diazaspiro[3.3]heptan-2-yl)pyridin-2-yl)-5-fluoropyrimidin-2-amine The title compound was synthesized by procedures analogous to those outlined in Example 55, Steps 8-10. Purification by prep-HPLC on a C18 column (5-95%, MeCN/0.1% TFA (aq.)) afforded the TFA salt of the title compound as an orange solid. $^1$H NMR (300 MHz, Methanol-d$_4$) δ 8.68 (d, J=2.9 Hz, 1H), 7.67 (dd, J=9.5, 2.8 Hz, 1H), 7.57-7.39 (m, 2H), 4.56-4.43 (m, 2H), 4.40-4.21 (m, 4H), 4.18-4.05 (m, 5H), 3.27 (q, J=7.3 Hz, 2H), 2.57 (d, J=3.2 Hz, 3H), 2.13 (tt, J=8.3, 5.1 Hz, 1H), 1.42-1.11 (m, 5H), 0.97-0.78 (m, 2H). LCMS calc. for $C_{26}H_{30}FN_8S$ [M+H]$^+$: m/z=505.2; Found: 504.9.

Example 102. 2-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)-1,1,1-trifluoropropan-2-ol

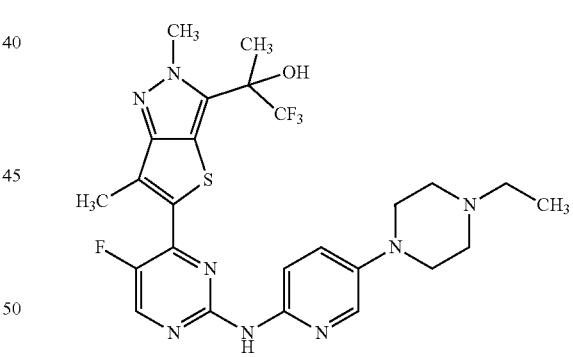

Step 1. 3-Iodo-2,6-dimethylthieno[3,2-c]pyrazole and 3-iodo-1,6-dimethyl-1H-thieno[3,2-c]pyrazole

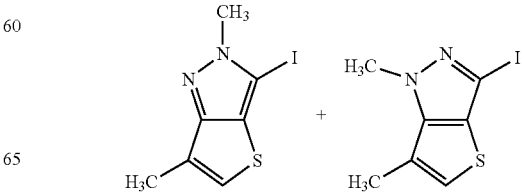

To a solution of 3-iodo-6-methyl-1H-thieno[3,2-c]pyrazole (2.2 g, 8.33 mmol, Example 55, Step 4) in THF (80 mL) at 0° C. was added potassium tert-butoxide solution (10.0 mL, 10 mmol, 1.0 M in THF). The resulting mixture was stirred at 0° C. for 5 min. Next, iodomethane (0.62 mL, 10 mmol) was added, and the reaction was stirred for 2 h. The reaction was quenched by adding sat. aq. NH$_4$Cl (50 mL). The reaction mixture was extracted with EtOAc (50 mL×3). The combined organic layers were dried over sodium sulfate, filtered, and concentrated under reduced pressure. The crude product was purified by flash chromatography to afford a mixture of the title compounds (2.2 g, 7.9 mmol, 94% yield). LCMS calc. for C$_7$H$_8$IN$_2$S [M+H]$^+$: m/z=278.9; Found: 278.9.

Step 2: 1-(2,6-Dimethyl-2H-thieno[3,2-c]pyrazol-3-yl)ethan-1-one

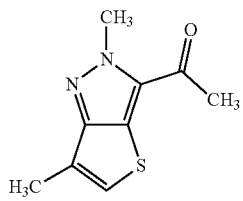

To a mixture of 3-iodo-1,6-dimethylthieno[3,2-c]pyrazole and 3-iodo-2,6-dimethylthieno[3,2-c]pyrazole (3.0 g, 10.8 mmol) in toluene (30 mL) was added tributyl(1-ethoxyvinyl)tin (5.46 mL, 16.2 mmol), followed by the addition of Pd(PPh$_3$)$_4$ (1.25 g, 1.08 mmol). The mixture was heated at 100° C. overnight. The reaction was quenched with 0.3 N KF solution (30 mL). The mixture was stirred at room temperature for 2 h, passed through a Celite pad and extracted with EtOAc (3×30 mL). The combined organic phase was dried over Na$_2$SO$_4$, concentrated under reduced pressure, and redissolved in THF (20 mL). Next 1N HCl (20 mL) was added. The mixture was stirred at rt overnight. The organic phase was separated and the aqueous phase was extracted with EtOAc (3×20 mL). The combined organic phase was dried over Na$_2$SO$_4$, concentrated under reduced pressure, and purified by silica gel column chromatography (0-35% EtOAc/hexanes) to afford the title compound (735 mg, 3.78 mmol, 35.0% yield, R$_f$=0.80, 30% EtOAc/hexanes). LCMS calc. for C$_9$H$_{11}$N$_2$OS [M+H]$^+$: m/z=195.0; Found: 195.1.

Step 3. 2-(2,6-Dimethyl-2H-thieno[3,2-c]pyrazol-3-yl)-1,1,1-trifluoropropan-2-ol

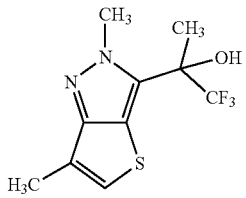

To a solution of 1-(2,6-dimethylthieno[3,2-c]pyrazol-3-yl)ethanone (535 mg, 2.75 mmol) in THF (10 mL) was added trimethyl(trifluoromethyl)silane (2.85 mL, 19.3 mmol) and TBAF solution (4.13 mL, 4.13 mmol, 1.00 M in THF) at 0° C. The mixture was stirred for 30 min. The reaction was quenched by adding sat. aq. NH$_4$Cl (10 mL). The organic phase was separated, and the aqueous phase was extracted with EtOAc (3×10 mL). The combined organic phases were dried over Na$_2$SO$_4$, concentrated, and purified by silica gel column chromatography (0-10% EtOAc/hexanes) to afford the title compound (264 mg, 1.00 mmol, 36.3% yield). LCMS calc. for C$_{10}$H$_{12}$F$_3$N$_2$OS [M+H]$^+$: m/z=265.0; Found: 265.1.

Step 4. 2-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)-1,1,1-trifluoropropan-2-ol The title compound is synthesized by procedures analogous to those outlined in Example 14, Steps 3-5. $^1$H NMR (300 MHz, Methanol-d4) δ 8.77 (d, J=2.8 Hz, 1H), 8.24 (dd, J=9.7, 2.9 Hz, 1H), 7.90 (d, J=2.8 Hz, 1H), 7.59 (d, J=9.6 Hz, 1H), 4.33 (s, 3H), 4.10-3.40 (m, 6H), 3.30-3.06 (m, 4H), 2.63 (d, J=3.2 Hz, 3H), 1.97 (s, 3H), 1.42 (t, J=7.3 Hz, 3H). LC-MS calc. for C$_{25}$H$_{29}$F$_4$N$_8$OS [M+H]$^+$: m/z=565.2; Found 565.1.

Example 103. 1-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)ethan-1-one

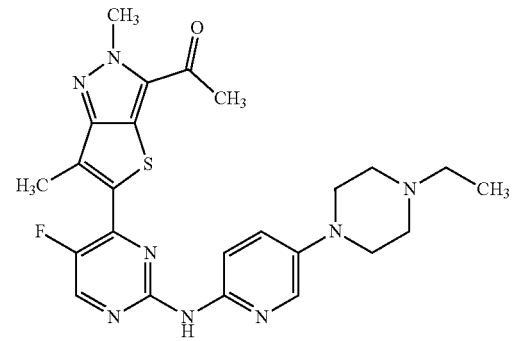 [SMILES: CCN1CCN(c2ccc(Nc3ncc(F)c(-c4sc5c(C(C)=O)n(C)nc5c4C)n3)nc2)CC1]

Step 1. 2,6-Dimethyl-3-(2-methyl-1,3-dioxolan-2-yl)-2H-thieno[3,2-c]pyrazole

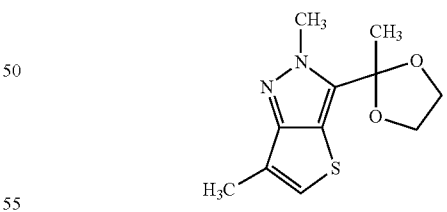

p-Toluenesulfonic acid monohydrate (66.1 mg, 0347 mmol) was added to a mixture of 1-(2,6-dimethyl-2H-thieno[3,2-c]pyrazol-3-yl)ethan-1-one (135 mg, 0.695 mmol, Example 102, Step 2) and ethylene glycol (0.155 mL, 2.78 mmol) in toluene (3.00 mL) at room temperature. The reaction mixture was heated at 110° C. overnight. The reaction mixture was cooled to room temperature and purified by silica gel chromatography using EtOAc in heptane (10%) to afford the title compound (132 mg, 0.554 mmol, 79.7% yield). LC-MS calc. for C$_{11}$H$_{15}$N$_2$O$_2$S [M+H]$^+$: m/z=239.1; Found 239.1.

Step 2. 5-(2-Chloro-5-fluoropyrimidin-4-yl)-2,6-dimethyl-3-(2-methyl-1,3-dioxolan-2-yl)-2H-thieno[3,2-c]pyrazole

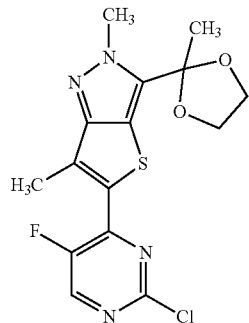 [SMILES: Cc1c(-c2nc(Cl)ncc2F)sc2c(C3(C)OCCO3)n(C)nc12]

The title compound is synthesized by procedures analogous to those outlined in Example 1, Steps 6-7. LC-MS calc. for $C_{15}H_{15}ClFN_4O_2S$ [M+H]$^+$: m/z=369.1; Found 368.9.

Step 3. 1-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)ethan-1-one To a solution of 5-(2-chloro-5-fluoropyrimidin-4-yl)-2,6-dimethyl-3-(2-methyl-1,3-dioxolan-2-yl)-2H-thieno[3,2-c]pyrazole, TFA salt (13.3 mg, 0.0275 mmol) and 5-(4-ethylpiperazin-1-yl)pyridin-2-amine (9.67 mg, 0.0469 mmol) in 1,4-dioxane (1.00 mL) was added $K_3PO_4$ (45.9 mg, 0.216 mmol) and XPhos Pd G2 (4.26 mg, 5.41 μmol, CAS 1310584-14-5). The reaction vessel was sealed, and the mixture was degassed with $N_2$ (3×). The reaction mixture was heated at 100° C. for 4 h. The reaction mixture was cooled to room temperature and 4N aq. HCl (1.50 mL) was added. The reaction was heated to 80° C. for 30 min. The reaction mixture was cooled to room temperature, filtered, and concentrated under reduced pressure. The dark residue was purified by prep-HPLC on a C18 column (5-50% MeCN/0.1% TFA (aq.)) afforded the title compound (13.0 mg, 0.022 mmol, 62.3% yield) as a tan solid $^1$H NMR (300 MHz, Methanol-d$_4$) δ 8.82 (d, J=2.9 Hz, 1H), 8.28 (dd, J=9.7, 2.9 Hz, 1H), 7.96 (d, J=2.9 Hz, 1H), 7.64 (d, J=9.7 Hz, 1H), 4.43 (s, 3H), 4.13-3.60 (m, 4H), 3.57-3.08 (m, 6H), 2.71 (d, J=3.3 Hz, 3H), 2.67 (s, 3H), 1.46 (t, J=7.3 Hz, 3H). LCMS calc. for $C_{24}H_{28}FN_8OS$ [M+H]$^+$: m/z=495.2; Found: 495.4.

Example 104. 1-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)ethan-1-ol

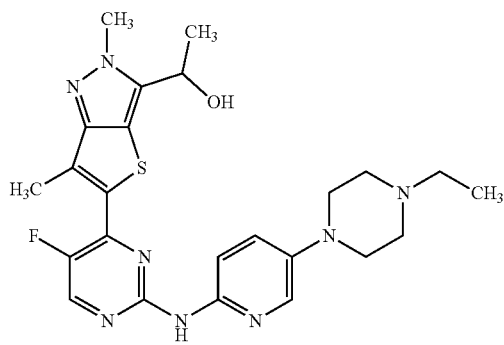 [SMILES: CCN1CCN(c2ccc(Nc3ncc(F)c(-c4sc5c(C(C)O)n(C)nc5c4C)n3)nc2)CC1]

To a solution of 1-(5-(2-((5-(4-ethylpiperazin-1-yl)pyridin-2-yl)amino)-5-fluoropyrimidin-4-yl)-2,6-dimethyl-2H-thieno[3,2-c]pyrazol-3-yl)ethan-1-one, TFA salt (5.80 mg, 0.012 mmol, Example 103) in MeOH (1.00 mL) was added sodium borohydride (0.444 mg, 0.012 mmol). The reaction mixture was stirred at room temperature for 30 min. The reaction mixture was purified by prep-HPLC on a C18 column (2-50%, MeCN/0.1% TFA (aq.)) to afford the TFA salt of the title compound (5.00 mg, 0.008 mmol, 69.8% yield) as a brown solid. $^1$H NMR (300 MHz, Methanol-d$_4$) δ 8.74 (s, 1H), 8.20 (d, J=9.3 Hz, 1H), 7.92 (s, 1H), 7.63 (d, J=9.6 Hz, 1H), 5.22 (q, J=6.6 Hz, 1H), 4.14 (s, 3H), 4.04-2.94 (m, 10H), 2.61 (d, J=3.3 Hz, 3H), 1.69 (d, J=6.5 Hz, 3H), 1.42 (t, J=7.3, 3H). LCMS calc. for $C_{24}H_{30}FN_8OS$ [M+H]$^+$: m/z=497.2; Found: 497.4.

Example 105. N-(5-(6-Ethyl-2,6-diazaspiro[3.3]heptan-2-yl)pyridin-2-yl)-5-fluoro-4-(3-(2-methoxypropan-2-yl)-2,6-dimethyl-2H-thieno[3,2-c]pyrazol-5-yl)pyrimidin-2-amine

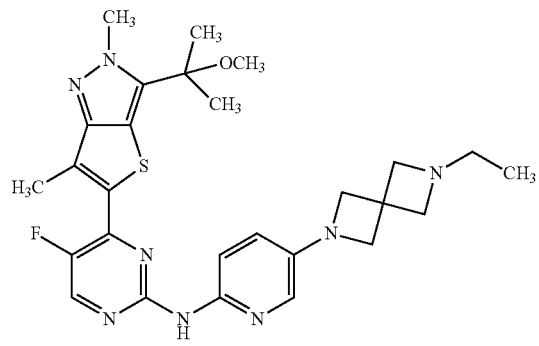 [SMILES: CCN1CC2(C1)CN(c1ccc(Nc3ncc(F)c(-c4sc5c(C(C)(C)OC)n(C)nc5c4C)n3)nc1)C2]

Step 1. 2-(2,6-Dimethyl-2H-thieno[3,2-c]pyrazol-3-yl)propan-2-ol

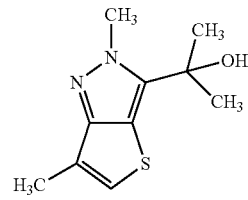

The title compound is synthesized by procedures analogous to those outlined in Example 17, Step 2. LCMS calc. for $C_{10}H_{15}N_2OS$ [M-OH]$^+$: m/z=211.1; Found: 211.0.

Step 2. 3-(2-methoxypropan-2-yl)-2,6-dimethyl-2H-thieno[3,2-c]pyrazole

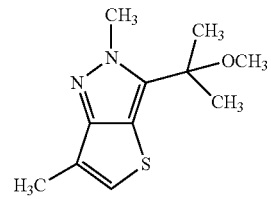

Iodomethane (0.139 mL, 2.23 mmol) and KOH (25.1 mg, 0.447 mmol) were added sequentially to a solution of 2-(2,6-dimethyl-2H-thieno[3,2-c]pyrazol-3-yl)propan-2-ol (47.0 mg, 0.223 mmol) in DMSO (1.00 mL). The reaction mixture was stirred at room temperature for 2 h. The reaction was quenched with 2N aq. HCl solution (2.00 mL), and the mixture was purified by prep-HPLC on a C18 column (10-80% MeCN/0.1% TFA (aq.)) to afford the title compound (39.0 mg, 0.174 mmol, 77.8% yield) as a colorless oil. LCMS calc. for $C_{11}H_{17}N_2OS$ [M+H]$^+$: m/z=225.1; Found: 224.9.

Step 3. N-(5-(6-Ethyl-2,6-diazaspiro[3.3]heptan-2-yl)pyridin-2-yl)-5-fluoro-4-(3-(2-methoxypropan-2-yl)-2,6-dimethyl-2H-thieno[3,2-c]pyrazol-5-yl)pyrimidin-2-amine The title compound is synthesized by procedures analogous to those outlined in Example 55, Steps 8-10. Purification by prep-HPLC on a C18 column (2-50%, MeCN/0.1% TFA (aq.)) afforded the TFA salt of the title compound (5.70 mg, 0.009 mmol, 42.0% yield) as a green solid. $^1$H NMR (300 MHz, Methanol-d$_4$) δ 8.74 (d, J=2.8 Hz, 1H), 7.69 (dd, J=9.5, 2.8 Hz, 1H), 7.57-7.46 (m, 2H), 4.52 (d, J=11.2 Hz, 2H), 4.38-4.27 (m, 4H), 4.26 (s, 3H), 4.20 (s, 2H), 3.30-3.25 (m, 2H), 3.17 (s, 3H), 2.62 (d, J=3.1 Hz, 3H), 1.76 (s, 6H), 1.25 (t, J=7.2 Hz, 3H). LCMS calc. for $C_{27}H_{34}FN_8OS$ [M+H]$^+$: m/z=537.2; Found: 536.9.

Example 106. 4-(1,6-Dimethyl-3-propan-2-ylthieno[3,2-c]pyrazol-5-yl)-N-[5-(4-ethylpiperazin-1-yl)pyridin-2-yl]-5-fluoropyrimidin-2-amine

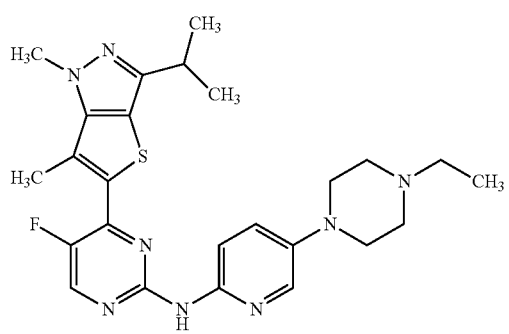 [SMILES: CCN1CCN(c2ccc(Nc3ncc(F)c(-c4sc5c(C(C)C)nn(C)c5c4C)n3)nc2)CC1]

Step 1: 1,6-Dimethyl-3-prop-1-en-2-ylthieno[3,2-c]pyrazole and 2,6-Dimethyl-3-(prop-1-en-2-yl)-2H-thieno[3,2-c]pyrazole

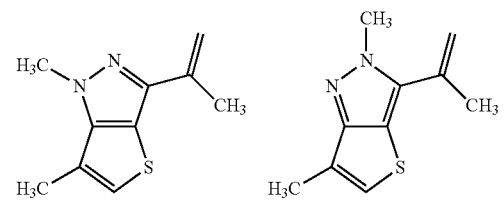

To a mixture of 2-isopropenyl-4,4,5,5-tetramethyl-1,3,2-dioxaborolane (0.91 mL, 4.85 mmol) and K$_3$PO$_4$ (2.06 g, 9.71 mmol) in 1,4-dioxane (13.5 mL) and water (4.5 mL) was added [1,1'-bis(diphenylphosphino)ferrocene]dichloropalladium(II) (237 mg, 0.32 mmol), followed by the addition of a mixture of 3-iodo-2,6-dimethylthieno[3,2-c]pyrazole and 3-iodo-1,6-dimethyl-1H-thieno[3,2-c]pyrazole (900 mg, 3.24 mmol, Example 102, Step 1). The reaction mixture was sparged with nitrogen for 5 min and stirred at 100° C. overnight. The reaction mixture was filtered, and the filtrate was concentrated. The residue was dissolved in EtOAc (50 mL) and washed with water (30 mL) and brine (30 mL). The organic layer was dried over sodium sulfate, filtered, and concentrated. The residue was purified by flash chromatography on a silica gel column using EtOAc/heptanes (0-25%) to afford 1,6-dimethyl-3-prop-1-en-2-ylthieno[3,2-c]pyrazole (333 mg, 1.73 mmol, 54% yield) as a light yellow solid. HPLC t$_R$=6.26 min, C18-column (4.6× 100 mm, 5 μm), Aq (0.1% TFA)/MeCN @ 1.0 mL/min; Gradient 5-95% B in 4 min). $^1$H NMR (300 MHz, CDCl$_3$) δ 6.95 (s, 1H), 5.35 (s, 1H), 5.23 (s, 1H), 4.09 (s, 3H), 2.44 (s, 3H), 2.23 (s, 3H). LCMS calc. for $C_{10}H_{13}N_2S$ [M+H]$^+$: m/z=193.1; Found: 193.2. The same purification also afforded 2,6-dimethyl-3-(prop-1-en-2-yl)-2H-thieno[3,2-c]pyrazole (180 mg, 0.94 mmol, 29% yield, Example 55, Step 6) as a yellow oil. HPLC t$_R$=5.94 min, C18-column (4.6×100 mm, 5 μm), Aq (0.1% TFA)/MeCN @ 1.0 mL/min, Gradient 5-95% B in 4 min).

Step 2. 1,6-Dimethyl-3-propan-2-ylthieno[3,2-c]pyrazole

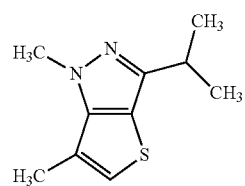

The title compound is synthesized by procedures analogous to those outlined in Example 100, Step 3. LCMS calc. for $C_{10}H_{15}N_2S$ [M+H]$^+$: m/z=195.1; Found: 195.2.

Step 3. 4-(1,6-Dimethyl-3-propan-2-ylthieno[3,2-c]pyrazol-5-yl)-N-[5-(4-ethylpiperazin-1-yl)pyridin-2-yl]-5-fluoropyrimidin-2-amine The title compound is synthesized by procedures analogous to those outlined in Example 1, Steps 6-8. $^1$H NMR (300 MHz, methanol-d$_4$) δ 8.74 (d, J=2.7 Hz, 1H), 8.15 (dd, J=9.6, 2.9 Hz, 1H), 7.93 (d, J=2.8 Hz, 1H), 7.69 (d, J=9.5 Hz, 1H), 4.14 (s, 3H), 4.01-3.44 (m, 6H), 3.18-3.06 (m, 5H), 2.69 (d, J=3.2 Hz, 3H), 1.47-1.35 (m, 9H). LCMS calc. for $C_{25}H_{32}FN_8S$ [M+H]$^+$: 495.2; Found: 495.2.

Example 107. N-(5-Fluoro-4-(3-isopropyl-2-methyl-3H-thieno[2,3-d]imidazol-5-yl)pyrimidin-2-yl)pyridazin-3-amine

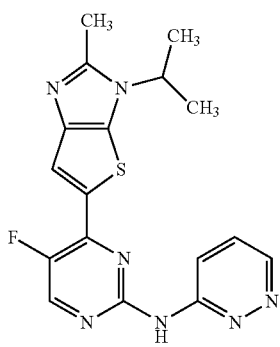 [SMILES: Cc1nc2cc(-c3nc(Nc4cccnn4)ncc3F)sc2n1C(C)C]

The title compound is synthesized by procedures analogous to those outlined in Example 52, Steps 1-8. ¹H NMR (300 MHz, methanol-$d_4$) δ 8.87 (d, J=4.3 Hz, 1H), 8.65 (d, J=3.1 Hz, 1H), 8.45 (d, J=9.0 Hz, 1H), 8.03 (s, 1H), 7.92 (dd, J=9.2, 4.6 Hz, 1H), 4.98-4.93 (m, 1H), 2.78 (s, 3H), 1.67 (d, J=6.7 Hz, 6H). LCMS calc. for $C_{17}H_{17}FN_7S$ [M+H]⁺: m/z=370.1; Found: 369.8.

Example 108. 5-Fluoro-4-(3-isopropyl-2,6-dimethyl-3H-thieno[2,3-d]imidazol-5-yl)-N-(5-(1-methylazetidin-3-yl)pyridin-2-yl)pyrimidin-2-amine

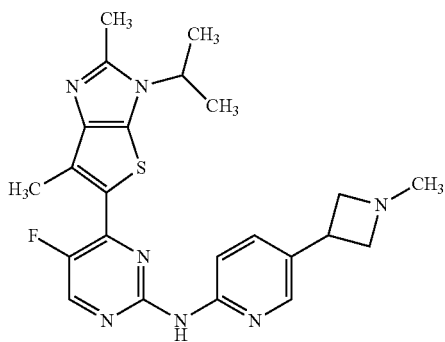 [SMILES: Cc1c(-c2nc(Nc3ccc(C4CN(C)C4)cn3)ncc2F)sc2c1nc(C)n2C(C)C]

Step 1. tert-Butyl 3-(6-chloropyridin-3-yl)azetidine-1-carboxylate

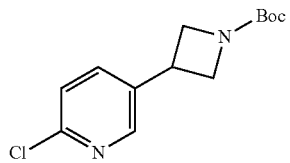 [SMILES: CC(C)(C)OC(=O)N1CC(c2ccc(Cl)nc2)C1]

1,2-Dibromoethane (12.2 µL, 0.141 mmol) was added to a suspension of zinc powder (127 mg, 1.94 mmol) in DMF (2.20 mL), and the resulting mixture was heated at 70° C. for 10 min. Upon cooling to room temperature, chlorotrimethylsilane (18.0 µL, 0.141 mmol) was added. The reaction was stirred for 30 min, and then a solution of tert-butyl 3-iodoazetidine-1-carboxylate (500 mg, 1.77 mmol) in DMF (2.20 mL) was added dropwise. The reaction was heated a 40° C. for 1 h and then 2-chloro-5-iodopyridine (423 mg, 1.77 mmol), tris(dibenzylideneacetone)dipalladium(0) (12.0 mg, 35.3 µmol), and tri(2-furyl)phosphine (16.4 mg, 70.6 µmol) were added. The reaction mixture was heated at 70° C. for 18 h. The reaction mixture was cooled to room temperature and diluted with sat. NH₄Cl (aq.) (10.0 mL) and EtOAc (15.0 mL). The two layers were separated, and the aqueous layer was extracted with EtOAc (15.0 mL×3). The combined organic layers were washed with brine, dried over magnesium sulfate, filtered, and concentrated. The residue was purified by silica gel chromotography using EtOAc/hexanes (0-100%) to afford the title compound (80.0 mg, 0.298 mmol, 16.9% yield) as an orange oil. LCMS calc. for $C_{13}H_{18}ClN_2O_2$[M+H]⁺: m/z=269.1; Found: 269.0.

Step 2. 5-Fluoro-4-(3-isopropyl-2,6-dimethyl-3H-thieno[2,3-d]imidazol-5-yl)-N-(5-(1-methylazetidin-3-yl)pyridin-2-yl)pyrimidin-2-amine The title compound is synthesized by procedures analogous to those outlined in Example 53, Steps 3-5. LCMS calc. for $C_{23}H_{27}FN_7S$ [M+H]⁺: m/z=452.2; Found: 452.1.

Example 109. tert-Butyl 3-(2-(2-((5-(6-ethyl-2,6-diazaspiro[3.3]heptan-2-yl)pyridin-2-yl)amino)-5-fluoropyrimidin-4-yl)-5-methyl-4-oxo-4,5-dihydrothieno[2,3-d]pyridazin-7-yl)azetidine-1-carboxylate

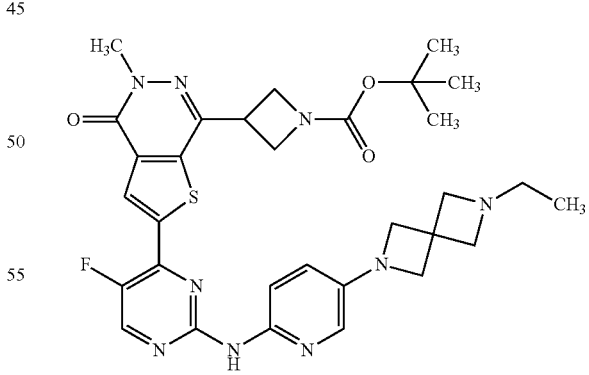

The title compound is synthesized by procedures analogous to those outlined in Example 63. Purification via by prep-HPLC on a C18 column (25.9-53.3%, MeCN/0.1% TFA (aq.)) afforded the title compound as the TFA salt, a white solid. LCMS calc. for $C_{31}H_{37}FN_9O_3S$ [M+H]⁺: m/z=634.3; Found: 634.0.

Example 110. 2-(5-Fluoro-2-((5-(1-methylpiperidin-4-yl)pyridin-2-yl)amino)pyrimidin-4-yl)-7-(3-fluorobicyclo[1.1.1]pentan-1-yl)-5-methylthieno[2,3-d]pyridazin-4(5H)-one

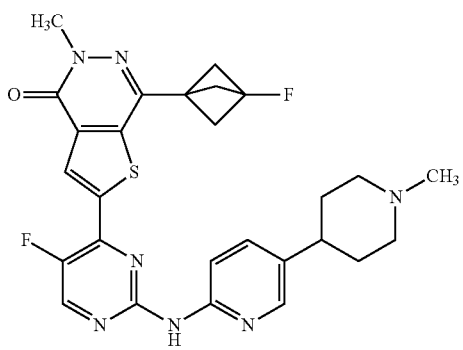 [SMILES: CN1CCC(c2ccc(Nc3ncc(F)c(-c4cc5c(=O)n(C)nc(C67CC(F)(C6)C7)c5s4)n3)nc2)CC1]

The title compound is synthesized by procedures analogous to those outlined in Example 63. Purification via by prep-HPLC on a C18 column (17.2-37.2%, MeCN/0.1% TFA (aq.)) afforded the title compound as the TFA salt, a white solid. LCMS calc. for $C_{27}H_{28}F_2N_7OS$ $[M+H]^+$: m/z=536.2; Found: 536.0.

Example 111. 5-(2-((5-(6-Ethyl-2,6-diazaspiro[3.3]heptan-2-yl)pyridin-2-yl)amino)-5-fluoropyrimidin-4-yl)-3-isopropyl-N,N,6-trimethyl-3H-thieno[2,3-d]imidazol-2-amine

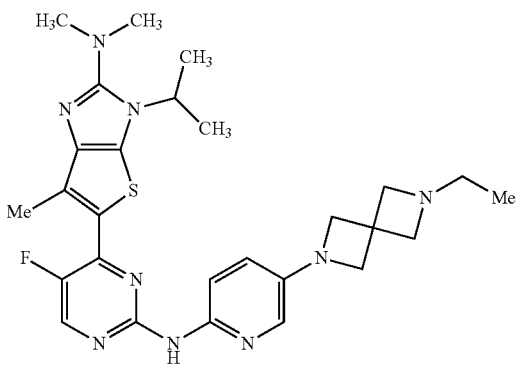 [SMILES: CCN1CC2(C1)CN(c1ccc(Nc3ncc(F)c(-c4sc5c(nc(N(C)C)n5C(C)C)c4C)n3)nc1)C2]

Step 1. 3-Isopropyl-6-methyl-1,3-dihydro-2H-thieno[2,3-d]imidazol-2-one

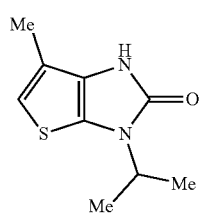

Diphenyl phosphoryl azide (1.78 g, 6.45 mmol) was added dropwise to a mixture of 4-methyl-2-(propan-2-ylamino)thiophene-3-carboxylic acid (1.03 g, 5.16 mmol, Example 52 Step 2) and triethylamine (1.80 mL, 13.0 mmol) in toluene (15.0 mL) at room temperature. The reaction mixture was stirred for 1 h. The reaction mixture washed with sat. NaHCO₃ (aq.) (15.0 mL) and water (15.0 mL), dried over MgSO₄, and filtered. The filtrate was heated at 100° C. for 18 h. The reaction mixture was cooled to room temperature and partitioned between sat. NaHCO₃ (aq.) (30.0 mL) and EtOAc (30.0 mL). The organic layer was separated, and the aqueous layer was extracted with EtOAc (15.0 mL×3). The combined organic layers were washed with sat. NaHCO₃ (aq.) (15.0 mL), water (15.0 mL), and brine (15.0 mL). The organic layer was then dried over MgSO₄, filtered, and concentrated under reduced pressure. The residue was purified by silica gel chromatography (0-50% EtOAc/heptanes) to give the title compound (600 mg, 3.10 mmol, 59.0% yield) as brown solid. LCMS calc. for $C_9H_{13}N_2OS$ $[M+H]^+$: m/z=197.1; Found: 197.1.

Step 2. 2-Chloro-3-isopropyl-6-methyl-3H-thieno[2,3-d]imidazole

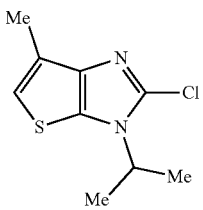 [SMILES: Cc1csc2c1nc(Cl)n2C(C)C]

A mixture of 3-isopropyl-6-methyl-1,3-dihydro-2H-thieno[2,3-d]imidazol-2-one (1.24 g, 6.30 mmol) and phosphorous oxychloride (5.80 g, 37.8 mmol) was stirred at 100° C. for 24 h. The reaction mixture was cooled to room temperature and poured into ice-cold sat. NaHCO₃ (aq.) with vigorous stirring. The mixture was extracted with EtOAc (20.0 mL×3), and the combined organic extracts were washed with brine (20.0 mL), dried over Na₂SO₄, filtered, and concentrated under reduced pressure. The crude residue was purified by silica gel chromatography (0-50% EtOAc/heptanes) to give the title compound (707 mg, 3.29 mmol, 52.2% yield) as colorless oil. LCMS calc. for $C_9H_{12}ClN_2S$ $[M+H]^+$: m/z=215.0; Found: 215.0.

Step 3. 3-Isopropyl-N,N,6-trimethyl-3H-thieno[2,3-d]imidazol-2-amine

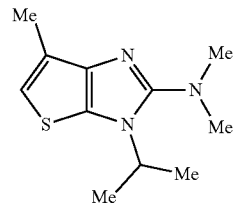 [SMILES: Cc1csc2c1nc(N(C)C)n2C(C)C]

A mixture of 2-chloro-3-isopropyl-6-methyl-3H-thieno[2,3-d]imidazole (521 mg, 2.43 mmol) and dimethylamine (5.00 mL, 40% in water) was heated at 140° C. in a sealed tube for 2 d. Upon cooling to room temperature, the reaction mixture was concentrated. The residue was purified via silica gel chromatography (0-50% EtOAc/heptanes) to afford the title compound (74.0 mg, 0.330 mmol, 14.0% yield) as colorless oil. LCMS calc. for $C_{11}H_{18}N_3S$ [M+H]$^+$: m/z=224.1; Found: 224.1.

Step 4. 5-(2-((5-(6-Ethyl-2,6-diazaspiro[3.3]heptan-2-yl)pyridin-2-yl)amino)-5-fluoropyrimidin-4-yl)-3-isopropyl-N,N,6-trimethyl-3H-thieno[2,3-d]imidazol-2-amine The title compound is synthesized by procedures analogous to those outlined in Example 1, Steps 6-8. Purification via by prep-HPLC on a C18 column (6-80%, MeCN/0.1% TFA (aq.)) afforded the title compound as the TFA salt, a yellow solid. $^1$H NMR (300 MHz, $CD_3OD$) δ 8.66 (d, J=3.4 Hz, 1H), 7.67 (dd, J=9.5, 2.8 Hz, 1H), 7.53-7.46 (m, 2H), 5.03-4.97 (m, 1H), 4.56-4.14 (m, 8H), 3.28-3.23 (m, 2H), 3.18 (s, 6H), 2.73 (d, J=2.8 Hz, 3H), 1.62 (d, J=6.7 Hz, 6H), 1.22 (t, J=7.2 Hz, 3H). LCMS calc. for $C_{27}H_{35}FN_9S$ [M+H]$^+$: m/z=536.3; Found: 536.0.

Example 112. N-(5-(2-Ethyl-2-azaspiro[3.3]heptan-6-yl)pyridin-2-yl)-5-fluoro-4-(3-isopropyl-2-methyl-3H-thieno[2,3-d]imidazol-5-yl)pyrimidin-2-amine

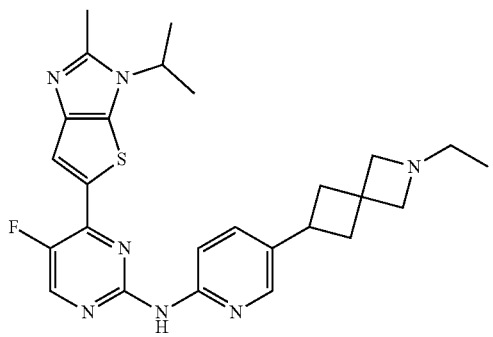 [SMILES: CCN1CC2(CC(c3ccc(Nc4ncc(F)c(-c5cc6nc(C)n(C(C)C)c6s5)n4)nc3)C2)C1]

Step 1. tert-Butyl 6-iodo-2-azaspiro[3.3]heptane-2-carboxylate

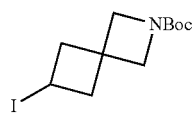

A vial was charged with tert-butyl 6-hydroxy-2-azaspiro[3.3]heptane-2-carboxylate (2.55 g, 12.0 mmol), imidazole (2.44 g, 35.9 mmol), triphenylphosphine (6.27 g, 23.9 mmol), and iodine (4.55 g, 17.9 mmol), toluene (40 mL) was added. The mixture was refluxed for 1 h. The mixture was cooled to room temperature, washed with $H_2O$ (40 mL), dried over $Na_2SO_4$, filtered, and concentrated to give a colorless solid. The crude residue was purified by silica gel chromatography (0-20% EtOAc/heptanes) to afford the title compound (3.55 g, 10.9 mmol, 91.8% yield) as a colorless solid. $R_f$=0.7 (20% EtOAc/hexane).

Step 2. tert-Butyl 6-(6-aminopyridin-3-yl)-2-azaspiro[3.3]heptane-2-carboxylate

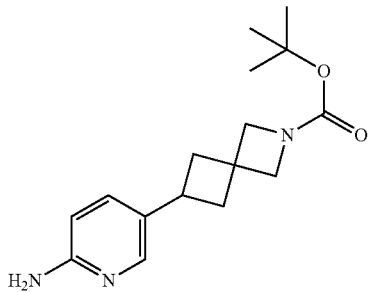 [SMILES: CC(C)(C)OC(=O)N1CC2(CC(c3ccc(N)nc3)C2)C1]

A vial was charged with 5-(4,4,5,5-tetramethyl-1,3,2-dioxaborolan-2-yl)pyridin-2-amine (82.1 mg, 0.373 mmol), tert-butyl 6-iodo-2-azaspiro[3.3]heptane-2-carboxylate (120.5 mg, 0.3729 mmol), [1,1'-bis(diphenylphosphino)ferrocene]dichloropalladium(II) (27.3 mg, 0.0373 mmol) and $K_3PO_4$ (237.4 mg, 1.119 mmol), 1,4-dioxane (3 mL), and water (1 mL) were added. The mixture was heated at 100° C. overnight. The mixture was concentrated and partitioned in DCM (10 mL) and water (10 mL). The biphasic mixture was then filtered via a syringe filter. The organic layer was separated, and the aqueous phase was extracted with DCM (10 mL×3). The combined organic phase was dried over $Na_2SO_4$, filtered, concentrated, and purified by silica gel chromatography (0-10% MeOH/DCM) to afford the title compound (40.1 mg, 0.138 mmol, 37.0% yield). LCMS calc. for $C_{16}H_{24}N_3O_2$ [M+H]$^+$: m/z=290.2; Found: 290.0.

Step 3. N-(5-(2-Azaspiro[3.3]heptan-6-yl)pyridin-2-yl)-5-fluoro-4-(3-isopropyl-2-methyl-3H-thieno[2,3-d]imidazol-5-yl)pyrimidin-2-amine

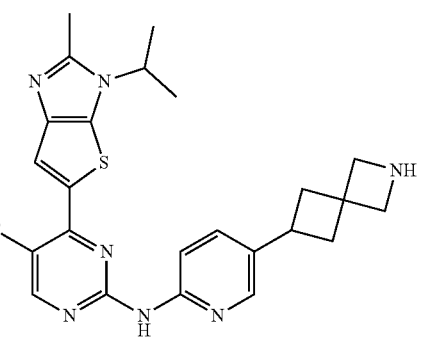

The title compound was synthesized according to procedures analogous to Example 1, Step 8 to afford the title compound as a TFA salt. LCMS calc. for $C_{24}H_{27}FN_7S$ [M+H]$^+$: m/z=464.2; Found: 464.0.

Step 4. N-[5-(2-Ethyl-2-azaspiro[3.3]heptan-6-yl)pyridin-2-yl]-5-fluoro-4-(2-methyl-3-propan-2-ylthieno[2,3-d]imidazol-5-yl)pyrimidin-2-amine To a suspension of N-[5-(2-azaspiro[3.3]heptan-6-yl)pyridin-2-yl]-5-fluoro-4-(2-methyl-3-propan-2-ylthieno[2, 3-d]imidazol-5-yl)pyrimidin-2-amine, TFA salt (41.6 mg, 0.0720 mmol) in methanol (5 mL) was added acetaldehyde (56.9 µL, 0.449 mmol, 40 wt. % in H$_2$O), acetic acid (18 µL, 0.31 mmol) and NaBH$_3$CN (56.4 mg, 0.0897 mmol). The suspension was stirred at room temperature for 30 min. To the mixture was added MeCN (2 mL) and H$_2$O (1 mL). The mixture was filtered and purified by prep-HPLC on a C18 column (2-40% MeCN/0.1% TFA (aq.)) to afford the title compound as a TFA salt (24.3 mg, 0.0401 mmol, 55.7% yield), a yellow solid. $^1$H NMR (300 MHz, methanol-d4) δ 8.74 (d, J=3.2 Hz, 1H), 8.29 (dd, J=9.1, 2.1 Hz, 1H), 8.22-8.11 (m, 2H), 7.59 (d, J=9.1 Hz, 1H), 5.03-4.94 (m, 1H), 4.46 (dd, J=10.8, 2.6 Hz, 1H), 4.29-4.14 (m, 2H), 4.03 (d, J=10.9 Hz, 1H), 3.68-3.56 (m, 1H), 3.23 (q, J=7.2 Hz, 2H), 2.92-2.78 (m, 4H), 2.76-2.65 (m, 1H), 2.61-2.40 (m, 2H), 1.68 (d, J=6.7 Hz, 6H), 1.21 (t, J=7.2 Hz, 3H). LCMS calc. for C$_{26}$H$_{31}$FN$_7$S [M+H]$^+$: m/z=492.2; Found 492.0.

Example 113. 4-(2,6-Dimethyl-3-propan-2-ylthieno[2,3-d]imidazol-5-yl)-N-[6-(4-ethylpiperazin-1-yl)pyridin-2-yl]-5-fluoropyrimidin-2-amine

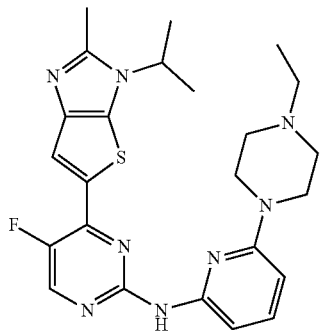 [SMILES: CCN1CCN(c2cccc(Nc3ncc(F)c(-c4cc5nc(C)n(C(C)C)c5s4)n3)n2)CC1]

Step 1. tert-Butyl N-[6-(4-ethylpiperazin-1-yl)pyridin-2-yl]carbamate

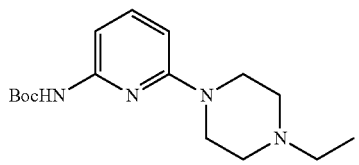 [SMILES: CCN1CCN(c2cccc(NC(=O)OC(C)(C)C)n2)CC1]

tert-Butyl N-(6-bromopyridin-2-yl)carbamate (600.0 mg, 2.197 mmol) was stirred in 1-ethylpiperazine (5.8 mL, 44 mmol) at 90° C. overnight. The reaction mixture was diluted with DCM and poured into saturated NaHCO$_3$ (aq.) (10 mL). After extraction with DCM (10 mL×3), the combined organic layers were dried over Na$_2$SO$_4$, filtered, and concentrated. The residue was purified by silica gel chromatography (10%-80% EtOAc/heptanes) to afford the title compound (588 mg, 1.92 mmol, 87.4% yield). LCMS calc. for C$_{16}$H$_{27}$N$_4$O$_2$ [M+H]$^+$: 307.2; Found: 307.1

Step 2. 6-(4-Ethylpiperazin-1-yl)pyridin-2-amine

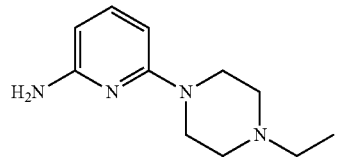

A solution of tert-butyl N-[6-(4-ethylpiperazin-1-yl)pyridin-2-yl]carbamate (588.0 mg, 1.919 mmol) in DCM (6 mL) was added TFA (26.1 mmol, 2 mL) at 0° C. The reaction was slowly warmed to room temperature and stirred for 6 h. The solvent was removed under vacuum. The residue was redissolved in 10:1 DCM/MeOH (20 mL). NaHCO$_3$ (100 mg) was added, and the mixture was stirred for 15 min and then filtered. The filtrate was concentrated and purified by silica gel chromatography (0-10% MeOH/DCM) to afford the title compound (362 mg, 1.75 mmol, 91.4% yield). LCMS calc. for C$_{11}$H$_{19}$N$_4$[M+H]$^+$: m/z=207.2; Found 207.1.

Step 3. 4-(2,6-Dimethyl-3-propan-2-ylthieno[2,3-d]imidazol-5-yl)-N-[6-(4-ethylpiperazin-1-yl)pyridin-2-yl]-5-fluoropyrimidin-2-amine The title compound was synthesized according to procedures analogous to Example 1, Step 8 to afford the title compound as a TFA salt, a light yellow solid. $^1$H NMR (300 MHz, CD$_3$OD) δ 8.60 (d, J=2.9 Hz, 1H), 7.76-7.60 (m, 2H), 6.64-6.52 (m, 1H), 4.97-4.80 (m, 1H), 3.81-3.45 (m, 2H), 3.29-3.13 (m, 8H), 2.85 (s, 3H), 2.62 (d, J=3.8 Hz, 3H), 1.68 (d, J=6.7 Hz, 6H), 1.40 (t, J=7.3 Hz, 3H). LCMS calc. for C$_{25}$H$_{31}$FN$_8$S [M+H]$^+$: m/z=495.2; Found 495.1.

Example 114. 5-Fluoro-4-(2-methyl-3-propan-2-ylthieno[2,3-d]imidazol-5-yl)-N-[5-(1-methylpyrrolidin-3-yl)oxypyridin-2-yl]pyrimidin-2-amine

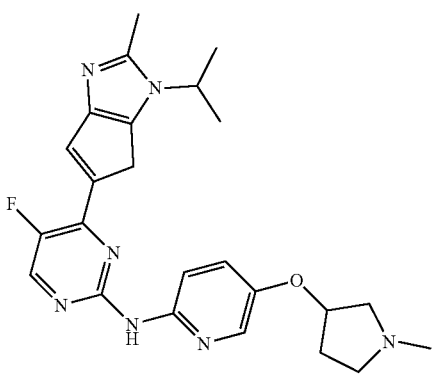 [SMILES: Cc1nc2c(n1C(C)C)CC(c1nc(Nc3ccc(OC4CCN(C)C4)cn3)ncc1F)=C2]

Step 1. 5-(1-Methylpyrrolidin-3-yl)oxy-2-nitropyridine

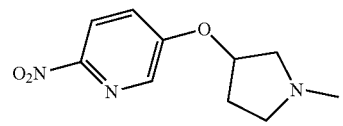 [SMILES: CN1CCC(Oc2ccc([N+](=O)[O-])nc2)C1]

To a solution of 1-methylpyrrolidin-3-ol (391.5 mg, 3.870 mmol) in N,N-dimethylacetamide (10 mL) at 0° C. was added potassium tert-butoxide (4.2 mL, 4.2 mmol, 1.0 M in THF) portion-wise and then 5-fluoro-2-nitropyridine (500.0 mg, 3.519 mmol) portion-wise. The resulting dark solution was stirred at 0° C. for 30 min and allowed to warm to room temperature, stirring for 18 h. The reaction mixture was quenched with water (20 mL) and extracted with EtOAc (10 mL×3). The combined organic layers were washed with water (10 mL) and brine (10 mL), dried over $Na_2SO_4$, filtered, and concentrated. The residue was purified by silica gel chromatography (0-75% MeOH/MTBE) to afford the title compound (693 mg, 3.10 mmol, 88.3% yield) as a yellow solid. $R_f$=0.3 (30% MeOH/MTBE).

Step 2.
5-(1-Methylpyrrolidin-3-yl)oxypyridin-2-amine

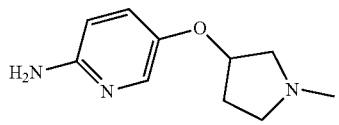

To a stirred solution of 5-(1-methylpyrrolidin-3-yl)oxy-2-nitropyridine (580.0 mg, 2.598 mmol) in methanol (30 mL) was added palladium on carbon (27.7 mg, 0.260 mmol, 10 wt %), and the reaction vessel was charged with $H_2$. The reaction mixture was stirred at room temperature for 2 h. The reaction mixture was filtered through Celite, and the filtrate was concentrated. The residue was purified by silica gel chromatography (5-30% MeOH/DCM) to afford the title compound (390 mg, 2.02 mmol, 77.7% yield). LCMS calc. for $C_{10}H_{16}N_3O$ $[M+H]^+$: m/z=194.1; Found 194.0.

Step 3. 5-Fluoro-4-(2-methyl-3-propan-2-ylthieno[2,3-d]imidazol-5-yl)-N-[5-(1-methylpyrrolidin-3-yl)oxypyridin-2-yl]pyrimidin-2-amine

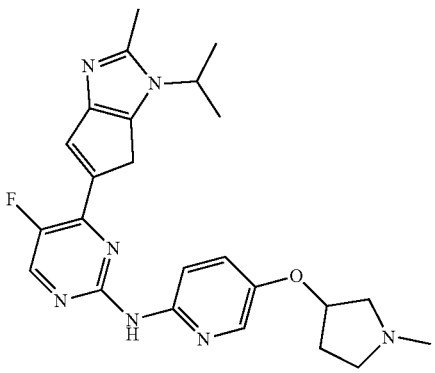 [SMILES: Cc1nc2c(n1C(C)C)CC(c1nc(Nc3ccc(OC4CCN(C)C4)cn3)ncc1F)=C2]

The title compound was synthesized according to procedures analogous to Example 1, Step 8 to afford the title compound as a TFA salt. $^1$H NMR (300 MHz, methanol-$d_4$) δ 8.67 (dd, J=3.3, 1.9 Hz, 1H), 8.10 (d, J=1.2 Hz, 1H), 8.07 (d, J=2.8 Hz, 1H), 7.97-7.88 (m, 1H), 7.83 (d, J=9.5 Hz, 1H), 5.32 (s, 1H), 5.00-4.95 (m, 1H), 4.08-3.49 (m, 4H), 3.06 (s, 3H), 2.84 (d, J=1.8 Hz, 3H), 2.36 (t, J=7.3 Hz, 2H), 1.69 (d, J=6.7 Hz, 6H). LCMS calc. for $C_{23}H_{27}FN_7OS$ $[M+H]^+$: m/z=468.2; Found 467.9.

Example 115. 5-Fluoro-4-(3-isopropyl-2,6-dimethyl-3H-thieno[2,3-d]imidazol-5-yl)-N-(5-(4-methylmorpholin-2-yl)pyridin-2-yl)pyrimidin-2-amine

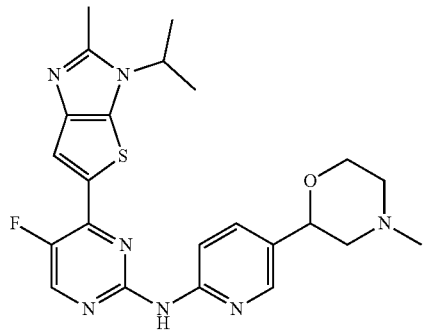 [SMILES: Cc1nc2cc(-c3nc(Nc4ccc(C5CN(C)CCO5)cn4)ncc3F)sc2n1C(C)C]

Step 1. 5-(1-Ethoxyethenyl)-2-nitropyridine

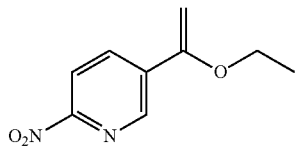

To a solution of tributyl(1-ethoxyvinyl)tin (2.08 mL, 6.17 mmol) and 5-bromo-2-nitropyridine (1.14 g, 5.61 mmol) in toluene (30 mL) was added tetrakis(triphenylphosphine)palladium(0) (454 mg, 0.392 mmol). The mixture was heated at 100° C. for 6 h. KF was added (2 g, 30 mmol), and the mixture was stirred at room temperature for 1 h. $H_2O$ (30 mL) and EtOAc (50 mL) were added. The mixture was passed through a Celite pad. The organic layer was separated, and the aqueous phase was extracted with EtOAc (30 mL×3). The combined organic layers were dried over $Na_2SO_4$, filtered, and concentrated. The residue was purified by silica gel chromatography (0%-10%, EtOAc/hexanes) to give the title compound (1.08 g, 5.56 mmol, 99.2% yield) as a yellow oil. LCMS calc. for $C_9H_{11}N_2O_3$ $[M+H]^+$: m/z=195.1; Found: 195.0.

Step 2. 2-Bromo-1-(6-nitropyridin-3-yl)ethanone

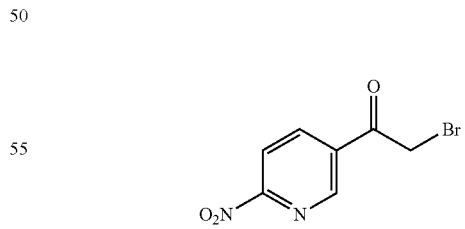

To a solution of 5-(1-ethoxyethenyl)-2-nitropyridine (1.08 g, 5.56 mmol) in THF (15 mL) and water (6 mL) was added N-bromosuccinimide (0.99 g, 5.6 mmol). The mixture was stirred for 2 h at room temperature. To the mixture was added hexanes (10 mL) and EtOAc (10 mL). The organic layer was separated, and the aqueous layer was extracted with EtOAc (10 mL×3). The combined organic layers were dried over $Na_2SO_4$, filtered, and concentrated. The residue was triturated with MTBE to give the title compound (1.11 g, 4.53 mmol, 81.4% yield) as a beige solid. LCMS calc. for $C_7H_4BrN_2O_3$ [M−H]⁻: m/z=242.9; Found: 242.8.

Step 3. 2-Nitro-5-(oxiran-2-yl)pyridine

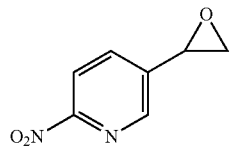 [SMILES: O=[N+]([O-])c1ccc(C2CO2)cn1]

To a solution of 2-bromo-1-(6-nitropyridin-3-yl)ethanone (55.0 mg, 0.224 mmol) in methanol (5 mL) was added sodium borohydride (8.5 mg, 0.22 mmol). The mixture was stirred for 2 h at room temperature. The mixture was diluted with water and purified by prep-HPLC on a C18 column (5%-60% MeCN/0.1% TFA(aq.)) to give the title compound (5.0 mg, 0.030 mmol, 13% yield) as a beige solid. ¹H NMR (300 MHz, DMSO-d₆) δ 8.64 (d, J=2.3 Hz, 1H), 8.36-8.25 (m, 1H), 8.09 (dd, J=8.4, 2.2 Hz, 1H), 4.23 (dd, J=4.3, 2.5 Hz, 1H), 3.28 (dd, J=5.3, 4.2 Hz, 1H), 3.04 (dd, J=5.3, 2.6 Hz, 1H).

Step 4. 2-((2-Hydroxyethyl)(methyl)amino)-1-(6-nitropyridin-3-yl)ethan-1-ol

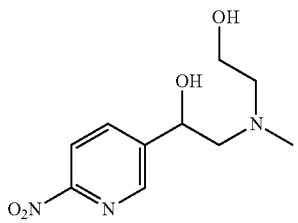

To a solution of 2-nitro-5-(oxiran-2-yl)pyridine (61.3 mg, 0.369 mmol) in DMF (1 mL) was added 2-(methylamino)ethanol (122.6 μL, 1.526 mmol). The mixture was heated at 80° C. for 6 h. The mixture was purified by prep-HPLC on a C18 column (0%-20% MeCN/0.1% TFA(aq.)) to give the title compound as a TFA salt (52.0 mg, 0.146 mmol, 39.7% yield), a colorless oil. LCMS calc. for $C_{10}H_{16}N_3O_4$ [M+H]⁺: m/z=242.1; Found: 241.9.

Step 5. 1-(6-Aminopyridin-3-yl)-2-[2-hydroxyethyl(methyl)amino]ethanol

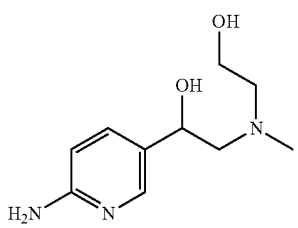

To a solution of 2-[2-hydroxyethyl(methyl)amino]-1-(6-nitropyridin-3-yl)ethanol, TFA salt (47.0 mg, 0.132 mmol, from Step 4) in methanol (4 mL) was added palladium on carbon (10 mg, 10 wt %). The mixture was stirred under an atmosphere of H₂ overnight. The mixture was filtered through a syringe filter and concentrated to afford the title compound, which was used without any further purification. LCMS calc. for $C_{10}H_{18}N_3O_2$ [M+H]⁺: m/z=212.1; Found: 212.0.

Step 6. 5-(4-Methylmorpholin-2-yl)pyridin-2-amine

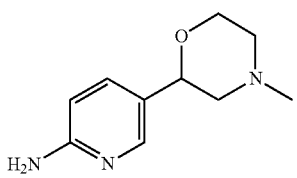

A mixture of 1-(6-aminopyridin-3-yl)-2-[2-hydroxyethyl(methyl)amino]ethanol (from Step 5) and conc. H₂SO₄ (1.0 mL, 18.37 mmol) was stirred for 1 h at room temperature. The mixture was cooled to 0° C., and water (3 mL) and DCM (3 mL) were added sequentially. NH₄OH (10 mL) was then added slowly. The organic layer was separated, and the aqueous layer was extracted with DCM (10 mL×3). The combined organic layers were dried over Na₂SO₄, filtered, and concentrated to afford the title compound (15.1 mg, 0.0781 mmol, 59.2% yield over two steps) as a colorless oil. LCMS calc. for $C_{10}H_{16}N_3O$ [M+H]⁺: m/z=194.1; Found: 194.0.

Step 7. 5-Fluoro-4-(3-isopropyl-2,6-dimethyl-3H-thieno[2,3-d]imidazol-5-yl)-N-(5-(4-methylmorpholin-2-yl)pyridin-2-yl)pyrimidin-2-amine The title compound was synthesized according to procedures analogous to Example 1, Step 8 to afford the title compound as a TFA salt. ¹H NMR (300 MHz, CD₃OD) δ 8.75 (d, J=3.0 Hz, 1H), 8.41 (d, J=2.1 Hz, 1H), 8.21 (dd, J=9.1, 2.2 Hz, 1H), 7.88 (d, J=9.0 Hz, 1H), 5.02-4.90 (m, 2H), 4.34 (dd, J=13.3, 3.7 Hz, 1H), 4.05 (t, J=12.7 Hz, 1H), 3.78 (d, J=12.5 Hz, 1H), 3.64-3.51 (m, 1H), 3.23-3.14 (m, 2H), 3.01 (s, 3H), 2.85 (s, 3H), 2.72 (d, J=3.2 Hz, 3H), 1.68 (d, J=6.7 Hz, 6H). LCMS calc. for $C_{24}H_{29}FN_7OS$ [M+H]⁺: m/z=482.2; Found 481.8.

Example 116. N-[5-[1-(4-Ethylpiperazin-1-yl)ethyl]pyridin-2-yl]-5-fluoro-4-(2-methyl-3-propan-2-ylthieno[2,3-d]imidazol-5-yl)pyrimidin-2-amine

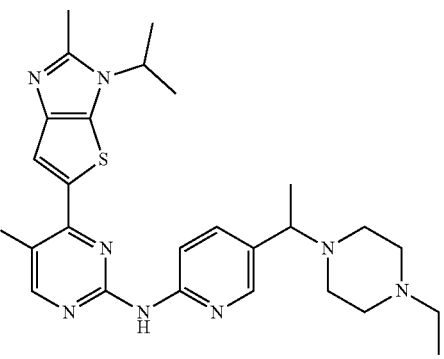

Step 1. 1-(6-Chloropyridin-3-yl)ethanol

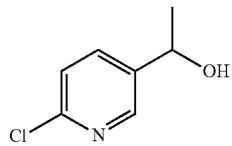

To methylmagnesium chloride (2.35 mL, 7.1 mmol, 3.0 M in THF) was added a solution of 2-chloro-5-formylpyridine (500.0 mg, 3.531 mmol) in THF (6 mL) dropwise at 0° C. The reaction mixture was stirred at 0° C. for 1 h. The reaction was quenched with sat. NH$_4$Cl (aq.) (5 mL) and extracted with EtOAc (5 mL×3). The combined organic layers were washed with brine (10 mL), dried over Na$_2$SO$_4$, filtered, and concentrated. The residue was purified by silica gel chromatography (0-40%, EtOAc/heptanes) to afford the title compound (495.1 mg, 3.141 mmol, 88.97% yield). LCMS calc. for C$_7$H$_9$ClNO [M+H]$^+$: m/z=158.0, 160.0; Found: 157.6, 159.8.

Step 2. 1-(6-Chloropyridin-3-yl)ethyl methanesulfonate

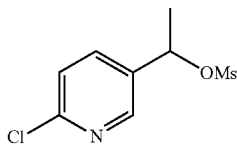

To a solution of 1-(6-chloropyridin-3-yl)ethanol (450.0 mg, 2.855 mmol) and triethylamine (1.19 mL, 8.57 mmol) in DCM (10 mL) was added methanesulfonyl chloride (0.33 mL, 4.9 mmol) dropwise at 0° C. The reaction mixture was then stirred at room temperature for 2 h. The reaction was diluted with DCM (10 mL), washed with water (10 mL) and brine (10 mL), dried over Na$_2$SO$_4$, filtered, and concentrated to afford the title compound (606.1 mg), which was used without further purification. LCMS calc. for C$_8$H$_{11}$ClNO$_3$S [M+H]+: m/z=236.0, 238.0; Found: 235.8, 237.8.

Step 3. tert-Butyl 4-[1-(6-chloropyridin-3-yl)ethyl]piperazine-1-carboxylate

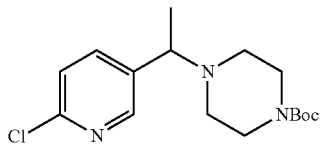 [SMILES: CC(c1ccc(Cl)nc1)N1CCN(C(=O)OC(C)(C)C)CC1]

To a solution of 1-(6-chloropyridin-3-yl)ethyl methanesulfonate (600.0 mg, from Step 2) and tert-butyl 1-piperazinecarboxylate (948.3 mg, 5.091 mmol) in DMF (6 mL) was added triethylamine (1.77 mL, 12.7 mmol). The reaction mixture was stirred at 50° C. for 1 h. The reaction was diluted with water (10 mL) and extracted with EtOAc (10 mL×3). The combined organic layers were washed with water (10 mL) and brine (10 mL), dried over Na$_2$SO$_4$, filtered, and concentrated. The residue was purified by silica gel chromatography (5-90%, EtOAc/heptanes) to afford the title compound (733.2 mg, 2.250 mmol). LCMS calc. for C$_{16}$H$_{25}$ClN$_3$O$_2$[M+H]$^+$: m/z=326.2, 328.2; Found: 326.0, 327.8.

Step 4. 1-[1-(6-Chloropyridin-3-yl)ethyl]piperazine

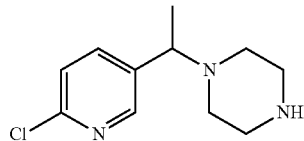

To a solution of tert-butyl 4-[1-(6-chloropyridin-3-yl)ethyl]piperazine-1-carboxylate (733.2 mg, 2.250 mmol) in DCM (1 mL) was added TFA (1.0 mL, 13 mmol). The reaction mixture was stirred at room temperature for 2 h. The mixture was concentrated to afford the title compound (505.3 mg), which was used without further purification. LCMS calc. for C$_{11}$H$_{17}$ClN$_3$ [M+H]$^+$: m/z=226.1, 228.1; Found: 225.9, 227.9.

Step 5. 1-[1-(6-Chloropyridin-3-yl)ethyl]-4-ethylpiperazine

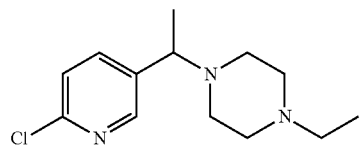 [SMILES: CCN1CCN(C(C)c2ccc(Cl)nc2)CC1]

To a solution of 1-[1-(6-chloropyridin-3-yl)ethyl]piperazine (490.0 mg, from Step 4) in methanol (10 mL) was added acetic acid (0.01 mL, 0.2 mmol) and acetaldehyde (1.38 mL, 10.9 mmol, 40 wt % in H$_2$O). The reaction mixture was stirred at room temperature for 10 min, and then sodium cyanoborohydride (409.3 mg, 6.513 mmol) was added. The resulting mixture was stirred at room temperature overnight. The solvent was removed under reduced pressure. The residue was dissolved in EtOAc (10 mL), washed with sat. NaHCO$_3$ (aq.) (10 mL) and brine, dried over Na$_2$SO$_4$, filtered, and concentrated. The residue was purified by silica gel chromatography (5-100%, EtOAc/heptanes) to afford the title compound (180.2 mg, 0.7100 mmol). LCMS calc. for C$_{13}$H$_{21}$ClN$_3$ [M+H]$^+$: m/z=254.1, 256.1; Found: 254.0, 255.9.

Step 6. 5-(2-Chloro-5-fluoropyrimidin-4-yl)-3-isopropyl-2-methyl-3H-thieno[2,3-d]imidazole

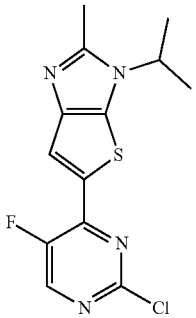 [SMILES: Cc1nc2cc(-c3nc(Cl)ncc3F)sc2n1C(C)C]

The title compound was synthesized to procedures analogous to Example 52, Steps 1-7. $^1$H NMR (300 MHz, CDCl$_3$) δ 8.55 (d, J=2.5 Hz, 1H), 8.11 (d, J=0.9 Hz, 1H), 4.75 (dq, J=13.3, 6.7 Hz, 1H), 2.90 (s, 3H), 1.71 (d, J=6.7 Hz, 6H). LCMS calc. for C$_{13}$H$_{13}$ClFN$_4$S [M+H]$^+$: m/z=311.1; Found: 311.1.

Step 7. N-[5-[1-(4-Ethylpiperazin-1-yl)ethyl]pyridin-2-yl]-5-fluoro-4-(2-methyl-3-propan-2-ylthieno[2,3-d]imidazol-5-yl)pyrimidin-2-amine The title compound was synthesized to procedures analogous to Example 53, Steps 1 and 5 to yield the title compound as a TFA salt. $^1$H NMR (300 MHz, CD$_3$OD) δ 8.75 (d, J=3.2 Hz, 1H), 8.37 (dd, J=9.1, 2.0 Hz, 1H), 8.33 (s, 1H), 8.14 (d, J=0.9 Hz, 1H), 7.67 (d, J=9.0 Hz, 1H), 4.99-4.92 (m, 1H), 3.85 (t, J=6.7 Hz, 1H), 3.70-3.34 (m, 3H), 3.29-3.00 (m, 7H), 2.82 (s, 3H), 1.69 (d, J=6.7 Hz, 6H), 1.48 (d, J=6.7 Hz, 3H), 1.35 (t, J=7.3 Hz, 3H). LCMS calc. for C$_{26}$H$_{34}$FN$_8$S [M+H]$^+$: m/z=509.3; Found: 509.3.

Example 117. 3-[6-[[5-Fluoro-4-(2-methyl-3-propan-2-ylthieno[2,3-d]imidazol-5-yl)pyrimidin-2-yl]amino]pyridin-3-yl]-1,4-dimethylpiperazin-2-one

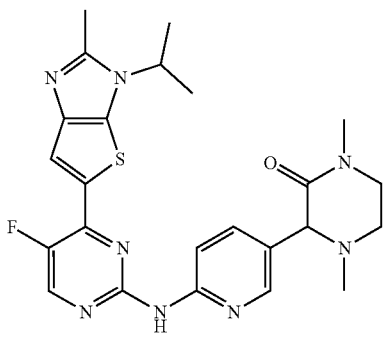 [SMILES: Cc1nc2cc(-c3nc(Nc4ccc(C5C(=O)N(C)CCN5C)cn4)ncc3F)sc2n1C(C)C]

Step 1. Methyl 2-bromo-2-(6-chloropyridin-3-yl)acetate

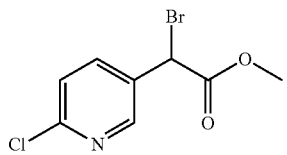

To a solution of methyl 2-(6-chloropyridin-3-yl)acetate (510.0 mg, 2.748 mmol) in acetonitrile (5 mL) was added N-bromosuccinimide (580.2 mg, 3.260 mmol) and 2,2'-azobisisobutyronitrile (45.1 mg, 0.275 mmol). The reaction mixture was stirred at room temperature for 5 h. The mixture was concentrated under reduced pressure and purified by silica gel chromatography (0-50%, EtOAc/heptanes) to afford the title compound (490.1 mg, 1.853 mmol, 67.43% yield). LCMS calc. for C$_8$H$_8$BrClNO$_2$ [M+H]$^+$: m/z=263.9, 265.9; Found: 264.0, 265.9.

Step 2. 3-(6-Chloropyridin-3-yl)-1,4-dimethylpiperazin-2-one

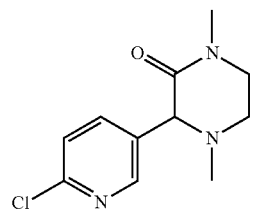 [SMILES: CN1CCN(C)C(c2ccc(Cl)nc2)C1=O]

To a solution of methyl 2-bromo-2-(6-chloropyridin-3-yl)acetate (490.1 mg, 1.853 mmol) in ethanol (10 mL) was added N,N'-dimethylethylenediamine (0.24 mL, 2.2 mmol). After stirring at room temperature overnight, the reaction mixture was concentrated. Purification via silica gel chromatography (5-100%, EtOAc/heptanes) afforded the title compound (250.5 mg, 1.045 mmol, 56.40% yield). LCMS calc. for C$_{11}$H$_{15}$ClN$_3$O [M+H]$^+$: m/z=240.0, 242.0; Found: 239.9, 242.0.

Step 3. 3-[6-[[5-Fluoro-4-(2-methyl-3-propan-2-ylthieno[2,3-d]imidazol-5-yl)pyrimidin-2-yl]amino]pyridin-3-yl]-1,4-dimethylpiperazin-2-one The title compound was synthesized to procedures analogous to Example 53, Step 5 to afford the title compound as a TFA salt. $^1$H NMR (300 MHz, CD$_3$OD) δ 8.76 (d, J=3.1 Hz, 1H), 8.42 (d, J=2.2 Hz, 1H), 8.29 (dd, J=9.1, 2.2 Hz, 1H), 8.14 (s, 1H), 7.72 (d, J=9.0 Hz, 1H), 5.07-4.97 (m, 1H), 4.36 (s, 1H), 3.91-3.79 (m, 1H), 3.47 (dt, J=12.4, 3.2 Hz, 1H), 3.40-3.33 (m, 1H), 3.09 (dd, J=11.6, 3.9 Hz, 1H), 3.04 (s, 3H), 2.88 (s, 3H), 2.47 (s, 3H), 1.71 (d, J=6.6 Hz, 6H). LCMS calc. for C$_{24}$H$_{28}$FN$_8$OS [M+H]$^+$: m/z=495.2; Found: 494.9.

Example 118. ((8aS)-6-(6-(((5-Fluoro-4-(3-isopropyl-2,6-dimethyl-3H-thieno[2,3-d]imidazol-5-yl)pyrimidin-2-yl)amino)pyridin-3-yl)-2-methylhexahydropyrrolo[1,2-a]pyrazin-3(4H)-one (single diastereomer)

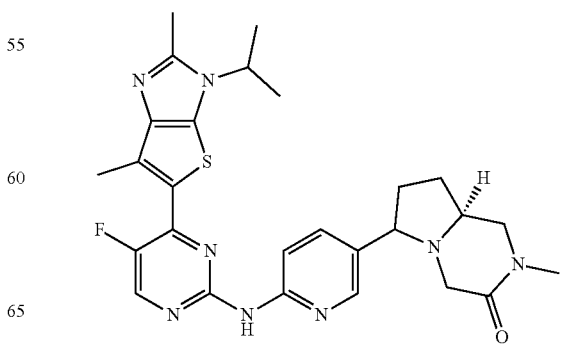

Step 1. Ethyl (2S)-5-(6-Chloropyridin-3-yl)-2-[(2-methylpropan-2-yl)oxycarbonylamino]-5-oxopentanoate

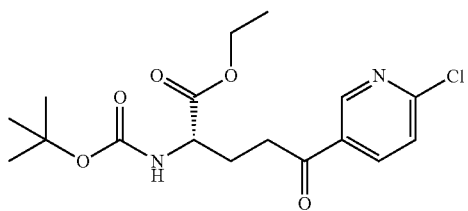 [SMILES: CCOC(=O)[C@H](CCC(=O)c1ccc(Cl)nc1)NC(=O)OC(C)(C)C]

To a solution of 2-chloro-5-iodopyridine (10 g, 42 mmol) in THF (50 mL) was added isopropyl magnesium chloride (19 mL, 38 mmol, 2.0 M in THF) dropwise at −60° C. The reaction mixture was warmed slowly to 0° C. over 30 min and then stirred for 1 h at 0° C. The reaction mixture was cooled to −20° C., and 1-O-tert-butyl 2-O-ethyl (2S)-5-oxopyrrolidine-1,2-dicarboxylate (8.6 g, 33 mmol) in THF (15 mL) was added. The reaction mixture was slowly warmed to room temperature over 30 min and stirred for 1 h. The reaction was quenched with 2 M HCl (20 mL) and stirred for 30 min. The organic layer was separated, and the aqueous layer was extracted with DCM (20 mL×3). The combined organic layers were dried over $Na_2SO_4$, filtered, and concentrated. The residue was purified by silica gel chromatography (5%-35%, EtOAc/heptanes) to afford the title compound (11 g, 29 mmol, 89% yield). $^1$H NMR (300 MHz, $CDCl_3$) δ 8.93 (d, J=2.28 Hz, 1H), 8.23-8.15 (m, 1H), 7.45 (d, J=8.35 Hz, 1H), 5.15 (bs, 1H), 4.43-4.30 (m, 1H), 4.28-4.18 (m, 2H), 3.20-2.97 (m, 2H), 2.44-2.31 (m, 1H), 2.14-2.00 (m, 1H), 1.42 (s, 9H), 1.33-1.27 (m, 3H). LCMS calc. for $C_{17}H_{24}ClN_2O_5[M+H]^+$: m/z=371.1; Found: 370.9.

Step 2. Ethyl (2S)-5-(6-chloropyridin-3-yl)-3,4-dihydro-2H-pyrrole-2-carboxylate

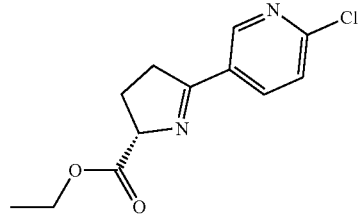 [SMILES: CCOC(=O)[C@@H]1CCC(c2ccc(Cl)nc2)=N1]

To a solution of ethyl (2S)-5-(6-chloropyridin-3-yl)-2-[(2-methylpropan-2-yl)oxycarbonylamino]-5-oxopentanoate (11 g, 29 mmol) in DCM (30 mL) was added TFA (9 mL). The reaction mixture was stirred at room temperature overnight. The reaction mixture was concentrated, dissolved in EtOAc (100 mL), and washed subsequently with sat. $K_2CO_3$ (aq.) (30 mL×2) and sat. $NH_4Cl$ (aq.) (30 mL). The organic layer was dried over $Na_2SO_4$, filtered, and concentrated to afford the title compound (7.2 g), which was used without further purification. LCMS for calc. for $C_{12}H_{14}ClN_2O_2[M+H]^+$: m/z=253.1; found 253.0.

Step 3. [(2S)-5-(6-Chloropyridin-3-yl)pyrrolidin-2-yl]methanol

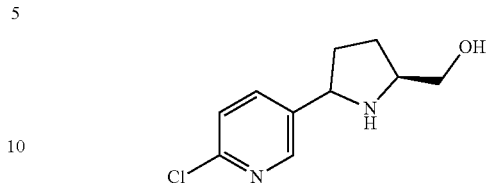

To a solution of ethyl (2S)-5-(6-chloropyridin-3-yl)-3,4-dihydro-2H-pyrrole-2-carboxylate (7.2 g, from Step 2) in ethanol (200 mL) was added sodium borohydride (5.29 g, 140 mmol) in three portions over 30 min. The reaction mixture was stirred overnight at room temperature. The reaction mixture was concentrated, redissolved in DCM (100 mL), and filtered through Celite. The mixture was washed with water (50 mL) and brine (50 mL), dried over $Na_2SO_4$, filtered, and concentrated. The residue was purified by chromatography (5%-30% EtOAc/heptanes with 10% MeOH) to afford the title compound (3.7 g, 18 mmol, 62% yield over two steps). $^1$H NMR (300 MHz, $CDCl_3$) δ 8.39 (dd, J=2.47, 0.57 Hz, 1H), 7.80-7.66 (m, 1H), 7.37-7.25 (m, 1H), 4.38-4.24 (m, 1H), 3.74-3.40 (m, 3H), 2.43 (bs, 2H), 2.38-2.16 (m, 1H), 2.12-1.93 (m, 1H), 1.85-1.57 (m, 2H). LCMS for calc. for $C_{10}H_{14}ClN_2O$ $[M+H]^+$: m/z=213.1; found 213.0.

Step 4. Ethyl 2-[(5S)-2-(6-Chloropyridin-3-yl)-5-(hydroxymethyl)pyrrolidin-1-yl]acetate (Single Diastereomer)

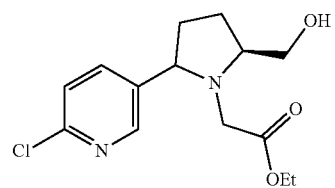 [SMILES: CCOC(=O)CN1C(c2ccc(Cl)nc2)CC[C@H]1CO]

To a solution of [(2S)-5-(6-chloropyridin-3-yl)pyrrolidin-2-yl]methanol (460.0 mg, 2.163 mmol) and ethyl 2-oxoacetate (0.43 mL, 4.3 mmol) in DCM (10 mL) was added sodium triacetoxyborohydride (900.0 mg, 4.247 mmol). The reaction mixture was stirred at room temperature overnight. The reaction was quenched with sat. $NaHCO_3$ (aq.) (10 mL). The organic layer was separated, and the aqueous layer was extracted with DCM (20 mL×3). The combined organic layers were washed with brine (20 mL), dried over $Na_2SO_4$, filtered, and concentrated. The residue was purified by chromatography (5%-20% EtOAc/heptanes with 10% MeOH) to afford the title compound (397.1 mg, 1.329 mmol, 61.44% yield), the major diastereomer. Major diastereomer: $R_f$=0.15 (1:2 EtOAc/heptane with 10% MeOH). Minor diastereomer: $R_f$=0.25 (1:2 EtOAc/heptane with 10% MeOH). LCMS calc. for $C_{14}H_{20}ClN_2O_3[M+H]^+$: m/z=299.1; found 299.2.

Step 5. Ethyl 2-((2S)-2-(azidomethyl)-5-(6-chloro-pyridin-3-yl)pyrrolidin-1-yl)acetate (Single Diastereomer)

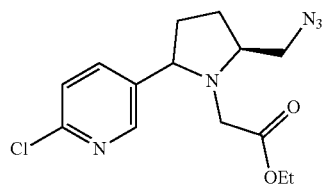 [SMILES: CCOC(=O)CN1C(c2ccc(Cl)nc2)CC[C@H]1CN=[N+]=[N-]]

To a solution of ethyl 2-[(5S)-2-(6-chloropyridin-3-yl)-5-(hydroxymethyl)pyrrolidin-1-yl]acetate (370.1 mg, 1.239 mmol, from Step 4) and triphenylphosphine (487.0 mg, 1.857 mmol) in THF (10 mL) at 0° C. was added diisopropyl azodicarboxylate (366 µL, 1.86 mmol). The reaction mixture was stirred at room temperature for 30 min, and then diphenyl phosphoryl azide (400 µL, 1.86 mmol]) was added dropwise. The reaction mixture was stirred overnight. The reaction was quenched with sat. NaHCO$_3$ (aq.) (20 mL). The organic layer was separated, and the aqueous layer was extracted with DCM (25 mL×3). The combined organic layers were washed with brine (25 mL), dried over Na$_2$SO$_4$, filtered, and concentrated. The residue was purified by silica gel chromatography (5-20%, EtOAc/heptanes) to afford the title compound (200.0 mg, 0.6177 mmol, 49.85% yield). LCMS calc. for C$_{14}$H$_{19}$ClN$_5$O$_2$[M+H]$^+$: m/z=324.1; found 323.9.

Step 6. (8aS)-6-(6-Chloropyridin-3-yl)hexahydropyrrolo[1,2-a]pyrazin-3(4H)-one (Single Diastereomer)

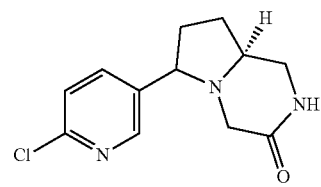 [SMILES: O=C1CN2C(c3ccc(Cl)nc3)CC[C@H]2CN1]

To a solution of ethyl 2-[(2S)-2-(azidomethyl)-5-(6-chloropyridin-3-yl)pyrrolidin-1-yl]acetate (190.0 mg, 0.5868 mmol, from Step 5) in THF (5 mL) and water (0.5 mL) was added triphenylphosphine (185.1 mg, 0.7057 mmol). The reaction mixture was stirred at 60° C. overnight. The reaction mixture was concentrated and purified by prep-HPLC on a C18 column (10-60%, MeCN/0.1% TFA (aq.)) to afford the title compound as a TFA salt (113.1 mg, 0.3092 mmol, 52.69% yield). $^1$H NMR (300 MHz, CD$_3$OD) δ 8.42 (d, J=2.47 Hz, 1H), 7.93 (dd, J=8.35, 2.47 Hz, 1H), 7.52 (d, J=8.35 Hz, 1H), 3.85 (t, J=8.64 Hz, 1H), 3.59 (dd, J=12.05, 3.89 Hz, 1H), 3.41-3.33 (m, 1H), 3.29-3.18 (m, 2H), 3.17-3.08 (m, 1H), 2.57-2.43 (m, 1H), 2.31-2.19 (m, 1H), 2.08-1.95 (m, 1H), 1.90-1.76 (m, 1H). LCMS calc. for C$_{12}$H$_{15}$ClN$_3$O [M+H$^+$]: m/z=252.1, found 252.0.

Step 7. (8aS)-6-(6-Chloropyridin-3-yl)-2-methyl-hexahydropyrrolo[1,2-a]pyrazin-3(4H)-one (Single Diastereomer)

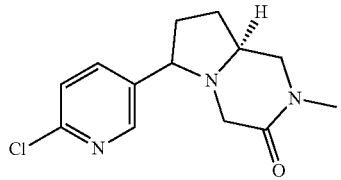 [SMILES: CN1C[C@@H]2CCC(c3ccc(Cl)nc3)N2CC1=O]

To a solution of (8aS)-6-(6-Chloropyridin-3-yl)hexahydropyrrolo[1,2-a]pyrazin-3(4H)-one, TFA salt (70.0 mg, 0.191 mmol, from Step 6) in DMF (2 mL) was added sodium hydride (24.5 mg, 0.612 mmol, 60% wt in mineral oil). The reaction mixture was stirred at room temperature for 30 min. Then methyl iodide (26 µL, 0.41 mmol) was added. The reaction mixture was stirred at room temperature for 1 h. The reaction was quenched with water (5 mL), and the reaction mixture was extracted with EtOAc (5 mL×3). The combined organic layers were washed with brine (4 mL×3), dried over Na$_2$SO$_4$, filtered, and concentrated. The residue was purified by silica gel chromatography (25-40%, EtOAc/heptanes with 0.5% MeOH) to afford the title compound (52.2 mg, 0.196 mmol, 97.4% yield). $^1$H NMR (300 MHz, CDCl$_3$) δ 8.24 (d, J=2.28 Hz, 1H), 7.61 (dd, J=8.35, 2.47 Hz, 1H), 7.27-7.20 (m, 1H), 3.35-3.22 (m, 4H), 2.92 (s, 3H), 2.80-2.63 (m, 2H), 2.32-2.20 (m, 1H), 2.04-1.95 (m, 1H), 1.72-1.58 (m, 2H). LCMS calc. for C$_{13}$H$_{17}$ClN$_3$O [M+H]$^+$: m/z=266.1, found 266.1.

Step 8. (8aS)-6-[6-[[4-(2,6-Dimethyl-3-propan-2-ylthieno[2,3-d]imidazol-5-yl)-5-fluoropyrimidin-2-yl]amino]pyridin-3-yl]-2-methyl-1,4,6,7,8,8a-hexahydropyrrolo[1,2-a]pyrazin-3-one (Single Diastereomer)

The title compound was synthesized to procedures analogous to Example 53, Step 5 to afford the title compound as a TFA salt. $^1$H NMR (300 MHz, CD$_3$OD) δ 8.79 (d, J=3.23 Hz, 1H), 8.35 (dd, J=9.11, 2.09 Hz, 1H), 8.30 (d, J=1.71 Hz, 1H), 7.63 (d, J=8.92 Hz, 1H), 5.04-4.90 (m, 1H), 3.63-3.49 (m, 2H), 3.42-3.33 (m, 2H), 3.01-2.94 (m, 4H), 2.86 (s, 4H), 2.73 (d, J=3.04 Hz, 3H), 2.51-2.38 (m, 1H), 2.21-2.07 (m, 1H), 1.90-1.72 (m, 2H), 1.67 (d, J=6.64 Hz, 6H). LCMS calc. for C$_{27}$H$_{32}$FN$_8$OS [M+H]$^+$: m/z=535.2, found 535.2.

Example 119. 4-(2,6-Dimethyl-3-propan-2-ylthieno[2,3-d]imidazol-5-yl)-N-[4-(4-ethylpiperazin-1-yl)pyridin-2-yl]-5-fluoropyrimidin-2-amine

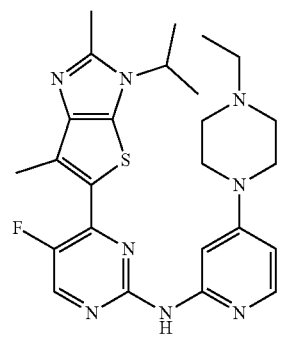 [SMILES: CCN1CCN(c2ccnc(Nc3ncc(F)c(-c4sc5c(nc(C)n5C(C)C)c4C)n3)c2)CC1]

Step 1. 1-(2-Bromopyridin-4-yl)-4-ethylpiperazine

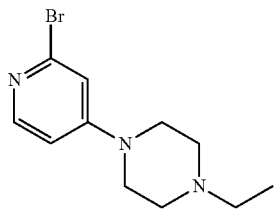

To a solution of tert-butyl 4-(2-bromopyridin-4-yl)piperazine-1-carboxylate (250 mg, 0.730 mmol) in DCM (5 mL) was added TFA (2.5 mL) at 0° C. The reaction was stirred at room temperature for 2 h. The reaction mixture was concentrated and dried in vacuum. The residue was dissolved in methanol (10 mL), and acetaldehyde (96.5 mg, 2.19 mmol) and sodium cyanoborohydride (413 mg, 6.57 mmol) were added. The reaction was stirred at room temperature for 2 h. The reaction was quenched with sat. NaHCO$_3$ (aq.) (10 mL) and extracted with DCM (10 mL×3). The combined organic layers were dried over Na$_2$SO$_4$, filtered, and concentrated. The residue was purified by silica gel chromatography (0-10%, MeOH/DCM) to give the title compound (152 mg, 0.563 mmol, 77.1% yield). LCMS calc. for C$_{11}$H$_{17}$BrN$_3$ [M+H]$^+$: 270.1, 272.1; Found: 270.1, 272.0.

Step 2. 4-(2,6-Dimethyl-3-propan-2-ylthieno[2,3-d]imidazol-5-yl)-N-[4-(4-ethylpiperazin-1-yl)pyridin-2-yl]-5-fluoropyrimidin-2-amine The title compound was synthesized by procedures analogous to those outlined in Example 53, Step 5. $^1$H NMR (300 MHz, CD$_3$OD) δ 8.74 (d, J=2.9 Hz, 1H), 8.04 (d, J=7.5 Hz, 1H), 7.04 (dd, J=7.6, 2.7 Hz, 1H), 6.78 (d, J=2.6 Hz, 1H), 5.04-4.99 (m, 1H), 4.25-3.41 (m, 8H), 3.30 (m, 2H), 2.89 (s, 3H), 2.73 (d, J=3.1 Hz, 3H), 1.68 (d, J=6.7 Hz, 6H), 1.42 (t, J=7.3 Hz, 3H). LCMS calc. for C$_{25}$H$_{32}$FN$_8$S [M+H]$^+$: m/z=495.2; Found 495.1.

Example 120. 4-(3-Isopropyl-2-methyl-3H-thieno[2,3-d]imidazol-5-yl)-N-(5-(1-methylpiperidin-4-yl)pyridin-2-yl)-5-(trifluoromethyl)pyrimidin-2-amine

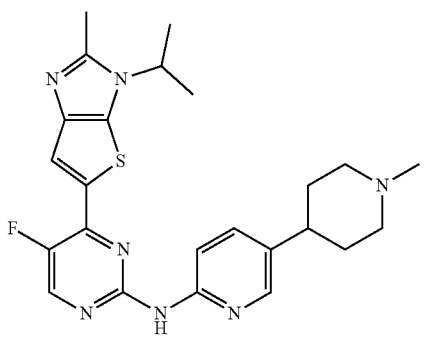 [SMILES: Cc1nc2cc(-c3nc(Nc4ccc(C5CCN(C)CC5)cn4)ncc3F)sc2n1C(C)C]

The title compound was synthesized by procedures analogous to those outlined in Example 52 to afford the title compound as its TFA salt. $^1$H NMR (300 MHz, CD$_3$OD) δ 9.08 (s, 1H), 8.38 (d, J=2.1 Hz, 1H), 8.34 (dd, J=9.1, 2.2 Hz, 1H), 8.05 (s, 1H), 7.82 (d, J=8.9 Hz, 1H), 5.01 (q, J=6.8 Hz, 1H), 3.69 (d, J=12.4 Hz, 2H), 3.22-3.08 (m, 3H), 2.96 (s, 3H), 2.88 (s, 3H), 2.24 (d, J=14.1 Hz, 2H), 2.16-2.02 (m, 2H), 1.71 (d, J=6.6 Hz, 6H). LCMS calc. for C$_{25}$H$_{29}$F$_3$N$_7$S [M+H]$^+$: m/z=516.2; Found: 515.9.

Example 121. N-[5-(4-Ethylpiperazin-1-yl)pyridin-2-yl]-5-fluoro-4-[7-propan-2-yl-3-(trifluoromethyl)thieno[3,2-b]pyridin-2-yl]pyrimidin-2-amine

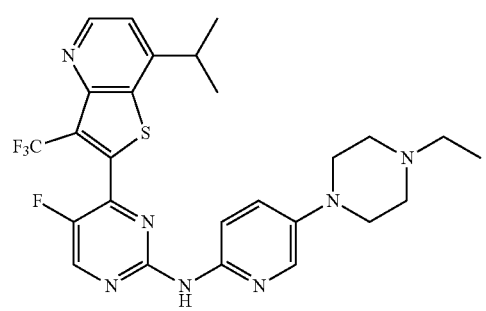 [SMILES: CCN1CCN(c2ccc(Nc3ncc(F)c(-c4sc5c(C(C)C)ccnc5c4C(F)(F)F)n3)nc2)CC1]

Step 1. 3-Iodo-7-propan-2-ylthieno[3,2-b]pyridine

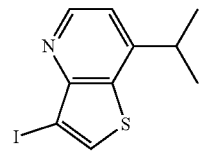

To a solution of 7-propan-2-ylthieno[3,2-b]pyridine (570 mg, 3.22 mmol) in trifluoromethanesulfonic acid (1.71 mL, 19.4 mmol) was added N-iodosuccinimide (720 mg, 3.22 mmol) portion-wise. The reaction mixture was stirred at room temperature for 1 h. The reaction was quenched with sat. NaHCO$_3$ (aq.) (20 mL) and extracted with EtOAc (20 mL×3). The combined organic layers were dried over Na$_2$SO$_4$, filtered, and concentrated. The residue was purified by silica gel chromatography (3-30% EtOAc/heptane) and further purified by prep-HPLC on a C18 column (20-100% MeCN/0.1% TFA(aq.)) to afford the title compound as a TFA salt (680 mg, 1.63 mmol, 50.6% yield), a red oil. LCMS calc. for C$_{10}$H$_{11}$INS [M+H]$^+$: m/z=304.0; Found: 304.1.

Step 2. 7-Propan-2-yl-3-(trifluoromethyl)thieno[3,2-b]pyridine

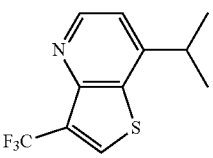

A mixture of 3-iodo-7-propan-2-ylthieno[3,2-b]pyridine, TFA salt (250 mg, 0.599 mmol, from Step 1), methyl 2,2-difluoro-2-(fluorosulfonyl)acetate (607 mg, 3.16 mmol), and copper(I) iodide (628 mg, 3.30 mmol) in DMF (3 mL) was stirred at 100° C. overnight. The reaction was quenched with water (5 mL), and the mixture extracted with EtOAc (5 mL×3). The combined organic layers were dried over Na$_2$SO$_4$, filtered, and concentrated. The residue was purified by prep-HPLC on a C$_{18}$ column (10-100% MeCN/0.1% TFA (aq.)) to yield the title compound as a TFA salt (30.1 mg, 0.0838 mmol, 14.0% yield). LCMS calc. for C$_{11}$H$_{11}$F$_3$NS [M+H]$^+$: m/z=246.1; Found 246.1.

Step 3. 2-(2-Chloro-5-fluoro-3,4-dihydropyrimidin-4-yl)-7-isopropyl-3-(trifluoromethyl)thieno[3,2-b]pyridine

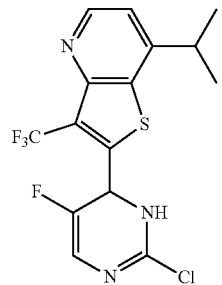

A solution of 7-propan-2-yl-3-(trifluoromethyl)thieno[3,2-b]pyridine, TFA salt (25.0 mg, 0.0696 mmol, from Step 2) in THF (2 mL) was added lithium diisopropylamide (0.25 mL, 0.50 mmol, 2.0 M in THF/ethylbenzene/hexanes) dropwise at −78° C. The resulting solution was stirred at −78° C. for 10 min. Then 2-chloro-5-fluoropyrimidine (10.3 mg, 0.153 mmol) was added, and the resulting solution was stirred at −78° C. After stirring for 20 min, the reaction mixture was slowly warmed to room temperature. The reaction was quenched with sat. NH$_4$Cl (aq.) (10 mL) and extracted with EtOAc (20 mL×3). The combined organic layers were dried over Na$_2$SO$_4$, filtered, and concentrated to afford the title compound, which was used without further purification. LCMS calc. for C$_{15}$H$_{13}$ClF$_4$N$_3$S [M+H]$^+$: m/z=378.0, 380.0; Found 378.0, 380.0.

Step 4. 2-(2-Chloro-5-fluoropyrimidin-4-yl)-7-propan-2-yl-3-(trifluoromethyl) thieno[3,2-b]pyridine

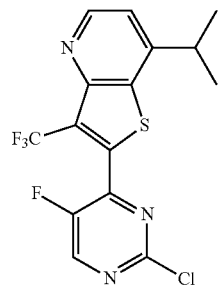 [SMILES: CC(C)c1ccnc2c(C(F)(F)F)c(-c3nc(Cl)ncc3F)sc12]

To a solution of 2-(2-chloro-5-fluoro-1,6-dihydropyrimidin-6-yl)-7-propan-2-yl-3-(trifluoromethyl)thieno[3,2-b]pyridine (from Step 5) in THF (5 mL) was added 2,3-dichloro-5,6-dicyano-p-benzoquinone (14.4 mg, 0.0634 mmol). The resulting mixture was stirred at room temperature for 1 h. The reaction was diluted with EtOAc (30 mL) and sat. NaHCO$_3$ (aq.) (30 mL). The organic layer was separated, and the aqueous layer was extracted with EtOAc (30 mL). The combined organic layers were dried over sodium Na$_2$SO$_4$, filtered and concentrated. The residue was purified by silica gel chromatography (1-30% EtOAc/heptane) to afford the title compound (19.2 mg, 0.0511 mmol, 73.4% yield over two steps) as a yellow oil. $^1$H NMR (300 MHz, CD$_3$OD) δ 8.92 (t, J=1.1 Hz, 1H), 8.80 (d, J=4.9 Hz, 1H), 7.55 (d, J=4.9 Hz, 1H), 3.41-3.20 (m, 1H), 1.48 (d, J=6.9 Hz, 6H). LCMS calc. for C$_{15}$H$_{11}$ClF$_4$N$_3$S [M+H]$^+$: m/z=376.0, 378.0; Found 375.8, 377.8.

Step 5. N-[5-(4-Ethylpiperazin-1-yl)pyridin-2-yl]-5-fluoro-4-[7-propan-2-yl-3-(trifluoromethyl) thieno[3,2-b]pyridin-2-yl]pyrimidin-2-amine The title compound was synthesized by procedures analogous to those outlined in Example 1, Step 8 to afford the title compound as a TFA salt. $^1$H NMR (300 MHz, CD$_3$OD) δ 8.90 (d, J=1.5 Hz, 1H), 8.82 (d, J=4.9 Hz, 1H), 8.22 (dd, J=9.6, 2.9 Hz, 1H), 7.93 (d, J=2.9 Hz, 1H), 7.63 (d, J=9.6 Hz, 1H), 7.56 (d, J=4.9 Hz, 1H), 4.09-3.51 (m, 6H), 3.40-3.34 (m, 2H), 3.30-3.25 (m, 3H), 1.49 (d, J=6.9 Hz, 6H), 1.42 (t, J=7.3 Hz, 3H). LCMS calc. for C$_{26}$H$_{28}$F$_4$N$_7$S [M+H]$^+$: m/z=546.2; Found 546.1.

Example 122. 2-(2-((5-(4-Ethylpiperazin-1-yl)pyridin-2-yl)amino)-5-fluoropyrimidin-4-yl)-7-isopropylthieno[3,2-b]pyridine-3-carbonitrile

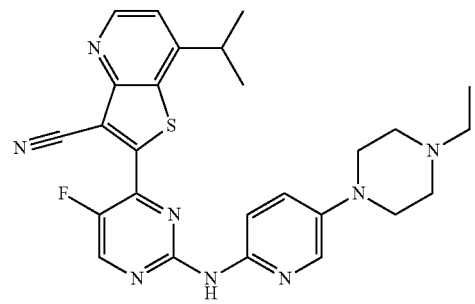 [SMILES: CCN1CCN(c2ccc(Nc3ncc(F)c(-c4sc5c(C(C)C)ccnc5c4C#N)n3)nc2)CC1]

Step 1. 7-Propan-2-ylthieno[3,2-b]pyridine-3-carbonitrile

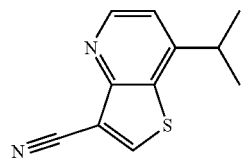

A mixture of 3-iodo-7-propan-2-ylthieno[3,2-b]pyridine (1.4 g, 4.6 mmol, Example 121, Step 1), zinc cyanide (250 mg, 2.13 mmol), XPhos Pd G3 (0.39 g, 0.46 mmol, CAS: 1445085-55-1), and N,N-diisopropylethylamine (0.91 mL, 5.5 mmol) in N,N-dimethylacetamide (20 mL) was stirred at 85° C. overnight. The reaction was quenched with water (20 mL) and extracted with EtOAc (20 mL×3). The combined organic layers were washed with brine (30 mL), dried over Na$_2$SO$_4$, filtered, and concentrated. The residue was purified by silica gel chromatography (0-20% EtOAc/heptane) to afford the title compound (174 mg, 0,860 mmol, 18.6% yield). LCMS calc. for $C_{11}H_{11}N_2S$ [M+H]$^+$: m/z=203.1; Found 203.1.

Step 2. 7-Isopropyl-2-(tributylstannyl)thieno[3,2-b]pyridine-3-carbonitrile

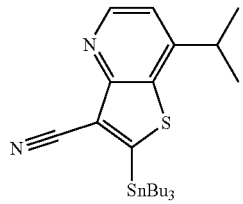

To a solution of 7-propan-2-ylthieno[3,2-b]pyridine-3-carbonitrile (40.1 mg, 0.198 mmol) in THF (1 mL) was added lithium diisopropylamide (0.11 mL, 0.22 mmol, 2.0 M in THF/ethylbenzene/hexanes) dropwise at −78° C. The mixture was stirred at −78° C. for 30 min. Then tributyl (chloro)stannane (0.060 mL, 0.22 mmol) was added. The mixture was stirred at room temperature for 1 h. The reaction was quenched with KF (aq.) (1 mL, 0.3 mmol, 0.3 N) and stirred at room temperature for 1 h. Then the mixture was passed through a Celite pad and extracted with EtOAc (1 mL×3). The combined organic layers were dried over $Na_2SO_4$, filtered, and concentrated. The residue was purified by silica gel chromatography (0-10% EtOAc/hexane) to give the title compound (72.0 mg, 0.146 mmol, 73.9% yield) as a colorless oil. $R_f$=0.5 (10% EtOAc/hexane).

Step 3. 2-(2-Chloro-5-fluoropyrimidin-4-yl)-7-isopropylthieno[3,2-b]pyridine-3-carbonitrile A mixture of 7-propan-2-yl-2-tributylstannylthieno[3,2-b]pyridine-3-carbonitrile (72.0 mg, 0.146 mmol), 2,4-dichloro-5-fluoropyrimidine (48.9 mg, 0.293 mmol), and tetrakis(triphenylphosphine)palladium(0) (25.4 mg, 0.0220 mmol) in toluene (1 mL) was stirred at 100° C. overnight. The solvent was removed, and the residue was purified by silica gel chromatography (0-35% EtOAc/hexane) to give the title compound (27.2 mg, 0.0817 mmol, 55.9% yield) as a colorless solid. LCMS calc. for $C_{15}H_{11}ClFN_4S$ [M+H]$^+$: m/z=333.0; Found: 332.9.

Step 4. 2-(2-((5-(4-Ethylpiperazin-1-yl)pyridin-2-yl)amino)-5-fluoropyrimidin-4-yl)-7-isopropylthieno[3,2-b]pyridine-3-carbonitrile The title compound was synthesized by procedures analogous to those outlined in Example 1, Step 8 to afford the title compound as a TFA salt. $^1$H NMR (300 MHz, CD$_3$OD) δ 8.98 (d, J=2.7 Hz, 1H), 8.86 (d, J=4.9 Hz, 1H), 8.18 (dd, J=9.5, 2.9 Hz, 1H), 8.01 (d, J=2.8 Hz, 1H), 7.74 (d, J=9.5 Hz, 1H), 7.60 (d, J=4.9 Hz, 1H), 4.09-3.52 (m, 4H), 3.50-3.33 (m, 7H), 1.50 (d, J=6.9 Hz, 6H), 1.43 (t, J=7.3 Hz, 3H). LCMS calc. for $C_{26}H_{28}FN_8S$ [M+H]$^+$: m/z=503.2; Found 503.1.

Example 123. 5-Fluoro-N-[5-(1-methylpiperidin-4-yl)pyridin-2-yl]-4-(3-methyl-7-propan-2-ylthieno[3,2-c]pyridin-2-yl)pyrimidin-2-amine

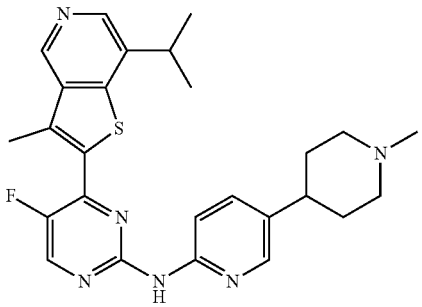

Step 1. 2,4-Dibromo-3-methyl-7-propan-2-ylthieno[3,2-c]pyridine

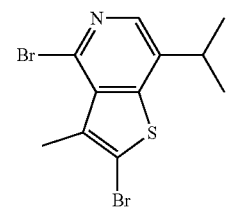

A mixture of 2-bromo-3-methyl-7-propan-2-yl-5H-thieno[3,2-c]pyridin-4-one (250 mg, 0.874 mmol, Example 51, Step 4) and phosphoryl bromide (376 mg, 1.31 mmol) in 1,4-dioxane (2 mL) was stirred at 100° C. for 5 h. The reaction was quenched with ice-cold water (3 mL) and extracted with EtOAc (3 mL×3). The combined organic layers were washed with sat. NaHCO$_3$ (aq.) (5 mL) and brine (5 mL), dried over Na$_2$SO$_4$, filtered, and concentrated. The residue was purified by silica gel chromatography (0-30% EtOAc/heptane) to afford the title compound (202 mg, 0.579 mmol, 66.2% yield). LCMS calc. for $C_{11}H_{12}Br_2NS$ [M+H]$^+$: m/z=347.9, 349.9, 351.9; Found: 347.8, 349.8, 351.8.

Step 2. 3-Methyl-7-propan-2-ylthieno[3,2-c]pyridine

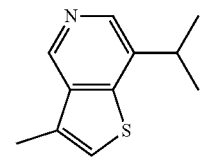

To a solution of 2,4-dibromo-3-methyl-7-propan-2-ylthieno[3,2-c]pyridine (200 mg, 0.573 mmol) in methanol (1 mL) was added Pd/C (20.0 mg, 0.0188 mmol, 10 wt %) and triethylamine (0.226 mL, 1.15 mmol). The reaction mixture was stirred under an atmosphere of hydrogen overnight. The reaction mixture was filtered, and the filtrate was concentrated. The residue was purified by silica gel chromatography (0-30% EtOAc/heptane) to afford the title compound (55.1 mg, 0.288 mmol, 50.2% yield). LCMS calc. for $C_{11}H_{14}NS$ [M+H]⁺: m/z=192.1; Found: 191.8.

Step 3. 2-(2-Chloro-5-fluoro-1,6-dihydropyrimidin-6-yl)-3-methyl-7-propan-2-ylthieno[3,2-c]pyridine

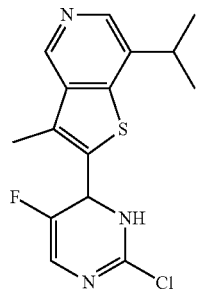 [SMILES: Cc1c(C2NC(Cl)=NC=C2F)sc2c(C(C)C)cncc12]

The title compound was synthesized by procedures analogous to those outlined in Example 121, Step 3. LCMS calc. for $C_{15}H_{16}ClFN_3S$ [M+H]⁺: m/z=324.1, 326.1; Found: 323.9, 325.9.

Step 4. 2-(2-Chloro-5-fluoropyrimidin-4-yl)-3-methyl-7-propan-2-ylthieno[3,2-c]pyridine

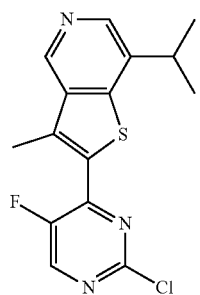 [SMILES: Cc1c(-c2nc(Cl)ncc2F)sc2c(C(C)C)cncc12]

The title compound was synthesized by procedures analogous to those outlined in Example 121, Step 4. LCMS calc. for $C_{15}H_{14}ClFN_3S$ [M+H]⁺: m/z=322.1, 324.1; Found: 321.9, 323.8.

Step 5. 5-Fluoro-N-[5-(1-methylpiperidin-4-yl)pyridin-2-yl]-4-(3-methyl-7-propan-2-ylthieno[3,2-c]pyridin-2-yl)pyrimidin-2-amine The title compound was synthesized by procedures analogous to those outlined in Example 1, Step 8 to afford the title compound as a TFA salt. ¹H NMR (300 MHz, CD₃OD) δ 9.47 (s, 1H), 8.96 (d, J=1.9 Hz, 1H), 8.65 (s, 1H), 8.37-8.27 (m, 2H), 7.77 (d, J=8.9 Hz, 1H), 3.72 (d, J=12.5 Hz, 2H), 3.56-3.50 (m, 1H), 3.26-3.18 (m, 2H), 3.16-3.09 (m, 1H), 2.98 (s, 3H), 2.87 (d, J=2.9 Hz, 3H), 2.31-2.19 (m, 2H), 2.16-2.04 (m, 2H), 1.60 (d, J=6.9 Hz, 6H). LCMS calc. for $C_{26}H_{30}FN_6S$ [M+H]⁺: m/z=477.2; Found: 477.1.

Example 124. N-[5-[(4-Ethylpiperazin-1-yl)methyl]pyridin-2-yl]-5-fluoro-4-(6-methyl-3-propan-2-ylthieno[2,3-d]imidazol-5-yl)pyrimidin-2-amine

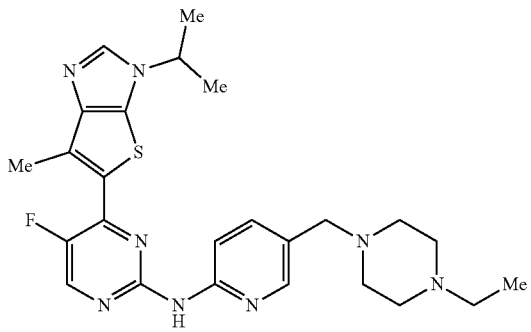 [SMILES: CCN1CCN(Cc2ccc(Nc3ncc(F)c(-c4sc5c(ncn5C(C)C)c4C)n3)nc2)CC1]

Step 1. 2-[Formyl(propan-2-yl)amino]-4-methylthiophene-3-carboxylic Acid

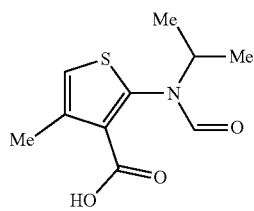 [SMILES: Cc1csc(N(C=O)C(C)C)c1C(=O)O]

To a solution of formic acid (1.00 mL, 0.264 mmol) in chloroform (20 mL) was added EDC (4.1 g, 0.26 mmol) at −15° C. The reaction vessel was removed from the cooling bath, and the reaction mixture stirred at room temperature for 10 min. A solution of 4-methyl-2-(propan-2-ylamino)thiophene-3-carboxylic acid (39.3 g, 197 mmol) in chloroform (2.5 L) was then added. The reaction solution was stirred at room temperature for 20 min, and another portion of formic acid (1.00 mL, 0.264 mmol) and EDC (4.10 g, 0.260 mmol) were added. This procedure was repeated 12 times. Upon stirring overnight, the reaction mixture was diluted with water and 1 N HCl (aq.). The resulting mixture was extracted with DCM (3×). The combined organic layers were dried over Na₂SO₄. After removal of solvent, the residue was purified by silica chromatography (5%-100% EtOAc/heptanes, then 2% AcOH in EtOAc to afford the title compound (26.5 g, 117 mmol, 59.1%). LCMS calc. for $C_{10}H_{14}NO_3S$ [M+H]⁺: m/z=228.2; Found: 228.1.

Step 2. N-(3-amino-4-methylthiophen-2-yl)-N-propan-2-ylformamide

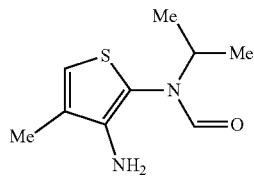

To a solution of 2-[formyl(propan-2-yl)amino]-4-methylthiophene-3-carboxylic acid (2.40 g, 10.6 mmol) and triethylamine (4.42 mL, 31.7 mmol) in 1,4-dioxane (150 mL) was added diphenylphosphoryl azide (3.41 mL, 15.8 mmol). The reaction mixture was stirred at room temperature for 1 h. Water (150 mL) was added, and the reaction mixture was stirred at 100° C. overnight. The reaction mixture was concentrated under reduced pressure and extracted with DCM (3×). The combined organic phases were dried over $Na_2SO_4$. After removal of solvent, the residue was purified by silica gel column chromatography (5%-60% EtOAc/heptane with 0.1% $Et_3N$) to afford the title compound (9.80 g). While not analytically pure, the material was used in the next step without further purification. LCMS calc. for $C_9H_{15}N_2OS$ [M+H]$^+$: m/z=199.1; Found: 198.9.

Step 3. 6-Methyl-3-propan-2-ylthieno[2,3-d]imidazole

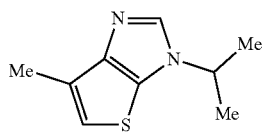 [SMILES: Cc1csc2c1ncn2C(C)C]

A mixture of N-(3-amino-4-methylthiophen-2-yl)-N-propan-2-ylformamide (19.0 g, 95.8 mmol) and $POCl_3$ (8.93 mL, 95.8 mmol) in toluene (150 mL) was stirred at 100° C. overnight. 10% $Na_2CO_3$ (aq.) was added, and the mixture was extracted with DCM (3×). The combined organic phases were dried over $Na_2SO_4$. After removal of solvent, the residue was purified by silica gel column chromatography (5%-80% EtOAc/heptanes) to afford the title compound (12.4 g, 68.8 mmol, 71.8%). LCMS calc. for $C_9H_{13}N_2S$ [M+H]: m/z=181.1; Found: 181.2.

Step 4. 6-Methyl-3-propan-2-yl-5-(4,4,5,5-tetramethyl-1,3,2-dioxaborolan-2-yl)thieno[2,3-d]imidazole

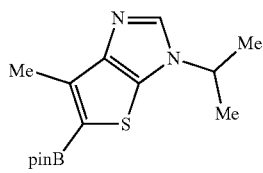

The title compound was synthesized according to procedures analogous to Example 52, Step 6. LCMS calc. for $C_{15}H_{24}BN_2O_2S$ [M+H]$^+$: m/z=307.2 Found: 307.1.

Step 5. 5-(2-Chloro-5-fluoropyrimidin-4-yl)-6-methyl-3-propan-2-ylthieno[2,3-d]imidazole

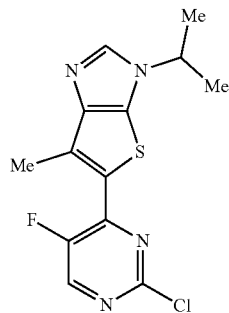 [SMILES: Cc1c(-c2nc(Cl)ncc2F)sc2c1ncn2C(C)C]

The title compound was synthesized according to procedures analogous to Example 52, Step 6 to afford the title compound as a TFA salt. $^1$H NMR (300 MHz, CDCl$_3$) δ 8.42 (dd, J=3.0, 0.7 Hz, 1H), 7.77 (s, 1H), 4.55 (hept, J=6.9 Hz, 1H), 2.74 (d, J=3.4 Hz, 3H), 1.62 (d, J=6.7 Hz, 6H). LCMS calc. for $C_{13}H_{13}ClFN_4S$ [M+H]$^+$: m/z=311.1 Found: 310.9.

Step 6. N-[5-[(4-ethylpiperazin-1-yl)methyl]pyridin-2-yl]-5-fluoro-4-(6-methyl-3-propan-2-ylthieno[2,3-d]imidazol-5-yl)pyrimidin-2-amine The title compound was synthesized according to procedures analogous to Example 1, Step 8 to afford the title compound as an HCl salt (630 mg, 1.27 mmol, 99%). $^1$H NMR (300 MHz, CD$_3$OD) δ 9.00 (s, 1H), 8.81 (d, J=3.0 Hz, 1H), 8.36 (m, 2H), 7.65 (d, J=8.9 Hz, 1H), 4.95-4.90 (m, 1H), 3.79 (s, 2H), 3.57 (br s, 2H), 3.27-3.11 (m, 6H), 2.76 (d, J=3.0 Hz, 3H), 2.65 (m, 2H), 1.70 (d, J=6.7 Hz, 6H), 1.37 (t, J=7.3 Hz, 3H). LCMS calc. for $C_{25}H_{32}FN_8S$ [M+H]+: m/z=495.2; Found: 495.2.

Example 125. 5-Fluoro-N-[5-[-1-methylpiperidin-3-yl]pyridin-2-yl]-4-(6-methyl-3-propan-2-ylthieno[2,3-d]imidazol-5-yl)pyrimidin-2-amine (Isomer 1)

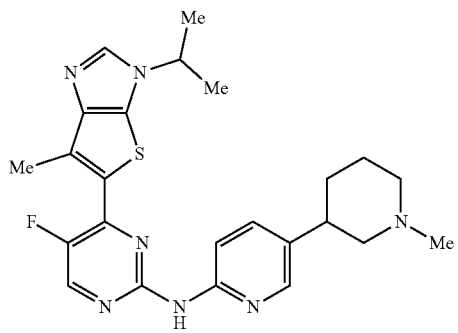 [SMILES: Cc1c(-c2nc(Nc3ccc(C4CCCN(C)C4)cn3)ncc2F)sc2c1ncn2C(C)C]

Step 1. Tert-Butyl 5-(6-chloropyridin-3-yl)-3,6-dihydro-2H-pyridine-1-carboxylate

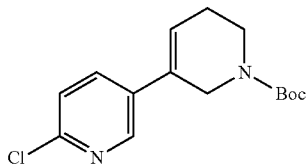 [SMILES: CC(C)(C)OC(=O)N1CCC=C(c2ccc(Cl)nc2)C1]

A suspension of 5-bromo-2-chloropyridine (6.00 g, 31.2 mmol), tert-butyl 3-(4,4,5,5-tetramethyl-1,3,2-dioxaborolan-2-yl)-5,6-dihydropyridine-1(2H)-carboxylate (9.64 g, 31.18 mmol), [1,1'-bis(diphenylphosphino)ferrocene]dichloropalladium(II) (1.14 g, 1.56 mmol), and potassium carbonate (17.24 g, 124.7 mmol) in 1,4-dioxane (90 mL) and water (30 mL) was stirred at 100° C. under a nitrogen atmosphere for 6 h. The reaction mixture was cooled to room temperature, concentrated, partitioned between EtOAc (100 mL) and water (100 mL), and filtered through a pad of celite. The organic layer was separated, and the aqueous layer was extracted with EtOAc (3×100 mL). The combined organic layers were washed with brine (100 mL), dried over $Na_2SO_4$, and concentrated to give a dark brown residue. The residue was purified by silica column chromatography (0-30% EtOAc/heptanes) to give the title compound (8.63 g, 29.3 mmol, 93.9% yield) as a colorless solid. LC-MS calc. for $C_{15}H_{20}ClN_2O_2[M+H]^+$: m/z=295.1; Found: 294.9.

Step 2. Tert-Butyl-3-(6-chloropyridin-3-yl)piperidine-1-carboxylate (Isomers 1 and 2)

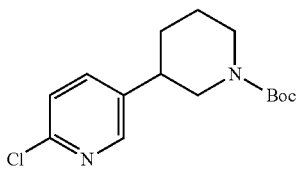 [SMILES: CC(C)(C)OC(=O)N1CCCC(c2ccc(Cl)nc2)C1]

To a solution of tert-butyl 5-(6-chloropyridin-3-yl)-3,6-dihydro-2H-pyridine-1-carboxylate (7.70 g, 26.1 mmol) in EtOAc (100 mL) was added $PtO_2$ (770 mg, 3.39 mmol). The mixture was stirred under a hydrogen atmosphere overnight. The suspension was filtered through Celite and concentrated to give the title compound (7.00 g, 23.6 mmol, 90.0% yield) as a gray oil. The isomers were separated using SFC on a Columntek Enantiocel A6 column (35% MeOH/$CO_2$, 100 bar) to afford the title compound as two isomers: isomer 1 (3 g) and isomer 2 (3 g). Isomer 1: LC-MS calc. for $C_{15}H_{22}ClN_2O_2[M+H]^+$: m/z=297.1; Found: 296.9. Isomer 2: LC-MS calc. for $C_{15}H_{22}ClN_2O_2[M+H]^+$: m/z=297.1; Found: 296.9.

Step 3. 5-Fluoro-4-(6-methyl-3-propan-2-ylthieno[2,3-d]imidazol-5-yl)pyrimidin-2-amine

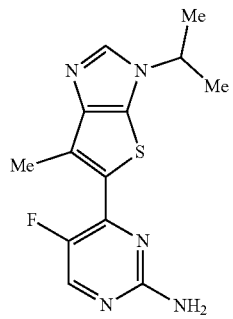 [SMILES: Cc1c(-c2nc(N)ncc2F)sc2c1ncn2C(C)C]

The title compound was synthesized according to procedures analogous to Example 53, Step 1. LCMS calc. for $C_{13}H_{14}FN_5S [M+H]^+$: m/z=292.1; Found: 292.0.

Step 4. 5-Fluoro-4-(6-methyl-3-propan-2-ylthieno[2,3-d]imidazol-5-yl)-N-[5-[-piperidin-3-yl]pyridin-2-yl]pyrimidin-2-amine (Isomer 1)

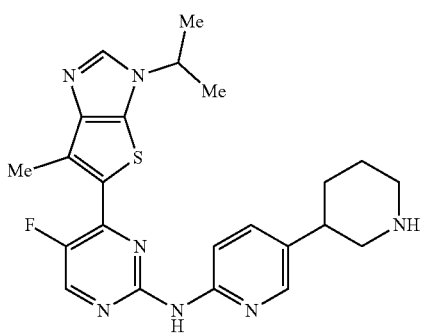 [SMILES: Cc1c(-c2nc(Nc3ccc(C4CCCNC4)cn3)ncc2F)sc2c1ncn2C(C)C]

A sealed tube was charged with 5-fluoro-4-(6-methyl-3-propan-2-ylthieno[2,3-d]imidazol-5-yl)pyrimidin-2-amine (53 mg, 0.18 mmol), tert-butyl-3-(6-chloropyridin-3-yl)piperidine-1-carboxylate (isomer 1) (56 mg, 0.19 mmol), XPhos Pd G2 (33 mg, 0.040 mmol, CAS 1310584-14-5), sodium tert-butoxide (69 mg, 0.72 mmol), and 1,4-dioxane (1 mL). The mixture was heated under a nitrogen atmosphere for 4 h. The solvent was removed under reduced pressure. To the resulting residue was added TFA (5 mL). The mixture was stirred for 10 min. The solvent was removed under reduced pressure. The crude material was purified by prep-HPLC on a $C_{18}$ column (2-25% MeCN/0.1% TFA (aq)) to yield the title compound as the TFA salt (90.0 mg, 0.190 mmol, quantitative). LC-MS calc. for $C_{23}H_{27}FN_7S [M+H]^+$: m/z=452.2; Found: 452.0.

Step 5. 5-Fluoro-N-[5-[1-methylpiperidin-3-yl]pyridin-2-yl]-4-(6-methyl-3-propan-2-ylthieno[2,3-d]imidazol-5-yl)pyrimidin-2-amine (Isomer 1)

To a suspension of 5-fluoro-4-(6-methyl-3-propan-2-ylthieno[2,3-d]imidazol-5-yl)-N-[5-[piperidin-3-yl]pyridin-2-yl]pyrimidin-2-amine (isomer 1) (90 mg, 0.20 mmol) in methanol (3 mL) was added acetic acid (34.2 µL, 0.600 mmol), $NaBH_3CN$ (63 mg, 1.0 mmol), and formaldehyde (74.2 uL, 1.00 mmol, 37 wt % aq.). The reaction mixture was stirred for 30 min. To the mixture was added MeCN (2 mL) and water (0.5 mL). The mixture was purified by prep-HPLC on C18 column (2 to 25% MeCN/0.1% TFA (aq)). The product-containing fractions were combined and concentrated, basified with $NaHCO_3$, and extracted with DCM (3×20 mL). The combined organic phases were dried over $Na_2SO_4$ and concentrated to give a yellow oil, which was then dissolved in EtOAc (1 mL). The desired product precipitated from the solution after 2 min. The resulting solid was dissolved in water (1 mL) and 2N HCl (0.23 mL, 2.3 equiv) and concentrated under reduced pressure to give the title compound (24.4 mg, 0.0524 mmol, 23% yield) as the HCl salt, a yellow solid. $^1$H NMR (300 MHz, $CD_3OD$) δ 8.75 (d, J=3.2 Hz, 1H), 8.66 (s, 1H), 8.39-8.26 (m, 2H), 7.69 (d, J=8.9 Hz, 1H), 4.80-4.78 (m, 1H), 3.73-3.50 (m, 2H), 3.25-3.18 (m, 2H), 3.17-3.01 (m, 1H), 2.94 (s, 3H), 2.76 (d, J=3.0 Hz, 3H), 2.21-2.06 (m, 2H), 2.05-1.93 (m, 1H), 1.91-1.76 (m, 1H), 1.67 (d, J=6.7 Hz, 6H). LC-MS calc. for $C_{24}H_{29}FN_7S [M+H]^+$: m/z=466.2; Found: 466.2.

Example 126. 5-Fluoro-N-[5-[-1-methylpiperidin-3-yl]pyridin-2-yl]-4-(6-methyl-3-propan-2-ylthieno[2,3-d]imidazol-5-yl)pyrimidin-2-amine (Isomer 2)

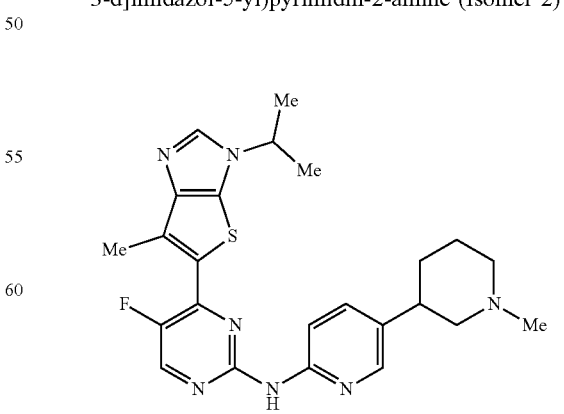

The title compound was synthesized according to procedures analogous to Example 125, Steps 4-5, utilizing tertbutyl-3-(6-chloropyridin-3-yl)piperidine-1-carboxylate (isomer 2) in Step 4, to afford the title compound as the HCl salt. ¹H NMR (300 MHz, CD₃OD) δ 8.74 (d, J=3.2 Hz, 1H), 8.59 (s, 1H), 8.36-8.25 (m, 2H), 7.70 (d, J=9.0 Hz, 1H), 4.81-4.75 (m, 1H), 3.71-3.56 (m, 2H), 3.26-3.19 (m, 2H), 3.14-3.02 (m, 1H), 2.95 (s, 3H), 2.76 (d, J=3.0 Hz, 3H), 2.11 (d, J=14.1 Hz, 2H), 2.05-1.96 (m, 1H), 1.92-1.76 (m, 1H), 1.66 (d, J=6.7 Hz, 6H). LC-MS calc. for $C_{24}H_{29}FN_7S$ [M+H]⁺: m/z=466.2; Found: 466.2.

Example 127. 4-(3-Isopropyl-2-methyl-3H-thieno[2,3-d]imidazol-5-yl)-5-methoxy-N-(5-(1-methylpiperidin-4-yl)pyridin-2-yl)pyrimidin-2-amine

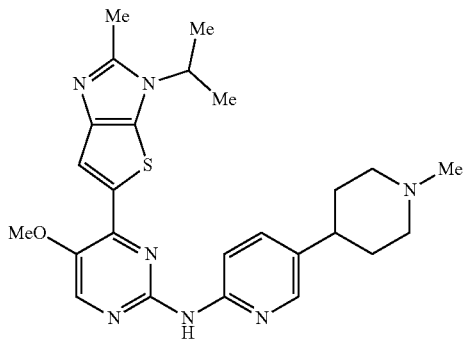 [SMILES: COc1cnc(Nc2ccc(C3CCN(C)CC3)cn2)nc1-c1cc2nc(C)n(C(C)C)c2s1]

The title compound was synthesized according to procedures analogous to Example 52 to afford the title compound as a TFA salt. ¹H NMR (300 MHz, DMSO-d₆) δ 11.38 (s, 1H), 10.11 (s, 1H), 8.51 (s, 1H), 8.24 (s, 2H), 8.09 (dd, J=9.0, 2.1 Hz, 1H), 7.80 (d, J=9.0 Hz, 1H), 4.84 (hept, J=6.3 Hz, 1H), 4.14 (s, 3H), 3.54 (d, J=11.9 Hz, 2H), 3.08 (q, J=10.4 Hz, 2H), 2.94-2.86 (m, 1H), 2.81 (d, J=4.1 Hz, 3H), 2.71 (s, 3H), 2.07 (d, J=13.6 Hz, 2H), 2.00-1.84 (m, 2H), 1.55 (d, J=6.6 Hz, 6H). LCMS calc. for $C_{25}H_{32}N_7OS$ [M+H]⁺: m/z=478.24; Found: 478.20.

Example 128. N-(5-(1-Ethylpiperidin-4-yl)pyridin-2-yl)-5-fluoro-4-(3-isopropyl-6-methyl-3H-thieno[2,3-d]imidazol-5-yl)pyrimidin-2-amine

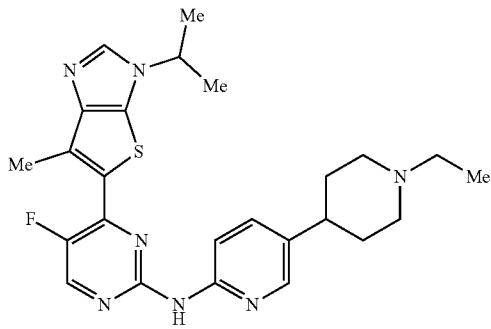 [SMILES: CCN1CCC(c2ccc(Nc3ncc(F)c(-c4sc5c(ncn5C(C)C)c4C)n3)nc2)CC1]

The title compound was synthesized according to procedures analogous to Example 124 to afford the title compound as an HCl salt. ¹H NMR (300 MHz, CD₃OD) δ 8.47 (d, J=3.2 Hz, 1H), 8.31 (d, J=8.7 Hz, 1H), 8.21 (d, J=2.1 Hz, 1H), 8.05 (s, 1H), 7.71 (dd, J=8.7, 2.4 Hz, 1H), 4.78-4.64 (m, 1H), 3.60 (d, J=12.3 Hz, 2H), 3.14 (q, J=7.3 Hz, 2H), 3.04-2.83 (m, 3H), 2.60 (d, J=3.8 Hz, 3H), 2.18-1.89 (m, 4H), 1.62 (d, J=6.7 Hz, 6H), 1.37 (t, J=7.3 Hz, 3H). LCMS calc. for $C_{25}H_{31}FN_7S$ [M+H]⁺: m/z=480.2; Found: 480.2.

Example 129. N-(5-(6-ethyl-2,6-diazaspiro[3.3]heptan-2-yl)pyridin-2-yl)-5-fluoro-4-(3-isopropyl-3H-thieno[2,3-d]imidazol-5-yl)pyrimidin-2-amine

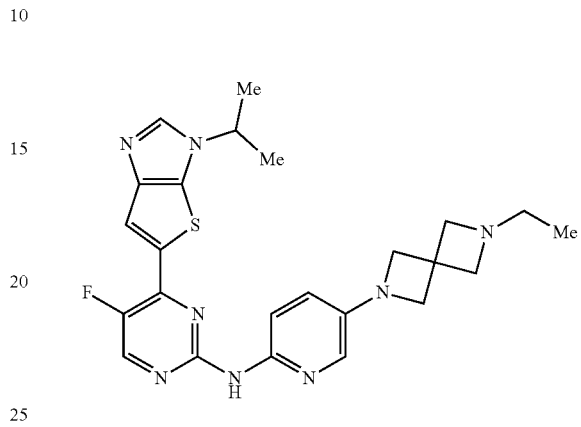

The title compound was synthesized according to procedures analogous to Example 124 to afford the title compound as the tartaric acid salt. ¹H NMR (300 MHz, DMSO-d₆) δ 9.55 (s, 1H), 8.54 (d, J=3.5 Hz, 1H), 8.16 (s, 1H), 7.99 (d, J=8.9 Hz, 1H), 7.94 (d, J=1.5 Hz, 1H), 7.61 (d, J=2.9 Hz, 1H), 7.03 (dd, J=8.9, 3.0 Hz, 1H), 4.73 (hept, J=6.7 Hz, 1H), 4.09 (s, 2H), 4.05 (s, 4H), 4.00 (s, 4H), 2.99 (q, J=7.2 Hz, 2H), 1.55 (d, J=6.6 Hz, 6H), 1.03 (t, J=7.2 Hz, 3H). LCMS calc. for $C_{24}H_{28}FN_8S$ [M+H]⁺: m/z=479.21; Found: 478.77.

Example 130. 5-Chloro-4-(3-isopropyl-6-methyl-3H-thieno[2,3-d]imidazol-5-yl)-N-(5-(1-methylpiperidin-3-yl)pyridin-2-yl)pyrimidin-2-amine

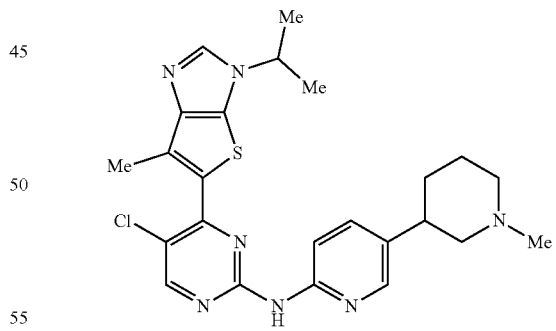

The title compound was synthesized according to procedures analogous to Example 124 to afford the title compound as a TFA salt. ¹H NMR (300 MHz, DMSO-d₆) δ 10.47 (s, 1H), 9.56 (s, 1H), 8.73 (s, 1H), 8.46 (s, 1H), 8.24 (d, J=2.1 Hz, 1H), 8.11 (d, J=8.7 Hz, 1H), 7.76 (dd, J=8.7, 2.2 Hz, 1H), 4.77 (hept, J=6.6 Hz, 1H), 3.50 (t, J=11.3 Hz, 2H), 3.85-3.20 (m, 3H), 2.80 (d, J=4.4 Hz, 3H), 2.44 (s, 3H), 2.05-1.59 (m, 4H), 1.54 (d, J=6.6 Hz, 6H). LC-MS calc. for $C_{24}H_{29}ClN_7S$ [M+H]⁺: m/z=482.19; Found 482.20.

Example 131. 2-(5-Fluoro-2-((5-(1-methylpiperidin-4-yl)pyridin-2-yl)amino)pyrimidin-4-yl)-7-isopropyl-3-methylthieno[3,2-c]pyridine 5-oxide

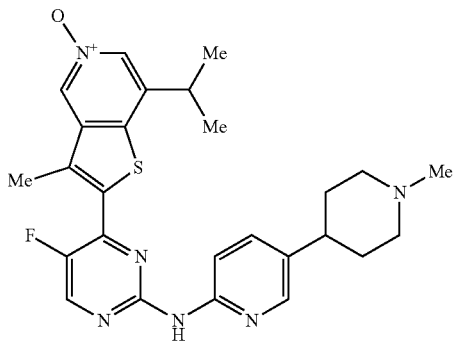 [SMILES: Cc1c(-c2nc(Nc3ccc(C4CCN(C)CC4)cn3)ncc2F)sc2c(C(C)C)c[n+](O)cc12]

The title compound was synthesized according to procedures analogous to Example 50 to afford the title compound as a TFA salt. $^1$H NMR (300 MHz, CD$_3$OD) δ 9.07 (s, 1H), 8.93 (d, J=2.3 Hz, 1H), 8.40-8.30 (m, 3H), 7.67 (d, J=9.0 Hz, 1H), 3.70 (d, J=12.5 Hz, 2H), 3.27-3.06 (m, 4H), 2.97 (s, 3H), 2.72 (d, J=2.8 Hz, 3H), 2.25 (d, J=14.1 Hz, 2H), 2.15-2.05 (m, 2H), 1.52 (d, J=6.9 Hz, 6H).

Example A: Enzymatic Activity and Cytotoxicity Studies

CDK4/CyclinD1 Enzymatic Activity Assay

The inhibitory activity of compounds was evaluated in vitro using TR-FRET assay with white 384-well low volume microplate (Greiner Bio-One). CDK4/Cyclin D1 catalyzed phosphorylation of peptide in the presence and absence of compounds was measured. IC$_{50}$ determination. Recombinant protein complex CDK4/Cyclin D1, expressed from insect cell, was purchased from ProQinase. Testing compounds were dissolved in DMSO at 0.1 mM and tested in 9-dose IC$_{50}$ mode. The reaction mixture was prepared by mixing CDK4/CyclinD1 (1 nM final), ULight-4E-BP1 (100 nM final, Perkinelmer, TRF0128-D), and ATP (2 mM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E). After 20 minutes preincubation at room temperature, MgCl$_2$ (10 mM final) was added to initiate the reaction. Following a 60 minutes incubation at 37° C., the reaction was stopped by addition of 2 μL of quenching buffer consisting of Lance detection buffer (Perkinelmer CR97-100C), 2 nM LANCE Ultra Europium-anti-P-4E-BP1 (Perkinelmer, TRF0216-D), 10 mM EDTA, and incubate at room temperature for additional 60 minutes in dark. The reaction signal was measured by Envision multimode plate reader (PerkinElmer, 2102-0010). IC$_{50}$ values were determined by fitting the data to the standard 4 parameters with Hill Slope using GraphPad Prism software. Table 4, below, shows the IC$_{50}$ values determined by this assay.

CDK6/CyclinD1 Enzymatic Activity Assay

The inhibitory activity of compounds was evaluated in vitro using TR-FRET assay with white 384-well low volume microplate (Greiner Bio-One). CDK6/Cyclin D1 catalyzed phosphorylation of peptide in the presence and absence of compounds was measured and used in IC$_{50}$ determination. Recombinant protein complex CDK6/Cyclin D1, expressed from insect cell, was purchased from ProQinase. Testing compounds were dissolved in DMSO at 0.1 mM and tested in 9-dose IC50 mode. The reaction mixture was prepared by mixing CDK6/Cyclin D1 (1 nM final), ULight-4E-BP1 (100 nM final, Perkinelmer, TRF0128-D), and ATP (250 μM final) in assay buffer (20 mM of HEPES pH 7.4, 1 mM of EGTA, 0.05% BSA, 0.005% Tween 20, and 1 mM TCEP). The compound of interest in DMSO was added to each well in 3-fold serial dilution by dispenser (TECAN D300E). After 20 minutes preincubation at room temperature, 0.1 μL MgCl$_2$ (10 mM final) was added to initiate the reaction. Following a 60 minutes incubation at 37° C., the reaction was stopped by addition of 2 μL of quenching buffer consisting of Lance detection buffer (Perkinelmer CR97-100C), 2 nM LANCE Ultra Europium-anti-P-4E-BP1 (Perkinelmer, TRF0216-D), 10 mM EDTA, and incubate at room temperature for additional 60 minutes in dark. The reaction signal was measured by Envision multimode plate reader (PerkinElmer, 2102-0010). IC$_{50}$ values were determined by fitting the data to the standard 4 parameters with Hill Slope using GraphPad Prism software. Table 4, below, shows the IC$_{50}$ values determined by this assay.

Cell Proliferation Studies in MCF7 Cells

Cell proliferation studies were conducted in MCF7 adenocarcinoma cell line. Cells were maintained in DMEM (Coming, Catalog #: 10-013-CV) supplemented with 10% v/v FBS (Gibco, Catalog #: 26140-079), 1% v/v Penicillin Streptomycin (Gibco, Catalog #15140-122) Cells were seeded in 384-well plates at a density of 100 or 200 cells/well. Compounds dissolved in DMSO were plated in quadruplicate using a digital dispenser (D300E, Tecan) and tested on a 9-point 3-fold serial dilution. Cells were incubated for 10 days in a 37° C. active humidified incubator at 5% CO$_2$. A media exchange and second compound addition were performed on day 5. Cell viability was measured using the ATP-Lite 1-Step Luminescence reagent (Perkin Elmer, Catalog #: 6016731) as per manufacturer's instructions. Luminescence signal was measured with a multimode plate reader (Envision 2105, Perkin Elmer). Raw data files were imported to Dotmatics Screening Ultra for IC$_{50}$ analysis. Luminescence values were normalized to both background and DMSO controls to obtain a percentage of viable cells relative to DMSO vehicle control. The results are shown in Table 7, below.

TABLE 7

| | IC$_{50}$ Values | | |
|---|---|---|---|
| Example | CDK4_D1 IC$_{50}$ (nM) | CDK6_D1 IC$_{50}$ (nM) | PROLIFERATION_CTG_MCF7 IC$_{50}$ (nM) |
| 1 | ++++ | +++ | +++ |
| 2 | ++++ | ++++ | ++++ |
| 3 | ++++ | +++ | +++ |
| 4 | ++++ | ++++ | +++ |
| 5 | +++ | — | +++ |

TABLE 7-continued

| | IC$_{50}$ Values | | |
|---|---|---|---|
| Example | CDK4_D1 IC$_{50}$ (nM) | CDK6_D1 IC$_{50}$ (nM) | PROLIFERATION_CTG_MCF7 IC$_{50}$ (nM) |
| 6 | ++++ | — | +++ |
| 7 | ++++ | — | +++ |
| 8 | ++++ | — | +++ |
| 9 | ++++ | ++++ | ++++ |
| 10 | ++++ | — | ++ |
| 11 | +++ | — | ++ |
| 12 | ++ | — | — |
| 13 | ++++ | — | +++ |
| 14 | ++++ | — | +++ |
| 15 | ++++ | — | — |
| 16 | ++++ | — | +++ |
| 17 | ++++ | +++ | +++ |
| 18 | +++ | — | +++ |
| 19 | +++ | — | ++ |
| 20 | ++++ | — | +++ |
| 21 | ++++ | — | +++ |
| 22 | +++ | — | ++ |
| 23 | ++++ | +++ | +++ |
| 24 | +++ | — | ++ |
| 25 | +++ | — | +++ |
| 26 | ++++ | — | +++ |
| 27 | +++ | — | ++ |
| 28 | +++ | — | ++ |
| 29 | +++ | — | +++ |
| 30 | ++++ | +++ | +++ |
| 31 | +++ | — | ++ |
| 32 | ++++ | — | ++ |
| 33 | ++++ | — | ++ |
| 34 | ++++ | — | +++ |
| 35 | ++++ | — | — |
| 36 | +++ | — | ++ |
| 37 | +++ | — | ++ |
| 38 | +++ | — | + |
| 39 | +++ | — | ++ |
| 40 | +++ | — | + |
| 41 | ++ | — | + |
| 42 | ++ | — | + |
| 43 | +++ | — | ++ |
| 44 | +++ | — | ++ |
| 45 | +++ | — | ++ |
| 46 | +++ | — | ++ |
| 47 | +++ | — | ++ |
| 48 | ++ | — | ++ |
| 49 | ++ | — | ++ |
| 50 | ++++ | ++++ | ++++ |
| 51 | ++++ | ++++ | +++ |
| 52 | ++++ | ++++ | ++++ |
| 53 | ++++ | ++++ | +++ |
| 54 | ++++ | +++ | +++ |
| 55 | ++++ | ++++ | +++ |
| 56 | ++++ | ++++ | +++ |
| 57 | ++++ | ++++ | +++ |
| 58 | ++++ | +++ | +++ |
| 59 | ++++ | +++ | +++ |
| 60 | ++++ | ++++ | ++++ |
| 61 | ++++ | ++++ | ++++ |
| 62 | ++++ | ++++ | +++ |
| 63 | +++ | — | ++ |
| 64 | +++ | +++ | ++ |
| 65 | +++ | — | — |
| 66 | +++ | +++ | — |
| 67 | ++++ | ++++ | +++ |
| 68 | +++ | — | — |
| 68 | ++++ | ++++ | +++ |
| 70 | ++++ | — | — |
| 71 | ++++ | +++ | +++ |
| 72 | ++++ | ++++ | +++ |
| 73 | ++++ | +++ | +++ |
| 74 | ++++ | +++ | +++ |
| 75 | ++++ | ++++ | ++++ |

TABLE 7-continued

IC$_{50}$ Values

| Example | CDK4_D1 IC$_{50}$ (nM) | CDK6_D1 IC$_{50}$ (nM) | PROLIFERATION_CTG_MCF7 IC$_{50}$ (nM) |
|---|---|---|---|
| 76 | ++++ | — | — |
| 77 | ++++ | ++++ | +++ |
| 78 | ++++ | ++++ | +++ |
| 79 | ++++ | ++++ | +++ |
| 80 | +++ | +++ | ++ |
| 81 | ++++ | ++++ | +++ |
| 82 | ++++ | ++++ | +++ |
| 83 | ++++ | — | +++ |
| 84 | ++++ | ++++ | +++ |
| 85 | ++++ | — | +++ |
| 86 | ++++ | +++ | +++ |
| 87 | ++++ | ++++ | +++ |
| 88 | ++++ | +++ | +++ |
| 89 | ++++ | ++++ | +++ |
| 90 | ++++ | +++ | +++ |
| 91 | ++++ | ++++ | +++ |
| 92 | ++++ | ++++ | +++ |
| 93 | ++++ | +++ | +++ |
| 94 | ++++ | ++++ | +++ |
| 95 | ++++ | +++ | +++ |
| 96 | +++ | — | ++ |
| 97 | ++++ | ++++ | ++++ |
| 98 | ++++ | — | +++ |
| 99 | ++++ | +++ | +++ |
| 100 | +++ | — | ++ |
| 101 | +++ | — | — |
| 102 | ++++ | ++++ | +++ |
| 103 | ++ | — | — |
| 104 | +++ | — | — |
| 105 | ++++ | — | +++ |
| 106 | ++ | — | — |
| 107 | +++ | — | — |
| 108 | ++++ | +++ | +++ |
| 109 | ++++ | +++ | +++ |
| 110 | ++ | — | — |
| 111 | +++ | — | +++ |
| 112 | ++++ | +++ | +++ |
| 113 | ++ | — | — |
| 114 | ++++ | +++ | +++ |
| 115 | ++++ | — | +++ |
| 116 | ++++ | — | — |
| 117 | ++++ | — | — |
| 118 | ++++ | — | ++ |
| 119 | ++ | — | — |
| 120 | ++++ | ++++ | +++ |
| 121 | ++++ | +++ | +++ |
| 122 | +++ | — | — |
| 123 | ++++ | +++ | +++ |
| 124 | ++++ | ++++ | +++ |
| 125 | ++++ | ++++ | +++ |
| 126 | ++++ | ++++ | +++ |
| 127 | +++ | — | — |
| 128 | ++++ | ++++ | ++++ |
| 129 | ++++ | ++++ | ++++ |
| 130 | ++++ | +++ | +++ |
| 131 | +++ | — | — |

In Table 7, a "+" denotes an IC$_{50}$ value of >2000 nM; a "++" denotes an IC$_{50}$ value of 200 nM < IC$_{50}$ ≤ 2000 nM; a "+++" denotes an IC$_{50}$ value of 20 nM < IC$_{50}$ ≤ 200 nM; and a "++++" denotes an IC$_{50}$ value of ≤20 nM.

Example B: Brain-to-Plasma Ratio Determination in Sprague-Dawley Rats

The brain-to-plasma ratio (K$_p$) was determined in male Sprague-Dawley rats (7-9 weeks old) four hours after a single oral dose. Rats were acclimated and given free access to standard rodent chow and water throughout the entire study. Test articles were formulated as a solution at 0.3, 0.4, 0.5, or 1.0 mg/mL in a vehicle comprised of 10:15:75 (v:v:v) dimethylacetamide (DMA):Solutol HS15:water and delivered orally at a rate of 10 mL/kg to three rats to achieve final doses of 3, 4, 5, or 10 mg/kg, respectively. At 4 hours post-dose, blood samples were collected via jugular vein cannula into tubes containing K$_2$EDTA as the anticoagulant and stored on ice. Blood samples were then centrifuged at 4° C. at 6000 rpm for 5 minutes, and the resulting plasma was placed into tubes and stored frozen at −80° C. until analysis. Whole brain samples were also collected at 4 hours post-dose. The weight of each brain was measured and recorded, and samples were immediately stored on dry ice. Brain samples were then transferred to storage at −80° C. until analysis.

Prior to analysis, brain samples were combined with water (4 mL/1 gram of brain) and homogenized. Prior to injection, plasma and brain homogenate samples and standards were prepared for analysis by precipitation with acetonitrile or 1:1 (v:v) methanol:acetonitrile. Samples were then thoroughly mixed, centrifuged at 4000 rpm for 15 minutes, and the resulting supernatant was transferred for analysis. Test article concentrations in plasma and brain homogenate were then determined by LC-MS/MS and quantified against calibration standards prepared to known concentrations in matched blank (analyte-free) biological matrix. The $K_p$ was then determined by dividing the dilution-corrected brain concentration by the plasma concentration from each rat. A brain density of 1 gram/mL was assumed for all calculations.

The results are shown in Table 8, below.

TABLE 8

| $K_p$ Values | |
|---|---|
| Example | $K_p$ |
| 1 | ++ |
| 2 | ++ |
| 3 | + |
| 4 | ++ |
| 8 | ++ |
| 9 | ++ |
| 18 | n.d. |
| 21 | + |
| 23 | +++ |
| 50 | ++ |
| 51 | +++ |
| 52 | ++ |
| 53 | n.d. |
| 54 | + |
| 55 | +++ |
| 56 | +++ |
| 57 | ++ |
| 60 | + |
| 61 | ++ |
| 62 | n.d. |
| 64 | + |
| 67 | n.d. |
| 68 | ++ |
| 71 | n.d. |
| 73 | ++ |
| 74 | + |
| 77 | ++ |
| 78 | ++ |
| 79 | + |
| 81 | n.d. |
| 82 | +++ |
| 84 | ++ |
| 85 | +++ |
| 86 | ++ |
| 87 | ++ |
| 88 | ++ |
| 89 | +++ |
| 90 | + |
| 91 | + |
| 93 | + |
| 94 | n.d. |
| 95 | ++ |
| 97 | + |
| 99 | +++ |
| 102 | ++ |
| 112 | + |
| 114 | ++ |
| 115 | + |
| 120 | ++ |
| 123 | +++ |
| 124 | ++ |
| 125 | ++ |
| 126 | ++ |

TABLE 8-continued

| $K_p$ Values | |
|---|---|
| Example | $K_p$ |
| 128 | ++ |
| 129 | ++ |
| 130 | ++ |

In Table 8, a "+" denotes a $K_p$ value <1.0; a "++" denotes $1.0 \le K_p < 3.0$; a "+++" denotes $K_p$ value $\ge 3.0$; and n.d. denotes a brain concentration below the detectable limit.

What is claimed:
1. A compound of Formula (I)

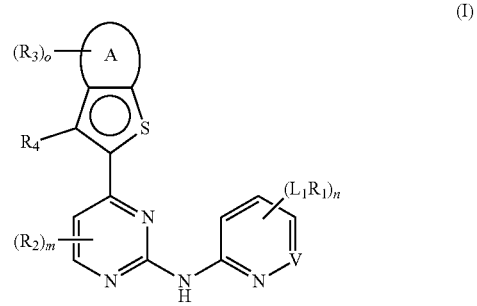

or a pharmaceutically acceptable salt or solvate or N-oxide thereof, wherein
ring A is a 5-7-membered heteroaryl;
V=C$L_1R_1$ or N
n is 1 or 2 or 3;
m is 1 or 2;
o is 1, 2, 3, 4, or 5;
each $L_1$ is independently a bond, O, NR or $C_1$-$C_6$ alkylene, wherein R is H or $C_1$-$C_6$alkyl;
each $R_1$ is independently H, D, halogen, —OH, —CN, —NO$_2$, —C$_1$-C$_6$alkyl, —C$_2$-C$_6$alkenyl, —C$_2$-C$_6$alkynyl, aryl, heteroaryl, cycloalkyl, cycloalkenyl, heterocycloalkyl, or heterocycloalkenyl, —OR$^a$, —SR$^a$, —NR$^c$R$^d$, —NR$^a$R$^c$, —C(O)R$^b$, —OC(O) R$^b$, —C(O)OR$^b$, —C(O)NR$^c$R$^d$, —S(O)R$^b$, —S(O)$_2$NR$^c$R$^d$, —S(O)(=NR$^b$)R$^b$, —SF$_5$, —P(O) R$^b$R$^b$, —P(O)(OR$^b$)(OR$^b$), —B(OR$^c$)(OR$^d$) or —S(O)$_2$R$^b$;
each $R_2$ is independently H, D, halogen, $C_1$-$C_8$ alkoxide $C_1$-$C_8$ alkyl, haloalkyl, or CN and
each $R_3$ is independently H, D, halogen, oxo, —OH, —CN, —NO$_2$, —C$_1$-C$_6$alkyl, —C$_2$-C$_6$alkenyl, —C$_2$-C$_6$alkynyl, C$_0$-C$_1$alk-aryl, C$_0$-C$_1$alk-heteroaryl, cycloalkyl, cycloalkenyl, heterocycloalkyl, or heterocycloalkenyl, —OR$^a$, —OR$^b$, —SR$^b$, —NR$^c$R$^d$, —NR$^a$R$^c$, —C(O)R$^b$, —OC(O)R$^b$, —C(O)OR$^b$, —C(O)NR$^c$R$^d$, —S(O)R$^b$, —S(O)$_2$ NR$^c$R$^d$, —S(O)(=NR)R$^b$, —SF$_5$, —P(O)R$^b$R$^b$, —P(O)(OR$^b$)(OR$^b$), —B(OR$^d$)(OR$^c$) or —S(O)$_2$R$^b$;
each $R^a$ is independently H, D, —C(O)R$^b$, —C(O) OR$^c$, —C(O)NR$^c$R$^d$, —C(=NR$^b$)NR$^b$R$^c$, —C(=NOR$^b$)NR$^b$R$^c$, —C(=NCN)NR$^b$R$^c$, —P(OR$^c$)$_2$, —P(O)R$^c$R$^b$, —P(O)OR$^c$R$^b$, —S(O) R$^b$, —S(O)NR$^c$R$^d$, —S(O)$_2$R$^b$, —S(O)$_2$NR$^c$R$^d$, SiR$^b_3$, —C$_1$-C$_{10}$alkyl, —C$_2$-C$_{10}$ alkenyl, —C$_2$-

C<sub>10</sub> alkynyl, aryl, cycloalkyl, cycloalkenyl, heteroaryl, heterocycloalkyl, or heterocycloalkenyl;

each $R^b$, is independently H, D, —$C_1$-$C_6$ alkyl, —$C_2$-$C_6$ alkenyl, —$C_2$-$C_6$ alkynyl, aryl, cycloalkyl, cycloalkenyl, heteroaryl, heterocycloalkyl, or heterocycloalkenyl;

each $R^c$ or $R^d$ is independently H, D, —$C_1$-$C_{10}$ alkyl, —$C_2$-$C_6$ alkenyl, —$C_2$-$C_6$ alkynyl, —$OC_1$-$C_6$alkyl, —O-cycloalkyl, aryl, heteroaryl, cycloalkyl, cycloalkenyl, heterocycloalkyl, or heterocycloalkenyl;

or $R^c$ and $R^d$, together with the atom to which they are both attached, form a monocyclic or multicyclic heterocycloalkyl, or a monocyclic or multicyclic heterocyclo-alkenyl group;

each $R_4$ is independently H, D, halogen, $C_1$-$C_8$ alkoxide or $C_1$-$C_8$ alkyl, haloalkyl or CN.

2. The compound of claim 1, wherein ring A is a 5-membered heteroaryl having at least one N atom.

3. The compound of claim 2, wherein the 5-membered heteroaryl having at least one N atom is an imidazole.

4. The compound of claim 1, wherein ring A is a 6-membered heteroaryl having at least one N atom.

5. The compound of claim 4, wherein the 6-membered heteroaryl having at least two N atom is a pyrimidine or a pyridazine.

6. The compound of claim 1, wherein n is 1.
7. The compound of claim 1, wherein n is 2.
8. The compound of claim 1, wherein n is 3.
9. The compound of claim 1, wherein m is 1.
10. The compound of claim 1, wherein m is 2.
11. The compound of claim 1, wherein o is 1.
12. The compound of claim 1, wherein o is 2.
13. The compound of claim 1, wherein o is 3.
14. The compound of claim 1, wherein o is 4.
15. The compound of claim 1, wherein o is 5.
16. The compound of claim 1, wherein at least one $R_2$ is H.
17. The compound of claim 1, wherein at least one $R_2$ is halogen.
18. The compound of claim 1, wherein at least one $R_2$ is $C_{1-6}$alkyl.
19. The compound of claim 1, wherein at least one $R_3$ is H.
20. The compound of claim 1, wherein at least one $R_3$ is $C_{1-6}$alkyl.
21. The compound of claim 1, wherein at least one $R_3$ is $C_{3-10}$cycloalkyl.
22. The compound of claim 1, wherein at least one $R^3$ is hydroxyalkyl.
23. The compound of claim 1, wherein at least one $R^3$ is isopropyl.
24. The compound of claim 1, wherein at least one $R^3$ is oxo bound to a nitrogen atom.
25. The compound of claim 1, wherein at least one $R_1$ is an unsubstituted or substituted 6-membered heterocyclalkyl.
26. The compound of claim 25, wherein $R_1$ is an unsubstituted or substituted piperazine.
27. The compound of claim 1, wherein at least one $R_1$ is an unsubstituted or substituted 7-membered heterocycloalkyl.

28. The compound of claim 1, wherein $R_4$ is hydrogen.
29. The compound of claim 1, wherein $R_4$ is methyl.
30. The compound of claim 1 in the form of a pharmaceutically acceptable salt.
31. The compound of claim 1 that is a compound of formula II, formula III, formula IV, formula V, formula VI or formula VII:

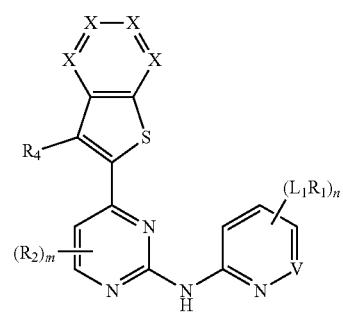

(II)

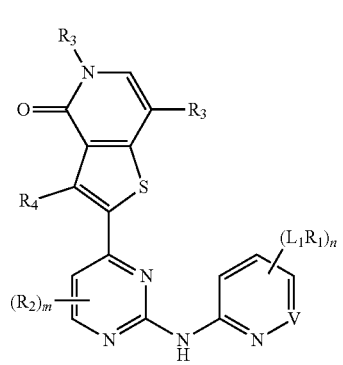

(III)

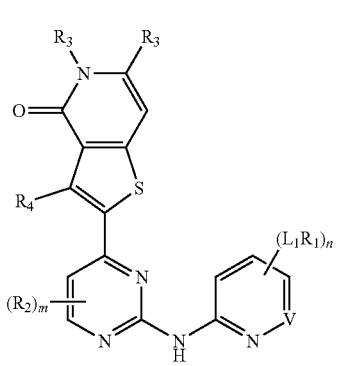

(IIIa)

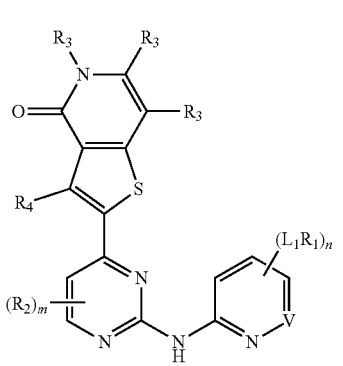

(IIIb)

(IV)
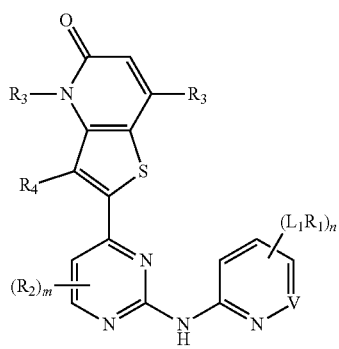
(IVa)
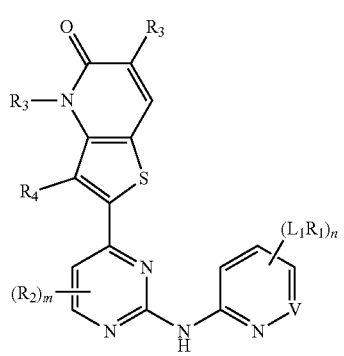
(IVb)
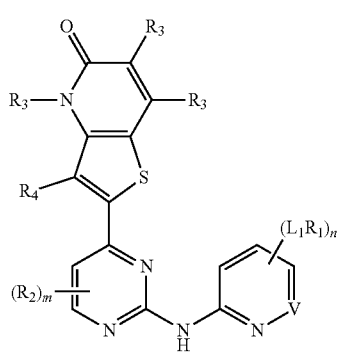
(V)
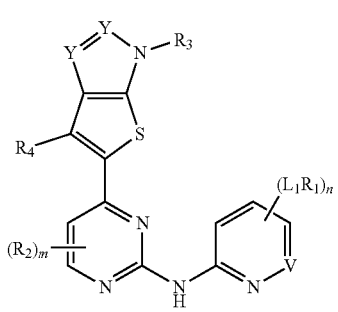
(VI), (VII)
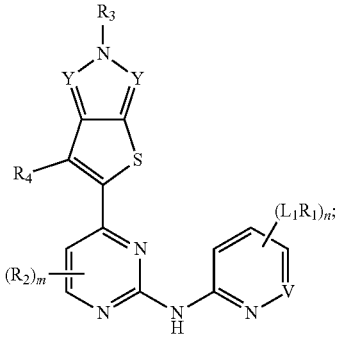
or a pharmaceutically acceptable salt thereof, wherein
each X is independently N, N-oxide or $CR_3$ and at least one X is N or N-oxide; and
each Y is independently N or $CR_3$ and at least one Y is N.
32. The compound of claim 1 that is a compound of formula VIII, formula IX, formula X, formula XI, formula XII, or formula XIII:
(VIII)
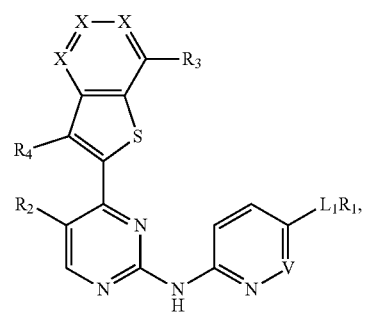
(IX)
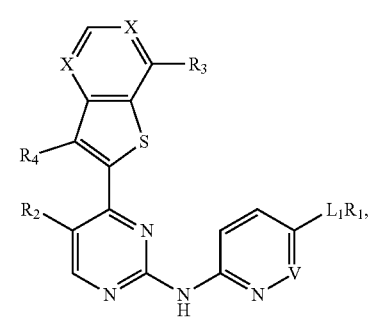
(X)
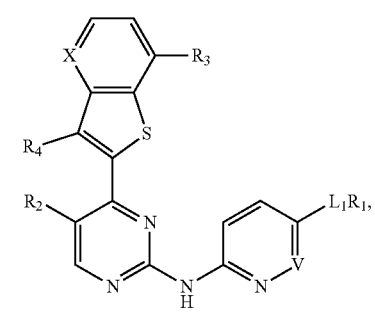

(XI)
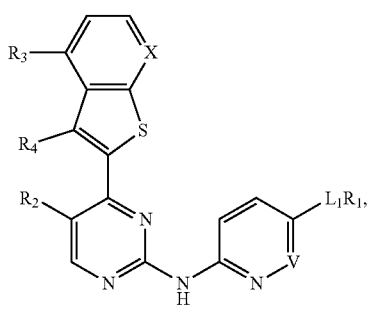

(XII)
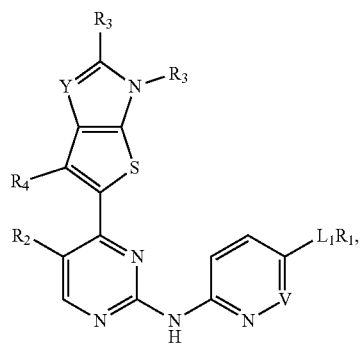

(XIII)
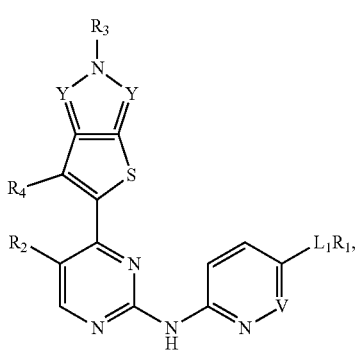

or a pharmaceutically acceptable salt thereof, wherein
each X is independently N, N-oxide or $CR_3$ and at least one X is N or N-oxide; and
Y is N or $CHR_3$.

33. The compound of claim 1 that is a compound of formula XV, formula XVI, formula XVII, formula XVIII, formula XIX, formula XX, formula XXI, formula XXII, formula XXIII, formula XXIV, formula XXV, formula XXVI, or formula XXVII:

(XV)
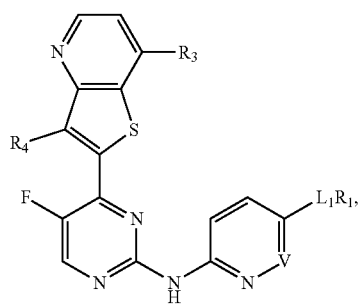

(XVI)
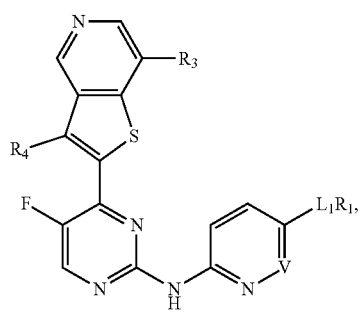

(XVII)
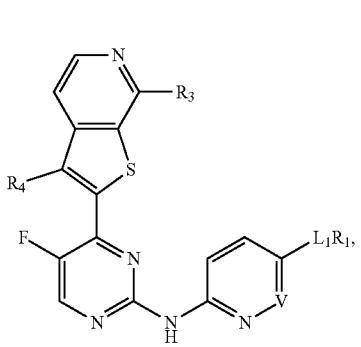

(XVIII)
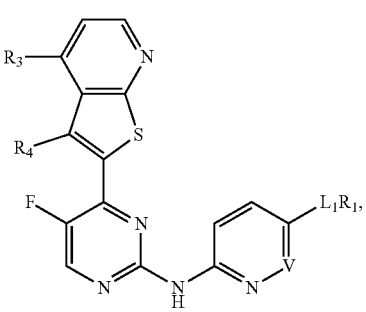

(XIX)
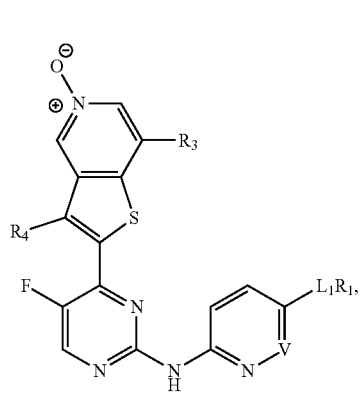

(XX)
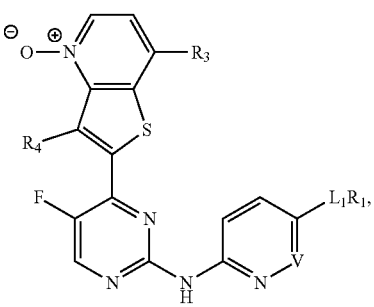

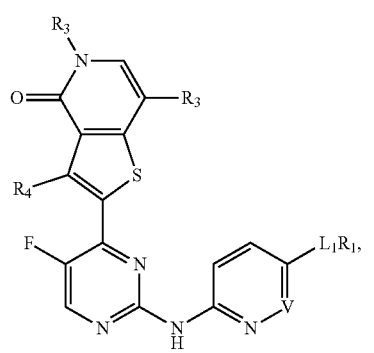
(XXI)
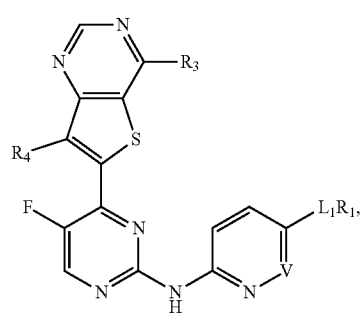
(XXII)
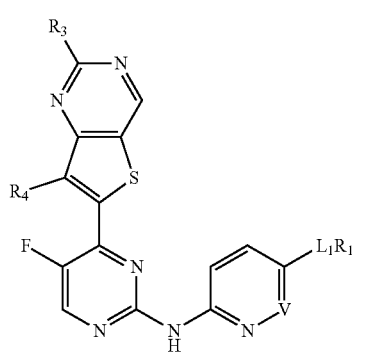
(XXIIIa)
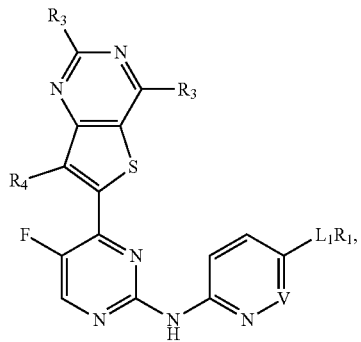
(XXIIIb)
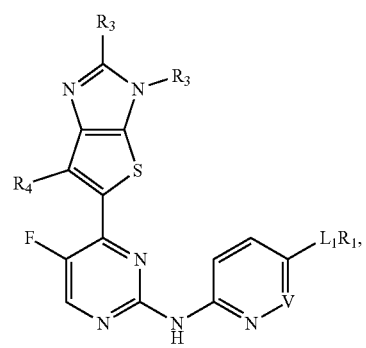
(XXIV)
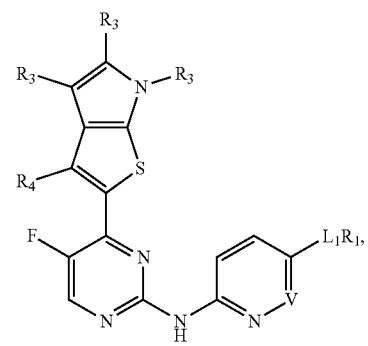
(XXV)
(XXIII)
(XXVI)

(XXVII)

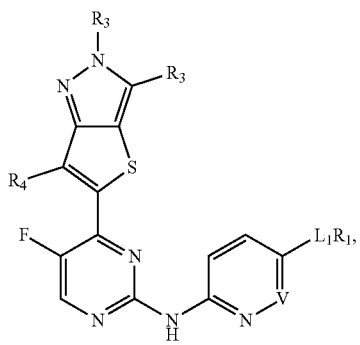

or a pharmaceutically acceptable salt thereof.

34. The compound of claim 1 that is a compound of formula XXIX, formula XXX, formula XXXI, or formula XXXII:

(XXIX)

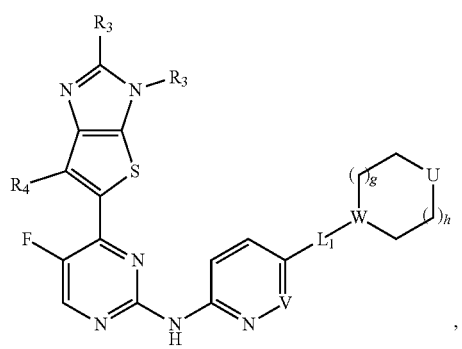

(XXX)

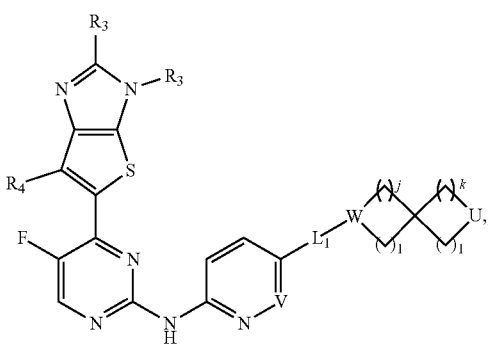

(XXXI)

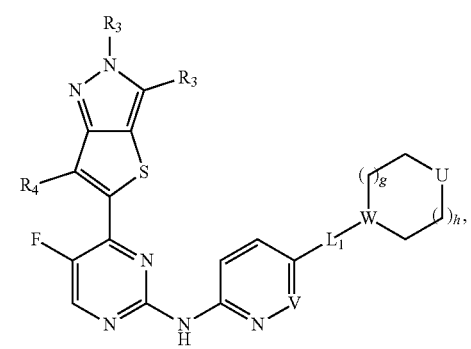

(XXXII)

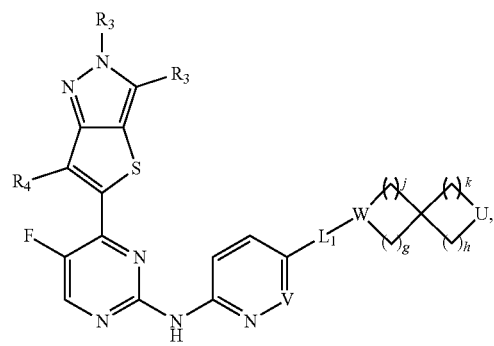

or a pharmaceutically acceptable salt thereof; wherein
W is CH or N;
U is $C(R_{10})_2$, $NR_{10}$, or O;
$R_{10}$ is H, fluoro, $C_{1-6}$alkyl, or $C_{1-6}$alkoxide; and
each g, h, j and k is independently 0, 1, 2 or 3.

35. The compound of claim 1 that is a compound of formula XXXV, formula XXXVI, formula XXXVII, formula XXXVIII, formula XXXIX, formula XL, formula XLI, formula XLII, formula XLIII, or formula XLIV:

(XXXV)

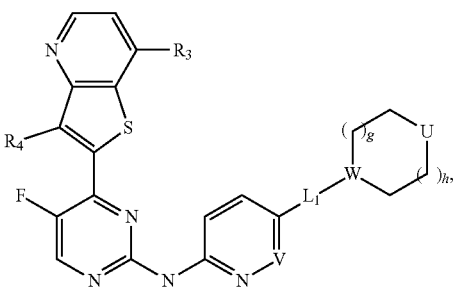

(XXXVI)

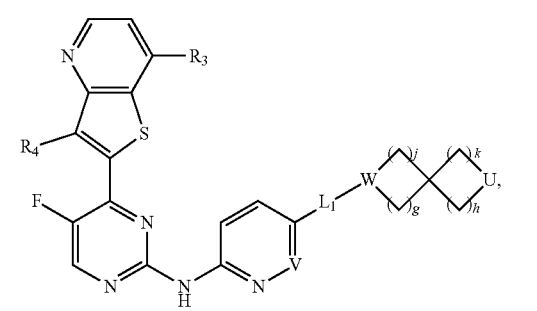

(XXXVII)

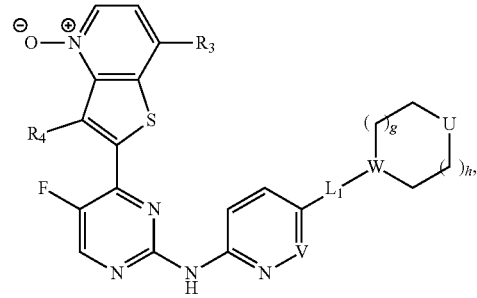

-continued
(XXXVIII)
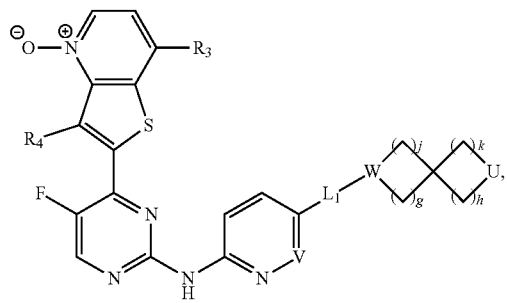
(XXXIX)
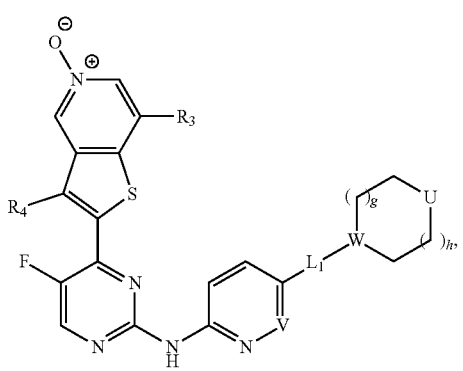
(XL)
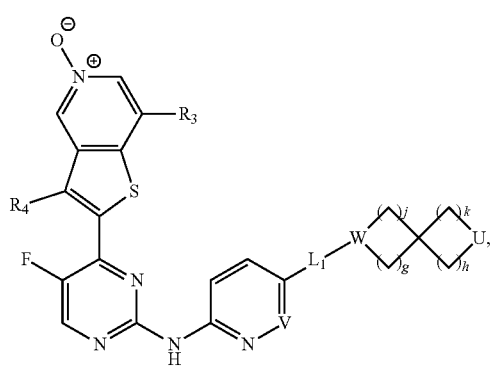
(XLI)
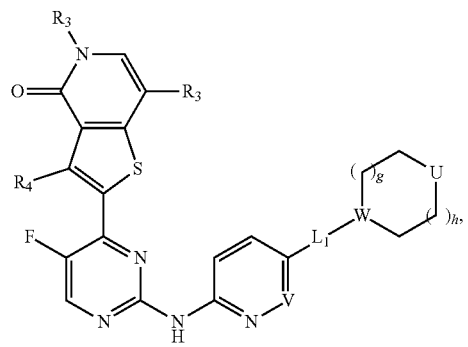
-continued
(XLII)
(XLIII)
(XLIV)
or a pharmaceutically acceptable salt thereof; wherein
W is CH or N;
U is C(R$_{10}$)$_2$, R$_{10}$ or O
R$_{10}$ is H, fluoro, C$_{1-4}$alkyl or C$_{1-4}$alkoxide; and
each g, h, j and k is independently 0, 1, 2 or 3.
36. The compound of claim 1 that is a compound of formula XLV, formula XLVI, formula XLVII, formula XLVIII, formula XLIX or formula L:
(XLV)
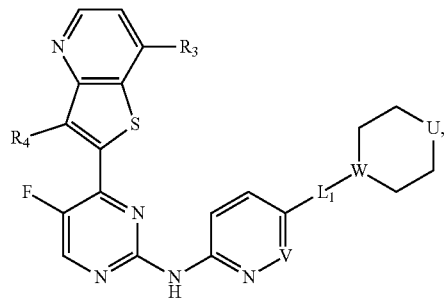

(XLVI)
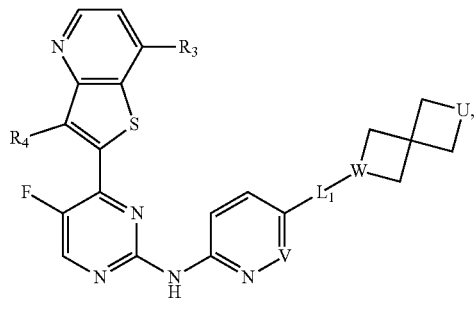
(L)
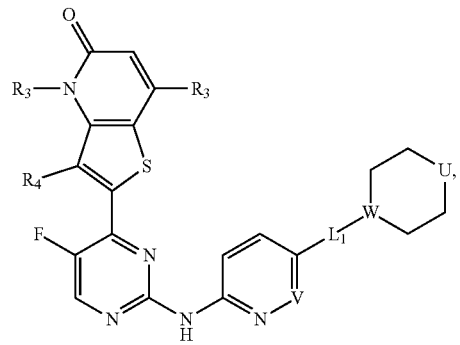
or a pharmaceutically acceptable salt thereof, wherein
W is CH or N;
U is $C(R_{10})_2$, $NR_{10}$ or O;
$R_{10}$ is H, fluoro, $C_{1-4}$alkyl or $C_{1-4}$alkoxide.
37. The compound of claim 1 that is a compound of formula LI, formula LII, formula LIII, or formula LIV:
(XLVII)
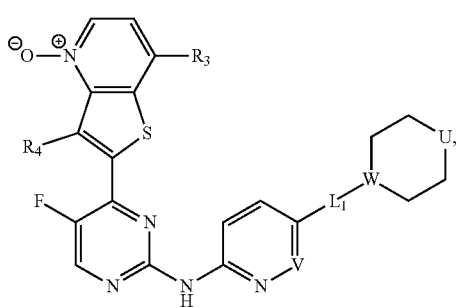
(LI)
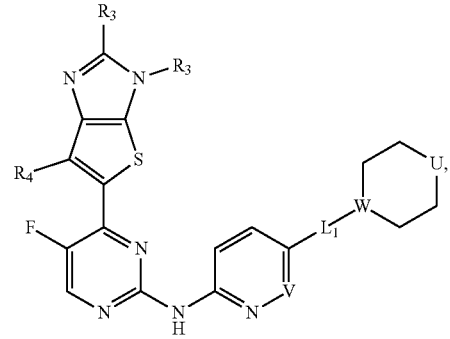
(XLVIII)
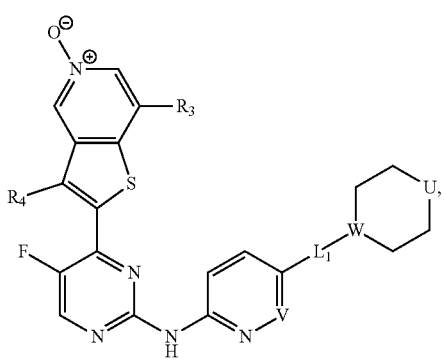
(LII)
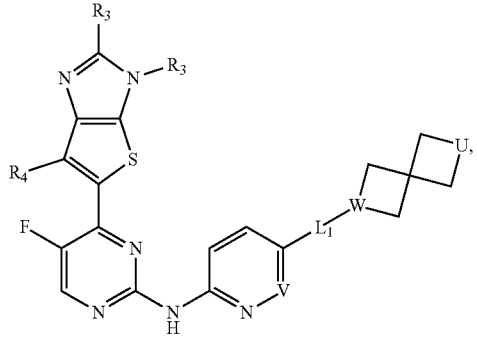
(XLIX)
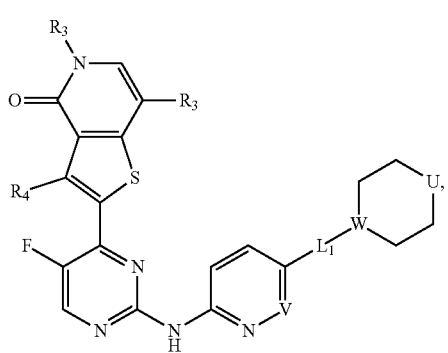
(LIII)
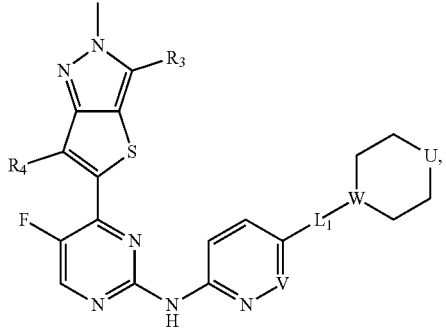

(LIV)

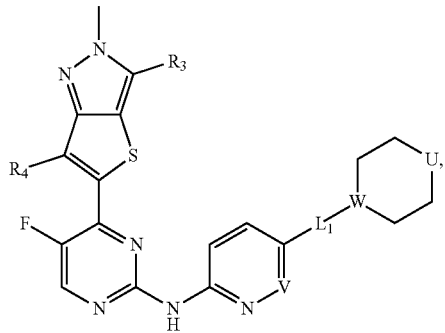

or a pharmaceutically acceptable salt thereof; wherein
W is CH or N;
U is C($R_{10}$)$_2$, N$R_{10}$ or O;
$R_{10}$ is H, fluoro, $C_{1-4}$alkyl or $C_{1-4}$alkoxide.

38. The compound of claim 1 that is a compound of formula LVII, formula LVIII, formula LIX, or formula LX:

(LVII)

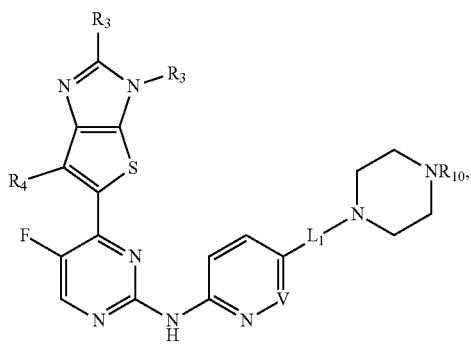

(LVIII)

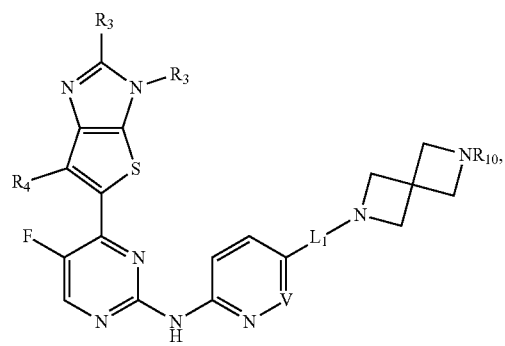

(LIX)

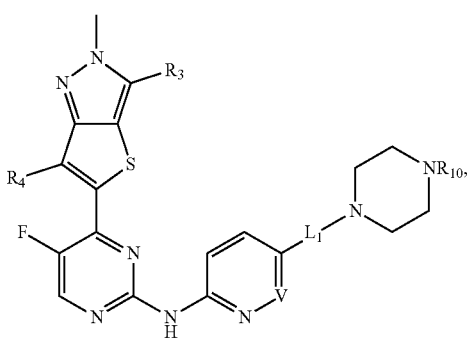

(LX)

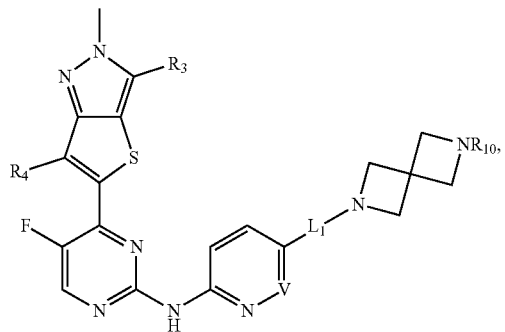

or a pharmaceutically acceptable salt thereof; wherein
$R_{10}$ is H, $C_{1-6}$alkyl, or $C_{1-6}$alkoxide.

39. The compound of claim 1 that is a compound of formula LXIII, formula LXIV, formula LXV, formula LXVI, formula LXVII or formula LXVIII:

(LXIII)

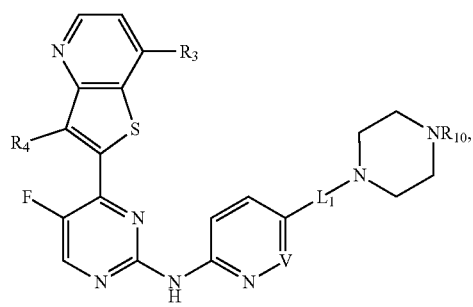

(LXIV)

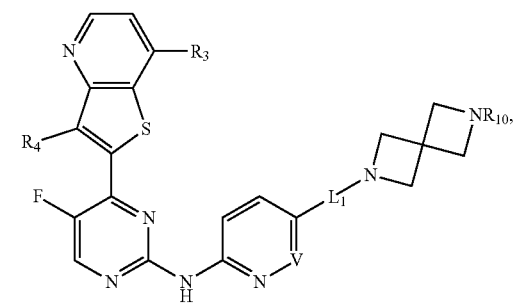

(LXV)

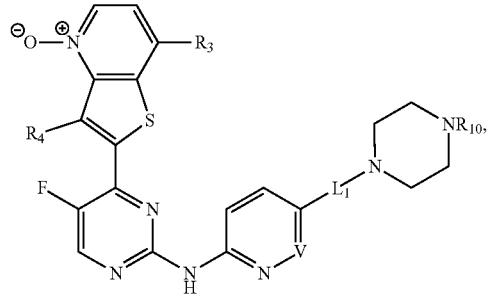

(LXVI)

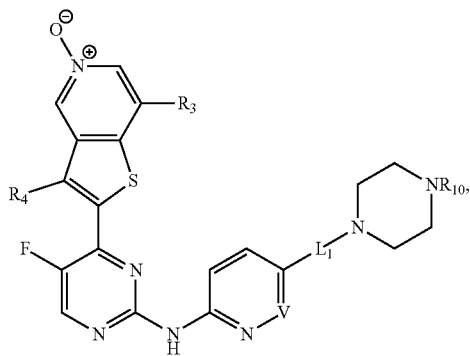

(LXVII)

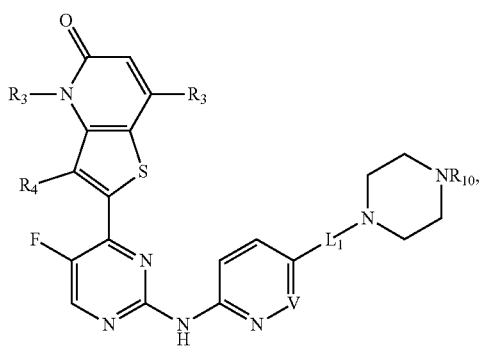

(LXVIII)

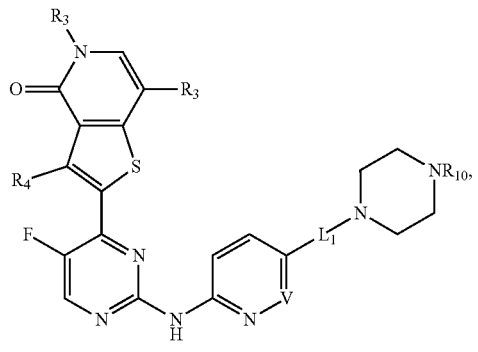

or a pharmaceutically acceptable salt thereof; wherein $R_{10}$ is H, $C_{1-4}$alkyl or $C_{1-4}$alkoxide.

40. The compound of claim 1 that is:
4-(3-Cyclopentyl-2,6-dimethyl-3H-thieno[2,3-d]imidazol-5-yl)-N-(5-(4-ethylpiperazin-1-yl)pyridin-2-yl)-5-fluoropyrimidin-2-amine;
N-(5-(4-Ethylpiperazin-1-yl)pyridin-2-yl)-5-fluoro-4-(3-isopropyl-2,6-dimethyl-3H-thieno[2,3-d]imidazol-5-yl)pyrimidin-2-amine;
N-(5-((4-Ethylpiperazin-1-yl)methyl)pyridin-2-yl)-5-fluoro-4-(3-isopropyl-2,6-dimethyl-3H-thieno[2,3-d]imidazol-5-yl)pyrimidin-2-amine;
4-(3-Cyclobutyl-2,6-dimethylthieno[2,3-d]imidazol-5-yl)-N-[5-(4-ethylpiperazin-1-yl)pyridin-2-yl]-5-fluoropyrimidin-2-amine;
4-(3-Cyclopentyl-2,6-dimethyl-3H-thieno[2,3-d]imidazol-5-yl)-N-(5-(1-ethylpiperidin-4-yl)pyridin-2-yl)-5-fluoropyrimidin-2-amine;
4-(3-Cyclopentyl-2,6-dimethyl-3H-thieno[2,3-d]imidazol-5-yl)-5-fluoro-N-(5-(1-methylpiperidin-4-yl)pyridin-2-yl)pyrimidin-2-amine;
4-(3-Cyclopentyl-2,6-dimethyl-3H-thieno[2,3-d]imidazol-5-yl)-5-fluoro-N-(5-(4-methylpiperazin-1-yl)pyridin-2-yl)pyrimidin-2-amine;
4-(3-Cyclobutyl-2,6-dimethyl-3H-thieno[2,3-d]imidazol-5-yl)-N-(5-(1-ethylpiperidin-4-yl)pyridin-2-yl)-5-fluoropyrimidin-2-amine;
5-Fluoro-4-(3-isopropyl-2,6-dimethyl-3H-thieno[2,3-d]imidazol-5-yl)-N-(5-(4-methylpiperazin-1-yl)pyridin-2-yl)pyrimidin-2-amine;
4-(3-Cyclobutyl-2,6-dimethylthieno[2,3-d]imidazol-5-yl)-N-[5-[(4-ethylpiperazin-1-yl)methyl]pyridin-2-yl]-5-fluoropyrimidin-2-amine;
4-(3-Cyclopentyl-2,6-dimethyl-3H-thieno[2,3-d]imidazol-5-yl)-N-(5-(3,3-difluoropyrrolidin-1-yl)pyridin-2-yl)-5-fluoropyrimidin-2-amine;
4-(3-Cyclopentyl-2,6-dimethyl-3H-thieno[2,3-d]imidazol-5-yl)-N-(5-((4-ethylpiperazin-1-yl)methyl)pyridin-2-yl)-5-fluoropyrimidin-2-amine;
4-(3-Cyclopentyl-2-methyl-3H-thieno[2,3-d]imidazol-5-yl)-5-fluoro-N-(5-(4-methylpiperazin-1-yl)pyridin-2-yl)pyrimidin-2-amine;
N-[5-(4-Ethylpiperazin-1-yl)pyridin-2-yl]-5-fluoro-4-(7-propan-2-ylthieno[3,2-b]pyridin-2-yl)pyrimidin-2-amine;
4-(7-Cyclopentylthieno[3,2-b]pyridin-2-yl)-N-[5-(6-ethyl-2,6-diazaspiro[3.3]heptan-2-yl)pyridin-2-yl]-5-fluoropyrimidin-2-amine;
4-(3-Chloro-7-cyclopentylthieno[3,2-b]pyridin-2-yl)-N-[5-(4-ethylpiperazin-1-yl)pyridin-2-yl]-5-fluoropyrimidin-2-amine;
2-[2-[2-[[5-(4-Ethylpiperazin-1-yl)pyridin-2-yl]amino]-5-fluoropyrimidin-4-yl]thieno[3,2-b]pyridin-7-yl]propan-2-ol;
2-[2-[2-[[5-(6-Ethyl-2,6-diazaspiro[3.3]heptan-2-yl)pyridin-2-yl]amino]-5-fluoropyrimidin-4-yl]thieno[3,2-b]pyridin-7-yl]-1,1,1-trifluoropropan-2-ol;
N-[5-[(4-Ethylpiperazin-1-yl)methyl]pyridin-2-yl]-5-fluoro-4-(7-propan-2-ylthieno[3,2-b]pyridin-2-yl)pyrimidin-2-amine;
4-(3-Chloro-7-cyclopentylthieno[3,2-b]pyridin-2-yl)-N-[5-(1-ethylpiperidin-4-yl)pyridin-2-yl]-5-fluoropyrimidin-2-amine;
2-[2-[2-[[5-(6-Ethyl-2,6-diazaspiro[3.3]heptan-2-yl)pyridin-2-yl]amino]-5-fluoropyrimidin-4-yl]thieno[3,2-b]pyridin-7-yl]propan-2-ol;
4-(7-Cyclopentyl-3-methylthieno[3,2-b]pyridin-2-yl)-N-(5-((4-ethylpiperazin-1-yl)methyl)pyridin-2-yl)-5-fluoropyrimidin-2-amine;
N-[5-(6-Ethyl-2,6-diazaspiro[3.3]heptan-2-yl)pyridin-2-yl]-5-fluoro-4-(7-propan-2-ylthieno[3,2-b]pyridin-2-yl)pyrimidin-2-amine;
4-(7-Cyclopentylthieno[3,2-b]pyridin-2-yl)-N-[5-(4-ethylpiperazin-1-yl)pyridin-2-yl]-5-fluoropyrimidin-2-amine;
2-[2-[2-[[5-[(4-Ethylpiperazin-1-yl)methyl]pyridin-2-yl]amino]-5-fluoropyrimidin-4-yl]thieno[3,2-b]pyridin-7-yl]-1,1,1-trifluoropropan-2-ol;
4-(7-Cyclopentyl-3-methylthieno[3,2-b]pyridin-2-yl)-5-fluoro-N-(5-(1-methylpiperidin-4-yl)pyridin-2-yl)pyrimidin-2-amine;
2-[2-[2-[[5-[(4-Ethylpiperazin-1-yl)methyl]pyridin-2-yl]amino]-5-fluoropyrimidin-4-yl]thieno[3,2-b]pyridin-7-yl]propan-2-ol;
4-(7-Cyclopentyl-3-methylthieno[3,2-b]pyridin-2-yl)-5-fluoro-N-(5-(4-methylpiperazin-1-yl)pyridin-2-yl)pyrimidin-2-amine;

2-[2-[2-[[5-(4-Ethylpiperazin-1-yl)pyridin-2-yl]amino]-5-fluoropyrimidin-4-yl]thieno[3,2-b]pyridin-7-yl]-1,1,1-trifluoropropan-2-ol;

4-(3-Chloro-7-cyclopentylthieno[3,2-b]pyridin-2-yl)-N-[5-[(4-ethylpiperazin-1-yl)methyl]pyridin-2-yl]-5-fluoropyrimidin-2-amine;

4-(7-Cyclopentyl-3-methylthieno[3,2-b]pyridin-2-yl)-N-(5-(4-ethylpiperazin-1-yl)pyridin-2-yl)-5-fluoropyrimidin-2-amine;

N-(5-(2,6-Diazaspiro[3.3]heptan-2-yl)pyridin-2-yl)-4-(7-cyclopentyl-3-methylthieno[3,2-b]pyridin-2-yl)-5-fluoropyrimidin-2-amine;

4-(7-Cyclopentylthieno[3,2-b]pyridin-2-yl)-N-[5-[(4-ethylpiperazin-1-yl)methyl]pyridin-2-yl]-5-fluoropyrimidin-2-amine;

4-(7-Cyclopentylthieno[3,2-b]pyridin-2-yl)-5-fluoro-N-(5-(1-methylpiperidin-4-yl)pyridin-2-yl)pyrimidin-2-amine;

4-(7-Cyclopentyl-3-methylthieno[3,2-b]pyridin-2-yl)-5-fluoro-N-(5-(piperazin-1-yl)pyridin-2-yl)pyrimidin-2-amine;

4-(7-Cyclopentylthieno[3,2-b]pyridin-2-yl)-5-fluoro-N-(5-piperazin-1-ylpyridin-2-yl)pyrimidin-2-amine;

4-(7-Cyclopentylthieno[3,2-b]pyridin-2-yl)-5-fluoro-N-[5-(4-methylpiperazin-1-yl)pyridin-2-yl]pyrimidin-2-amine;

4-(7-Cyclopentyl-3-methylthieno[3,2-b]pyridin-2-yl)-5-fluoro-N-(5-morpholinopyridin-2-yl)pyrimidin-2-amine;

4-(7-Cyclopentylthieno[3,2-b]pyridin-2-yl)-5-fluoro-N-[5-(4-methoxypiperidin-1-yl)pyridin-2-yl]pyrimidin-2-amine;

4-(7-Cyclopentylthieno[3,2-b]pyridin-2-yl)-5-fluoro-N-(5-morpholinopyridin-2-yl)pyrimidin-2-amine;

4-(7-Cyclopentylthieno[3,2-b]pyridin-2-yl)-N-[5-(3,3-difluoropyrrolidin-1-yl)pyridin-2-yl]-5-fluoropyrimidin-2-amine;

4-(4-Cyclopentylthieno[2,3-b]pyridin-2-yl)-5-fluoro-N-(5-morpholin-4-ylpyridin-2-yl)pyrimidin-2-amine;

4-(4-Cyclopentylthieno[2,3-b]pyridin-2-yl)-5-fluoro-N-(5-(1-methylpiperidin-4-yl)pyridin-2-yl)pyrimidin-2-amine;

4-(4-Cyclopentylthieno[2,3-b]pyridin-2-yl)-N-[5-(4-ethylpiperazin-1-yl)pyridin-2-yl]-5-fluoropyrimidin-2-amine;

4-(4-Cyclopentylthieno[2,3-b]pyridin-2-yl)-5-fluoro-N-[5-(4-methylpiperazin-1-yl)pyridin-2-yl]pyrimidin-2-amine;

4-(4-Cyclopentylthieno[2,3-b]pyridin-2-yl)-5-fluoro-N-(5-piperazin-1-ylpyridin-2-yl)pyrimidin-2-amine;

4-(4-Cyclopentylthieno[2,3-b]pyridin-2-yl)-N-[5-(6-ethyl-2,6-diazaspiro[3.3]heptan-2-yl)pyridin-2-yl]-5-fluoropyrimidin-2-amine;

4-(7-Cyclopentyl-3-methylthieno[2,3-c]pyridin-2-yl)-5-fluoro-N-(5-(4-methylpiperazin-1-yl)pyridin-2-yl)pyrimidin-2-amine;

4-(4-Cyclopentyl-7-methylthieno[3,2-d]pyrimidin-6-yl)-5-fluoro-N-(5-(1-methylpiperidin-4-yl)pyridin-2-yl)pyrimidin-2-amine;

N-[5-(4-Ethylpiperazin-1-yl)pyridin-2-yl]-5-fluoro-4-(4-oxido-7-propan-2-ylthieno[3,2-b]pyridin-4-ium-2-yl)pyrimidin-2-amine;

2-[5-Fluoro-2-[[5-(4-methylpiperazin-1-yl)pyridin-2-yl]amino]pyrimidin-4-yl]-3,5-dimethyl-7-propan-2-ylthieno[3,2-c]pyridin-4-one;

4-(2,6-Dimethyl-3-propan-2-ylthieno[2,3-d]imidazol-5-yl)-N-[5-(6-ethyl-2,6-diazaspiro [3.3]heptan-2-yl)pyridin-2-yl]-5-fluoropyrimidin-2-amine;

6-(6-Ethyl-2,6-diazaspiro[3.3]heptan-2-yl)-N-(5-fluoro-4-(3-isopropyl-2,6-dimethyl-3H-thieno[2,3-d]imidazol-5-yl)pyridin-2-yl)pyridazin-3-amine;

(4-Ethylpiperazin-1-yl)-[6-[[5-fluoro-4-(2-methyl-3-propan-2-ylthieno[2,3-d]imidazol-5-yl)pyrimidin-2-yl]amino]pyridin-3-yl]methanone;

4-(2,6-Dimethyl-3-propan-2-ylthieno[3,2-c]pyrazol-5-yl)-N-[5-(6-ethyl-2,6-diazaspiro[3.3]heptan-2-yl)pyridin-2-yl]-5-fluoropyrimidin-2-amine;

2-(5-Fluoro-2-((5-(1-methylpiperidin-4-yl)pyridin-2-yl)amino)pyrimidin-4-yl)-7-isopropyl-3,5-dimethylthieno[3,2-c]pyridin-4(5H)-one;

2-(2-((5-(6-Ethyl-2,6-diazaspiro[3.3]heptan-2-yl)pyridin-2-yl)amino)-5-fluoropyrimidin-4-yl)-7-isopropyl-3,5-dimethylthieno[3,2-c]pyridin-4(5H)-one;

2-(2-((5-(6-Ethyl-3,6-diazabicyclo[3.1.1]heptan-3-yl)pyridin-2-yl)amino)-5-fluoropyrimidin-4-yl)-7-isopropyl-5-methylthieno[3,2-c]pyridin-4(5H)-one;

2-(2-((5-(4-Ethylpiperazine-1-carbonyl)pyridin-2-yl)amino)-5-fluoropyrimidin-4-yl)-7-isopropyl-5-methylthieno[3,2-c]pyridin-4(5H)-one;

2-(5-Fluoro-2-((5-(1-methylpiperidin-4-yl)pyridin-2-yl)amino)pyrimidin-4-yl)-7-isopropyl-3-methylthieno[3,2-c]pyridin-4(5H)-one;

2-(5-Fluoro-2-((5-(6-methyl-2,6-diazaspiro[3.4]octan-2-yl)pyridin-2-yl)amino)pyrimidin-4-yl)-7-isopropyl-3,5-dimethylthieno[3,2-c]pyridin-4(5H)-one;

6-(2-((5-(6-Ethyl-2,6-diazaspiro[3.3]heptan-2-yl)pyridin-2-yl)amino)-5-fluoropyrimidin-4-yl)-1-isopropyl-5-methylthieno[2,3-d]pyrimidin-4(1H)-one;

2-(2-((5-(6-Ethyl-2,6-diazaspiro[3.3]heptan-2-yl)pyridin-2-yl)amino)-5-fluoropyrimidin-4-yl)-7-isopropyl-3,5-dimethylthieno[2,3-d]pyridazin-4(5H)-one;

or a pharmaceutically acceptable salt thereof.

41. The compound of claim 1 that is:

N-[5-[[4-(2,2-Difluoroethyl)piperazin-1-yl]methyl]pyridin-2-yl]-5-fluoro-4-(2-methyl-3-propan-2-ylthieno[2,3-d]imidazol-5-yl) pyrimidin-2-amine;

1-[[6-[[5-Fluoro-4-(2-methyl-3-propan-2-ylthieno[2,3-d]imidazol-5-yl)pyrimidin-2-yl]amino]pyridin-3-yl]methyl]-N,N-dimethylpyrrolidine-3-carboxamide;

4-(2,6-Dimethyl-3-propan-2-ylthieno[2,3-d]imidazol-5-yl)-5-fluoro-N-pyridin-2-ylpyrimidin-2-amine;

4-(2,6-Dimethyl-3-propan-2-ylthieno[2,3-d]imidazol-5-yl)-5-fluoro-N-[5-(1-methyl-1,6-diazaspiro[3.3]heptan-6-yl) pyridin-2-yl]pyrimidin-2-amine;

4-(2,6-Dimethyl-3-propan-2-ylthieno[2,3-d]imidazol-5-yl)-N-[5-(4-ethyl-6,6-difluoro-1,4-diazepan-1-yl)pyridin-2-yl]-5-fluoropyrimidin-2-amine;

4-(2,6-Dimethyl-3-propan-2-ylthieno[2,3-d]imidazol-5-yl)-5-fluoro-N-[5-[2,2,3,3,5,5,6,6-octadeuterio-4-(trideuteriomethyl)piperazin-1-yl]pyridin-2-yl]pyrimidin-2-amine;

N-[5-(5,5-Difluoro-7-methyl-2,7-diazaspiro[3.4]octan-2-yl)pyridin-2-yl]-4-(2,6-dimethyl-3-propan-2-ylthieno[2,3-d] imidazol-5-yl)-5-fluoropyrimidin-2-amine;

(6-Dthyl-2,6-diazaspiro[3.3]heptan-2-yl)-[6-[[5-fluoro-4-(2-methyl-3-propan-2-ylthieno[2,3-d] imidazol-5-yl)pyrimidin-2-yl]amino]pyridin-3-yl]methanone;

N-[5-[3-(Dimethylamino) azetidin-1-yl]pyridin-2-yl]-5-fluoro-4-(2-methyl-3-propan-2-ylthieno[2,3-d]imidazol-5-yl)pyrimidin-2-amine;

N-[5-[3-(Dimethylamino) pyrrolidin-1-yl]pyridin-2-yl]-4-(2,6-dimethyl-3-propan-2-ylthieno[2,3-d]imidazol-5-yl)-5-fluoropyrimidin-2-amine;

N-[5-(6-ethyl-3,6-Diazabicyclo[3.1.1]heptan-3-yl)pyridin-2-yl]-5-fluoro-4-(2-methyl-3-propan-2-ylthieno[2,3-d]imidazol-5-yl)pyrimidin-2-amine;

1-[6-[[4-(2,6-Dimethyl-3-propan-2-ylthieno[2,3-d]imidazol-5-yl)-5-fluoropyrimidin-2-yl]amino]pyridin-3-yl]-4-methylpiperazin-2-one;

2-(5-Fluoro-2-((5-(7-methyl-2,7-diazaspiro[4.4]nonan-2-yl)pyridin-2-yl)amino) pyrimidin-4-yl)-7-isopropyl-3,5-dimethylthieno[3,2-c]pyridin-4(5H)-one;

2-(5-Fluoro-2-((5-(7-methyl-2,7-diazaspiro[3.5]nonan-2-yl)pyridin-2-yl)amino) pyrimidin-4-yl)-7-isopropyl-3,5-dimethylthieno[3,2-c]pyridin-4(5H)-one;

2-(5-Fluoro-2-((5-((3aR,6aS)-5-methylhexahydropyrrolo[3,4-c]pyrrol-2(1H)-yl)pyridin-2-yl)amino)pyrimidin-4-yl)-7-isopropyl-3,5-dimethylthieno [3,2-c]pyridin-4(5H)-one;

2-(5-Fluoro-2-((5-((3aS,6aS)-5-methylhexahydropyrrolo[3,4-c]pyrrol-2(1H)-yl)pyridin-2-yl)amino)pyrimidin-4-yl)-7-isopropyl-3,5-dimethylthieno [3,2-c]pyridin-4(5H)-one;

2-(5-Fluoro-2-((5-(4-(2,2,2-trifluoroethyl)piperazin-1-yl)pyridin-2-yl)amino) pyrimidin-4-yl)-7-isopropyl-3,5-dimethylthieno [3,2-c]pyridin-4(5H)-one;

2-(2-((5-(5-Ethyl-2,5-diazabicyclo[2.2.1]heptan-2-yl)pyridin-2-yl)amino)-5-fluoropyrimidin-4-yl)-7-isopropyl-5-methylthieno [3,2-c]pyridin-4(5H)-one;

2-(5-Fluoro-2-((5-(1-(methyl-d3)piperidin-4-yl)pyridin-2-yl)amino) pyrimidin-4-yl)-7-isopropyl-3,5-dimethylthieno[3,2-c]pyridin-4(5H)-one;

2-(2-((5-(1,4-Diazabicyclo[3.2.2]nonan-4-yl)pyridin-2-yl)amino)-5-fluoropyrimidin-4-yl)-7-isopropyl-3,5-dimethylthieno [3,2-c]pyridin-4(5H)-one;

2-(5-Fluoro-2-((5-(1-(tetrahydrofuran-3-yl)piperidin-4-yl)pyridin-2-yl)amino)pyrimidin-4-yl)-7-isopropyl-3,5-dimethylthieno [3,2-c]pyridin-4(5H)-one;

2-(5-Fluoro-2-((5-(1-methylpiperidin-4-yl)pyridin-2-yl)amino) pyrimidin-4-yl)-7-isopropyl-3-methyl-5-(methyl-d3)thieno[3,2-c]pyridin-4(5H)-one;

2-(5-Fluoro-2-((5-(1-methylpiperidin-4-yl)pyridin-2-yl)amino) pyrimidin-4-yl)-7-isopropyl-5-methylthieno[3,2-c]pyridin-4(5H)-one;

2-(2-((5-(1-Ethylpiperidin-4-yl)pyridin-2-yl)amino)-5-fluoropyrimidin-4-yl)-7-isopropyl-3,5-dimethylthieno [3,2-c]pyridin-4(5H)-one;

2-(5-Fluoro-2-((5-(1-methylpiperidin-3-yl)pyridin-2-yl)amino) pyrimidin-4-yl)-7-isopropyl-3,5-dimethylthieno [3,2-c]pyridin-4(5H)-one;

2-(5-Fluoro-2-((5-(4-isopropylpiperazin-1-yl)pyridin-2-yl)amino) pyrimidin-4-yl)-7-isopropyl-3,5-dimethylthieno[3,2-c]pyridin-4(5H)-one;

2-(2-((5-((4-Ethylpiperazin-1-yl)methyl)pyridin-2-yl)amino)-5-fluoropyrimidin-4-yl)-7-isopropyl-3,5-dimethylthieno[3,2-c] pyridin-4(5H)-one;

2-(5-Fluoro-2-((5-(2-methyl-2,7-diazaspiro[3.5]nonan-7-yl)pyridin-2-yl)amino) pyrimidin-4-yl)-7-isopropyl-3,5-dimethylthieno[3,2-c]pyridin-4(5H)-one;

2-(5-Fluoro-2-((5-(6-isopropyl-2,6-diazaspiro[3.3]heptan-2-yl)pyridin-2-yl)amino) pyrimidin-4-yl)-7-isopropyl-3,5-dimethylthieno[3,2-c]pyridin-4(5H)-one;

2-(5-Fluoro-2-((6-(1-methylpiperidin-4-yl)pyridazin-3-yl)amino)pyrimidin-4-yl)-7-isopropyl-3,5-dimethylthieno [3,2-c]pyridin-4(5H)-one;

2-(5-Fluoro-2-((5-(piperidin-4-yl)pyridin-2-yl)amino) pyrimidin-4-yl)-7-isopropyl-3,5-dimethylthieno [3,2-c]pyridin-4(5H)-one;

2-(5-Fluoro-2-((5-(1-isopropylpyrrolidin-3-yl)pyridin-2-yl)amino)pyrimidin-4-yl)-7-isopropyl-3,5-dimethylthieno [3,2-c]pyridin-4(5H)-one;

7-Isopropyl-5-methyl-2-(2-((5-(1-methylpiperidin-4-yl)pyridine-2-yl)amino) pyrimidin-4-yl)thieno[3,2-c]pyridin-4(5H)-one;

7-Isopropyl-5-methyl-2-(5-methyl-2-((5-(1-methylpiperidin-4-yl)pyridin-2-yl)amino)pyrimidin-4-yl)thieno [3,2-c]pyridin-4(5H)-one;

4-(6-((5-Fluoro-4-(7-isopropyl-3,5-dimethyl-4-oxo-4,5-dihydrothieno[3,2-c]pyridin-2-yl)pyrimidin-2-yl) amino) pyridin-3-yl)-1-methylpiperidine 1-oxide;

5-Fluoro-4-(3-isopropyl-2-methyl-2H-thieno[3,2-c]pyrazol-5-yl)-N-(5-(1-methylpiperidin-4-yl)pyridin-2-yl) pyrimidin-2-amine;

N-(5-((4-Ethylpiperazin-1-yl)methyl)pyridin-2-yl)-5-fluoro-4-(3-isopropyl-6-methyl-2H-thieno[3,2-c]pyrazol-5-yl)pyrimidin-2-amine;

4-(3-Cyclopropyl-2,6-dimethyl-2H-thieno[3,2-c]pyrazol-5-yl)-N-(5-(6-ethyl-2,6-diazaspiro[3.3]heptan-2-yl) pyridin-2-yl)-5-fluoropyrimidin-2-amine;

2-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)-1,1,1-trifluoropropan-2-ol;

1-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)ethan-1-one;

1-(5-(2-((5-(4-Ethylpiperazin-1-yl)pyridin-2-yl)amino)-5-fluoropyrimidin-4-yl)-2,6-dimethyl-2H-thieno[3,2-c]pyrazol-3-yl)ethan-1-ol;

N-(5-(6-Ethyl-2,6-diazaspiro[3.3]heptan-2-yl)pyridin-2-yl)-5-fluoro-4-(3-(2-methoxypropan-2-yl)-2,6-dimethyl-2H-thieno[3,2-c]pyrazol-5-yl)pyrimidin-2-amine;

4-(1,6-dimethyl-3-propan-2-ylthieno[3,2-c]pyrazol-5-yl)-N-[5-(4-ethylpiperazin-1-yl) pyridin-2-yl]-5-fluoropyrimidin-2-amine;

N-(5-Fluoro-4-(3-isopropyl-2-methyl-3H-thieno[2,3-d]imidazol-5-yl)pyrimidin-2-yl)pyridazin-3-amine;

5-Fluoro-4-(3-isopropyl-2,6-dimethyl-3H-thieno[2,3-d]imidazol-5-yl)-N-(5-(1-methylazetidin-3-yl)pyridin-2-yl)pyrimidin-2-amine;

tert-Butyl 3-(2-(2-((5-(6-ethyl-2,6-diazaspiro[3.3]heptan-2-yl)pyridin-2-yl)amino)-5-fluoropyrimidin-4-yl)-5-methyl-4-oxo-4,5-dihydrothieno[2,3-d]pyridazin-7-yl)azetidine-1-carboxylate;

2-(5-Fluoro-2-((5-(1-methylpiperidin-4-yl)pyridin-2-yl)amino)pyrimidin-4-yl)-7-(3-fluorobicyclo[1.1.1]pentan-1-yl)-5-methylthieno[2,3-d]pyridazin-4(5H)-one;

5-(2-((5-(6-Ethyl-2,6-diazaspiro[3.3]heptan-2-yl)pyridin-2-yl)amino)-5-fluoropyrimidin-4-yl)-3-isopropyl-N,N,6-trimethyl-3H-thieno[2,3-d]imidazol-2-amine;

N-(5-(2-Ethyl-2-azaspiro [3.3]heptan-6-yl)pyridin-2-yl)-5-fluoro-4-(3-isopropyl-2-methyl-3H-thieno[2,3-d]imidazol-5-yl)pyrimidin-2-amine;

4-(2,6-Dimethyl-3-propan-2-ylthieno[2,3-d]imidazol-5-yl)-N-[6-(4-ethylpiperazin-1-yl) pyridin-2-yl]-5-fluoropyrimidin-2-amine;

5-Fluoro-4-(2-methyl-3-propan-2-ylthieno[2,3-d]imidazol-5-yl)-N-[5-(1-methylpyrrolidin-3-yl)oxypyridin-2-yl]pyrimidin-2-amine;

5-Fluoro-4-(3-isopropyl-2,6-dimethyl-3H-thieno[2,3-d]imidazol-5-yl)-N-(5-(4-methylmorpholin-2-yl)pyridin-2-yl)pyrimidin-2-amine;

N-[5-[1-(4-Ethylpiperazin-1-yl)ethyl]pyridin-2-yl]-5-fluoro-4-(2-methyl-3-propan-2-ylthieno[2,3-d]imidazol-5-yl) pyrimidin-2-amine;

3-[6-[[5-Fluoro-4-(2-methyl-3-propan-2-ylthieno[2,3-d]imidazol-5-yl)pyrimidin-2-yl]amino]pyridin-3-yl]-1,4-dimethylpiperazin-2-one;

((8aS)-6-(6-((5-Fluoro-4-(3-isopropyl-2,6-dimethyl-3H-thieno[2,3-d]imidazol-5-yl) pyrimidin-2-yl)amino) pyridin-3-yl)-2-methylhexahydropyrrolo [1,2-a]pyrazin-3(4H)-one;

4-(2,6-Dimethyl-3-propan-2-ylthieno[2,3-d]imidazol-5-yl)-N-[4-(4-ethylpiperazin-1-yl) pyridin-2-yl]-5-fluoropyrimidin-2-amine;

4-(3-Isopropyl-2-methyl-3H-thieno[2,3-d]imidazol-5-yl)-N-(5-(1-methylpiperidin-4-yl) pyridin-2-yl)-5-(trifluoromethyl) pyrimidin-2-amine;

N-[5-(4-Ethylpiperazin-1-yl)pyridin-2-yl]-5-fluoro-4-[7-propan-2-yl-3-(trifluoromethyl) thieno[3,2-b]pyridin-2-yl]pyrimidin-2-amine;

2-(2-((5-(4-Ethylpiperazin-1-yl) pyridin-2-yl)amino)-5-fluoropyrimidin-4-yl)-7-isopropylthieno[3,2-b]pyridine-3-carbonitrile;

5-Fluoro-N-[5-(1-methylpiperidin-4-yl)pyridin-2-yl]-4-(3-methyl-7-propan-2-ylthieno[3,2-c]pyridin-2-yl) pyrimidin-2-amine;

N-[5-[(4-Ethylpiperazin-1-yl)methyl]pyridin-2-yl]-5-fluoro-4-(6-methyl-3-propan-2-ylthieno[2,3-d]imidazol-5-yl)pyrimidin-2-amine;

5-Fluoro-N-[5-[-1-methylpiperidin-3-yl]pyridin-2-yl]-4-(6-methyl-3-propan-2-ylthieno[2,3-d]imidazol-5-yl) pyrimidin-2-amine (isomer 1);

5-Fluoro-N-[5-[-1-methylpiperidin-3-yl]pyridin-2-yl]-4-(6-methyl-3-propan-2-ylthieno[2,3-d]imidazol-5-yl) pyrimidin-2-amine (isomer 2);

4-(3-Isopropyl-2-methyl-3H-thieno[2,3-d]imidazol-5-yl)-5-methoxy-N-(5-(1-methylpiperidin-4-yl)pyridin-2-yl)pyrimidin-2-amine;

N-(5-(1-Ethylpiperidin-4-yl)pyridin-2-yl)-5-fluoro-4-(3-isopropyl-6-methyl-3H-thieno[2,3-d]imidazol-5-yl) pyrimidin-2-amine;

N-(5-(6-ethyl-2,6-diazaspiro[3.3]heptan-2-yl) pyridin-2-yl)-5-fluoro-4-(3-isopropyl-3H-thieno[2,3-d] imidazol-5-yl)pyrimidin-2-amine;

5-Chloro-4-(3-isopropyl-6-methyl-3H-thieno[2,3-d]imidazol-5-yl)-N-(5-(1-methylpiperidin-3-yl)pyridin-2-yl) pyrimidin-2-amine;

2-(5-Fluoro-2-((5-(1-methylpiperidin-4-yl)pyridin-2-yl) amino)pyrimidin-4-yl)-7-isopropyl-3-methylthieno[3,2-c] pyridine 5-oxide;

or a pharmaceutically acceptable salt thereof.

42. A pharmaceutical composition comprising a compound according to claim 1, or a pharmaceutically acceptable salt thereof, and a pharmaceutically acceptable excipient.

43. A method of inhibiting CDK4 and CDK6 comprising administering a compound according to claim 1, or a pharmaceutically acceptable salt thereof, or a pharmaceutically acceptable composition thereof.

44. A method for treating a CDK4-mediated and a CDK6-mediated disorder in a patient in need thereof, comprising administering to said patient a compound according to claim 1, or a pharmaceutically acceptable salt thereof, or a pharmaceutically acceptable composition thereof.

45. The method according to claim 44, wherein the CDK4-mediated and CDK6-mediated disorder is a cancer.

46. The method according to claim 45, wherein the cancer is breast cancer, malignant brain tumors, colon cancer, small-cell lung cancer, non-small-cell lung cancer, bladder cancer, ovarian cancer, prostate cancer, chronic lymphoid leukemia, lymphoma, myeloma, acute myeloid leukemia, secondary pancreatic cancer or secondary brain metastases.

47. The method according to claim 46, wherein the breast cancer is HR+/HER2− or HR+/HER2+ advanced or metastatic breast cancer; and the malignant brain tumors are glioblastoma, astrocytoma, or pontine glioma.

48. The method according to claim 44, wherein the patient is administered the pharmaceutically acceptable composition.

49. The method according to claim 44, wherein the administration is oral administration.

50. The method according to claim 44, further comprising administering an additional therapeutic agent to the patient.

51. The method according to claim 50, wherein the additional therapeutic agent is a PRMT5 inhibitor, a HER2 kinase inhibitor, an aromatase inhibitor, an estrogen receptor antagonist or an alkylating agent.

52. The method according to claim 51, wherein the aromatase inhibitor is letrozole.

53. The method according to claim 51 wherein estrogen receptor antagonist is fulvestrant.

54. The method according to claim 51, wherein the alkylating agent is temozolomide.

* * * * *

UNITED STATES PATENT AND TRADEMARK OFFICE
CERTIFICATE OF CORRECTION

| | | |
|---|---|---|
| PATENT NO. | : 11,685,744 B2 | Page 1 of 3 |
| APPLICATION NO. | : 17/480323 | |
| DATED | : June 27, 2023 | |
| INVENTOR(S) | : Andrew W. Buesking et al. | |

It is certified that error appears in the above-identified patent and that said Letters Patent is hereby corrected as shown below:

On the Title Page

Delete the title page and substitute therefore with the attached title page, showing the corrected number of claims.

In the Claims

Column 246, Line 46 after Claim 54 Please add the following Claims 55-62:

55. The compound of claim 1 that is:

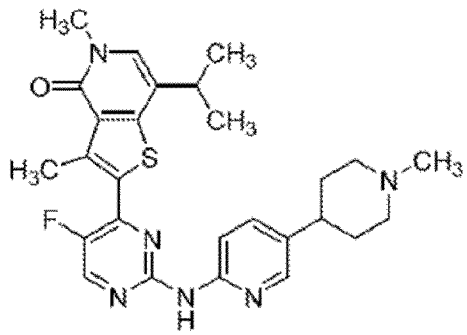

or a pharmaceutically acceptable salt thereof.

Signed and Sealed this
Nineteenth Day of March, 2024

Katherine Kelly Vidal
*Director of the United States Patent and Trademark Office*

56. The compound of claim 55 that is:

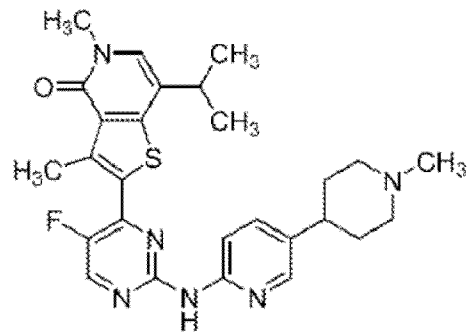

57. A pharmaceutical composition comprising a compound according to claim 55, or a pharmaceutically acceptable salt thereof, and a pharmaceutically acceptable excipient.

58. A method of inhibiting CDK4 and CDK6 comprising administering a compound according to claim 55, or a pharmaceutically acceptable salt thereof, or a pharmaceutically acceptable composition thereof.

59. A method for treating a CDK4-mediated and a CDK6-mediated disorder in a patient in need thereof, comprising administering to said patient a compound according to claim 55, or a pharmaceutically acceptable salt thereof, or a pharmaceutically acceptable composition thereof.

60. The method according to claim 59, wherein the CDK4-mediated and CDK6-mediated disorder is a cancer.

61. The method according to claim 60, wherein the cancer is breast cancer, malignant brain tumors, colon cancer, small-cell lung cancer, non-small-cell lung cancer, bladder cancer, ovarian cancer, prostate cancer, chronic lymphoid leukemia, lymphoma, myeloma, acute myeloid leukemia, secondary pancreatic cancer or secondary brain metastases.

62. The method according to claim 61, wherein the breast cancer is HR+/HER2- or HR+/HER2+ advanced or metastatic breast cancer; and the malignant brain tumors are glioblastoma, astrocytoma, or pontine glioma.

(12) United States Patent
Buesking et al.

(10) Patent No.: US 11,685,744 B2
(45) Date of Patent: Jun. 27, 2023

(54) CDK INHIBITORS AND THEIR USE AS PHARMACEUTICALS

(71) Applicant: Prelude Therapeutics, Incorporated, Wilmington, DE (US)

(72) Inventors: Andrew W. Buesking, Wilmington, DE (US); Andrew Paul Combs, Kennett Square, PA (US); Jincong Zhuo, Garnet Valley, PA (US); Ryan Holmes, Wilmington, DE (US); Sarah Pawley, Landenberg, PA (US); Xiaowei Wu, Wilmington, DE (US)

(73) Assignee: Prelude Therapeutics Incorporated, Wilmington, DE (US)

( * ) Notice: Subject to any disclaimer, the term of this patent is extended or adjusted under 35 U.S.C. 154(b) by 0 days.

(21) Appl. No.: 17/480,323

(22) Filed: Sep. 21, 2021

(65) Prior Publication Data

US 2022/0089608 A1 Mar. 24, 2022

Related U.S. Application Data

(60) Provisional application No. 63/221,959, filed on Jul. 15, 2021, provisional application No. 63/081,126, filed on Sep. 21, 2020.

(51) Int. Cl.
| | |
|---|---|
| *A61K 31/4188* | (2006.01) |
| *A61K 31/4196* | (2006.01) |
| *A61K 31/506* | (2006.01) |
| *A61K 31/5355* | (2006.01) |
| *A61K 31/551* | (2006.01) |
| *A61K 31/565* | (2006.01) |
| *A61P 35/00* | (2006.01) |
| *C07D 495/04* | (2006.01) |
| *C07D 519/00* | (2006.01) |

(52) U.S. Cl.
CPC ........ *C07D 495/04* (2013.01); *A61K 31/4188* (2013.01); *A61K 31/4196* (2013.01); *A61K 31/506* (2013.01); *A61K 31/5355* (2013.01); *A61K 31/551* (2013.01); *A61K 31/565* (2013.01); *A61P 35/00* (2018.01); *C07D 519/00* (2013.01)

(58) Field of Classification Search
CPC ............... C07D 495/04; C07D 519/00; A61K 31/4188; A61K 31/4196; A61K 31/506; A61K 31/5355; A61K 31/551; A61K 31/565; A61P 35/00
See application file for complete search history.

(56) References Cited

U.S. PATENT DOCUMENTS

| | | | |
|---|---|---|---|
| 3,657,744 | A | 4/1972 | Ersek |
| 4,739,762 | A | 4/1988 | Palmaz |
| 4,992,445 | A | 2/1991 | Lawter et al. |
| 5,001,139 | A | 3/1991 | Lawter et al. |
| 5,023,252 | A | 6/1991 | Hsieh |
| 5,040,548 | A | 8/1991 | Yock |
| 5,061,273 | A | 10/1991 | Yock |
| 5,195,984 | A | 3/1993 | Schatz |
| 5,292,331 | A | 3/1994 | Boneau |
| 5,451,233 | A | 8/1995 | Yock |
| 5,496,346 | A | 3/1996 | Horewski |
| 5,674,278 | A | 10/1997 | Boneau |
| 5,879,382 | A | 3/1999 | Boneau |
| 6,344,053 | B1 | 2/2002 | Boneau |

FOREIGN PATENT DOCUMENTS

| | | | | |
|---|---|---|---|---|
| CN | 112457326 A | * | 3/2021 | ............ A61P 35/00 |
| WO | 2009036082 | | 3/2009 | |
| WO | 2009046416 | | 4/2009 | |
| WO | 2014149164 | | 9/2014 | |
| WO | 2017114351 | | 7/2017 | |
| WO | 2017133701 | | 8/2017 | |
| WO | 2019223632 | | 11/2019 | |

OTHER PUBLICATIONS

CN-112457326-A; (2021) WIPO English machine translation—Description: p. 1-31.*
Berge_etal_J_Pharm Sci_1977.
Bronner_etal_Bioorg_MedChem_Lett_2019.
Cho_etal_J_Med_Chem_2010.
De_Gooijer_etal_Invest_New_Drugs_2015.
Parrish, Pokorny et al. 2015.
Raub_etal_Drug_Metabolism _Disposition_2015.
Remington's_Pharmaceutical_Science_17_ed_chapter_76.

* cited by examiner

*Primary Examiner* — John M Mauro

(74) *Attorney, Agent, or Firm* — BakerHostetler

(57) ABSTRACT

The disclosure is directed to compounds of Formula I

Pharmaceutical compositions comprising compounds of Formula I, as well as methods of their use and preparation, are also described.

62 Claims, No Drawings